(12) United States Patent
Liu et al.

(10) Patent No.: US 11,261,190 B2
(45) Date of Patent: Mar. 1, 2022

(54) DIHYDROPYRIMIDINE COMPOUNDS AND USES THEREOF IN MEDICINE

(71) Applicant: SUNSHINE LAKE PHARMA CO., LTD., Guangdong (CN)

(72) Inventors: Xinchang Liu, Dongguan (CN); Qingyun Ren, Dongguan (CN); Guanghua Yan, Dongguan (CN); Siegfried Goldmann, Wuppertal (DE); Yingjun Zhang, Dongguan (CN)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 71 days.

(21) Appl. No.: 16/754,220

(22) PCT Filed: Oct. 17, 2018

(86) PCT No.: PCT/CN2018/110592
§ 371 (c)(1),
(2) Date: Apr. 7, 2020

(87) PCT Pub. No.: WO2019/076310
PCT Pub. Date: Apr. 25, 2019

(65) Prior Publication Data
US 2020/0283445 A1    Sep. 10, 2020

(30) Foreign Application Priority Data

Oct. 18, 2017  (CN) .......................... 201710978074.6
Jan. 30, 2018  (CN) .......................... 201810088129.0
Sep. 10, 2018  (CN) .......................... 201811049241.X

(51) Int. Cl.
*A61K 31/50*      (2006.01)
*C07D 471/00*   (2006.01)
(Continued)

(52) U.S. Cl.
CPC ............ *C07D 487/04* (2013.01); *A61P 31/20* (2018.01); *A61K 45/06* (2013.01)

(58) Field of Classification Search
CPC ......................... A61K 31/4985; C07D 487/04
(Continued)

(56) References Cited

U.S. PATENT DOCUMENTS 9,758,530  B2     9/2017  Guo et al.
10,081,627 B2     9/2018  Guo et al.
(Continued)

FOREIGN PATENT DOCUMENTS

CN          108567783 A        9/2018
WO     WO-2015132276 A1  *  9/2015  ........... C07D 498/04
(Continued)

OTHER PUBLICATIONS

Harbeson et al. "Deuterium Medicinal Chemistry: A New Approach to drug Discovery and Development," Medchem News, 2014, No. 2, p. 8-22 (Year: 2014).*

(Continued)

*Primary Examiner* — Shengjun Wang
(74) *Attorney, Agent, or Firm* — Oliff PLC

(57) ABSTRACT

A dihydropyrimidine compound and use as a medicament, especially application as a medicament used for treating and preventing hepatitis B, specifically, is a compound having Formula (I) or (Ia), or a stereoisomer, a tautomer, an N-oxide, a solvate, a metabolite, a pharmaceutically acceptable salt or a prodrug thereof, wherein the variables of the formulas are as defined in the specification; and also includes the use of the compound having Formula (I) or (Ia), or an enantiomer, a diastereoisomer, a tautomer, a hydrate, a solvate, or a pharmaceutically acceptable salt thereof as a medicament, especially use as a medicament for treating and preventing hepatitis B.

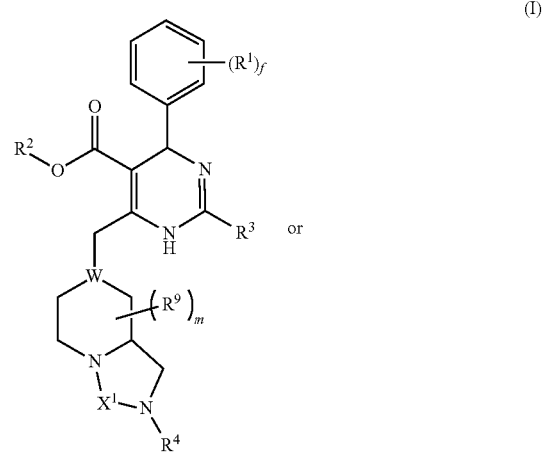

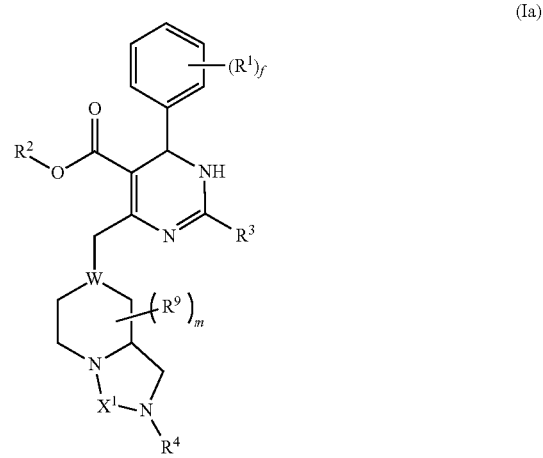

19 Claims, No Drawings

(51) Int. Cl.
    *C07D 487/04*     (2006.01)
    *A61P 31/20*     (2006.01)
    *A61K 45/06*     (2006.01)

(58) Field of Classification Search
    USPC .......................................... 514/249; 544/350
    See application file for complete search history.

(56) References Cited

U.S. PATENT DOCUMENTS

| | | |
|---|---|---|
| 10,179,131 B2 | 1/2019 | Qiu et al. |
| 10,428,069 B2 | 10/2019 | Guo et al. |
| 2018/0000824 A1 | 1/2018 | Dai et al. |
| 2019/0010155 A1 | 1/2019 | Chen |

FOREIGN PATENT DOCUMENTS

| | | |
|---|---|---|
| WO | 2017/064156 A1 | 4/2017 |
| WO | 2017/108630 A1 | 6/2017 |
| WO | 2018/045911 A1 | 3/2018 |
| WO | 2019/001396 A1 | 1/2019 |

OTHER PUBLICATIONS

Jan. 8, 2019 Search Report issued in International Patent Application No. PCT/CN2018/110592.
Jan. 8, 2019 Written Opinion of the International Searching Authority issued in International Patent Application No. PCT/CN2018/110592.

\* cited by examiner

DIHYDROPYRIMIDINE COMPOUNDS AND USES THEREOF IN MEDICINE

CROSS-REFERENCE TO RELATED APPLICATIONS

This application claims priority to Chinese Patent Application Serial Nos 201710978074.6, 201810088129.0 and 201811049241.X, filed with the State Intellectual Property Office of china respectively on Oct. 18, 2017, Jan. 30, 2018 and Sep. 10, 2018, which are hereby incorporated by reference in its entirety.

FIELD

The invention relates to use of dihydropyrimidine compounds as a medicine, especially for treating and preventing HBV diseases. The invention also relates to compositions of dihydropyrimidine compounds and other anti-viral agent, and applications in treating and preventing hepatitis B virus (HBV) infection diseases.

BACKGROUND OF THE INVENTION

The hepatitis B virus belongs to the family of hepadnaviridae. It can cause acute and/or persistent or progressive chronic diseases. Many other clinical manifestations in the pathological morphology can be also caused by HBV in particular chronic hepatitis, cirrhosis and hepatocellular carcinoma. Additionally, coinfection with hepatitis D virus may have adverse effects on the progress of the disease.

The conventional medicaments approved to be used for treating chronic hepatitis are interferon and lamivudine. However, the interferon has just moderate activity but has an adverse side reaction. Although lamivudine has good activity, its resistance develops rapidly during the treatment and relapse effects often appear after the treatment has stopped. The IC50 value of lamivudine (3-TC) is 300 nM (*Science*, 2003, 299, 893-896).

Deres, et al., have reported heteroaryl-substituted dihydropyrimidine (HAP) compounds including Bay41-4109 and Bay39-5493, and these compounds play a role in blocking HBV replication by preventing the proper formation of viral core particles (nucleocapsids). Bay41-4109 has a good drug metabolism properties in clinical research (Science, 299(2003), 893-896). The study of these compounds' mechanism indicated that through reacting with 113-143 amino acid residues of a core protein, heteroaryl-substituted dihydropyrimidine compounds have changed the angle between dimers which can form nucleocapsids, and thus led to forming unstably expanded nucleocapsids, which accelerate the degradation of the core protein (Biochem. Pharmacol, 2003, 66, 2273-2279).

Novel compounds with effective antiviral effects are still desired at present, especially drugs used for the treatment and/or prevention of hepatitis B.

SUMMARY OF THE INVENTION

The present invention relates to novel dihydropyrimidine compounds and use thereof in the manufacture of a medicament for treating and preventing an HBV infection. In particular, the present invention relates to a novel dihydropyrimidine compound, and a pharmaceutically acceptable composition thereof the compound have advantages like good pharmacokinetic properties, good solubility, good stability, no inducing effect on liver enzymes and small toxicity, and so on, and it can inhibit HBV infection effectively. It has a good application prospect in the field of anti HBV virus.

In one aspect, provided herein is a compound having Formula (I) or Formula (Ia) or a stereoisomer, a tautomer, an N-oxide, a solvate, a metabolite, a pharmaceutically acceptable salt or a prodrug thereof.

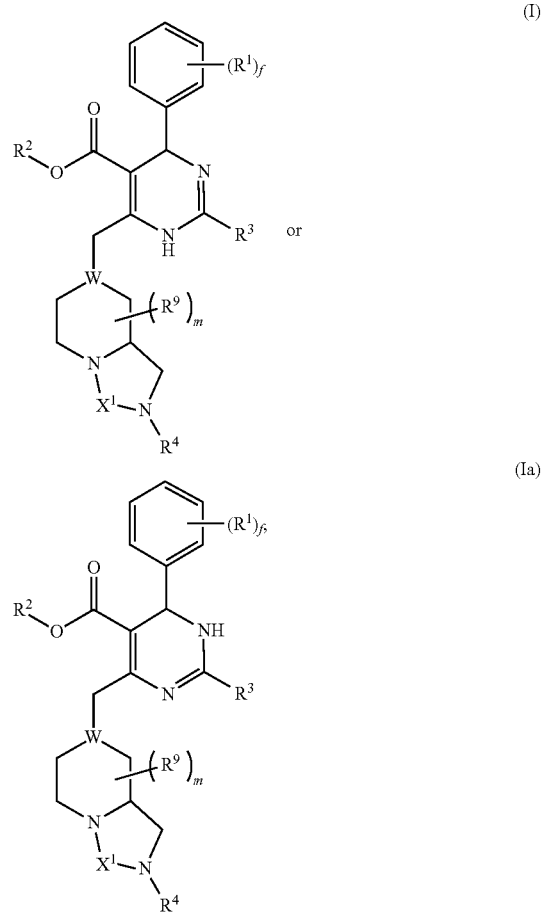

wherein each $R^1$ is independently H, deuterium, F, Cl, Br, I, cyano, methyl, ethyl, methoxy, ethoxy, methylamino, ethylamino, nitro, 4-trifluoromethylphenyl, 3,5-di(trifluoromethyl)phenyl or trifluoromethyl;

each $R^2$ is independently $C_{1-6}$ alkyl, deuterium substituted $C_{1-6}$ alkyl, $C_{1-6}$ haloalkyl, $C_{3-6}$ cycloalkyl-$C_{1-6}$ alkylene or 5-6 membered heterocyclyl-$C_{1-6}$ alkylene;

each $R^3$ is independently $C_{6-10}$ aryl or 5-6 membered heteroaryl, wherein each of $C_{6-10}$ aryl or 5-6 membered heteroaryl is independently unsubstituted or substituted with one, two, three, four or five substituents independently selected from deuterium, F, Cl, Br, OH, CN, $C_{1-6}$ alkyl, hydroxy $C_{1-6}$ alkyl, $C_{1-6}$ alkyl-OC(=O)—, $C_{1-6}$-alkyl-OC(=O)—$C_{1-6}$ alkylene, HOOC—$C_{1-6}$ alkylene, $C_{1-6}$ alkoxy-$C_{1-6}$ alkylene and $C_{1-6}$ alkyl-S(=O)$_2$—;

each W is independently CH or N;

each $X^1$ is independently —C(=O)—, —S(=O)$_2$— or —(CR$^7$R$^8$)$_j$—;

each $R^7$, $R^8$ and $R^9$ is independently H, deuterium, F, Cl, Br, amino, $C_{1-6}$ alkyl, NH$_2$C(=O)—, $C_{1-6}$ alkyl-OC(=O)—, carboxy, carboxy $C_{1-6}$ alkylene, hydroxy $C_{1-6}$ alkyl, $C_{1-4}$ alkoxy-$C_{1-4}$ alkyl or $C_{1-6}$ haloalkyl, or $R^7$ and $R^8$, together with the carbon atom to which they are attached, form $C_{3-6}$ cycloalkyl or carbonyl;

$R^4$ is 5-7 membered monocyclic heterocyclyl, 7-12 membered bicyclic heterocyclyl, $C_{2-12}$ alkynyl, pyridyl, 1,3,5-triazinyl, pyrazinyl, pyridazinyl, pyrimidinyl, 5 membered monocyclic heteroaryl, 7-12 membered bicyclic heteroaryl, phenyl, naphthyl, phenyl-$(CR^7R^8)$—, HOOC—$C_{1-6}$ alkylene or $R^{10}$—$(CR^7R^8)_j$—, wherein the 5-7 membered monocyclic heterocyclyl, 7-12 membered bicyclic heterocyclyl, $C_{2-12}$ alkynyl, 1,3,5-triazinyl, pyrazinyl, pyridazinyl, pyrimidinyl, 5 membered monocyclic heteroaryl, 7-12 membered bicyclic heteroary and naphthyl are each independently unsubstituted or substituted with one, two, three, four or five $R^w$, the pyridyl, phenyl and phenyl of phenyl-$(CR^7R^8)$— are each independently substituted with one, two, three or four $R^x$, the $C_{1-6}$ alkylene of HOOC—$C_{1-6}$ alkylene is substituted with one, two, three or four $R^{18}$;

$R^{10}$ is naphthyl, 5-7 membered monocyclic heteroaryl, 7-12 membered bicyclic heteroaryl, 5-7 membered monocyclic heterocyclyl or 7-12 membered bicyclic heterocyclyl, wherein the naphthyl, 5-7 membered monocyclic heteroaryl, 7-12 membered bicyclic heteroaryl, 5-7 membered monocyclic heterocyclyl and 7-12 membered bicyclic heterocyclyl are each independently substituted with one, two, three, four or five $R^w$;

each $R^w$ is independently deuterium, F, Cl, Br, OH, CN, $R^aR^bNC(=O)$—, $R^cR^dP(=O)$—, HOOC—$(CR^7R^8)_k$—, amino, $C_{1-8}$ alkyl, $C_{2-8}$ alkenyl, hydroxy $C_{1-8}$ alkyl, $C_{1-8}$ alkyl-C(=O)—, $C_{1-8}$ alkoxy, $C_{1-8}$ alkyl-OC(=O)— or $C_{1-8}$ alkyl-S(=O)$_2$—, wherein the amino, $C_{1-8}$ alkyl, $C_{2-8}$ alkenyl, hydroxy $C_{1-8}$ alkyl, $C_{1-8}$ alkyl-C(=O)—, $C_{1-8}$ alkoxy, $C_{1-8}$ alkyl-OC(=O)— and $C_{1-8}$ alkyl-S(=O)$_2$— are each independently unsubstituted or substituted with one, two, three, four or five BY;

each $R^x$ is independently deuterium, F, Cl, Br, OH, CN, $R^aR^bN$—, $R^aR^bNC(=O)$—, $R^cR^dP(=O)$—, HOOC—$(CR^7R^8)_k$—, tetrazolyl-$(CH_2)_n$—, amino, $C_{1-8}$ alkyl, $C_{2-8}$ alkenyl, hydroxy $C_{1-8}$ alkyl, $C_{1-8}$ alkyl-C(=O)—, $C_{1-8}$ alkoxy, $C_{1-8}$ alkyl-OC(=O)—, HOOC-methylene-O-methylene-, $C_{1-4}$ alkyl-OC(=O)-methylene-O-methylene, $C_{1-4}$ alkyl-C(=O)O-methylene or $C_{1-8}$ alkyl-S(=O)$_2$—, wherein the amino, $C_{1-8}$ alkyl, $C_{2-8}$ alkenyl, hydroxy $C_{1-8}$ alkyl, $C_{1-8}$ alkyl-C(=O)—, $C_{1-8}$ alkoxy, $C_{1-8}$ alkyl-OC(=O)—, HOOC-methylene-O-methylene-, $C_{1-4}$ alkyl-OC(=O)-methylene-O-methylene, $C_{1-4}$ alkyl-C(=O)O-methylene and $C_{1-8}$ alkyl-S(=O)$_2$— are each independently unsubstituted or substituted with one, two, three, four or five BY;

each $R^{18}$ is independently $R^aR^bN$—, 5-7 membered monocyclic heteroaryl, 7-12 membered bicyclic heteroaryl, 5-7 membered monocyclic heterocyclyl, 7-12 membered bicyclic heterocyclyl, benzyl or $C_{6-10}$ aryl, wherein the 5-7 membered monocyclic heteroaryl, 7-12 membered bicyclic heteroaryl, 5-7 membered monocyclic heterocyclyl, 7-12 membered bicyclic heterocyclyl, benzyl and $C_{6-10}$ aryl are each independently substituted with one, two, three, four or five $R^y$;

each $R^y$ is independently deuterium, F, Cl, Br, OH, CN, $R^aR^bNC(=O)$—, $R^cR^dP(=O)$—, HOOC—$(CR^7R^8)_h$—, amino, $C_{1-6}$ alkyl-S(=O)$_2$—NH—, $C_{1-8}$ alkyl, $C_{1-8}$ alkoxy, $C_{1-8}$ alkyl-S(=O)$_2$—, $C_{1-8}$ alkyl-C(=O)—, $C_{1-8}$ alkyl-OC(=O)—, benzyl-OC(=O)—, phenyl-OC(=O)— or $C_{1-8}$ alkylamino-S(=O)$_2$—, wherein the amino, $C_{1-6}$ alkyl-S(=O)$_2$—NH—, $C_{1-8}$ alkyl, $C_{1-8}$ alkoxy, $C_{1-8}$ alkyl-S(=O)$_2$—, $C_{1-8}$ alkyl-C(=O)—, $C_{1-8}$ alkyl-OC(=O)—, benzyl-OC(=O)—, phenyl-OC(=O)— and $C_{1-8}$ alkylamino-S(=O)$_2$— are each independently unsubstituted or substituted with one, two, three, four or five substituents selected from deuterium, F, Cl, Br, OH, $C_{1-8}$ alkoxy, $C_{1-8}$ alkyl, HOOC—$(CR^7R^8)_h$— or $C_{1-8}$ alkoxy-$(CR^7R^8)_n$—O—;

each $R^a$, $R^b$, $R^c$ and $R^d$ is independently H, deuterium, HOOC—$(CR^7R^8)_q$—, $C_{1-8}$ alkyl, $C_{1-8}$ alkyl-OC(=O)—, $C_{1-8}$ alkoxy, $C_{3-7}$ cycloalkyl or 3-12 membered heterocyclyl, wherein the $C_{1-8}$ alkyl, $C_{1-8}$ alkyl-OC(=O)—, $C_{1-8}$ alkoxy, $C_{3-7}$ cycloalkyl and 3-12 membered heterocyclyl are each independently unsubstituted or substituted with one, two, three, four or five substituents selected from deuterium, F, Cl, Br, OH, amino, $C_{1-8}$ alkyl, $C_{1-8}$ alkoxy, HOOC—$(CR^7R^8)_q$— or $C_{1-8}$ alkoxy-$(CR^7R^8)_n$—O—;

each f m, k, h and q is independently 0, 1, 2, 3 or 4;

each n is independently 1, 2, 3 or 4;

each j is independently 1, 2 or 3.

In some embodiments, provided herein is a compound having Formula (II) or Formula (IIa):

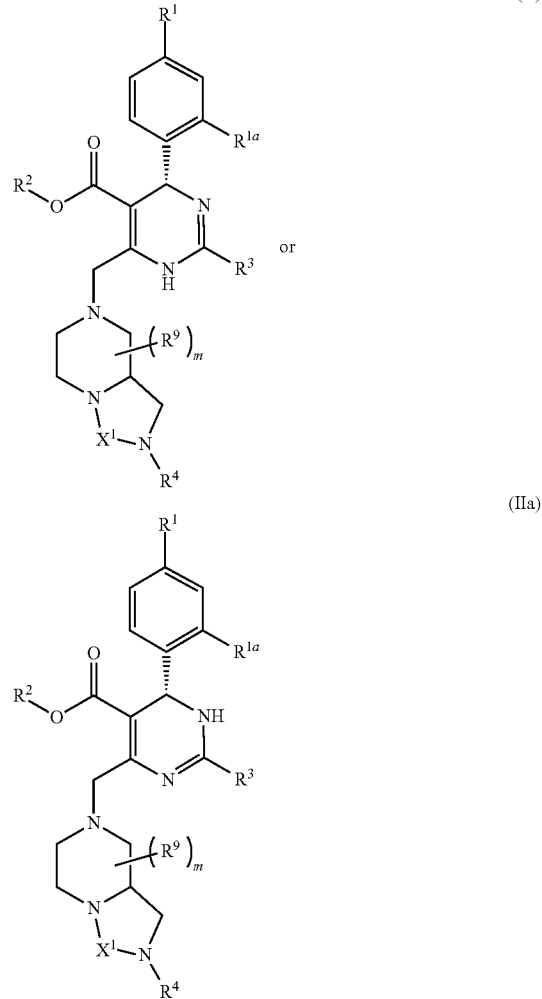

wherein each $R^2$, $R^3$, $R^4$, $R^9$, $X^1$ and m is as defined herein;

each $R^1$ and $R^{1a}$ is independently H, deuterium, F, Cl, Br, I, cyano, methyl, ethyl, methoxy, ethoxy, methylamino, ethylamino, nitro, 4-trifluoromethylphenyl, 3,5-di(trifluoromethyl)phenyl or trifluoromethyl.

In some embodiments, provided herein is a compound having Formula (III) or Formula (IIIa):

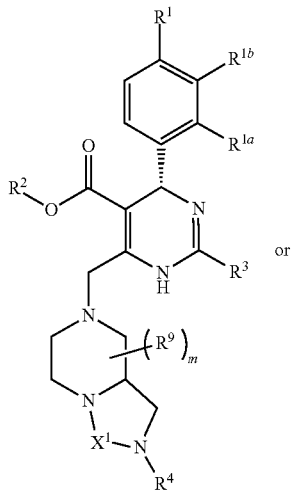
(III)

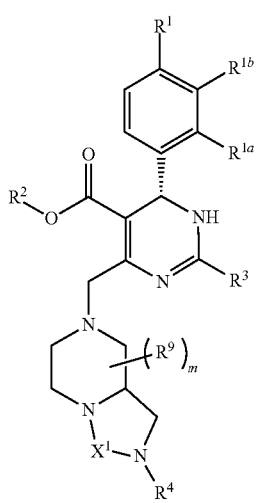
(IIIa)

wherein each $R^1$, $R^{1b}$ and $R^{1a}$ is independently H, deuterium, F, Cl, Br, I, cyano, methyl, ethyl, methoxy, ethoxy, methylamino, ethylamino, nitro, 4-trifluoromethylphenyl, 3,5-di(trifluoro methyl)phenyl or trifluoromethyl;

wherein each $R^2$, $R^3$, $R^4$, $R^9$, $X^1$ and m is as defined herein.

In some embodiments, provided herein is a compound having Formula (IV) or Formula (IVa):

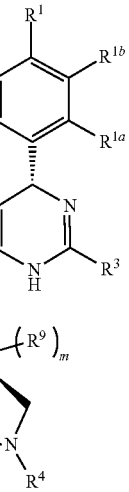
(IV)

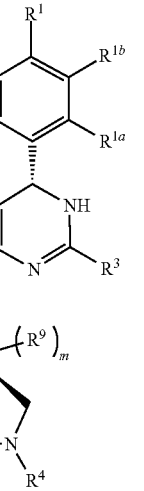
(IVa)

wherein each $R^1$, $R^{1b}$ and $R^{1a}$ is independently H, deuterium, F, Cl, Br, I, cyano, methyl, ethyl, methoxy, ethoxy, methylamino, ethylamino, nitro, 4-trifluoromethylphenyl, 3,5-di(trifluoro methyl)phenyl or trifluoromethyl;

wherein each $R^2$, $R^3$, $R^4$, $R^9$, $X^1$ and m is as defined herein.

In some embodiments, wherein each $R^2$ is independently methyl, deuterated methyl, ethyl, n-propyl, i-propyl, $C_{1-4}$ haloalkyl, $C_{3-6}$ cycloalkyl-$C_{1-3}$ alkylene or 5-6 membered heterocyclyl-$C_{1-3}$ alkylene;

$R^3$ is phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each of phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with one, two, three, four or five substituents independently selected from deuterium, F, Cl, Br, OH, CN, $C_{1-4}$ alkyl, hydroxy $C_{1-4}$ alkyl, $C_{1-4}$ alkyl-OC(=O)—, $C_{1-4}$ alkyl-OC(=O)—$C_{1-3}$ alkylene, HOOC—$C_{1-3}$ alkylene, $C_{1-4}$ alkoxy-$C_{1-3}$ alkylene or $C_{1-4}$ alkyl-S(=O)$_2$—;

each $R^7$, $R^8$ and $R^9$ is independently H, deuterium, F, Cl, Br, amino, methyl, ethyl, n-propyl, i-propyl, $NH_2C(=O)$—, $C_{1-4}$ alkyl-OC(=O)—, carboxy, carboxy $C_{1-3}$ alkylene, hydroxy $C_{1-4}$ alkyl, ethoxyethyl, methoxyethyl, isopropoxymethyl, methoxymethyl or $C_{1-4}$ haloalkyl, or $R^7$ and $R^8$, together with the carbon atom to which they are attached, form cyclopropyl, cyclobutyl, cyclopentyl, cyclohexyl or carbonyl;

In other embodiments, each $R^2$ is independently methyl, deuterated methyl, ethyl, n-propyl, i-propyl, $C_{1-4}$ haloalkyl, $C_{3-6}$ cycloalkyl-$C_{1-3}$ alkylene or 5-6 membered heterocyclyl-$C_{1-3}$ alkylene;

$R^3$ is phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each of phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with one, two, three, four or five substituents independently selected from deuterium, F, Cl, Br, OH, CN, $C_{1-4}$ alkyl, hydroxy $C_{1-4}$ alkyl, $C_{1-4}$ alkyl-OC(=O)—, $C_{1-4}$ alkyl-OC(=O)—$C_{1-3}$ alkylene, HOOC—$C_{1-3}$ alkylene, $C_{1-4}$ alkoxy-$C_{1-3}$ alkylene or $C_{1-4}$ alkyl-S(=O)$_2$—;

each $R^7$, $R^8$ and $R^9$ is independently H, deuterium, F, Cl, Br, amino, methyl, ethyl, n-propyl, i-propyl, $NH_2C(=O)$—, $C_{1-4}$ alkyl-OC(=O)—, methyl-OC(=O)—, ethyl-OC(=O)—, n-propyl-OC(=O)—, i-propyl-OC(=O)—, n-butyl-OC(=O)—, t-butyl-OC(=O)—, carboxy, carboxy-$C_{1-3}$ alkylene, hydroxymethyl, hydroxyethyl, hydroxypropyl, ethoxyethyl, methoxyethyl, isopropoxymethyl, methoxymethyl or $C_{1-4}$ haloalkyl, or $R^7$ and $R^8$, together with the carbon atom to which they are attached, form cyclopropyl, cyclobutyl, cyclopentyl, cyclohexyl or carbonyl.

In some embodiments, wherein $R^4$ is 5-6 membered monocyclic heterocyclyl, 8-10 membered bicyclic heterocyclyl, $C_{2-6}$ alkynyl, pyridyl, 1,3,5-triazinyl, pyrazinyl, pyridazinyl, pyrimidinyl, 5 membered monocyclic heteroaryl, 8-10 membered bicyclic heteroaryl, phenyl, naphthyl, phenyl-(CR$^7$R$^8$)—, HOOC—$C_{1-4}$ alkylene or $R^{10}$—(CR$^8$R$^8$)$_j$—, wherein the 5-6 membered monocyclic heterocyclyl, 8-10 membered bicyclic heterocyclyl, $C_{2-6}$ alkynyl, 1,3,5-triazinyl, pyrazinyl, pyridazinyl, pyrimidinyl, 5 membered monocyclic heteroaryl, 8-10 membered bicyclic heteroary and naphthyl are each independently unsubstituted or substituted with one, two, three, four or five $R^w$, the pyridyl, phenyl and phenyl of phenyl-(CR$^7$R$^8$)— are each independently substituted with one, two, three or four $R^x$, the $C_{1-4}$ alkylene of HOOC—$C_{1-4}$ alkylene is substituted with one, two, three or four $R^{18}$;

$R^{10}$ is naphthyl, 5-6 membered monocyclic heteroaryl, 8-10 membered bicyclic heteroaryl, 5-6 membered monocyclic heterocyclyl or 8-10 membered bicyclic heterocyclyl, wherein the naphthyl, 5-6 membered monocyclic heteroaryl, 8-10 membered bicyclic heteroaryl, 5-6 membered monocyclic heterocyclyl and 8-10 membered bicyclic heterocyclyl are each independently substituted with one, two, three, four or five $R^w$;

wherein each $R^7$, $R^8$, $R^w$, $R^x$, $R^{18}$ and j is as defined herein.

In some embodiments, wherein $R^4$ is pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, 8-10 membered bicyclic heterocyclyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, benzothiazolyl, benzoimidazolyl, benzofuryl, benzothienyl, indolyl, isoquinolyl, phenyl, naphthyl, phenyl-(CR$^7$R$^8$)—, HOOC—$C_{1-3}$ alkylene or $R^{10}$—(CR$^7$R$^8$)$_j$—, wherein each of pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, 8-10 membered bicyclic heterocyclyl, ethynyl, propargyl, propynyl, butynyl, pentynyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, benzothiazolyl, benzoimidazolyl, benzofuryl, benzothienyl, indolyl, isoquinolyl and naphthyl is independently unsubstituted or substituted with one, two, three, four or five $R^w$; the pyridyl, phenyl and phenyl of phenyl-(CR$^7$R$^8$)— are each independently substituted with one, two, three or four $R^x$; the $C_{1-3}$ alkylene of HOOC—$C_{1-3}$ alkylene is independently substituted with one, two, three or four $R^{18}$;

$R^{10}$ is naphthyl, 5-6 membered monocyclic heteroaryl, 8-10 membered bicyclic heteroaryl, 5-6 membered monocyclic heterocyclyl or 8-10 membered bicyclic heterocyclyl, wherein the naphthyl, 5-6 membered monocyclic heteroaryl, 8-10 membered bicyclic heteroaryl, 5-6 membered monocyclic heterocyclyl and 8-10 membered bicyclic heterocyclyl are each independently substituted with one, two, three, four or five $R^w$;

wherein each $R^7$, $R^8$, $R^w$, $R^x$, $R^{18}$ and j is as defined herein.

In some embodiments, wherein each $R^w$ is independently deuterium, F, Cl, Br, OH, CN, $R^aR^bNC(=O)$—, $R^cR^dP(=O)$—, HOOC—(CR$^7$R$^8$)$_k$—, amino, $C_{1-6}$ alkyl, hydroxy $C_{1-6}$ alkyl, $C_{2-6}$ alkenyl, $C_{1-6}$ alkyl-C(=O)—, $C_{1-6}$ alkoxy, $C_{1-6}$ alkyl-OC(=O)— or $C_{1-6}$ alkyl-S(=O)$_2$—, wherein the amino, $C_{1-6}$ alkyl, $C_{2-6}$ alkenyl, hydroxy $C_{1-6}$ alkyl, $C_{1-6}$ alkyl-C(=O)—, $C_{1-6}$ alkoxy, $C_{1-6}$ alkyl-OC(=O)— and $C_{1-6}$ alkyl-S(=O)$_2$— are each independently unsubstituted or substituted with one, two, three, four or five BY;

each $R^x$ is independently deuterium, F, Cl, Br, OH, CN, $R^aR^bN$—, $R^aR^bNC(=O)$—, $R^cR^dP(=O)$—, HOOC—(CR$^7$R$^8$)$_k$—, tetrazolyl-(CH$_2$)$_n$—, amino, $C_{1-6}$ alkyl, $C_{2-6}$ alkenyl, hydroxy $C_{1-6}$ alkyl, $C_{1-6}$ alkyl-C(=O)—, $C_{1-6}$ alkoxy, $C_{1-6}$ alkyl-OC(=O)—, HOOC-methylene-O-methylene-, $C_{1-4}$ alkyl-OC(=O)-methylene-O-methylene, $C_{1-4}$ alkyl-C(=O)O-methylene or $C_{1-6}$ alkyl-S(=O)$_2$—, wherein the amino, $C_{1-6}$ alkyl, $C_{2-6}$ alkenyl, hydroxy $C_{1-6}$ alkyl, $C_{1-6}$ alkyl-C(=O)—, $C_{1-6}$ alkoxy, $C_{1-6}$ alkyl-OC(=O)—, HOOC-methylene-O-methylene-, $C_{1-4}$ alkyl-OC(=O)-methylene-O-methylene, $C_{1-4}$ alkyl-C(=O)O-methylene and $C_{1-6}$ alkyl-S(=O)$_2$— are each independently unsubstituted or substituted with one, two, three, four or five BY;

each $R^{18}$ is independently $R^aR^bN$—, 5-6 membered monocyclic heteroaryl, 8-10 membered bicyclic heteroaryl, 5-6 membered monocyclic heterocyclyl, 8-10 membered bicyclic heterocyclyl, benzyl, phenyl or naphthyl, wherein the 5-6 membered monocyclic heteroaryl, 8-10 membered bicyclic heteroaryl, 5-6 membered monocyclic heterocyclyl, 8-10 membered bicyclic heterocyclyl, benzyl, phenyl and naphthyl are each independently substituted with one, two, three, four or five $R^y$;

wherein each $R^a$, $R^b$, $R^c$, $R^d$, $R^7$, $R^8$, $R^y$, k and n is as defined herein.

In some embodiments, wherein each $R^w$ is independently deuterium, F, Cl, Br, OH, CN, $R^aR^bNC(=O)$—, $R^cR^dP(=O)$—, HOOC—(CR$^7$R$^8$)$_k$—, amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)— or $C_{1-4}$ alkyl-S(=O)$_2$—, wherein the amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)— and $C_{1-4}$ alkyl-S(=O)$_2$— are each independently unsubstituted or substituted with one, two, three, four or five BY;

each $R^x$ is independently deuterium, F, Cl, Br, OH, CN, $R^aR^bN$—, $R^aR^bNC(=O)$—, $R^cR^dP(=O)$—, HOOC—$(CR^7R^8)_1$—, tetrazolyl-$(CH_2)_n$—, amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)—, HOOC-methylene-O-methylene-, methyl-OC(=O)-methylene-O-methylene, ethyl-OC(=O)-methylene-O-methylene, methyl-C(=O)O-methylene or $C_{1-4}$ alkyl-S(=O)$_2$—, wherein the amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)—, HOOC-methylene-O-methylene-, methyl-OC(=O)-methylene-O-methylene, ethyl-OC(=O)-methylene-O-methylene, methyl-C(=O)O-methylene and $C_{1-4}$ alkyl-S(=O)$_2$— are each independently unsubstituted or substituted with one, two, three, four or five BY;

each $R^{18}$ is independently $R^aR^bN$—, 5-6 membered monocyclic heteroaryl, 9-10 membered bicyclic heteroaryl, 5-6 membered monocyclic heterocyclyl, 8-10 membered bicyclic heterocyclyl, benzyl, phenyl or naphthyl, wherein the 5-6 membered monocyclic heteroaryl, 9-10 membered bicyclic heteroaryl, 5-6 membered monocyclic heterocyclyl, 8-10 membered bicyclic heterocyclyl, benzyl, phenyl and naphthyl are each independently substituted with one, two, three, four or five BY;

wherein each $R^a$, $R^b$, $R^c$, $R^d$, $R^7$, $R^8$, $R^y$, k and n is as defined herein.

In some embodiments, wherein each $R^y$ is independently deuterium, F, Cl, Br, OH, CN, $R^aR^bNC(=O)$—, $R^cR^dP(=O)$—, HOOC—$(CR^7R^8)_h$—, amino, $C_{1-4}$ alkyl-S(=O)$_2$—NH—, $C_{1-6}$ alkyl, $C_{1-6}$ alkoxy, $C_{1-6}$ alkyl-S(=O)$_2$—, $C_{1-6}$ alkyl-C(=O)—, $C_{1-6}$ alkyl-OC(=O)—, benzyl-OC(=O)—, phenyl-OC(=O)— or $C_{1-6}$ alkylamino-S(=O)$_2$—, wherein the amino, $C_{1-4}$ alkyl-S(=O)$_2$—NH—, $C_{1-6}$ alkyl, $C_{1-6}$ alkoxy, $C_{1-6}$ alkyl-S(=O)$_2$—, alkyl-C(=O)—, $C_{1-6}$ alkyl-OC(=O)—, benzyl-OC(=O)—, phenyl-OC(=O)— and $C_{1-6}$ alkylamino-S(=O)$_2$— are each independently unsubstituted or substituted with one, two, three, four or five substituents selected from deuterium, F, Cl, Br, OH, $C_{1-6}$ alkoxy, $C_{1-6}$ alkyl, HOOC—$(CR^7R^8)_h$— or $C_{1-6}$ alkoxy-$(CR^7R^8)_n$—O—;

each $R^a$, $R^b$, $R^c$ and $R^d$ is independently H, deuterium, HOOC—$(CR^7R^8)_q$—, $C_{1-6}$ alkyl, $C_{1-6}$ alkyl-OC(=O)—, $C_{1-6}$ alkoxy, $C_{3-6}$ cycloalkyl or 5-10 membered heterocyclyl, wherein the $C_{1-6}$ alkyl, $C_{1-6}$ alkyl-OC(=O)—, $C_{1-6}$ alkoxy, $C_{3-6}$ cycloalkyl and 5-10 membered heterocyclyl are each independently unsubstituted or substituted with one, two, three, four or five substituents selected from deuterium, F, Cl, Br, OH, amino, $C_{1-6}$ alkyl, $C_{1-6}$ alkoxy, HOOC—$(CR^7R^8)_q$— or $C_{1-6}$ alkoxy-$(CR^7R^8)_n$—O—;

wherein $R^7$, $R^8$, h, n and q are as defined herein.

In some embodiments, wherein each $R^y$ is independently deuterium, F, Cl, Br, OH, CN, $R^aR^bNC(=O)$—, $R^cR^dP(=O)$—, HOOC—$(CR^7R^8)_k$—, amino, methyl-S(=O)$_2$—NH—, ethyl-S(=O)$_2$—NH—, $C_{1-4}$ alkyl, $C_{1-4}$ alkoxy, $C_{1-4}$ alkyl-S(=O)$_2$—, $C_{1-4}$ alkyl-C(=O)—, $C_{1-4}$ alkyl-OC(=O)—, benzyl-OC(=O)—, phenyl-OC(=O)— or $C_{1-4}$ alkylamino-S(=O)$_2$—, wherein the amino, methyl-S(=O)$_2$—NH—, ethyl-S(=O)$_2$—NH—, $C_{1-4}$ alkyl, $C_{1-4}$ alkoxy, $C_{1-4}$ alkyl-S(=O)$_2$—, $C_{1-4}$ alkyl-C(=O)—, $C_{1-4}$ alkyl-OC(=O)—, benzyl-OC(=O)—, phenyl-OC(=O)— and $C_{1-4}$ alkylamino-S(=O)$_2$— are each independently unsubstituted or substituted with one, two, three, four or five substituents selected from deuterium, F, Cl, Br, OH, $C_{1-4}$ alkoxy, $C_{1-4}$ alkyl, HOOC—$(CR^7R^8)_h$— or $C_{1-4}$ alkoxy-$(CR^7R^8)_6$—O—;

each $R^a$, $R^b$, $R^c$ and $R^d$ is independently H, deuterium, HOOC—$(CR^7R^8)_q$—, $C_{1-4}$ alkyl, $C_{1-4}$ alkyl-OC(=O)—, $C_{1-4}$ alkoxy, $C_{3-6}$ cycloalkyl or 5-6 membered heterocyclyl, wherein the $C_{1-4}$ alkyl, $C_{1-4}$ alkyl-OC(=O)—, $C_{1-4}$ alkoxy, $C_{3-6}$ cycloalkyl and 5-6 membered heterocyclyl are each independently unsubstituted or substituted with one, two, three, four or five substituents selected from deuterium, F, Cl, Br, OH, amino, $C_{1-4}$ alkyl, $C_{1-4}$ alkoxy, HOOC—$(CR^7R^8)_q$— or $C_{1-4}$ alkoxy-$(CR^7R^8)_n$—O—;

wherein $R^7$, $R^8$, h, n and q are as defined herein.

In some embodiments, each $R^y$ is independently deuterium, F, Cl, Br, OH, CN, $R^aR^bNC(=O)$—, $R^cR^dP(=O)$—, HOOC—$(CR^7R^8)_k$—, amino, methyl-S(=O)$_2$—NH—, ethyl-S(=O)$_2$—NH—, $C_{1-4}$ alkyl, $C_{1-4}$ alkoxy, methyl-S(=O)$_2$—, ethyl-S(=O)$_2$—, n-propyl-S(=O)$_2$—, i-propyl-S(=O)$_2$—, $C_{1-4}$ alkyl-C(=O)—, methyl-OC(=O)—, ethyl-OC(=O)—, n-propyl-OC(=O)—, i-propyl-OC(=O)—, benzyl-OC(=O)—, phenyl-OC(=O)— or $C_{1-4}$ alkylamino-S(=O)$_2$—, wherein the amino, methyl-S(=O)$_2$—NH—, ethyl-S(=O)$_2$—NH—, $C_{1-4}$ alkyl, $C_{1-4}$ alkoxy, methyl-S(=O)$_2$—, ethyl-S(=O)$_2$—, n-propyl-S(=O)$_2$—, i-propyl-S(=O)$_2$—, $C_{1-4}$ alkyl-C(=O)—, methyl-OC(=O)—, ethyl-OC(=O)—, n-propyl-OC(=O)—, i-propyl-OC(=O)—, benzyl-OC(=O)—, phenyl-OC(=O)— and $C_{1-4}$ alkylamino-S(=O)$_2$— are each independently unsubstituted or substituted with one, two, three, four or five substituents selected from deuterium, F, Cl, Br, OH, $C_{1-4}$ alkoxy, $C_{1-4}$ alkyl, HOOC—$(CR^7R^8)_h$— or $C_{1-4}$ alkoxy-$(CR^7R^8)_n$—O—;

each $R^a$, $R^b$, $R^c$ and $R^d$ is independently H, deuterium, HOOC—$(CR^7R^8)_q$—, methyl, ethyl, n-propyl, i-propyl, $C_{1-4}$ alkyl-OC(=O)—, $C_{1-4}$ alkoxy, cyclopropyl, cyclobutyl, cyclopentyl, cyclohexyl or 5-6 membered heterocyclyl, wherein the methyl, ethyl, n-propyl, i-propyl, $C_{1-4}$ alkyl-OC(=O)—, $C_{1-4}$ alkoxy, cyclopropyl, cyclobutyl, cyclopentyl, cyclohexyl and 5-6 membered heterocyclyl are each independently unsubstituted or substituted with one, two, three, four or five substituents selected from deuterium, F, Cl, Br, OH, amino, $C_{1-4}$ alkyl, $C_{1-4}$ alkoxy, HOOC—$(CR^7R^8)_q$— or $C_{1-4}$ alkoxy-$(CR^7R^8)_n$—O—;

wherein $R^7$, $R^8$, h, n and q are as defined herein.

In other aspect, provided herein is a pharmaceutical composition comprising the compound disclosed herein and a pharmaceutically acceptable adjuvant.

In some embodiments, the pharmaceutical composition disclosed herein further comprises other anti-HBV drug.

In some embodiments of the pharmaceutical composition disclosed herein, wherein the other anti-HBV drug is an HBV polymerase inhibitor, immunomodulator or interferon.

In some embodiments of the pharmaceutical composition, wherein the other anti-HBV drug is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, Euforavac, rintatolimod, Phosphazid, Heplisav, interferon α-2b, levamisole, or propagermanium.

In another aspect, also provided herein is use of the compound or the pharmaceutical composition disclosed herein in the manufacture of a medicament for preventing, treating or lessening a virus disease in a patient.

In some embodiments of the use, wherein the virus disease disclosed herein is hepatitis B infection or a disease caused by hepatitis B infection.

In other embodiments of the use, the disease caused by hepatitis B infection disclosed herein is hepatic cirrhosis or hepatocellular carcinogenesis.

In other aspect, provided herein is use of the compound or the pharmaceutical composition in the manufacture of a medicament for preventing, treating or lessening an HBV disease in a patient, comprising administering to the patient a therapeutically effective amount of the compound or the pharmaceutical composition of the invention.

In other embodiments, the present invention relates to a method of preventing, treating or lessening an HBV disease in a patient, comprising administering a therapeutically effective amount of a pharmaceutically acceptable effective amount of the compound to a patient.

In other embodiments, the present invention relates to a method of preventing, treating or lessening an HBV disease in a patient, comprising administering a therapeutically effective amount of a pharmaceutically acceptable effective amount of the compound to a patient.

In other aspect, provided herein is use of the compound disclosed herein in the manufacture of a medicament for preventing, managing or treating an HBV disease in a patient, and lessening the severity thereof.

In other aspect, provided herein is use of the composition containing the compound disclosed herein in the manufacture of a medicament for preventing, managing or treating an HBV disease in a patient, and lessening the severity thereof.

In other embodiments, provided herein is a method of inhibiting HBV infection, comprising contacting cells with an effective amount of the compound or the composition to HBV. In other some embodiments, the method further comprises contacting cells with other anti-HBV therapeutic agent.

In other aspect, the present invention relates to a method of treating an HBV disease in a patient, comprising administrating a therapeutically effective amount of the compound or composition thereof to a patient in need. In other some embodiments, the method further comprises administrating a therapeutically effective amount of other anti-HBV therapeutic agent.

In other aspect, the present invention relates to a method of inhibiting an HBV infection in a patient, comprising administrating a therapeutically effective amount of the compound or composition thereof to a patient in need. In other some embodiments, the method further comprises administrating a therapeutically effective amount of other anti-HBV therapeutic agent.

In other aspect, the present invention relates to the compound or the pharmaceutical composition for use in preventing, treating or lessening a virus disease in a patient.

In some embodiments, wherein the virus disease is hepatitis B infection or a disease caused by hepatitis B infection.

In other embodiments, wherein the disease caused by hepatitis B infection is hepatic cirrhosis or hepatocellular carcinogenesis.

In other aspect, the present invention relates to a method of preventing, treating or lessening a virus disease comprising administering the compound or the pharmaceutical composition to the patient.

In some embodiments, the virus disease is hepatitis B infection or a disease caused by hepatitis B infection.

In other embodiments, the disease caused by hepatitis B infection is hepatic cirrhosis or hepatocellular carcinogenesis.

In other aspect, provided herein is a method of preparing, separating or purifying the compound of Formula (I) or Formula (Ia).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and the Handbook of Chemistry and Physics, 75 th Ed. 1994. Additionally, general principles of organic chemistry are described in Sorrell et al., "Organic Chemistry", University Science Books, Sausalito: 1999, and "March's Advanced Organic Chemistry", by Michael B. Smith and Jerry March, John Wiley & Sons, New York: 2007, all of which are incorporated herein by reference in their entireties.

As described herein, compounds disclosed herein may optionally be substituted with one or more substituents, such as are illustrated generally below, or as exemplified by particular classes, subclasses, and species of the invention.

In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituent may be, but are not limited to, deuterium, F, Cl, Br, OH, $C_{1-8}$ alky, $C_{1-8}$ alkoxy, HOOC—$(CR^7R^8)_q$— or $C_{1-8}$ alkoxy-$(CR^7R^8)_k$—O—, and wherein q, k, $R^7$ and $R^8$ are as defined herein.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "alkyl" or "alkyl group" refers to a saturated linear or branched-chain monovalent hydrocarbon radical of 1 to 20 carbon atoms, wherein the alkyl radical may be optionally and independently substituted with one or more substituents described herein. In some embodiments, the alkyl group contains 1-12 carbon atoms. In other embodiments, the alkyl group contains 1-10 carbon atoms. In other embodiments, the alkyl group contains 1-8 carbon atoms. In still other embodiments, the alkyl group contains 1-6 carbon atoms. In yet other embodiments, the alkyl group contains 1-4 carbon atoms and in still yet other embodiments, the alkyl group contains 1-3 carbon atoms. Some non-limiting examples of the alkyl group further include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), 2-methylpropyl or isobutyl (i-Bu, —CH$_2$CH(CH$_3$)$_2$), 1-methylpropyl or sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$) CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$) CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$) CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_{2,3}$CH(CH$_3$)$_2$), 3,3-dimethyl-2-butyl (—CH(CH$_3$)C (CH$_{3,3}$)$_3$, n-heptyl and n-octyl, etc.

The term "alkylene" refers to a saturated divalent or multivalent hydrocarbon group derived from a straight or branched chain saturated hydrocarbon by the removal of two or multi hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. And alkylene group is exemplified by, but not limited to, methylene (—CH$_2$—), ethylene (—CH$_2$CH$_2$—), isopropylene (—CH (CH$_3$)CH$_2$—), and the like.

The term "hydroxyalkyl" or "hydroxyalkoxy" refers to alkyl or alkoxy, as the case may be, substituted with one or more hydroxy groups. Wherein hydroxyalkyl and hydroxyalkylene may be used interchangeably, some non-limiting examples of the hydroxyalkyl group include hydroxymethyl (—CH$_2$OH), hydroxyethyl (—CH$_2$CH$_2$OH, —CHOHCH$_3$), hydroxypropyl (—CH$_2$CH$_2$CH$_2$OH, —CH$_2$CHOHCH$_3$— CHOHCH$_2$CH$_3$ hydroxymethoxy (—OCH$_2$OH), and the like.

The terms "haloalkyl", "haloalkenyl" or "haloalkoxy" refer to alkyl, alkenyl or alkoxy, as the case may be, substituted with one or more halogen atoms. Wherein the alkyl, alkenyl and alkoxy are as defined herein. Some non-limiting examples of such groups include difluoroethyl (—CH$_2$CHF$_2$, —CF$_2$CH$_3$, —CHFCH$_2$F), trifluoroethyl (—CH$_2$CF$_3$, —CF$_2$CH$_2$F, —CFHCHF$_2$), trifluoromethyl (—CF$_3$), trifluoromethoxy (—OCF$_3$), fluorovinyl (—CH=CHF, —CF=CH$_2$), and the like.

The term "alkenyl" refers to a linear or branched chain monovalent hydrocarbon radical of 2-12 carbon atoms, wherein at least one carbon-carbon bond is sp$^2$ double bond, wherein the alkenyl radical may be independently and optionally substituted with one or more substituents described herein, and includes radicals having "cis" and "trans" orientations, or alternatively, "E" and "Z" orientations. Examples of the alkenyl group include, but are not limited to, vinyl (—CH=CH$_2$), propenylallyl (—CH=CH$_2$CH$_3$), allyl (—CH$_2$CH=CH$_2$), and the like.

The term "alkoxy" refers to an alkyl group, as previously defined, attached to the parent molecular moiety via an oxygen atom. Unless otherwise specified, the alkoxy group contains 1-12 carbon atoms. In some embodiments, the alkoxy group contains 1-8 carbon atoms. In other embodiments, the alkoxy group contains 1-6 carbon atoms. In still other embodiments, the alkoxy group contains 1-4 carbon atoms. In yet other embodiments, the alkoxy group contains 1-3 carbon atoms. The alkoxy group may be optionally substituted with one or more substituents disclosed herein.

Some non-limiting examples of the alkoxy group include, but are not limited to, methoxy (MeO, —OCH$_3$), ethoxy (EtO, —OCH$_2$CH$_3$), 1-propoxy (n-PrO, n-propoxy, —OCH2CH$_2$CH$_3$), 2-propoxy (i-PrO, i-propoxy, —OCH (CH$_3$)$_2$), 1-butoxy (n-BuO, n-butoxy, —OCH$_2$CH$_2$CH$_2$CH$_3$), 2-methyl-1-propoxy i-butoxy, —OCH$_2$CH(CH$_3$)$_2$), 2-butoxy (s-BuO, s-butoxy, —OCH (CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$) CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH (CH$_3$)CH$_2$CH$_3$), and the like.

The term "alkynyl" refers to a linear or branched chain monovalent hydrocarbon radical of 2 to 12 carbon atoms, with at least one carbon-carbon bond is sp triple bond, wherein the alkynyl radical is optionally substituted independently with one or more substituents described herein. In some embodiments, the alkynyl group contained 2 to 12 carbon atoms; In other embodiments, the alkynyl group contained 2 to 8 carbon atoms; the alkynyl group contained 2 to 6 carbon atoms; the alkynyl group contained 2 to 4 carbon atoms. Some specific examples include, but are not limited to, ethynyl (—CCH), propargyl (—CH$_2$CCH), propinyl (—C≡C—CH$_3$), butynyl (—CH$_2$CH$_2$CCH, —CH$_2$C≡CCH$_3$, —C≡CCH$_2$CH$_3$ and —CH(CH$_3$)CCH) and pentynyl (—CH$_2$CH$_2$CH$_2$CCH, —CH$_2$CH$_2$C≡CCH$_3$, —CH$_2$C≡CCH$_2$CH$_3$, —C≡CCH$_2$CH$_2$CH$_3$, —CH$_2$CH(CH$_3$) CCH, —CH(CH$_3$)CH$_2$CCH), —C(CH$_3$)$_2$CCH, —CH(CH$_3$) C≡CCH$_3$ and —C≡CCH(CH$_3$)$_2$) and the like.

The term "cycloalkyl" refers to a monovalent or multivalent saturated ring having 3 to 12 carbon atoms as a monocyclic, bicyclic, or tricyclic ring system, In some embodiments, the cycloalkyl group contains 3 to 12 carbon atoms. In other embodiments, the cycloalkyl group contains 3 to 8 carbon atoms. In other embodiments, the cycloalkyl group contains 3 to 7 carbon atoms. In still other embodiments, the cycloalkyl group contains 3 to 6 carbon atoms. The cycloalkyl group may be optionally substituted with one or more substituents disclosed herein.

The term "X-membered" or "X membered", where X is an integer typically describes the number of ring-forming atoms in a moiety where the number of ring-forming atoms is X. For example, piperidinyl is an example of a 6-membered heterocyclyl.

The term "heterocyclyl" refers to a non-aromatic, saturated or partially unsaturated, monovalent or multivalent, monocyclic, bicyclic or tricyclic ring containing 3 to 12 ring atoms, in which at least one ring member is selected from nitrogen, sulfur and oxygen. Wherein, the heterocyclyl group may be optionally substituted with one or more substituents disclosed herein. Unless otherwise specified, the heterocyclyl group may be carbon or nitrogen linked, and a —CH$_2$— group can be optionally replaced by a —C(=O)— or —C(=S)— group. In which, the sulfur can be optionally oxygenized to S-oxide. In which, the nitrogen can be optionally oxygenized to N-oxide. In some embodiment, heterocyclyl refers to a 5-7 membered monocyclic heterocyclyl. In some embodiment, heterocyclyl refers to a 5-6 membered monocyclic heterocyclyl. In some embodiment, heterocyclyl refers to a 7-12 membered bicyclic heterocyclyl. In some embodiment, heterocyclyl refers to an 8-10 membered bicyclic heterocyclyl. In some embodiments, heterocyclyl may be 4 membered heterocyclyl, which refers to a monovalent or multivalent, saturated or partially unsaturated, non-aromatic monocyclic ring containing 4 ring atoms, of which at least one ring atom is selected from nitrogen, sulfur and oxygen. In other embodiments, heterocyclyl may be 5 membered heterocyclyl, which refers to a monovalent or multivalent, saturated or partially unsaturated, non-aromatic monocyclic ring containing 5 ring atoms, of which at least one ring atom is selected from nitrogen, sulfur and oxygen. In other embodiments, heterocyclyl may be 6 membered heterocyclyl, which refers to a monovalent or multivalent, saturated or partially unsaturated, non-aromatic monocyclic ring containing 6 ring atoms, of which at least one ring atom is selected from nitrogen, sulfur and oxygen.

Some non-limiting examples of the heterocyclyl group include pyrrolidyl, tetrahydrofuryl, dihydrofuryl, tetrahydrothienyl, tetrahydropyranyl, dihydropyranyl, tetraphydrothiopyranyl, piperidyl, morpholinyl, thiomorpholinyl, thioxanyl, piperazinyl, homopiperazinyl, azetidinyl, oxetanyl, thietanyl, homopiperidinyl, epoxypropyl, azapanyl, oxepanyl, thiepanyl, oxoazepinyl, diazepinyl, thiazepinyl, 2-pyrrolidinyl, 3-pyrrolidinyl, dihydroindolyl, 2H-pyranyl, 4H-pyranyl, dioxanyl, 1,3-dioxolanyl, pyrrazolinyl, dithianyl, dithiolanyl, dihydrothienyl, pyrazolidyl, imidazolinyl, imidazolidinyl, 1,2,3,4-tetrahydroisoquinolinyl, 3-azabicyclo[3.1.0]hexyl, 3-azabicyclo[4.1.0]heptyl, azabicyclo[2.2.2]hexyl, 3H-indolyl, quinolyl and N-pyridyl. Examples of the heterocyclyl group also include 1,1-dioxothiomorpholinyl, some examples, of which carbon atom replaced with oxo (=O), include but are not limited to pyrimidinyldione, 1,2,4-thiadiazolyl-5(4H)-one, 1,2,4-oxadiazolyl-5 (4H)-one,1H-1,2,4-triazolyl-5(4H)-one, and the like, some examples, of which carbon atom replaced with =S, include but are not limited to 1,2,4-oxadiazolyl-5(4H)-thione, 1,3,4-oxadiazolyl-2(3H)-thione, and the like.

The term "heterocyclylalkyl" or "heterocyclylalkylene" can be used interchangeably, which refers to heterocyclyl-substituted alkyl. Examples of such groups include, but are not limited to, pyrrolidin-2-ylmethyl, morpholin-4-ylmethyl, and the like.

The term "heterocyclylalkoxy" refers to a heterocyclyl-substituted alkoxy, attached to the rest of molecular through an oxygen atom. Examples of such groups include, but are not limited to, pyrrolidin-2-ylmethoxy, piperid-2-ylethoxy, and the like.

The term "heterocyclylalkylamino" refers to a heterocyclyl-substituted alkylamino, attached to the rest of molecular through a nitrogen atom. Wherein the heterocyclyl, alkyl and alkylamino are defined as the invention described herein. Examples of such groups include, but are not limited to, 2-morpholin-ethylamino, and the like.

The term "heteroatom" refers to one or more of oxygen, sulfur, nitrogen, phosphorus and silicon, including any oxidized form of nitrogen, sulfur, or phosphorus; the primary, secondary, tertiary or quaternary ammonium salts; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" or "halo" or "halogen atom" refers to F (fluorine), Cl (chlorine), Br (bromine), or I (iodine).

The term "unsaturated" refers to a moiety having one or more units of unsaturation.

The term "aryl" refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members and that has a single point or multipoint of attachment to the rest of the molecule. The term "aryl" and "aromatic ring" can be used interchangeably herein. Examples of aryl ring may include phenyl, naphthyl and anthryl. The aryl group may be optionally and independently substituted with one or more substituents disclosed herein.

The term "heteroaryl" refers to monocyclic, bicyclic and tricyclic carbocyclic ring systems having a total of five to twelve ring members, wherein at least one ring in the system is aromatic, and in which at least one aromatic ring member is selected from heteroatom, and wherein each ring in the system contains 5 to 7 ring members and that has a single point or multipoint of attachment to the rest of the molecule. The term "heteroaryl" and "heteroaromatic ring" or "heteroaromatic compound" can be used interchangeably herein. In some embodiment, the heteroaryl group is a 5-7 membered monocyclic heteroaryl comprising 1, 2, 3 or 4 heteroatoms independently selected from O, S and N. In some embodiment, the heteroaryl group is a 5-6 membered monocyclic heteroaryl comprising 1, 2, 3 or 4 heteroatoms independently selected from O, S and N. In some embodiment, the heteroaryl group is a 7-12 membered bicyclic heteroaryl comprising 1, 2, 3 or 4 heteroatoms independently selected from O, S and N. In some embodiment, the heteroaryl group is a 8-10 membered bicyclic heteroaryl comprising 1, 2, 3 or 4 heteroatoms independently selected from O, S and N. In some embodiment, the heteroaryl group is a 9-10 membered bicyclic heteroaryl comprising 1, 2, 3 or 4 heteroatoms independently selected from O, S and N. The heteroaryl is optionally substituted or unsubstituted, wherein the substituent may be, but are not limited to, deuterium, F, Cl, Br, OH, $C_{1-8}$ alky, $C_{1-8}$ alkoxy, HOOC—$(CR^7R^8)_q$— or $C_{1-8}$ alkoxy-$(CR^7R^8)_k$—O—, and wherein q, k, $R^7$ and $R^8$ are as defined herein.

Some non-limiting examples of the heteroaryl group include the following monocyclic ring, 1,2,4-oxadiazolyl-5 (4H)-thione, 1,2,4-thiadiazolyl-5 (4H)-one, 1,2,4-oxadiazolyl-5 (4H)-one, 1,3,4-oxadiazolyl-2 (3H)-thione, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl, 5-triazolyl), 2-thienyl, 3-thienyl, pyranyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, diazolyl, thiadiazolyl triazinyl, and the following bicycles, but are not limited to: benzothiazolyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), isoquinolinyl (e.g., 1-isoquinolinyl, 3-isoquinolinyl or 4-isoquinolinyl), and the like.

The term "M-$M_1$ membered" refers to consisted of M to $M_1$ ring atoms, the ring atoms include carbon atom and/or heteroatoms such as O, N, S, P, and so on. For example, "6-10 membered heteroaryl" refers to heteroaryl consisted of 6, 7, 8, 9 or 10 atoms.

The term "heteroarylalkyl" "heteroarylalkylene" may be used interchangeably, refers to an alkyl group substituted with one or more same or different heteroaryl groups, wherein the alkyl group and heteroaryl group are as defined herein. Some non-limiting examples of the heteroarylalkyl group include (pyrid-2-yl)ethyl, (thiazol-2-yl)methyl, (imidazol-2-yl)ethyl, (pyrimidin-2-yl)propyl, and the like.

The term "sulfonyl", whether used alone or in conjunction with other term like "alkylsulfonyl", refers to a divalent group —$SO_2$—. The term "alkylsulfonyl" refers to alkyl-substituted sulfonyl (e.g. —$SO_2CH_3$).

The term "aralkyl" or "arylalkyl" may be used interchangeably, refers to aryl-substituted alkyl, wherein the aryl and the alkyl are as defined herein. In some embodiments, the aralkyl or arylalkyl radical refers to a "lower aralkyl" radical, i.e. aryl attaches to $C_{1-6}$ alkyl. In other embodiments, the aralkyl or arylalkyl radical refers to aryl attaches to $C_{1-3}$ alkyl. Specific examples include phenylmethyl (i.e. benzyl), diphenylmethyl, phenylethyl, and the like. And aryl of the arylalkyl may be further substituted with the substituent selected from deuterium, F, Cl, Br, OH, $C_{1-8}$ alky, $C_{1-8}$ alkoxy, HOOC—$(CR^7R^8)_q$— or $C_{1-8}$ alkoxy-$(CR^7R^8)_k$—O—, and wherein q, k, $R^7$ and $R^8$ are as defined herein.

The term "alkylamino" refers to "N-alkylamino" and "N,N-dialkylamino" wherein amino group is independently substituted with one or two alkyl radicals, respectively. In some embodiments, the alkylamino group is lower alkylamino group having one or two alkyl groups of 1 to 12 carbon atoms attached to nitrogen atom. In other embodiments, the alkylamino radical is a "lower alkylamino" radical having one or two $C_1$-$C_6$ alkyl radicals attached to a nitrogen atom. In other embodiments, the alkylamino radical is a "lower alkylamino" radical having one or two $C_1$-$C_4$ alkyl radicals attached to a nitrogen atom. In yet other embodiments, the alkylamino radical is a "lower alkylamino" radical having one or two $C_1$-$C_3$ alkyl radicals attached to a nitrogen atom. Some non-limiting examples of suitable alkylamino radical include mono or dialkylamino. Some examples include, but not limited to, N-methylamino, N-ethylamino, N,N-dimethylamino and N,N-diethylamino, N-ethyl-N-prop-2-yl-amino, and the like.

The term "cycloalkylalkyl" "cycloalkylalkylene" may be used interchangeably, refers to an alkyl group substituted with one or more the same or different cycloalkyl groups, wherein the alkyl and cycloalkyl groups are as defined herein. Some non-limiting examples of such group include cyclohexylmethylene, cyclopropylethylene, etc.

The term "alkoxyalkyl" "alkoxyalkylene" may be used interchangeably, refers to an alkyl group substituted with one or more the same or different alkoxy groups, wherein the alkoxy and alkyl groups are as defined herein. Some non-limiting examples of such group include cyclohexylmethyl, cyclopropylethyl, methoxyethyl, ethoxymethyl, etc.

As described herein, a bond drawn from a substituent to the center of one ring within a ring system (as shown in Formula b) represents substitution of the substituent at any substitutable or reasonable position on the ring, and optionally including any substitution case on an enantiomer, for example, as shown as formula b, c, d, e, f, g and h.

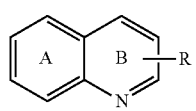

Formual a

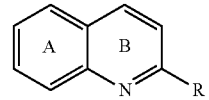

Formual b

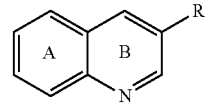

Formual c

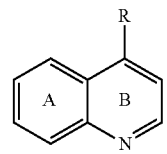

Formual d

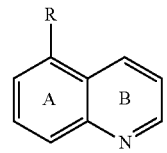

Formual e

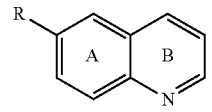

Formual f

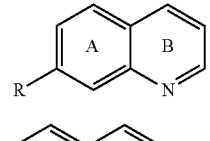

Formual g

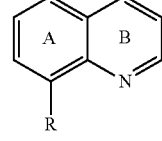

Formual h

Furthermore, unless otherwise stated, the phrase "each . . . is independently" is used interchangeably with the phrase "each (of) . . . and . . . is independently". It should be understood broadly that the specific options expressed by the same symbol are independently of each other in different radicals; or the specific options expressed by the same symbol are independently of each other in same radicals. Such as Formula (p), specific options of $R^9$ are not affect each other between multiple $R^9$.

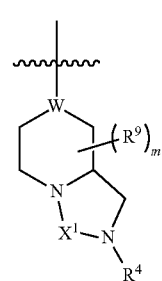

Formula p

As described herein, a system may have two attachment points attached to the rest of the molecule, for example, Formula q represents that it may connect with the rest of the molecule through either E or the two connect manners are interchangeable with each other in the case of reasonable molecular structure.

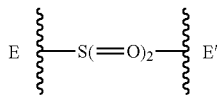

Formula q

Unless otherwise stated, structures depicted herein are also meant to include all isomeric (e.g., enantiomeric, diastereomeric, and geometric (conformational isomerism)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric mixtures of the present compounds are within the scope disclosed herein.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, all of which are incorporated herein by reference in their entireties.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley&Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons. Unless otherwise stated, all tautomeric forms of the compounds disclosed herein are within the scope of the invention.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66:1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydro iodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl)4 salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl) ethoxy-methy-1,2-(p-toluenesulfonyl) ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

DESCRIPTION OF COMPOUNDS OF THE INVENTION

The compound and the pharmaceutically acceptable composition thereof of the present invention all can inhibit HBV infection effectively.

In one aspect, provided herein is a compound having Formula (I) or Formula (Ia) or a stereoisomer, a tautomer, an N-oxide, a solvate, a metabolite, a pharmaceutically acceptable salt or a prodrug thereof;

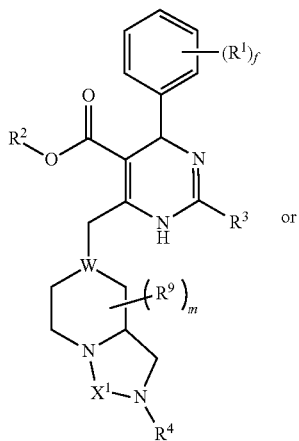

(I)

or

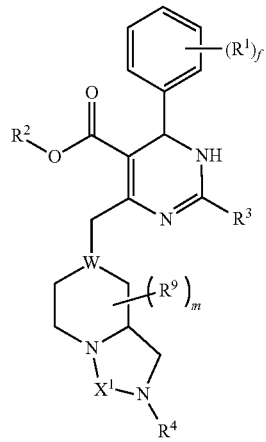

(Ia)

wherein each $R^1$ is independently H, deuterium, F, Cl, Br, I, cyano, methyl, ethyl, methoxy, ethoxy, methylamino, ethylamino, nitro, 4-trifluoromethylphenyl, 3,5-di(trifluoromethyl)phenyl or trifluoromethyl;

each $R^2$ is independently $C_{1-6}$ alkyl, deuterium substituted $C_{1-6}$ alkyl, $C_{1-6}$ haloalkyl, $C_{3-6}$ cycloalkyl-$C_{1-6}$ alkylene or (5-6 membered heterocyclyl)-$C_{1-6}$ alkylene;

each $R^3$ is independently $C_{6-10}$ aryl or 5-6 membered heteroaryl, wherein each of $C_{6-10}$ aryl or 5-6 membered heteroaryl is independently unsubstituted or substituted with one, two, three, four or five substituents independently selected from deuterium, F, Cl, Br, OH, CN, $C_{1-6}$ alkyl, hydroxy $C_{1-6}$ alkyl, $C_{1-6}$ alkyl-OC(=O)—, alkylene, HOOC—$C_{1-6}$ alkylene, $C_{1-6}$ alkoxy-$C_{1-6}$ alkylene and $C_{1-6}$ alkyl-S(=O)$_2$—;

each W is independently CH or N;

each $X^1$ is independently —C(=O)—, —S(=O)$_2$— or —(CR$^7$R$^8$)$_j$—;

each $R^7$, $R^8$ and $R^9$ is independently H, deuterium, F, Cl, Br, amino, $C_{1-6}$ alkyl, $NH_2C$(=O)—, $C_{1-6}$ alkyl-OC(=O)—, carboxy, carboxy $C_{1-6}$ alkylene, hydroxy $C_{1-6}$ alkyl, $C_{1-4}$ alkoxy-$C_{1-4}$ alkyl or $C_{1-6}$ haloalkyl, or $R^7$ and $R^8$, together with the carbon atom to which they are attached, form $C_{3-6}$ cycloalkyl or carbonyl;

$R^4$ is 5-7 membered monocyclic heterocyclyl, 7-12 membered bicyclic heterocyclyl, $C_{2-12}$ alkynyl, pyridyl, 1,3,5-triazinyl, pyrazinyl, pyridazinyl, pyrimidinyl, 5 membered monocyclic heteroaryl, 7-12 membered bicyclic heteroaryl, phenyl, naphthyl, phenyl-(CR$^7$R$^8$)—, HOOC—$C_{1-6}$ alkylene or $R^{10}$—(CR$^7$R$^8$)$_j$—, wherein the 5-7 membered monocyclic heterocyclyl, 7-12 membered bicyclic heterocyclyl, $C_{2-12}$ alkynyl, 1,3,5-triazinyl, pyrazinyl, pyridazinyl, pyrimidinyl, 5 membered monocyclic heteroaryl, 7-12 membered bicyclic heteroary and naphthyl are each independently unsubstituted or substituted with one, two, three, four or five $R^w$, the pyridyl, phenyl and phenyl of phenyl-(CR$^7$R$^8$)— are each independently substituted with one, two, three or four $R^x$, the $C_{1-6}$ alkylene of HOOC—$C_{1-6}$alkylene is substituted with one, two, three or four $R^{18}$;

$R^{10}$ is naphthyl, 5-7 membered monocyclic heteroaryl, 7-12 membered bicyclic heteroaryl, 5-7 membered monocyclic heterocyclyl or 7-12 membered bicyclic heterocyclyl, wherein the naphthyl, 5-7 membered monocyclic heteroaryl, 7-12 membered bicyclic heteroaryl, 5-7 membered monocyclic heterocyclyl and 7-12 membered bicyclic heterocyclyl are each independently substituted with one, two, three, four or five $R^w$;

each $R^w$ is independently deuterium, F, Cl, Br, OH, CN, $R^aR^bNC(\!=\!O)\!-\!$, $R^cR^dP(\!=\!O)\!-\!$, HOOC—$(CR^7R^8)_k\!-\!$, amino, $C_{1\text{-}8}$ alkyl, $C_{2\text{-}8}$ alkenyl, hydroxy $C_{1\text{-}8}$ alkyl, $C_{1\text{-}8}$ alkyl-C(=O)—, $C_{1\text{-}8}$ alkoxy, $C_{1\text{-}8}$ alkyl-OC(=O)— or $C_{1\text{-}8}$ alkyl-S(=O)$_2$—, wherein the amino, $C_{1\text{-}8}$ alkyl, $C_{2\text{-}8}$ alkenyl, hydroxy $C_{1\text{-}8}$ alkyl, $C_{1\text{-}8}$ alkyl-C(=O)—, $C_{1\text{-}8}$ alkoxy, $C_{1\text{-}8}$ alkyl-OC(=O)— and $C_{1\text{-}8}$ alkyl-S(=O)$_2$— are each independently unsubstituted or substituted with one, two, three, four or five BY;

each $R^x$ is independently deuterium, F, Cl, Br, OH, CN, $R^aR^bN\!-\!$, $R^aR^bNC(\!=\!O)\!-\!$, $R^cR^dP(\!=\!O)\!-\!$, HOOC—$(CR^7R^8)_k\!-\!$, tetrazolyl-$(CH_2)_n\!-\!$, amino, $C_{1\text{-}8}$ alkyl, $C_{2\text{-}8}$ alkenyl, hydroxy $C_{1\text{-}8}$ alkyl, $C_{1\text{-}8}$ alkyl-C(=O)—, $C_{1\text{-}8}$ alkoxy, $C_{1\text{-}8}$ alkyl-OC(=O)—, HOOC-methylene-O-methylene-, $C_{1\text{-}4}$ alkyl-OC(=O)-methylene-O-methylene, $C_{1\text{-}4}$ alkyl-C(=O)O-methylene or $C_{1\text{-}8}$ alkyl-S(=O)$_2$—, wherein the amino, $C_{1\text{-}8}$ alkyl, $C_{2\text{-}8}$ alkenyl, hydroxy $C_{1\text{-}8}$ alkyl, $C_{1\text{-}8}$ alkyl-C(=O)—, $C_{1\text{-}8}$ alkoxy, $C_{1\text{-}8}$ alkyl-OC(=O)—, HOOC-methylene-O-methylene-, $C_{1\text{-}4}$ alkyl-OC(=O)-methylene-O-methylene, $C_{1\text{-}4}$ alkyl-C(=O)O-methylene and $C_{1\text{-}8}$ alkyl-S(=O)$_2$— are each independently unsubstituted or substituted with one, two, three, four or five BY;

each $R^{18}$ is independently $R^aR^bN\!-\!$, 5-7 membered monocyclic heteroaryl, 7-12 membered bicyclic heteroaryl, 5-7 membered monocyclic heterocyclyl, 7-12 membered bicyclic heterocyclyl, benzyl or $C_{6\text{-}10}$ aryl, wherein the 5-7 membered monocyclic heteroaryl, 7-12 membered bicyclic heteroaryl, 5-7 membered monocyclic heterocyclyl, 7-12 membered bicyclic heterocyclyl, benzyl and $C_{6\text{-}10}$ aryl are each independently substituted with one, two, three, four or five BY;

each $R^y$ is independently deuterium, F, Cl, Br, OH, CN, $R^aR^bNC(\!=\!O)\!-\!$, $R^cR^dP(\!=\!O)\!-\!$, HOOC—$(CR^7R^8)_k\!-\!$, amino, $C_{1\text{-}6}$ alkyl-S(=O)$_2$—NH—, $C_{1\text{-}8}$ alkyl, $C_{1\text{-}8}$ alkoxy, $C_{1\text{-}8}$ alkyl-S(=O)$_2$—, $C_{1\text{-}8}$ alkyl-C(=O)—, $C_{1\text{-}8}$ alkyl-OC(=O)—, benzyl-OC(=O)—, phenyl-OC(=O)— or $C_{1\text{-}8}$ alkylamino-S(=O)$_2$—, wherein the amino, $C_{1\text{-}6}$ alkyl-S(=O)$_2$—NH—, $C_{1\text{-}8}$ alkyl, $C_{1\text{-}8}$ alkoxy, $C_{1\text{-}8}$ alkyl-S(=O)$_2$—, $C_{1\text{-}8}$ alkyl-C(=O)—, $C_{1\text{-}8}$ alkyl-OC(=O)—, benzyl-OC(=O)—, phenyl-OC(=O)— and $C_{1\text{-}8}$ alkylamino-S(=O)$_2$— are each independently unsubstituted or substituted with one, two, three, four or five substituents selected from deuterium, F, Cl, Br, OH, $C_{1\text{-}8}$ alkoxy, $C_{1\text{-}8}$ alkyl, HOOC—$(CR^7R^8)_h\!-\!$ or $C_{1\text{-}8}$ alkoxy-$(CR^7R^8)_n\!-\!$O—;

each $R^a$, $R^b$, $R^c$ and $R^d$ is independently H, deuterium, HOOC—$(CR^7R^8)_q\!-\!$, $C_{1\text{-}8}$ alkyl, $C_{1\text{-}8}$ alkyl-OC(=O)—, $C_{1\text{-}8}$ alkoxy, $C_{3\text{-}7}$ cycloalkyl or 3-12 membered heterocyclyl, wherein the $C_{1\text{-}8}$ alkyl, $C_{1\text{-}8}$ alkyl-OC(=O)—, $C_{1\text{-}8}$ alkoxy, $C_{3\text{-}7}$ cycloalkyl and 3-12 membered heterocyclyl are each independently unsubstituted or substituted with one, two, three, four or five substituents selected from deuterium, F, Cl, Br, OH, amino, $C_{1\text{-}8}$ alkyl, $C_{1\text{-}8}$ alkoxy, HOOC—$(CR^7R^8)_q\!-\!$ or $C_{1\text{-}8}$ alkoxy-$(CR^7R^8)_n\!-\!$O—;

each f m, k, h and q is independently 0, 1, 2, 3 or 4;
each n is independently 1, 2, 3 or 4;
each j is independently 1, 2 or 3.

In some embodiments, provided herein is a compound having Formula (II) or Formula (IIa):

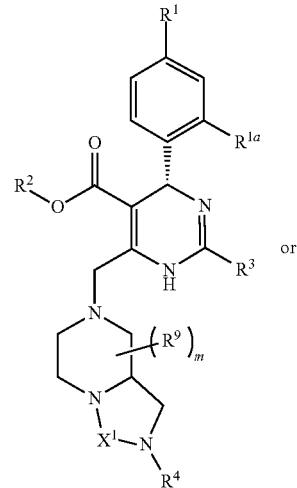

(II)

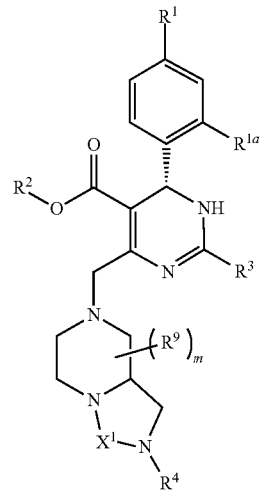

(IIa)

wherein each $R^2$, $R^3$, $R^4$, $R^9$, $X^1$ and m is as defined herein;

each $R^1$ and $R^{1a}$ is independently H, deuterium, F, Cl, Br, I, cyano, methyl, ethyl, methoxy, ethoxy, methylamino, ethylamino, nitro, 4-trifluoromethylphenyl, 3,5-di(trifluoromethyl)phenyl or trifluoromethyl.

In some embodiments, provided herein is a compound having Formula (III) or Formula (IIIa):

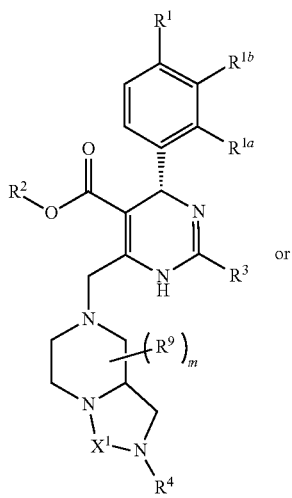

(III)

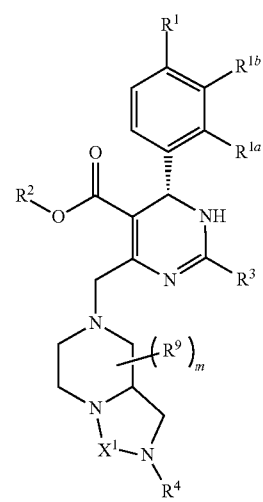

(IIIa)

wherein each $R^1$, $R^{1b}$ and $R^{1a}$ is independently H, deuterium, F, Cl, Br, I, cyano, methyl, ethyl, methoxy, ethoxy, methylamino, ethylamino, nitro, 4-trifluoromethylphenyl, 3,5-di(trifluoromethyl)phenyl or trifluoromethyl;

wherein each $R^2$, $R^3$, $R^4$, $R^9$, $X^1$ and m is as defined herein.

In some embodiments, provided herein is a compound having Formula (IV) or Formula (IVa):

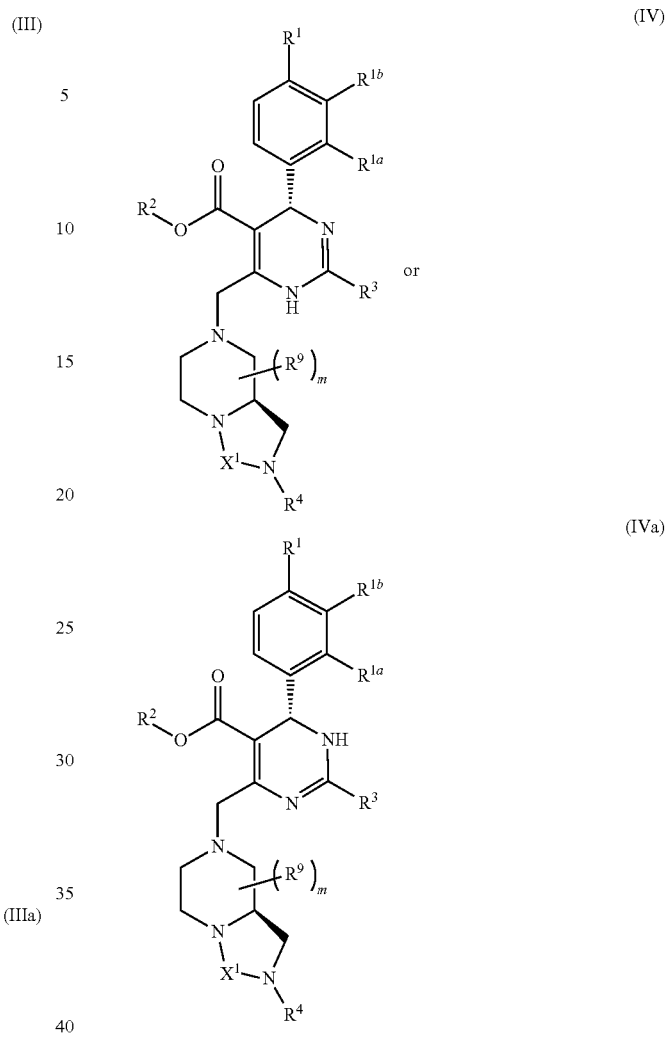

wherein each $R^1$, $R^{1b}$ and $R^{1a}$ is independently H, deuterium, F, Cl, Br, I, cyano, methyl, ethyl, methoxy, ethoxy, methylamino, ethylamino, nitro, 4-trifluoromethylphenyl, 3,5-di(trifluoro methyl)phenyl or trifluoromethyl;

wherein each $R^2$, $R^3$, $R^4$, $R^9$, $X^1$ and m is as defined herein.

In some embodiments, each $R^2$ is independently methyl, deuterated methyl, ethyl, n-propyl, i-propyl, $C_{1-4}$ haloalkyl, $C_{3-6}$ cycloalkyl-$C_{1-3}$ alkylene or 5-6 membered heterocyclyl-$C_{1-3}$ alkylene;

$R^3$ is phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each of phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with one, two, three, four or five substituents independently selected from deuterium, F, Cl, Br, OH, CN, $C_{1-4}$ alkyl, hydroxy $C_{1-4}$ alkyl, $C_{1-4}$ alkyl-OC(=O)—, $C_{1-4}$ alkyl-OC(=O)—$C_{1-3}$ alkylene, HOOC—$C_{1-3}$ alkylene, $C_{1-4}$ alkoxy-$C_{1-3}$ alkylene or $C_{1-4}$ alkyl-S(=O)$_2$—;

each $R^7$, $R^8$ and $R^9$ is independently H, deuterium, F, Cl, Br, amino, methyl, ethyl, n-propyl, i-propyl, $NH_2C(=O)$—, $C_{1-4}$ alkyl-OC(=O)—, carboxy, carboxy $C_{1-3}$ alkylene, hydroxy $C_{1-4}$ alkyl, ethoxyethyl, methoxyethyl, isopropoxymethyl, methoxymethyl or $C_{1-4}$ haloalkyl, or $R^7$ and $R^8$, together with the carbon atom to which they are attached, form cyclopropyl, cyclobutyl, cyclopentyl, cyclohexyl or carbonyl;

In some embodiments, wherein each $R^2$ is independently methyl, deuterated methyl, ethyl, n-propyl, i-propyl, $C_{1-4}$ haloalkyl, $C_{3-6}$ cycloalkyl-$C_{1-3}$ alkylene or 5-6 membered heterocyclyl-$C_{1-3}$ alkylene;

$R^3$ is phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each of phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with one, two, three, four or five substituents independently selected from deuterium, F, Cl, Br, OH, CN, $C_{1-4}$ alkyl, hydroxy $C_{1-4}$ alkyl, $C_{1-4}$ alkyl-OC(=O)—, $C_{1-4}$ alkyl-OC(=O)—$C_{1-3}$ alkylene, HOOC—$C_{1-3}$ alkylene, $C_{1-4}$alkoxy-$C_{1-3}$ alkylene- or $C_{1-4}$ alkyl-S(=O)$_2$—;

each $R^7$, $R^8$ and $R^9$ is independently H, deuterium, F, Cl, Br, amino, methyl, ethyl, n-propyl, i-propyl, NH$_2$C(=O)—, $C_{1-4}$ alkyl-OC(=O)—, methyl-OC(=O)—, ethyl-OC(=O)—, n-propyl-OC(=O)—, i-propyl-OC(=O)—, n-butyl-OC(=O)—, t-butyl-OC(=O)—, carboxy, carboxy $C_{1-3}$ alkylene, hydroxymethyl, hydroxyethyl, hydroxypropyl, ethoxyethyl, methoxyethyl, isopropoxymethyl, methoxymethyl or $C_{1-4}$ haloalkyl, or $R^7$ and $R^8$, together with the carbon atom to which they are attached, form cyclopropyl, cyclobutyl, cyclopentyl, cyclohexyl or carbonyl.

In some embodiments, wherein $R^4$ is 5-6 membered monocyclic heterocyclyl, 8-10 membered bicyclic heterocyclyl, $C_{2-10}$ alkynyl, pyridyl, 1,3,5-triazinyl, pyrazinyl, pyridazinyl, pyrimidinyl, 5 membered monocyclic heteroaryl, 8-10 membered bicyclic heteroaryl, phenyl, naphthyl, phenyl-(CR$^7$R$^8$)—, HOOC—$C_{1-4}$ alkylene or $R^{10}$—(CR$^8$R$^8$)$_j$—, wherein the 5-6 membered monocyclic heterocyclyl, 8-10 membered bicyclic heterocyclyl, $C_{2-6}$ alkynyl, 1,3,5-triazinyl, pyrazinyl, pyridazinyl, pyrimidinyl, 5 membered monocyclic heteroaryl, 8-10 membered bicyclic heteroary and naphthyl are each independently unsubstituted or substituted with one, two, three, four or five $R^w$, the pyridyl, phenyl and phenyl of phenyl-(CR$^7$R$^8$)— are each independently substituted with one, two, three or four $R^x$, the $C_{1-4}$ alkylene of HOOC—$C_{1-4}$ alkylene is substituted with one, two, three or four $R^{18}$;

$R^{10}$ is naphthyl, 5-6 membered monocyclic heteroaryl, 8-10 membered bicyclic heteroaryl, 5-6 membered monocyclic heterocyclyl or 8-10 membered bicyclic heterocyclyl, wherein the naphthyl, 5-6 membered monocyclic heteroaryl, 8-10 membered bicyclic heteroaryl, 5-6 membered monocyclic heterocyclyl and 8-10 membered bicyclic heterocyclyl are each independently substituted with one, two, three, four or five $R^w$;

wherein each $R^7$, $R^8$, $R^w$, $R^x$, $R^{18}$ and j is as defined herein.

In some embodiments, wherein $R^4$ is pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, 8-10 membered bicyclic heterocyclyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, benzothiazolyl, benzoimidazolyl, benzofuryl, benzothienyl, indolyl, isoquinolyl, phenyl, naphthyl, phenyl-(CR$^7$R$^8$)—, HOOC—$C_{1-3}$ alkylene or $R^{10}$—(CR$^7$R$^8$)$_j$—, wherein each of pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, 8-10 membered bicyclic heterocyclyl, ethynyl, propargyl, propynyl, butynyl, pentynyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, benzothiazolyl, benzoimidazolyl, benzofuryl, benzothienyl, indolyl, isoquinolyl and naphthyl is independently unsubstituted or substituted with one, two, three, four or five $R^w$; pyridyl, phenyl and phenyl of phenyl-(CR$^7$R$^8$)— are each independently substituted with one, two, three or four $R^x$; $C_{1-3}$ alkylene of HOOC—$C_{1-3}$ alkylene is independently substituted with one, two, three or four $R^{18}$;

$R^{10}$ is naphthyl, 5-6 membered monocyclic heteroaryl, 8-10 membered bicyclic heteroaryl, 5-6 membered monocyclic heterocyclyl or 8-10 membered bicyclic heterocyclyl, wherein the naphthyl, 5-6 membered monocyclic heteroaryl, 8-10 membered bicyclic heteroaryl, 5-6 membered monocyclic heterocyclyl and 8-10 membered bicyclic heterocyclyl are each independently substituted with one, two, three, four or five $R^w$.

wherein each $R^7$, $R^8$, $R^w$, $R^x$, $R^{18}$ and j is as defined herein.

In some embodiments, wherein each $R^w$ is independently deuterium, F, Cl, Br, OH, CN, $R^aR^bNC$(=O)—, $R^cR^dP$(=O)—, HOOC—(CR$^7$R$^8$)$_k$—, amino, $C_{1-6}$ alkyl, $C_{1-6}$ alkenyl, hydroxy $C_{2-6}$ alkyl, $C_{1-6}$ alkyl-C(=O)—, $C_{1-6}$ alkoxy, $C_{1-6}$ alkyl-OC(=O)— or $C_{1-6}$ alkyl-S(=O)$_2$—, wherein the amino, $C_{ho}$ alkyl, $C_{2-6}$ alkenyl, hydroxy $C_{1-6}$ alkyl, $C_{1-6}$ alkyl-C(=O)—, $C_{1-6}$ alkoxy, $C_{1-6}$ alkyl-OC(=O)— and $C_{1-6}$ alkyl-S(=O)$_2$— are each independently unsubstituted or substituted with one, two, three, four or five BY;

each $R^x$ is independently deuterium, F, Cl, Br, OH, CN, $R^aR^bN$—, $R^aR^bNC$(=O)—, $R^cR^dP$(=O)—, HOOC—(CR$^7$R$^8$)$_k$—, tetrazolyl-(CH$_2$)$_n$—, amino, $C_{1-6}$ alkyl, $C_{2-6}$ alkenyl, hydroxy $C_{1-6}$ alkyl, $C_{1-6}$ alkyl-C(=O)—, $C_{1-6}$ alkoxy, $C_{1-6}$ alkyl-OC(=O)—, HOOC-methylene-O-methylene-, $C_{1-4}$ alkyl-OC(=O)-methylene-O-methylene, $C_{1-4}$ alkyl-C(=O)O-methylene or $C_{1-6}$ alkyl-S(=O)$_2$—, wherein the amino, $C_{1-6}$ alkyl, $C_{2-6}$ alkenyl, hydroxy $C_{1-6}$ alkyl, $C_{1-6}$ alkyl-C(=O)—, $C_{1-6}$ alkoxy, $C_{1-6}$ alkyl-OC(=O)—, HOOC-methylene-O-methylene-, $C_{1-4}$ alkyl-OC(=O)-methylene-O-methylene, $C_{1-4}$ alkyl-C(=O)O-methylene and $C_{1-6}$ alkyl-S(=O)$_2$— are each independently unsubstituted or substituted with one, two, three, four or five BY;

each $R^{18}$ is independently $R^aR^bN$—, 5-6 membered monocyclic heteroaryl, 8-10 membered bicyclic heteroaryl, 5-6 membered monocyclic heterocyclyl, 8-10 membered bicyclic heterocyclyl, benzyl, phenyl or naphthyl, wherein the 5-6 membered monocyclic heteroaryl, 8-10 membered bicyclic heteroaryl, 5-6 membered monocyclic heterocyclyl, 8-10 membered bicyclic heterocyclyl, benzyl, phenyl and naphthyl are each independently substituted with one, two, three, four or five $R^y$;

wherein each $R^a$, $R^b$, $R^c$, $R^d$, $R^7$, $R^8$, $R^y$, k and n is as defined herein.

In some embodiments, wherein each $R^w$ is independently deuterium, F, Cl, Br, OH, CN, $R^aR^bNC$(=O)—, $R^cR^dP$(=O)—, HOOC—(CR$^7$R$^8$)$_k$—, amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)— or $C_{1-4}$ alkyl-S(=O)$_2$—, wherein the amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)— and $C_{1-4}$ alkyl-S(=O)$_2$— are each independently unsubstituted or substituted with one, two, three, four or five BY;

each $R^x$ is independently deuterium, F, Cl, Br, OH, CN, $R^aR^bN$—, $R^aR^bNC(=O)$—, $R^cR^dP(=O)$—, HOOC—$(CR^7R^8)_n$—, tetrazolyl-$(CH_2)_n$, amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)—, HOOC-methylene-O-methylene-, methyl-OC(=O)-methylene-O-methylene, ethyl-OC(=O)-methylene-O-methylene, methyl-C(=O)O-methylene or $C_{1-4}$ alkyl-S(=O)$_2$—, wherein the amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)—, HOOC-methylene-O-methylene-, methyl-OC(=O)-methylene-O-methylene, ethyl-OC(=O)-methylene-O-methylene, methyl-C(=O)O-methylene and $C_{1-4}$ alkyl-S(=O)$_2$— are each independently unsubstituted or substituted with one, two, three, four or five BY;

each $R^{18}$ is independently $R^aR^bN$—, 5-6 membered monocyclic heteroaryl, 9-10 membered bicyclic heteroaryl, 5-6 membered monocyclic heterocyclyl, 8-10 membered bicyclic heterocyclyl, benzyl, phenyl or naphthyl, wherein the 5-6 membered monocyclic heteroaryl, 9-10 membered bicyclic heteroaryl, 5-6 membered monocyclic heterocyclyl, 8-10 membered bicyclic heterocyclyl, benzyl, phenyl and naphthyl are each independently substituted with one, two, three, four or five R.

wherein each $R^a$, $R^b$, $R^c$, $R^d$, $R^7$, $R^8$, $R^y$, k and n is as defined herein.

In some embodiments, wherein each $R^y$ is independently deuterium, F, Cl, Br, OH, CN, $R^aR^bNC(=O)$—, $R^cR^dP(=O)$—, HOOC—$(CR^7R^8)_h$—, amino, $C_{1-4}$ alkyl-S(=O)$_2$—NH—, $C_{1-6}$ alkyl, $C_{1-6}$ alkoxy, $C_{1-6}$ alkyl-S(=O)$_2$—, $C_{1-6}$ alkyl-C(=O)—, $C_{1-6}$ alkyl-OC(=O)—, benzyl-OC(=O)—, phenyl-OC(=O)— or $C_{1-6}$ alkylamino-S(=O)$_2$—, wherein the amino, $C_{1-4}$ alkyl-S(=O)$_2$—NH—, $C_{1-6}$ alkyl, $C_{1-6}$ alkoxy, $C_{1-6}$ alkyl-S(=O)$_2$—, $C_{1-6}$ alkyl-C(=O)—, $C_{1-6}$ alkyl-OC(=O)—, benzyl-OC(=O)—, phenyl-OC(=O)— and $C_{1-6}$ alkylamino-S(=O)$_2$— are each independently unsubstituted or substituted with one, two, three, four or five substituents selected from deuterium, F, Cl, Br, OH, $C_{1-6}$ alkoxy, $C_{1-6}$ alkyl, HOOC—$(CR^7R^8)_h$— or $C_{1-6}$ alkoxy-$(CR^7R^8)_n$—O—;

each $R^a$, $R^b$, $R^c$ and $R^d$ is independently H, deuterium, HOOC—$(CR^7R^8)_q$—, $C_{1-6}$ alkyl, $C_{1-6}$ alkyl-OC(=O)—, $C_{1-6}$ alkoxy, $C_{3-6}$ cycloalkyl or 5-10 membered heterocyclyl, wherein the $C_{1-6}$ alkyl, $C_{1-6}$ alkyl-OC(=O)—, $C_{1-6}$ alkoxy, $C_{3-6}$ cycloalkyl and 5-10 membered heterocyclyl are each independently unsubstituted or substituted with one, two, three, four or five substituents selected from deuterium, F, Cl, Br, OH, amino, $C_{1-6}$ alkyl, $C_{1-6}$ alkoxy, HOOC—$(CR^7R^8)_q$— or $C_{1-6}$ alkoxy-$(CR^7R^8)_n$—O—.

wherein each $R^7$, $R^8$, h, n and q is as defined herein.

In some embodiments, wherein each $R^y$ is independently deuterium, F, Cl, Br, OH, CN, $R^aR^bNC(=O)$—, $R^cR^dP(=O)$—, HOOC—$(CR^7R^8)_h$—, amino, methyl-S(=O)$_2$—NH—, ethyl-S(=O)$_2$—NH—, $C_{1-4}$ alkyl, $C_{1-4}$ alkoxy, $C_{1-4}$ alkyl-S(=O)$_2$—, $C_{1-4}$ alkyl-C(=O)—, $C_{1-4}$ alkyl-OC(=O)—, benzyl-OC(=O)—, phenyl-OC(=O)— or $C_{1-4}$ alkylamino-S(=O)$_2$—, wherein the amino, methyl-S(=O)$_2$—NH—, ethyl-S(=O)$_2$—NH—, $C_{1-4}$ alkyl, $C_{1-4}$ alkoxy, $C_{1-4}$ alkyl-S(=O)$_2$—, $C_{1-4}$ alkyl-C(=O)—, $C_{1-4}$ alkyl-OC(=O)—, benzyl-OC(=O)—, phenyl-OC(=O)— and $C_{1-4}$ alkylamino-S(=O)$_2$— are each independently unsubstituted or substituted with one, two, three, four or five substituents selected from deuterium, F, Cl, Br, OH, $C_{1-4}$ alkoxy, $C_{1-4}$ alkyl, HOOC—$(CR^7R^8)_h$— or $C_{1-4}$ alkoxy-$(CR^7R^8)_n$—O—;

each $R^a$, $R^b$, $R^c$ and $R^d$ is independently H, deuterium, HOOC—$(CR^7R^8)_q$—, $C_{1-4}$ alkyl, $C_{1-4}$ alkyl-OC(=O)—, $C_{1-4}$ alkoxy, $C_{3-6}$ cycloalkyl or 5-6 membered heterocyclyl, wherein the $C_{1-4}$ alkyl, $C_{1-4}$ alkyl-OC(=O)—, $C_{1-4}$ alkoxy, $C_{3-6}$ cycloalkyl and 5-6 membered heterocyclyl are each independently unsubstituted or substituted with one, two, three, four or five substituents selected from deuterium, F, Cl, Br, OH, amino, $C_{1-4}$ alkyl, $C_{1-4}$ alkoxy, HOOC—$(CR^7R^8)_q$— or $C_{1-4}$ alkoxy-$(CR^7R^8)_n$—O—.

wherein $R^7$, $R^8$, h, n and q are as defined herein.

In some embodiments, each $R^y$ is independently deuterium, F, Cl, Br, OH, CN, $R^aR^bNC(=O)$—, $R^cR^dP(=O)$—, HOOC—$(CR^7R^8)_h$—, amino, methyl-S(=O)$_2$—NH—, ethyl-S(=O)$_2$—NH—, $C_{1-4}$ alkyl, $C_{1-4}$ alkoxy, methyl-S(=O)$_2$—, ethyl-S(=O)$_2$—, n-propyl-S(=O)$_2$—, i-propyl-S(=O)$_2$—, $C_{1-4}$ alkyl-C(=O)—, methyl-OC(=O)—, ethyl-OC(=O)—, n-propyl-OC(=O)—, i-propyl-OC(=O)—, benzyl-OC(=O)—, phenyl-OC(=O)— or $C_{1-4}$ alkylamino-S(=O)$_2$—, wherein the amino, methyl-S(=O)$_2$—NH—, ethyl-S(=O)$_2$—NH—, $C_{1-4}$ alkyl, $C_{1-4}$ alkoxy, methyl-S(=O)$_2$—, ethyl-S(=O)$_2$—, n-propyl-S(=O)$_2$—, i-propyl-S(=O)$_2$—, $C_{1-4}$ alkyl-C(=O)—, methyl-OC(=O)—, ethyl-OC(=O)—, n-propyl-OC(=O)—, i-propyl-OC(=O)—, benzyl-OC(=O)—, phenyl-OC(=O)— and $C_{1-4}$ alkylamino-S(=O)$_2$— are each independently unsubstituted or substituted with one, two, three, four or five substituents selected from deuterium, F, Cl, Br, OH, $C_{1-4}$ alkoxy, $C_{1-4}$ alkyl, HOOC—$(CR^7R^8)_h$— or $C_{1-4}$ alkoxy-$(CR^7R^8)_n$—O—;

each $R^a$, $R^b$, $R^c$ and $R^d$ is independently H, deuterium, HOOC—$(CR^7R^8)_q$—, methyl, ethyl, n-propyl, i-propyl, $C_{1-4}$ alkyl-OC(=O)—, $C_{1-4}$ alkoxy, cyclopropyl, cyclobutyl, cyclopentyl, cyclohexyl or 5-6 membered heterocyclyl, wherein the methyl, ethyl, n-propyl, i-propyl, $C_{1-4}$ alkyl-OC(=O)—, $C_{1-4}$ alkoxy, cyclopropyl, cyclobutyl, cyclopentyl, cyclohexyl and 5-6 membered heterocyclyl are each independently unsubstituted or substituted with one, two, three, four or five substituents selected from deuterium, F, Cl, Br, OH, amino, $C_{1-4}$ alkyl, $C_{1-4}$ alkoxy, HOOC—$(CR^7R^8)_q$— or $C_{1-4}$ alkoxy-$(CR^7R^8)_n$—O—;

wherein $R^7$, $R^8$, h, n and q are as defined herein.

In still some embodiments, provided herein is a compound having one of the following structures, or a stereoisomer, a tautomer, an N-oxide, a solvate, a metabolite, a pharmaceutically acceptable salt or a prodrug thereof; but not limited to these compounds:

(1)
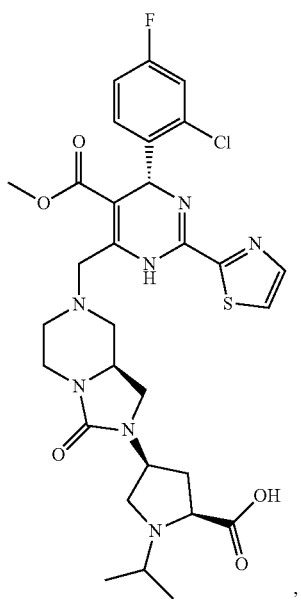
(2)
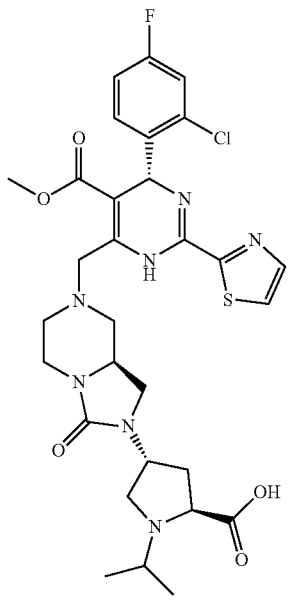
(3)
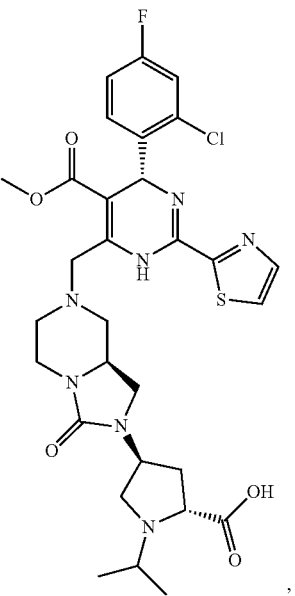
(4)
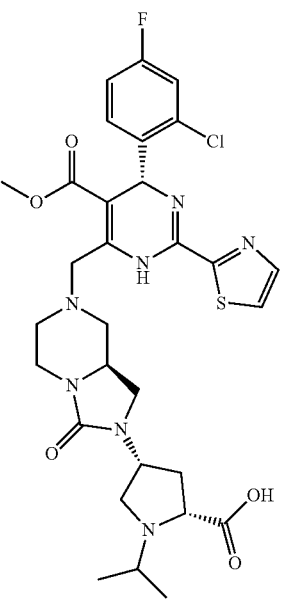

(5)
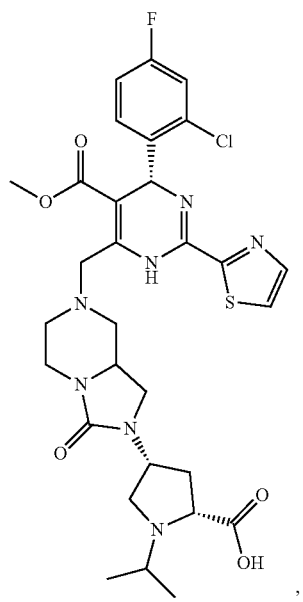
,
(6)
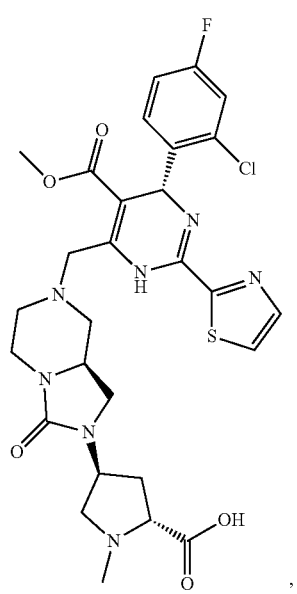
,
(7)
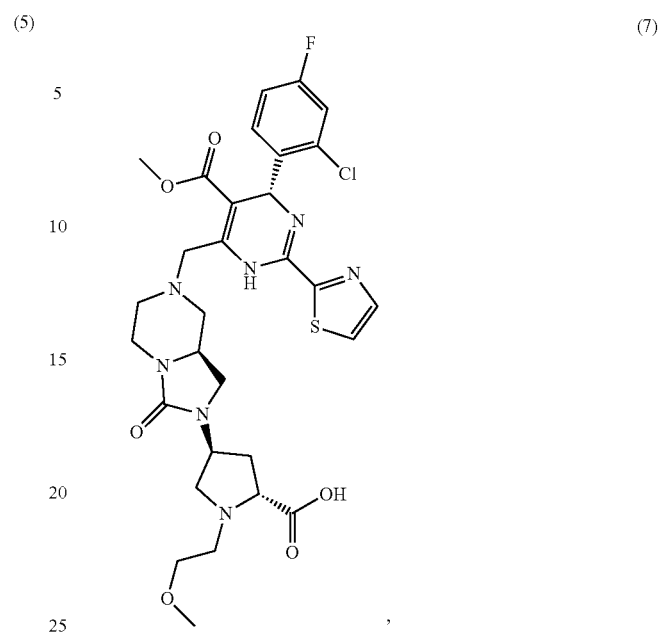
,
(8)
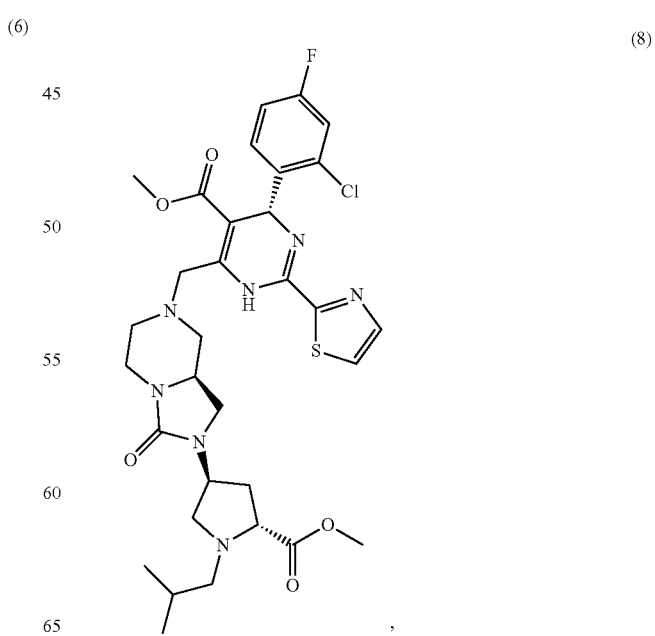
, (9)
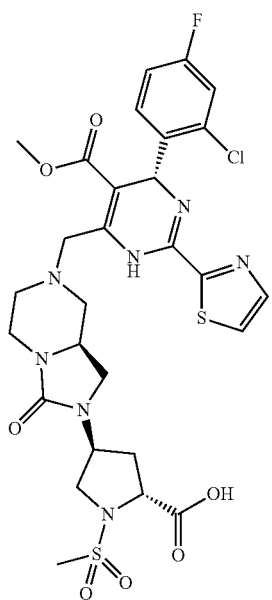
(10)
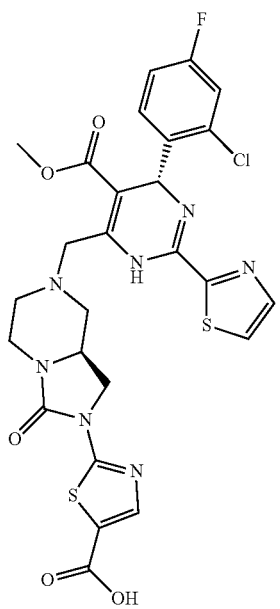
(11)
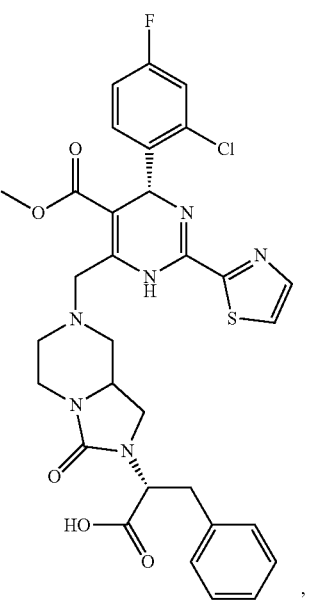
(12)
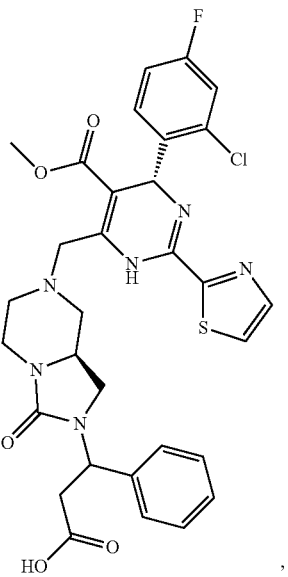

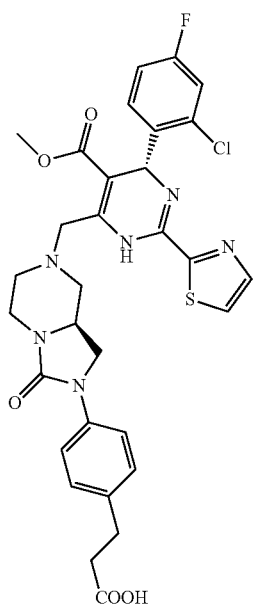
(13)
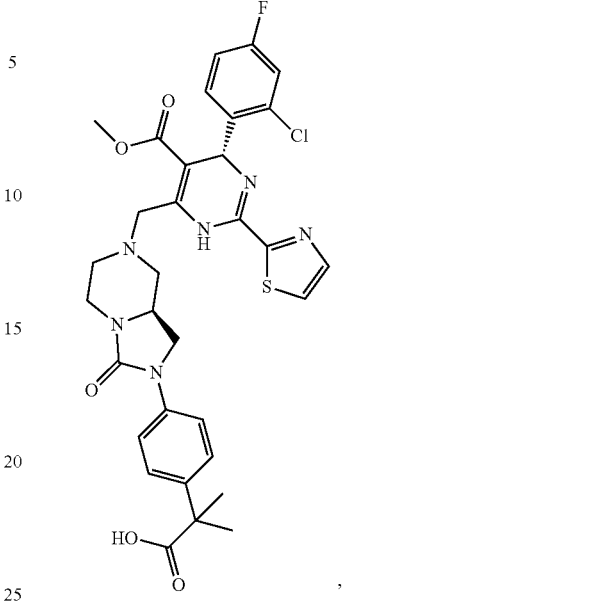
(15)
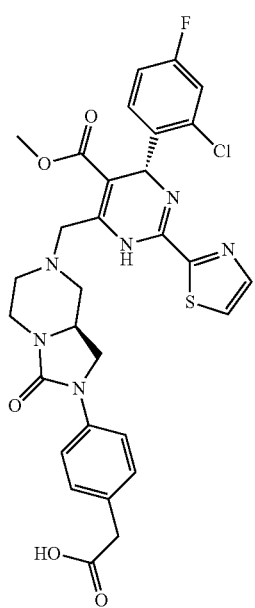
(14)
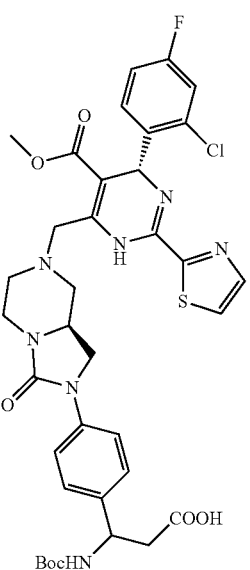
(16)

(17)
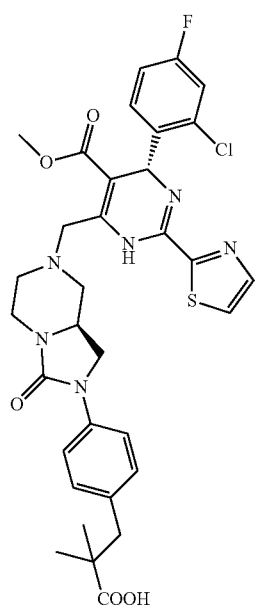
(18)
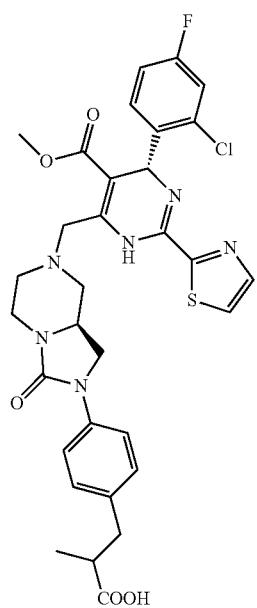
(19)
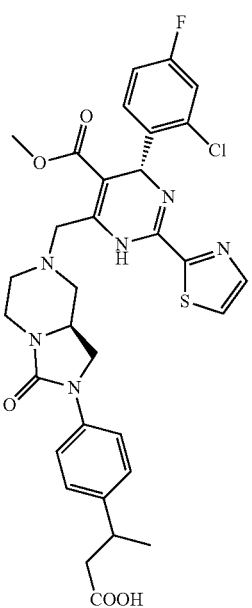
(20)
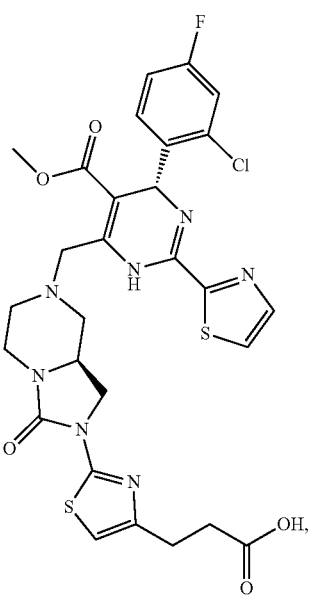

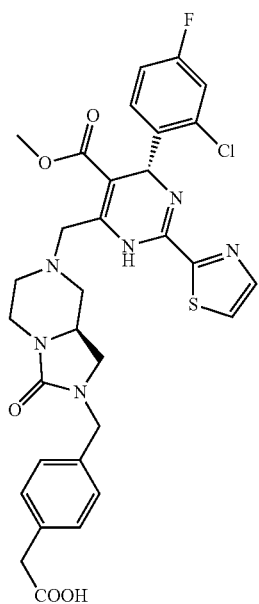
(21)
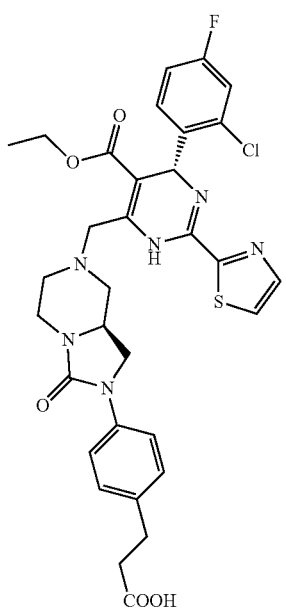
(23)
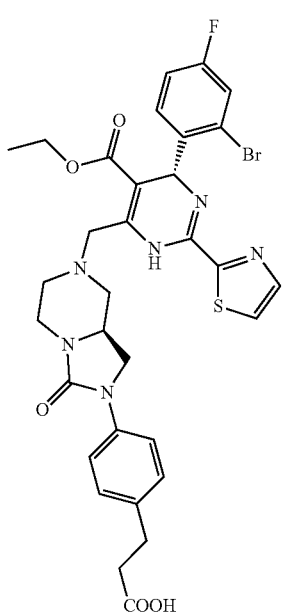
(22)
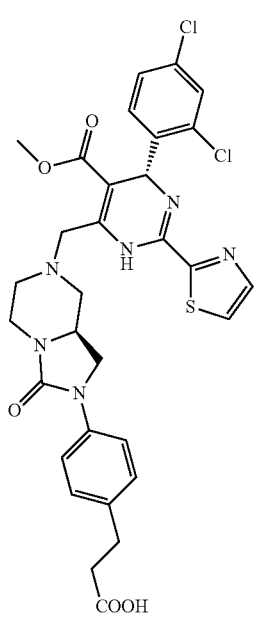
(24)

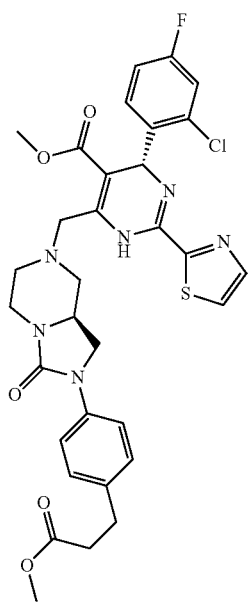
(25)
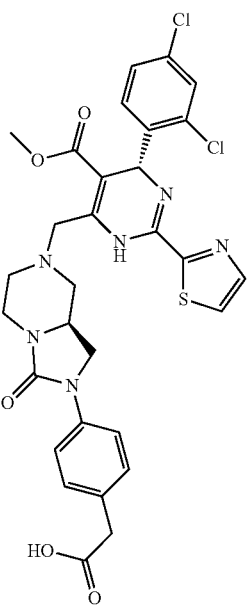
(27)
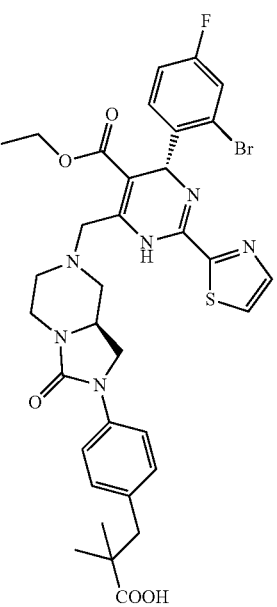
(26)
(28)

(29)
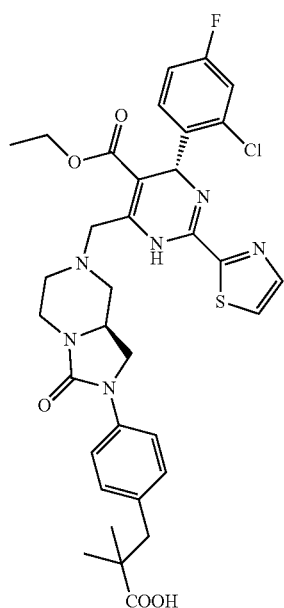
(30)
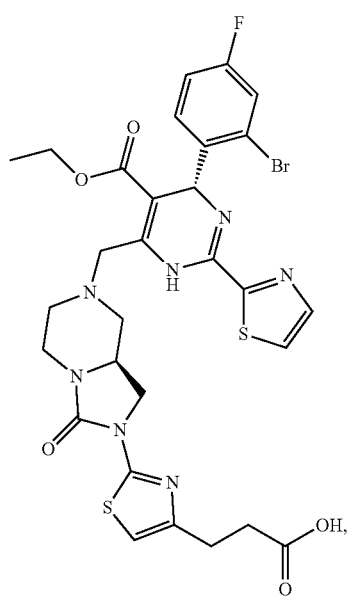
(31)
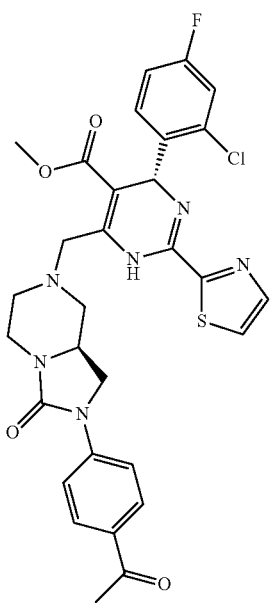
(32)
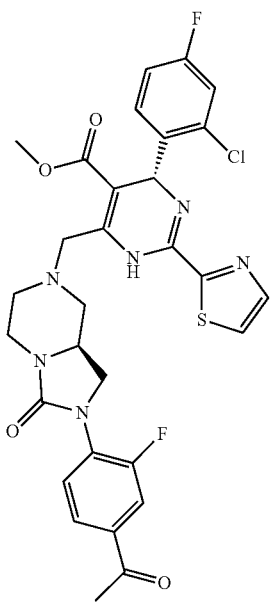

(33)
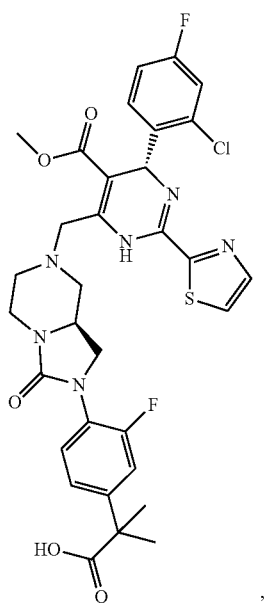
(34)
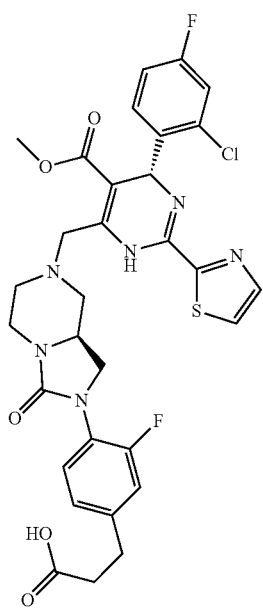
(35)
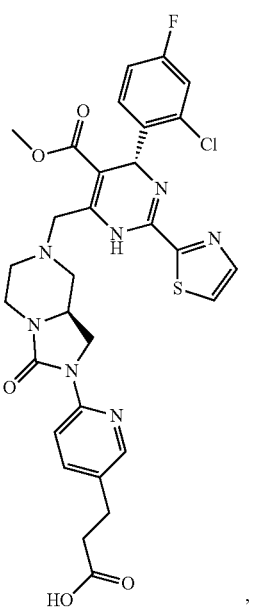
(36)
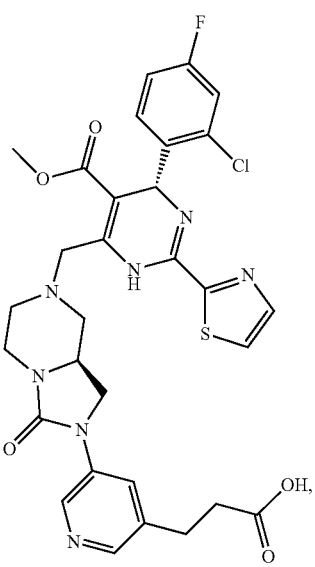

(37)
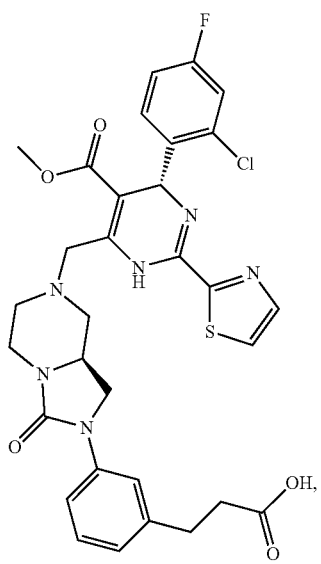
(38)
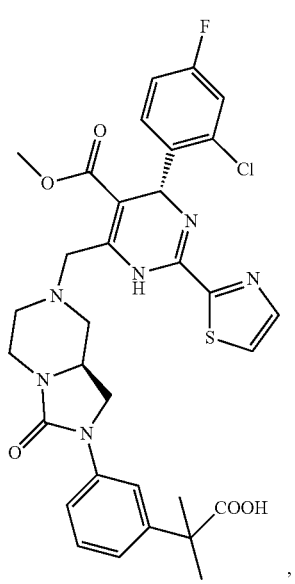
(39)
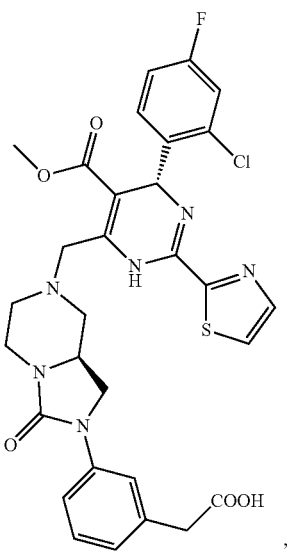
(40)
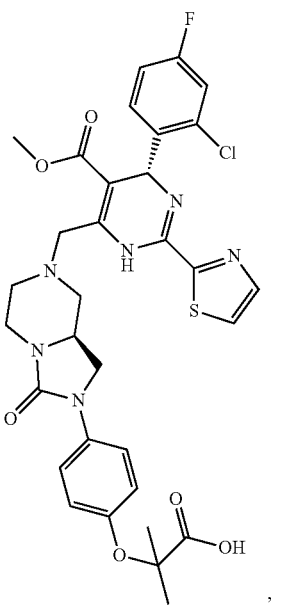

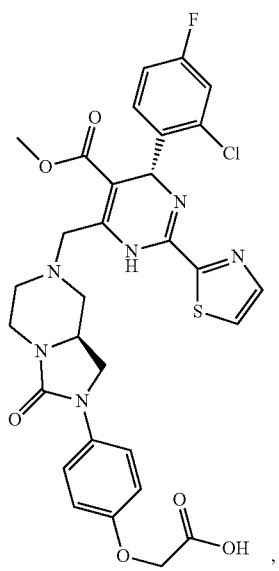
(41)
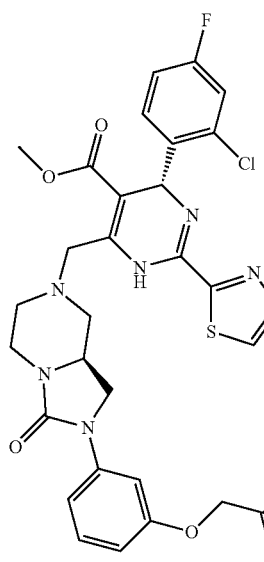
(43)
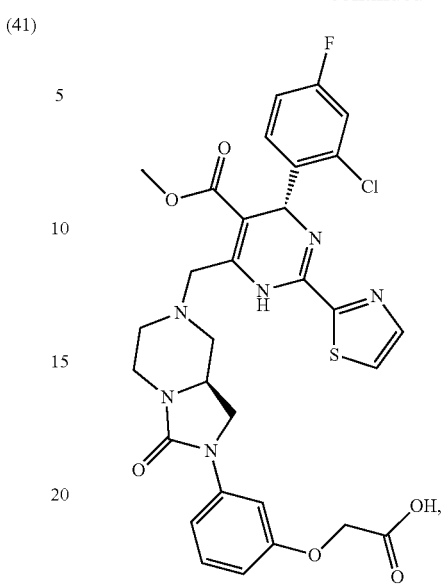
(42)
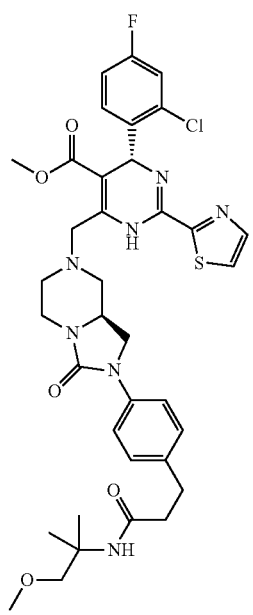
(44)

(45)
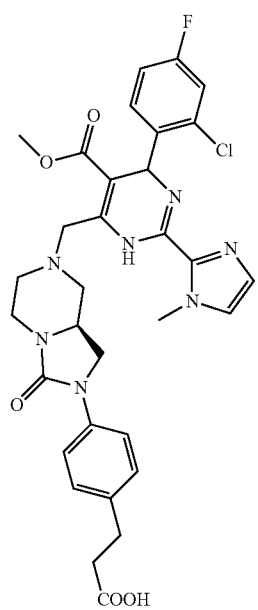
(46)
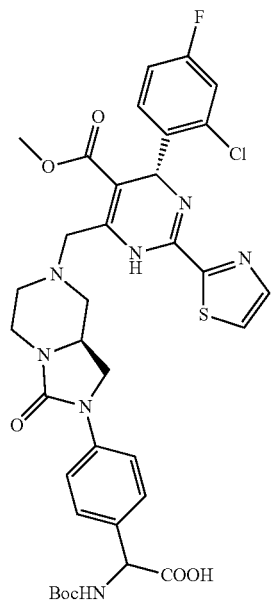
(47)
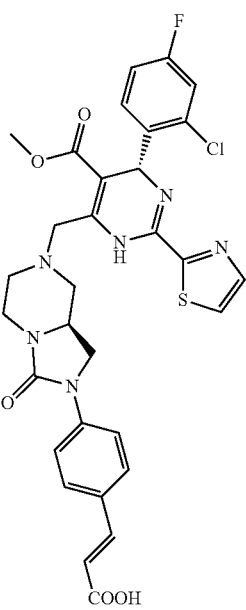
(48)
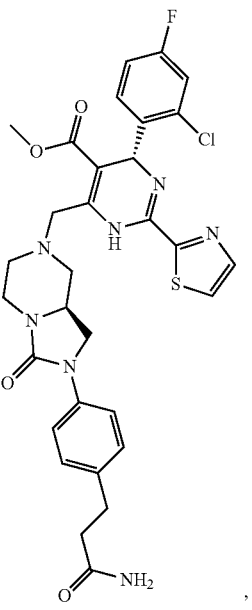

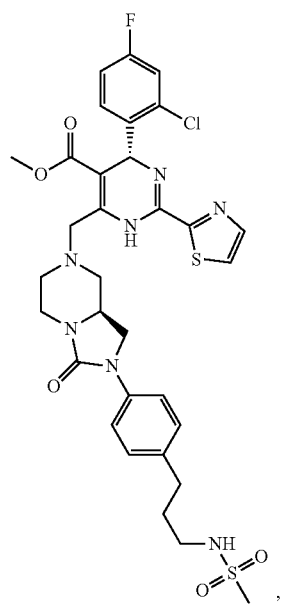
(49)
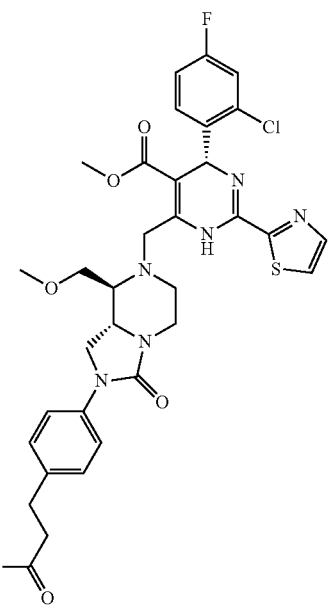
(50B)
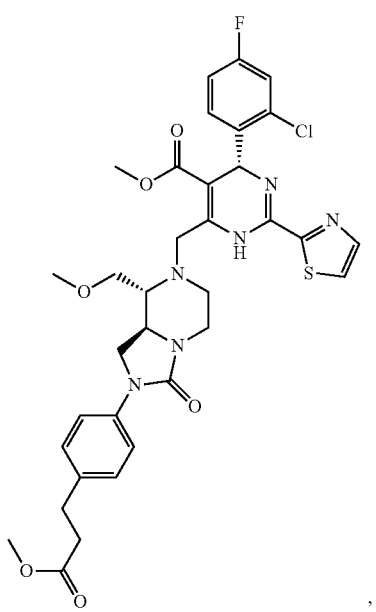
(50A)
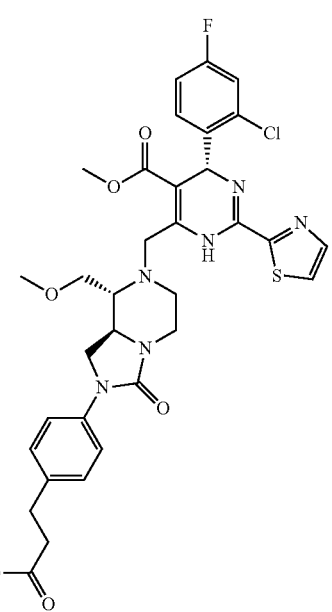
(51A)

(51B)
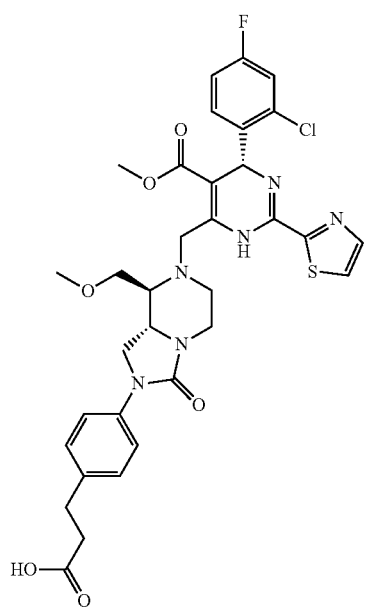
(52)
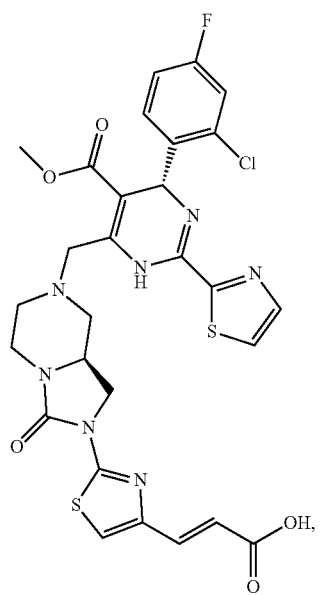
(53)
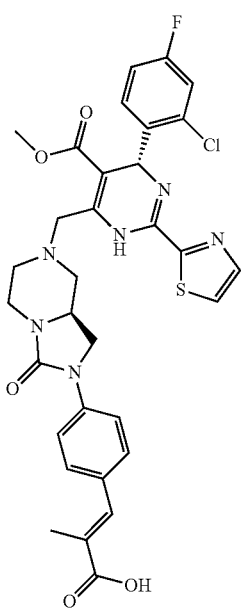
(54)
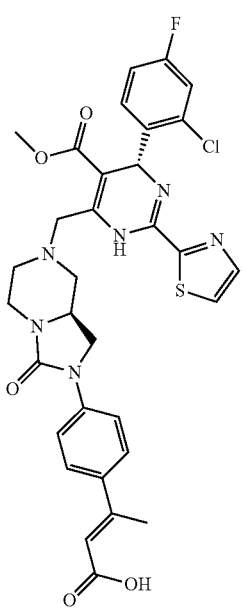

(55)
(56)
(57)
(58A)
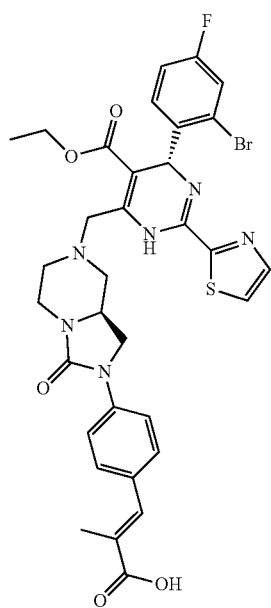
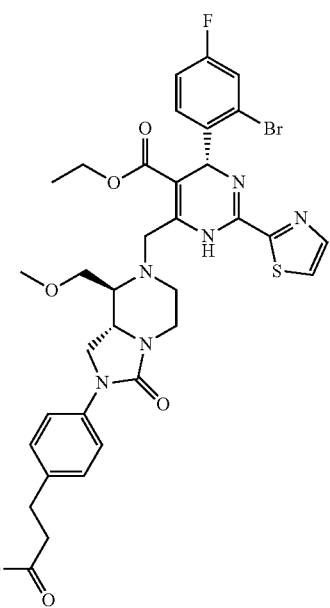

(58B)
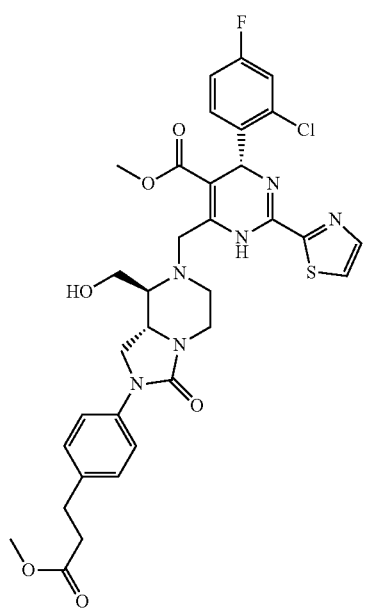
(59A)
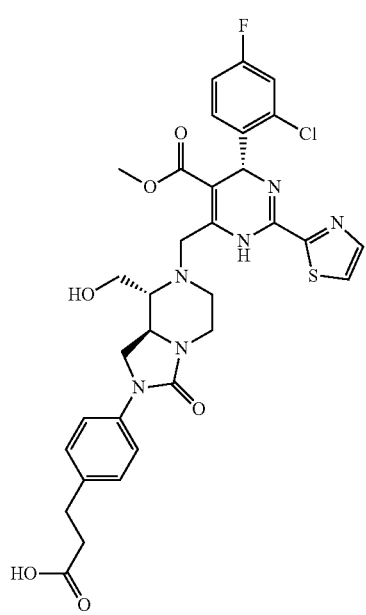
(59B)
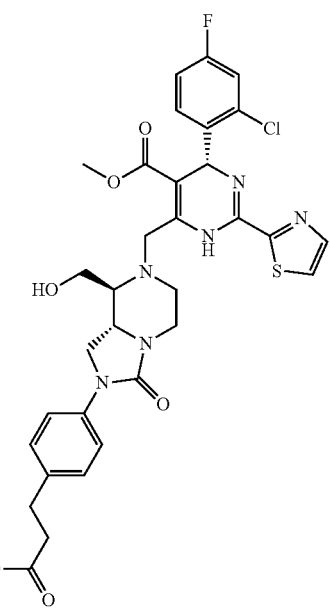
(60A)
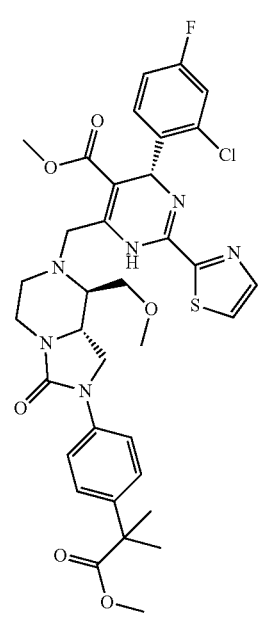

(60B)
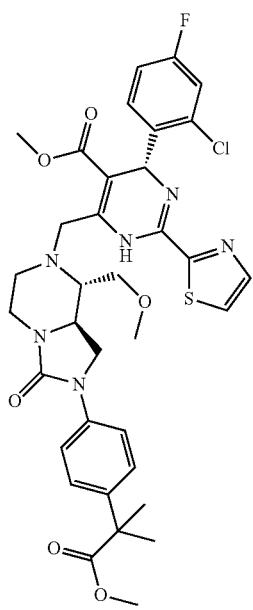
(61A)
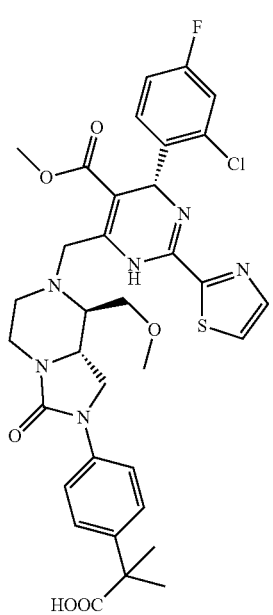
(61B)
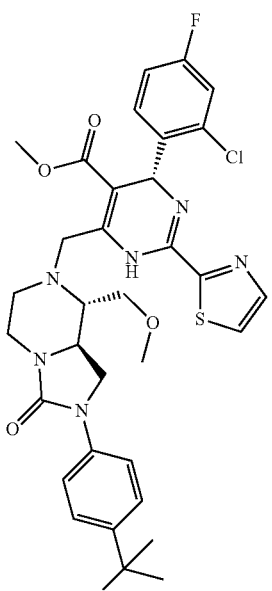
(62)
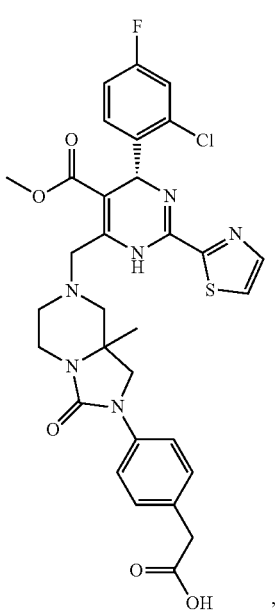

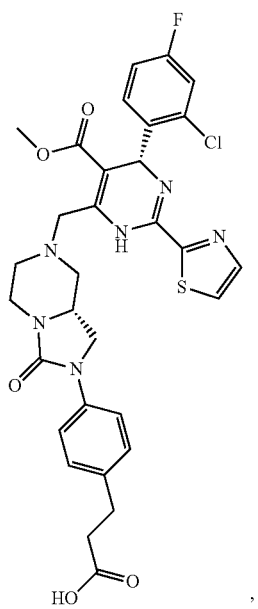
(63)
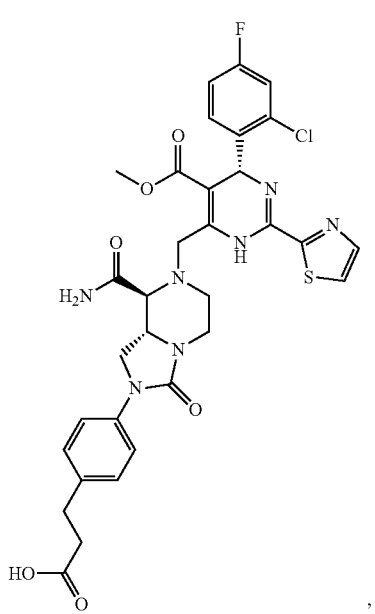
(64)
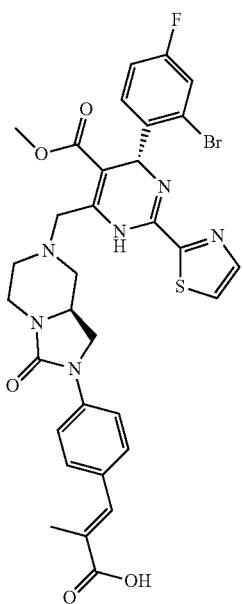
(65)
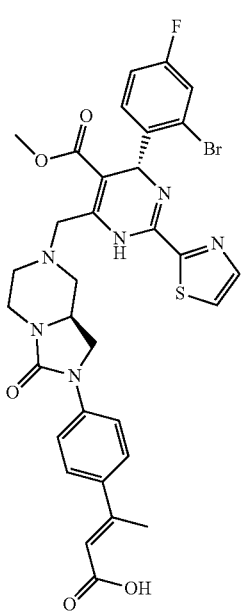
(66)

(67)
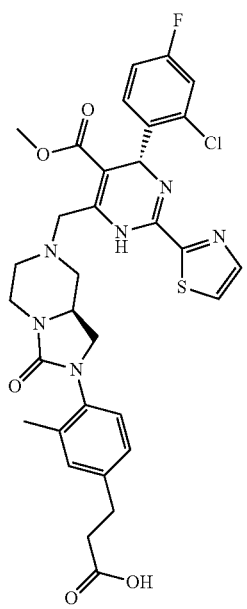
(68)
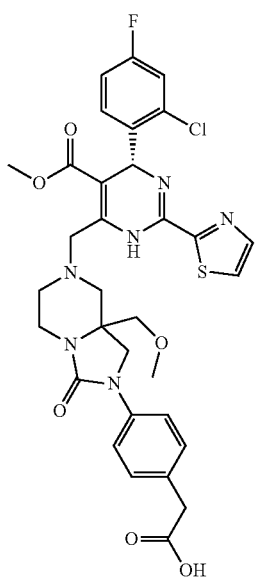
(69)
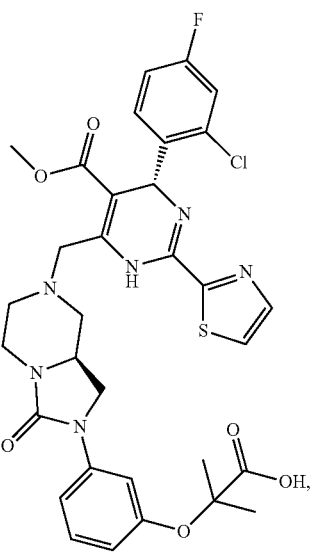
(70)
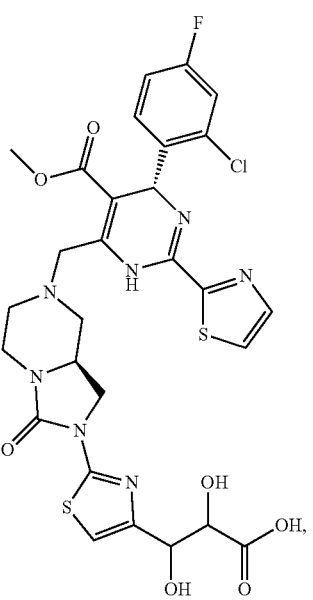

(71)
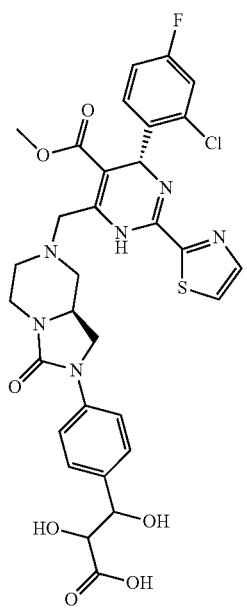
(72)
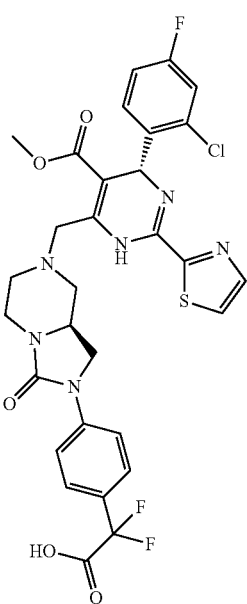
(73)
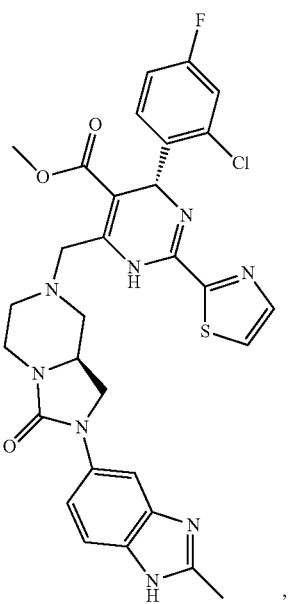
(74)

(75)
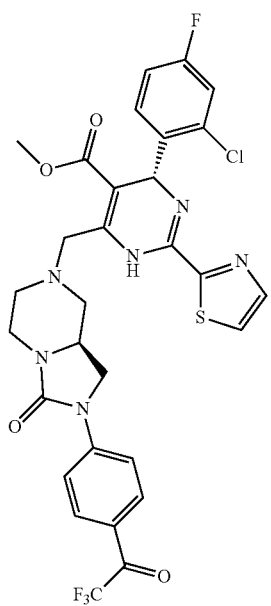
,
(76)
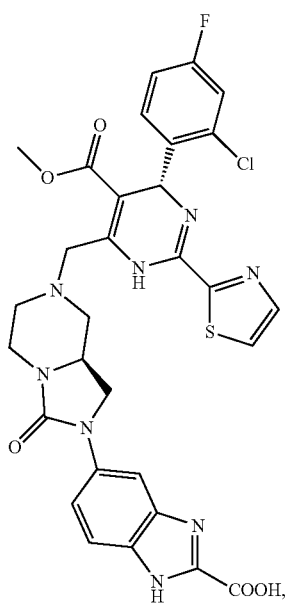
,
(77)
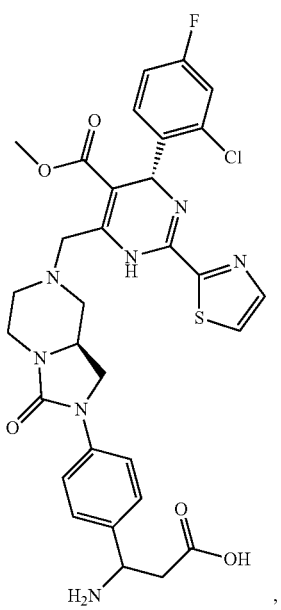
,
(78)
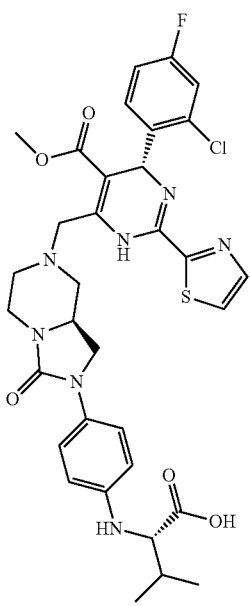
,

(79)
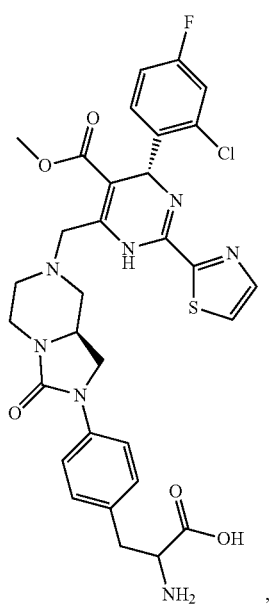
(81)
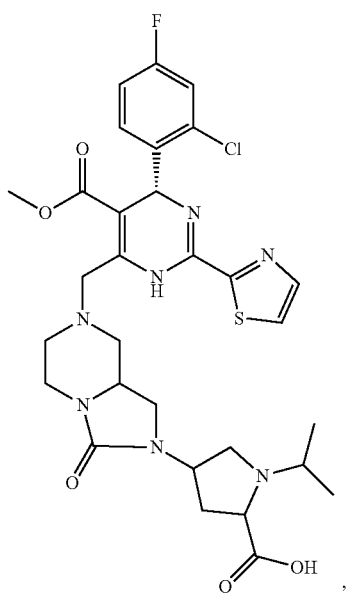
(80)
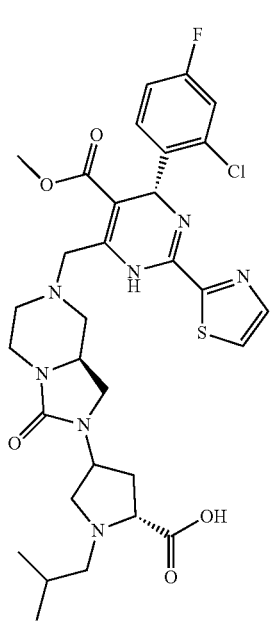
(82)

(83)
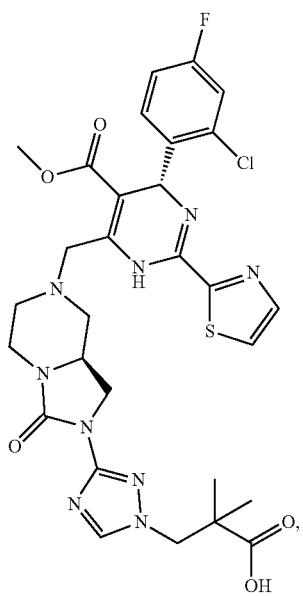
(84)
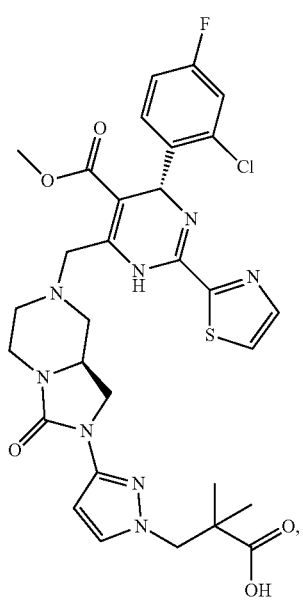
(85)
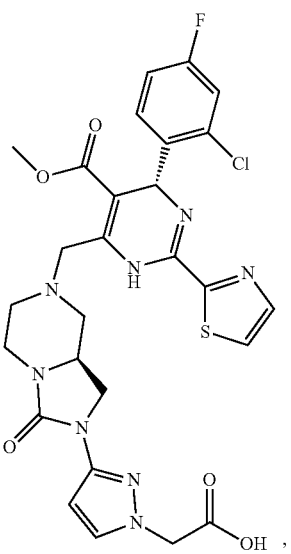
(86)
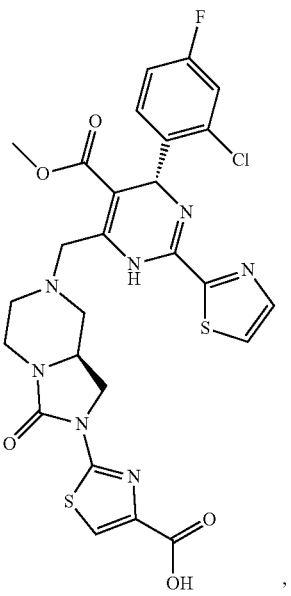

(87)
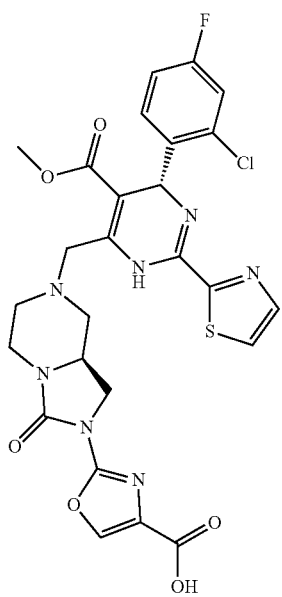
(88)
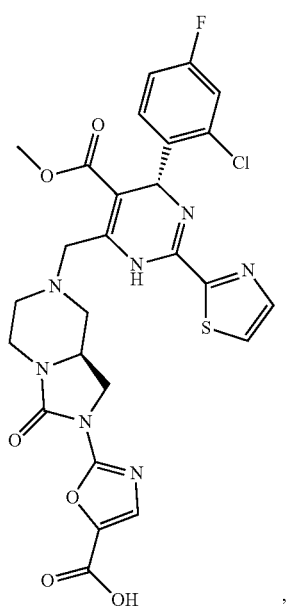
(89)
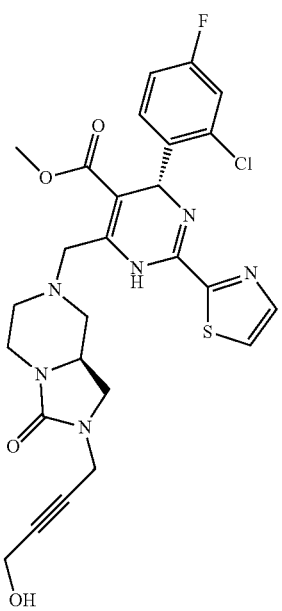
(90)
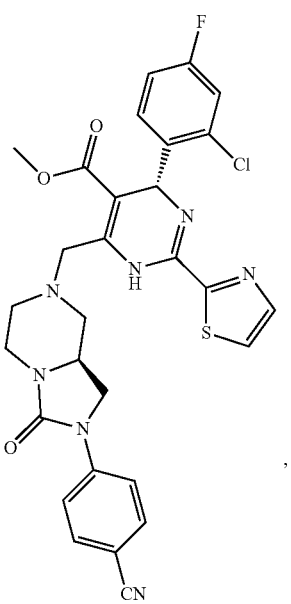

(91)
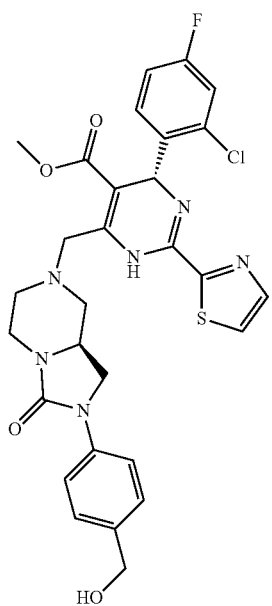
(92)
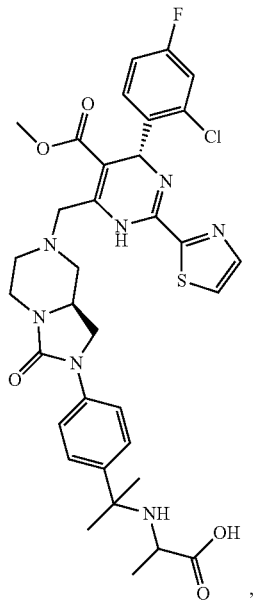
(93)
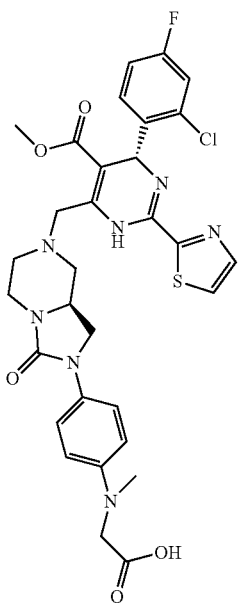
(94)
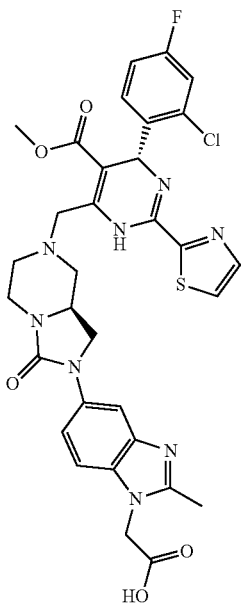

(95)
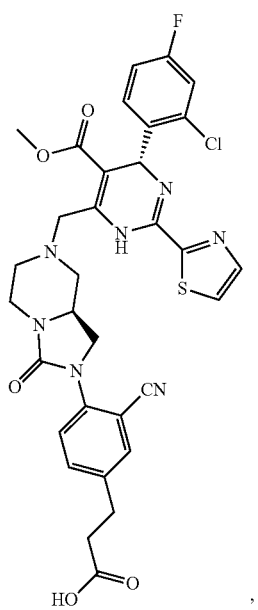
(97)
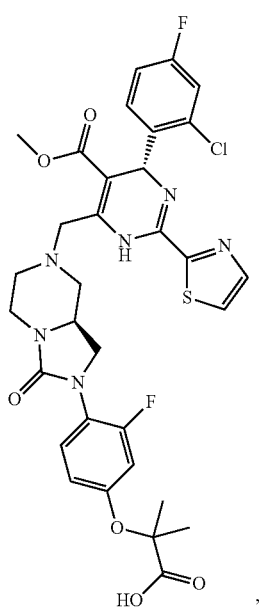
(96)
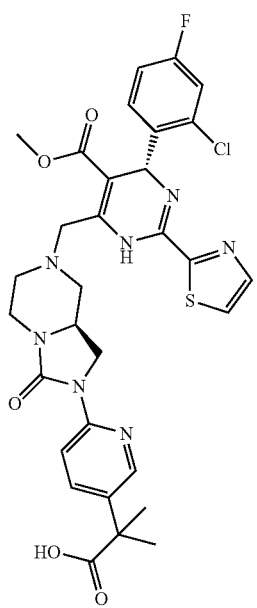
(98)
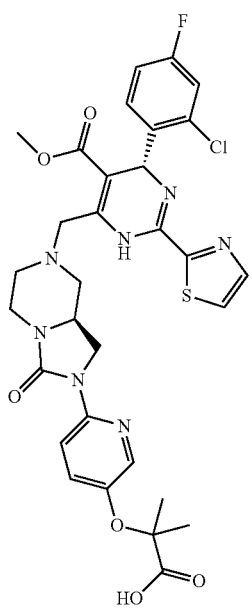

(99)
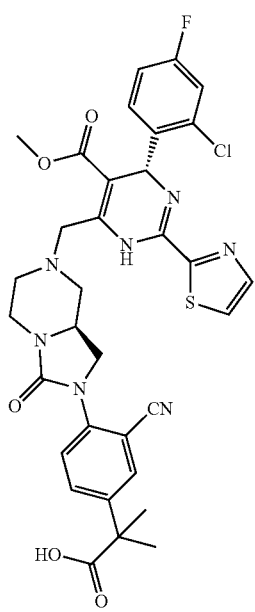
(101)
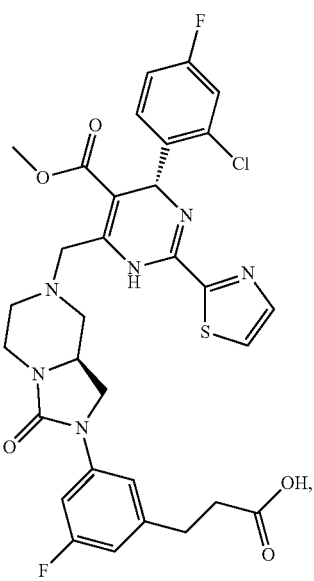
(100)
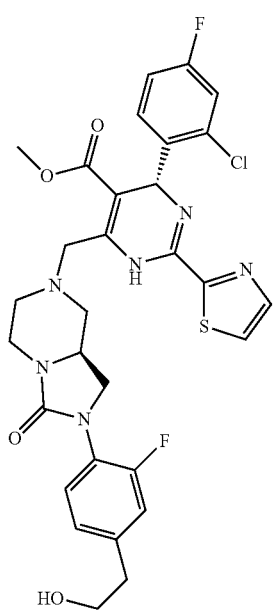
(102)
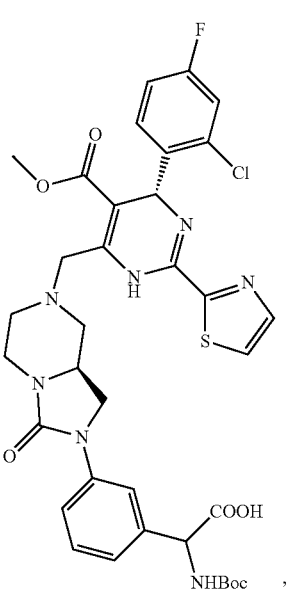

(103)
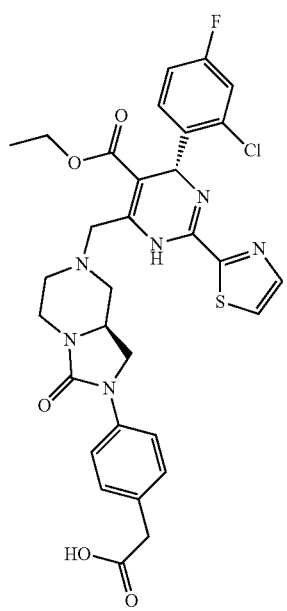
(104)
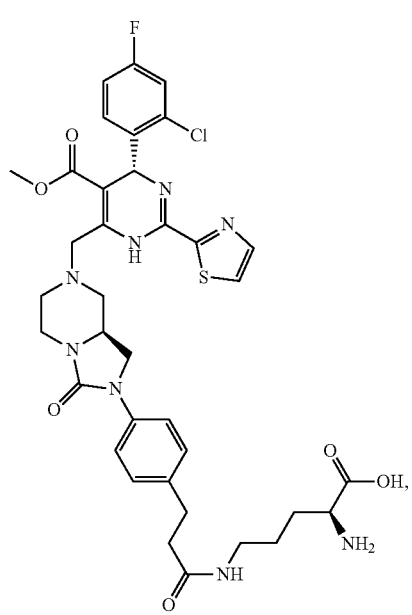
(105)
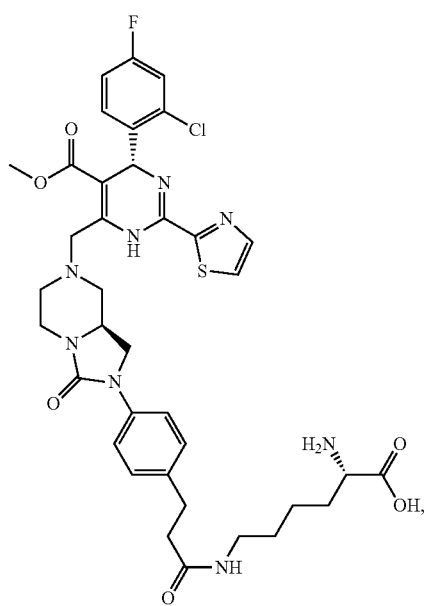
(106)
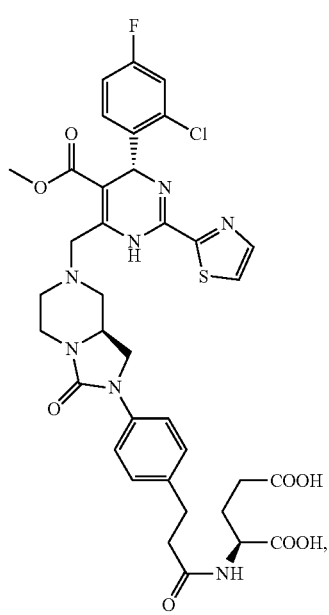

(107)
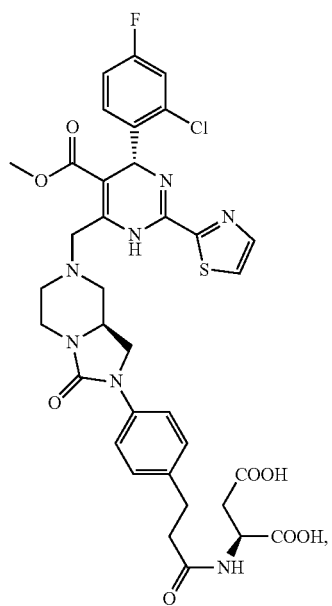
(108)
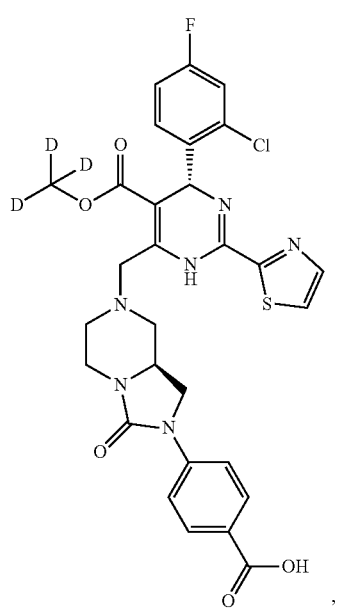
(109)
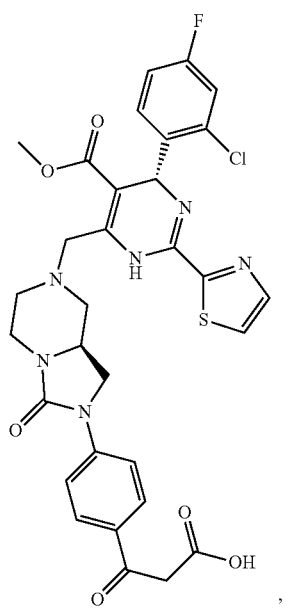
(110)
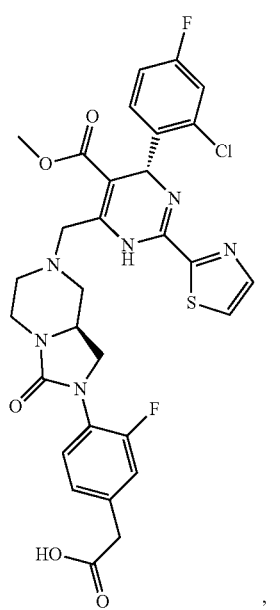

(111)
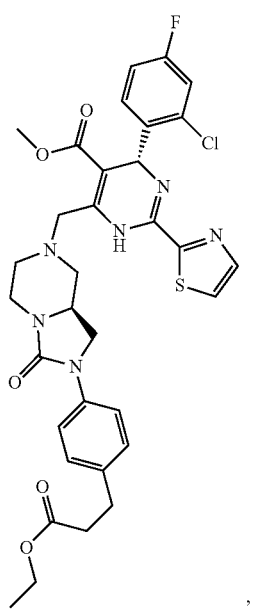
(112)
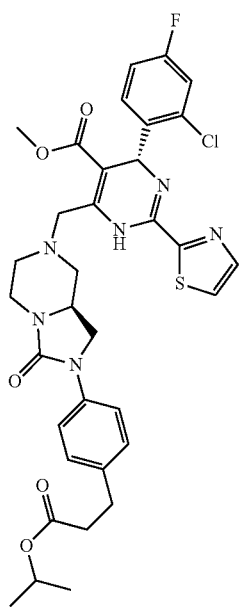
(113)
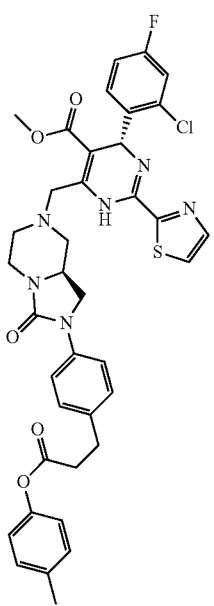
(114)
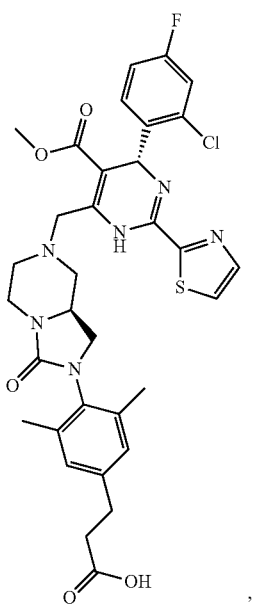

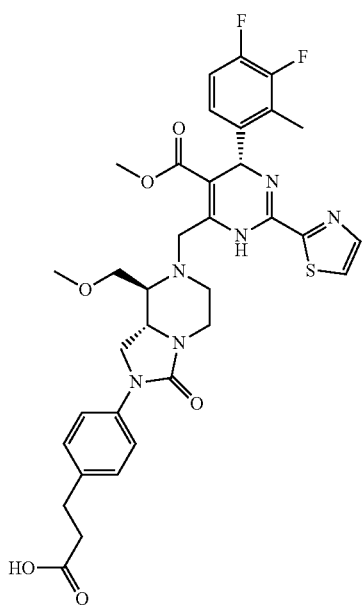
(115)
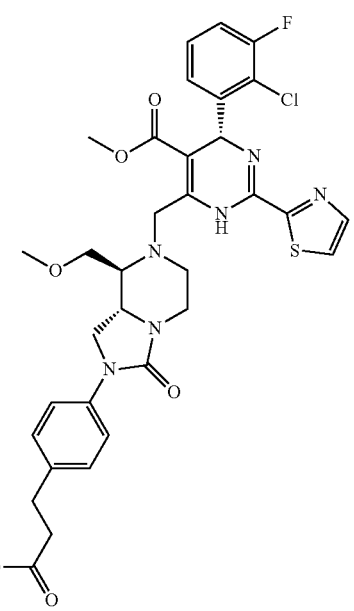
(117)
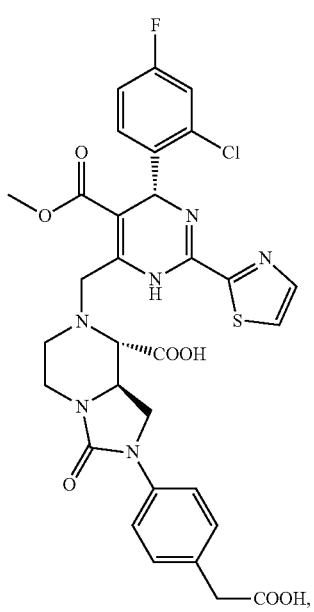
(116)
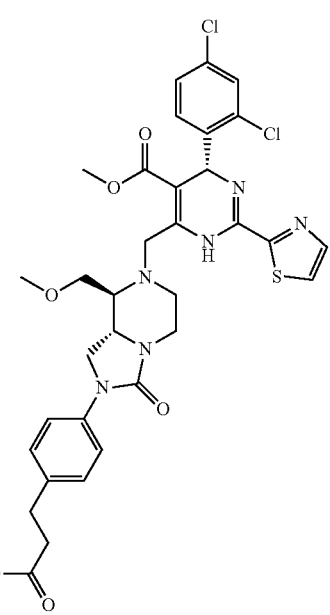
(118)

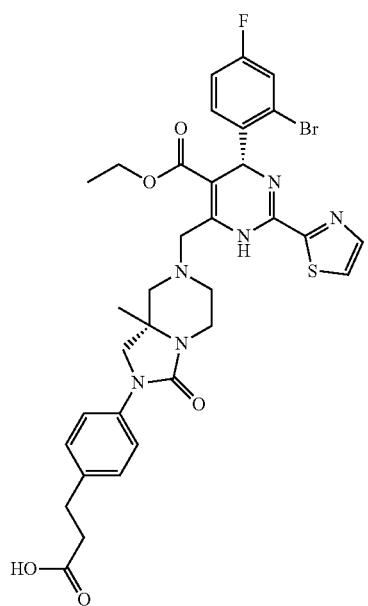
(119)
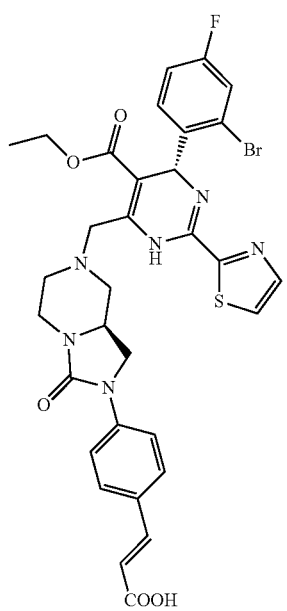
(121)
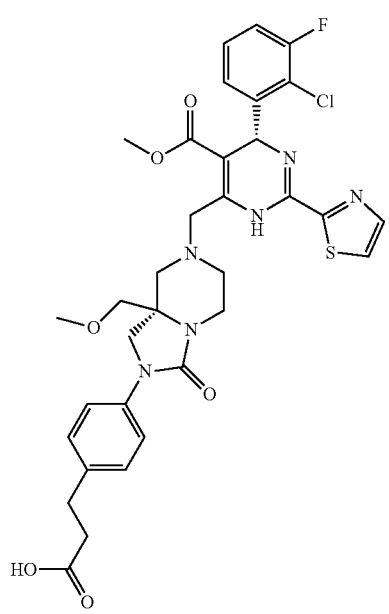
(120)
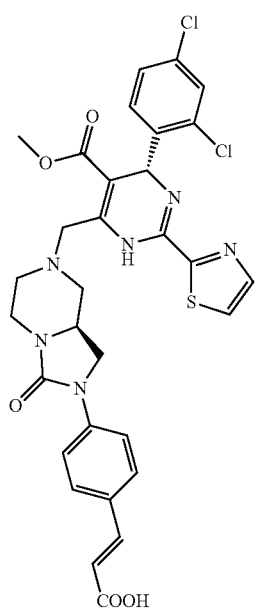
(122)

(123)
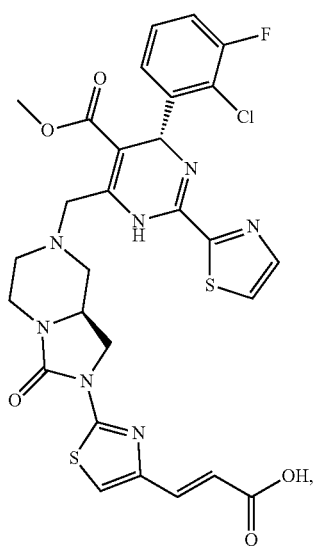
(124)
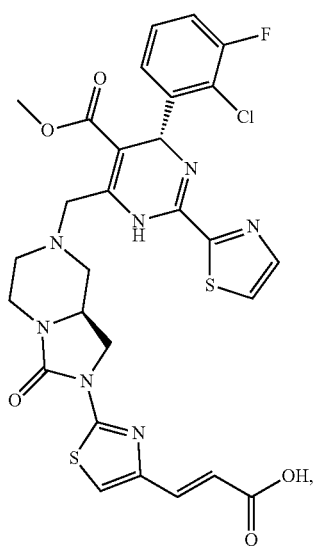
(125)
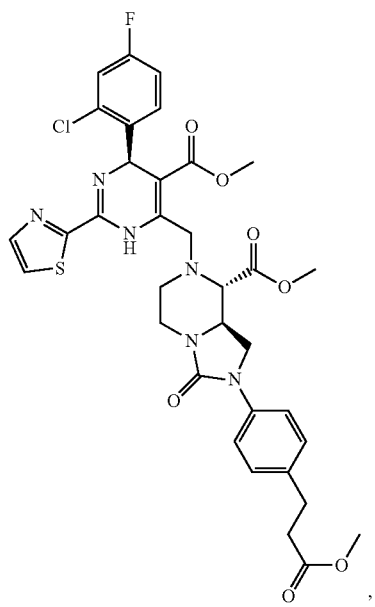
(126)
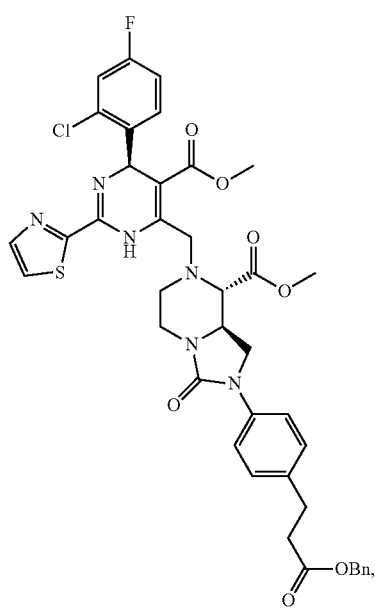

(127)
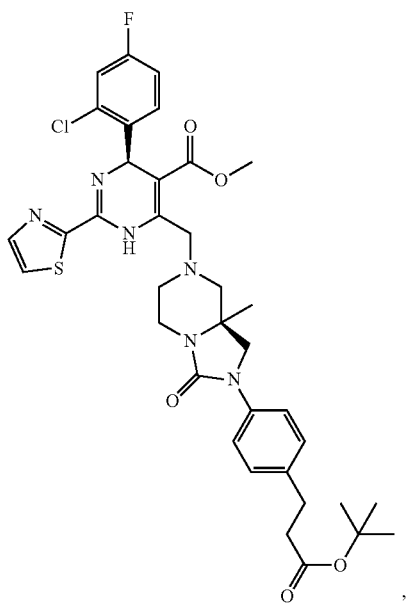
(128)
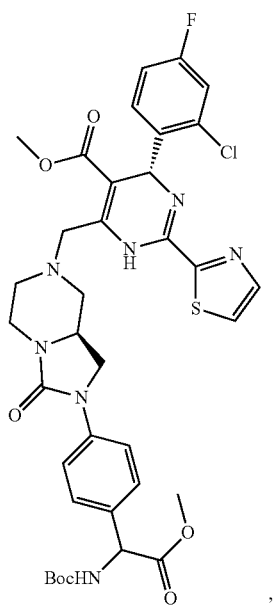
(129)
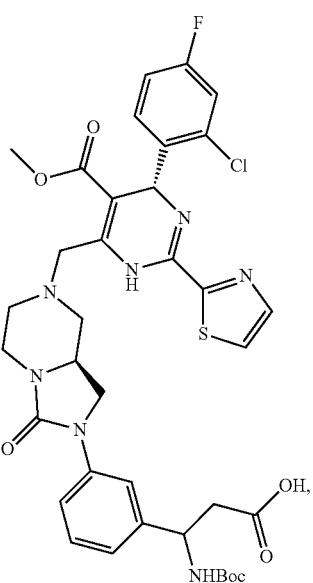
(130)
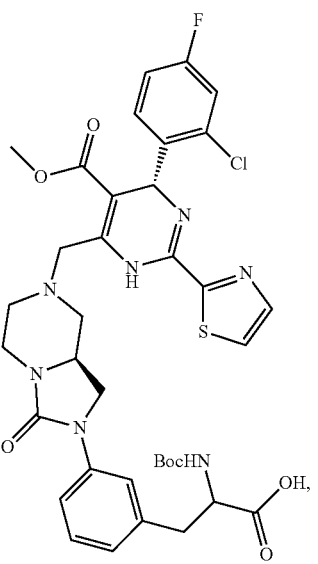

(131)
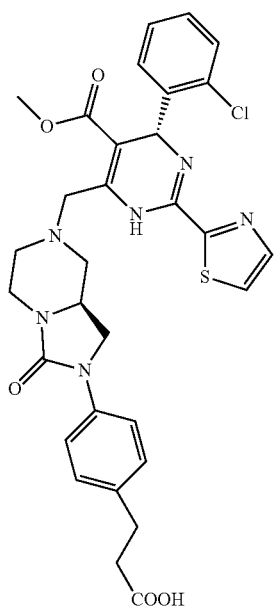
,
(132)
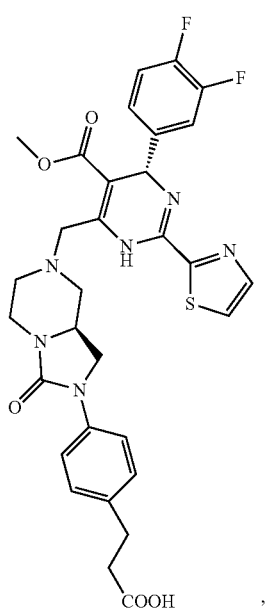
,
(133)
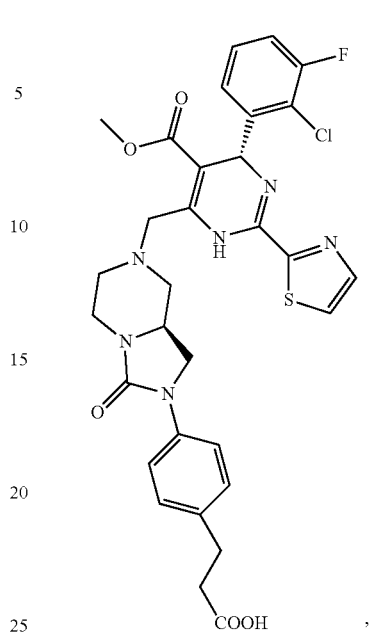
,
(134)
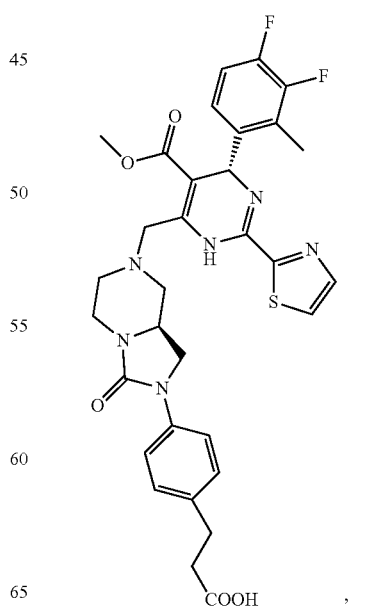
, (135)
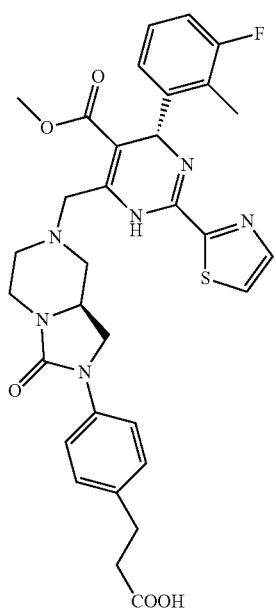
(137)
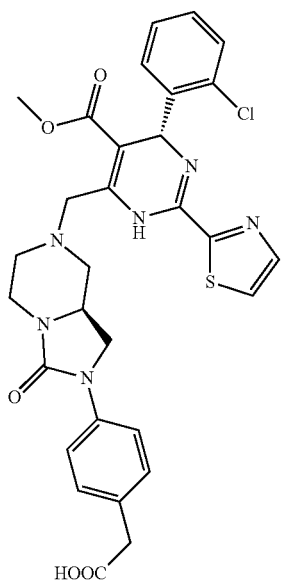
(136)
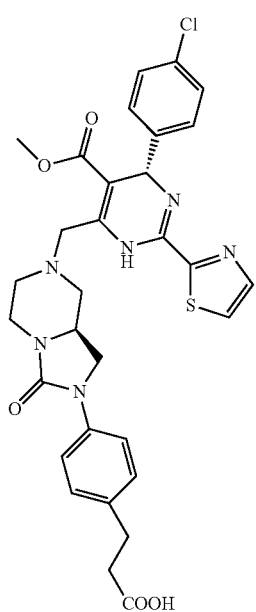
(138)
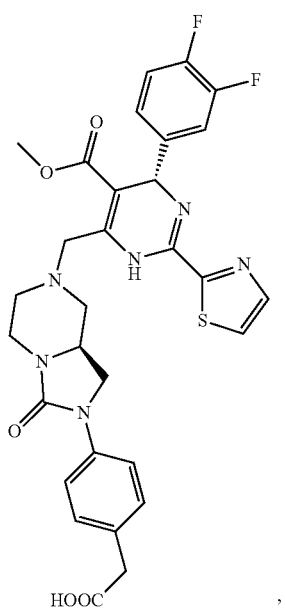

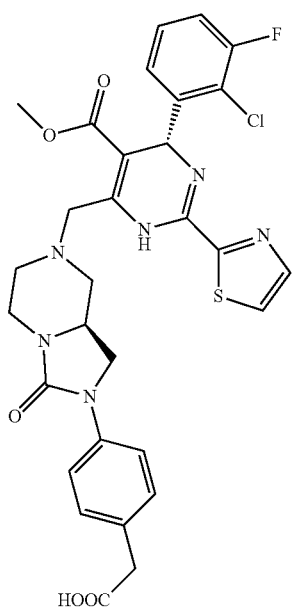
(139)
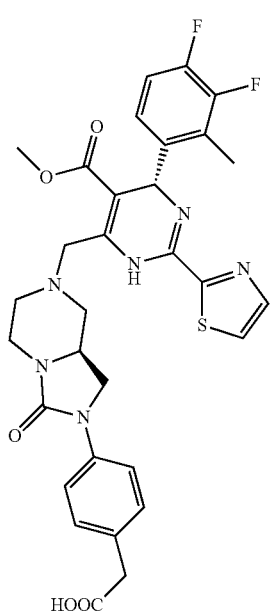
(140)
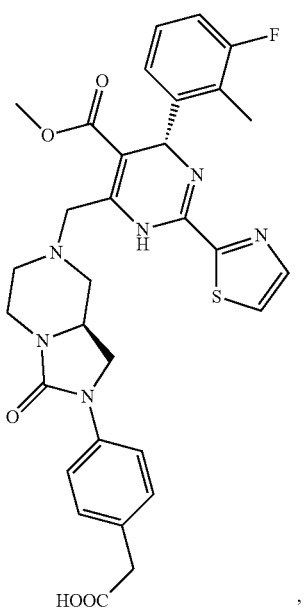
(141)
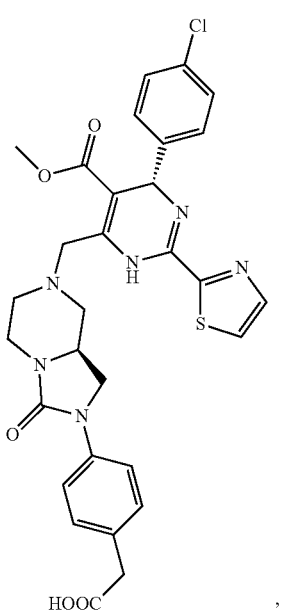
(142)

(143)
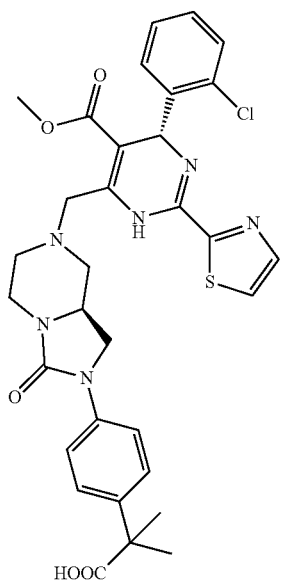
(144)
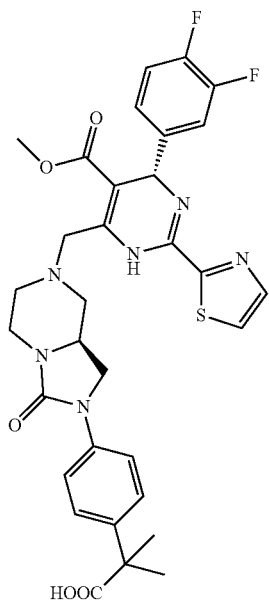
(145)
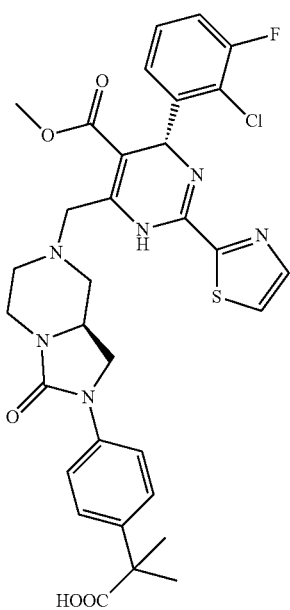
(146)
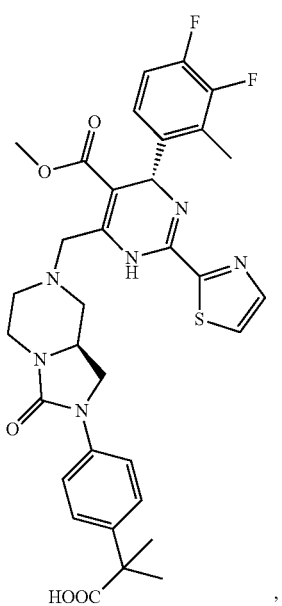

(147)
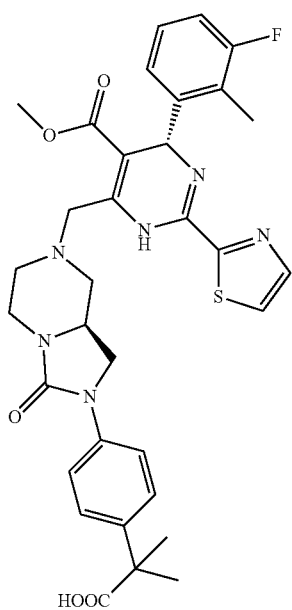
(148)
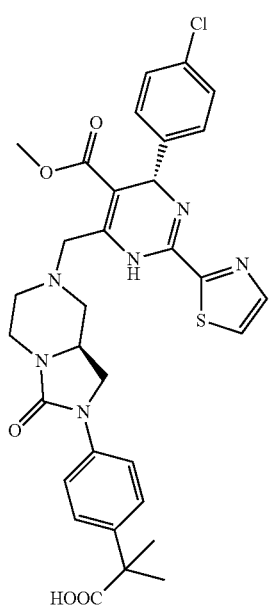
(149)
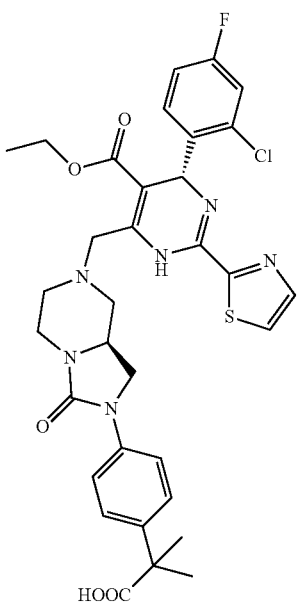
(150)
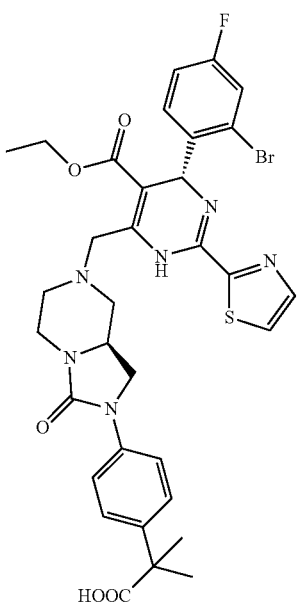

(151)
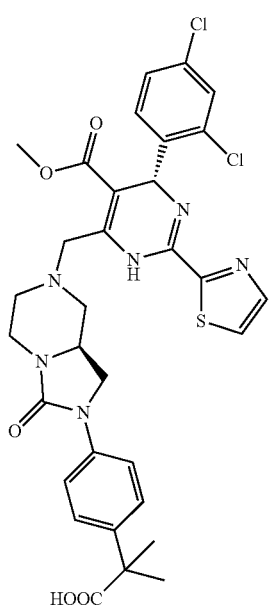
(152)
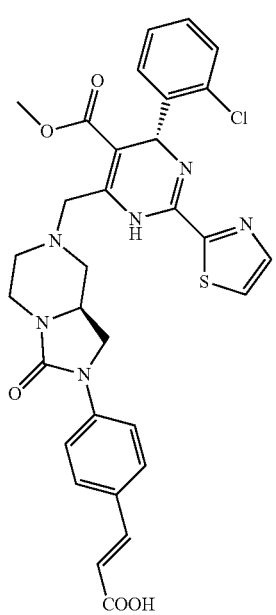
(153)
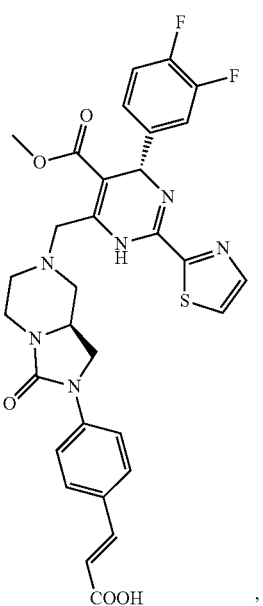
(154)
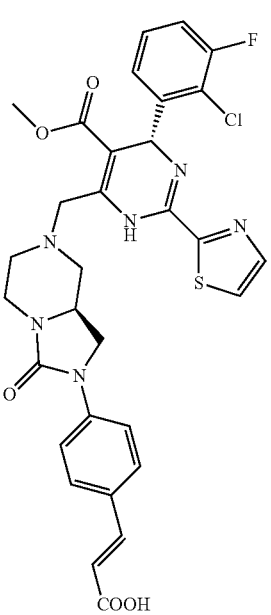

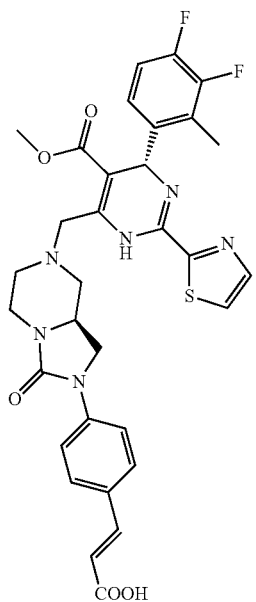
(155)
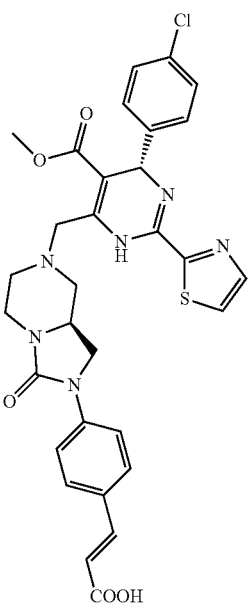
(157)
(156)
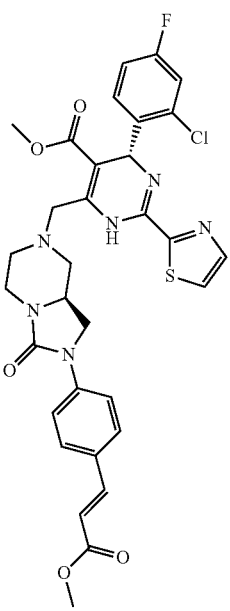
(158)

(159)
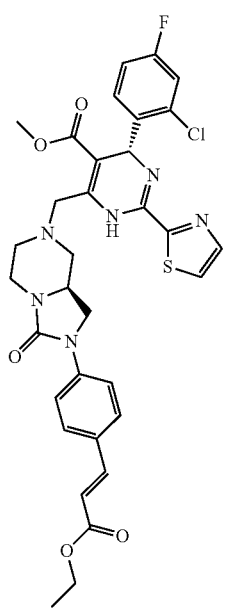
(160)
(161)
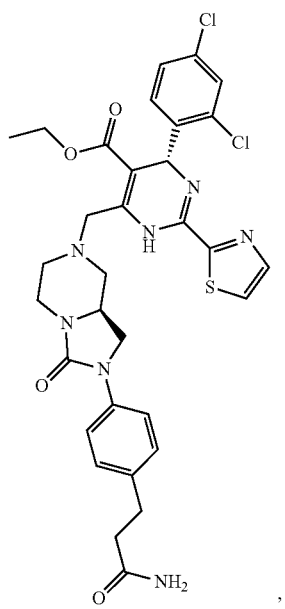
(162)
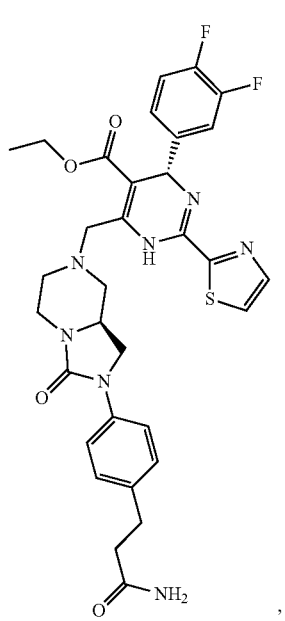

(163)
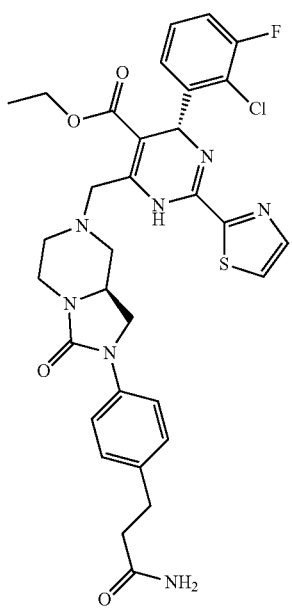
(164)
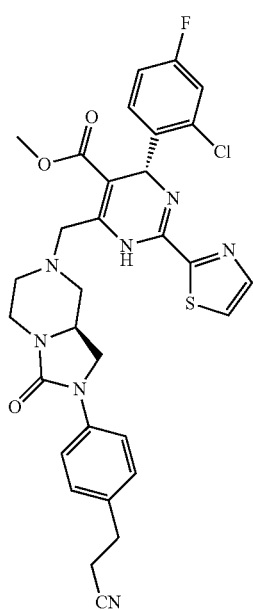
(165)
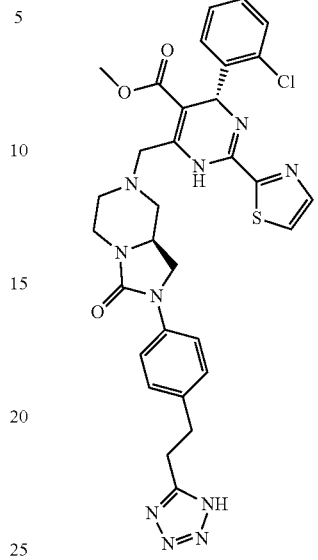
(166)
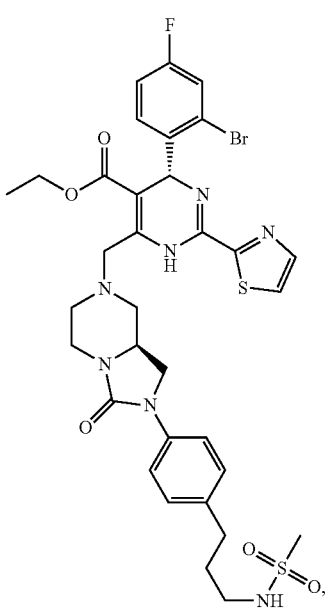

(167)
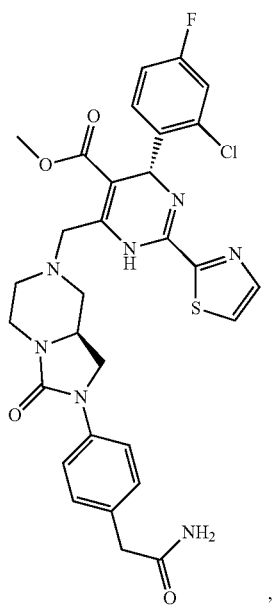
(168)
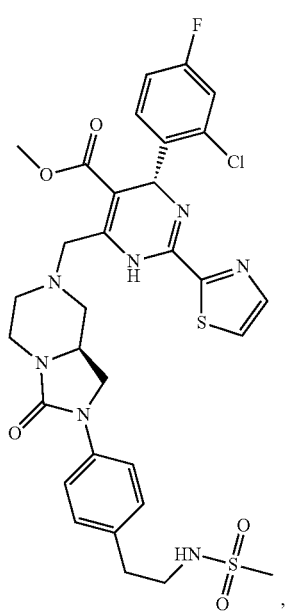
(169)
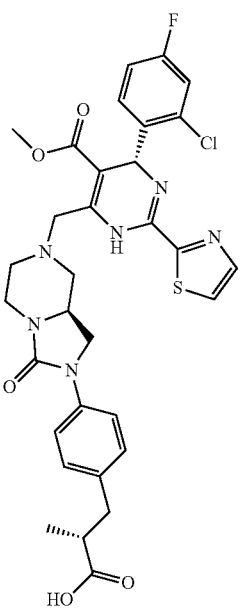
(170)
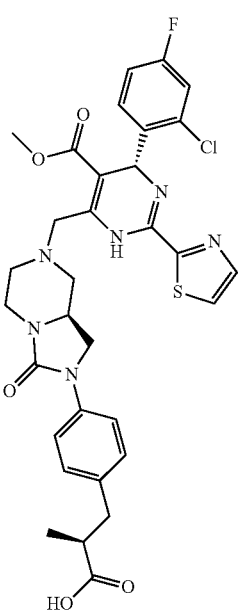

(171)
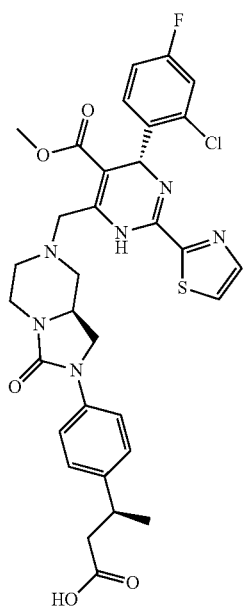
(172)
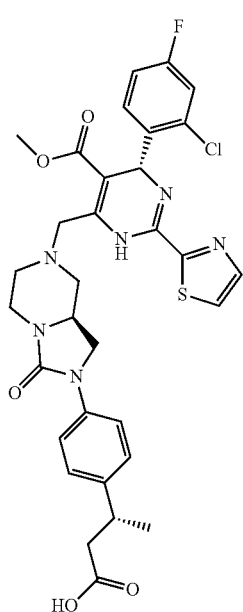
(173)
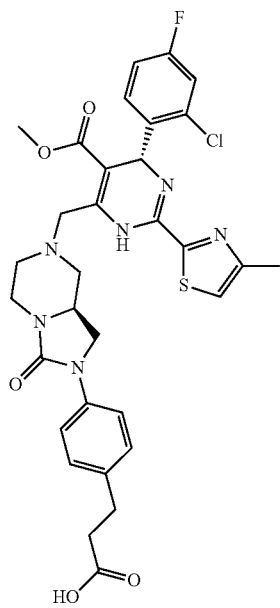
(174)
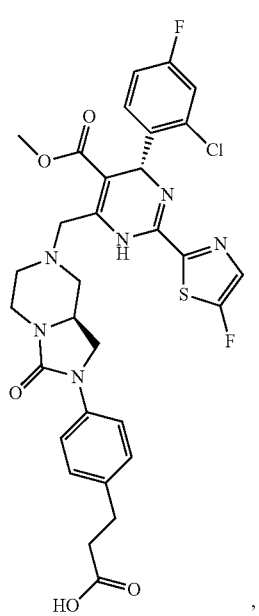

(175)
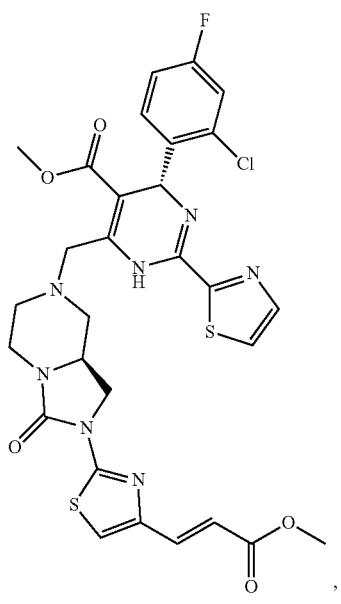
(176)
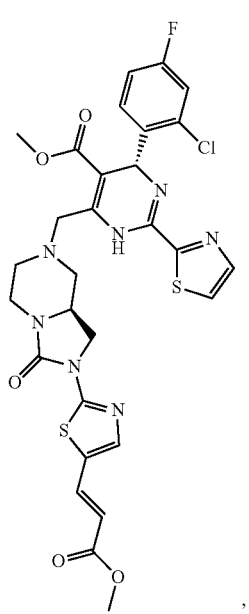
(177)
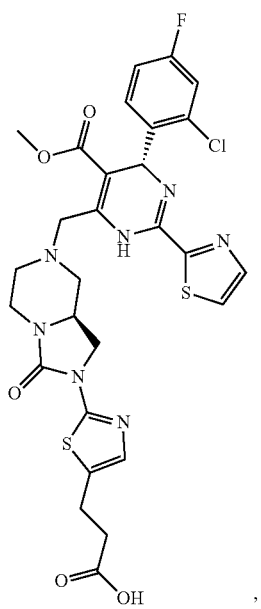
(178)
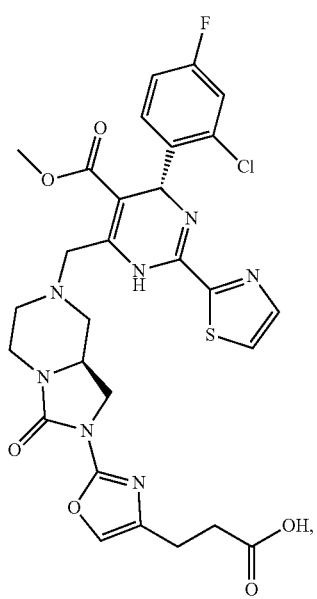

123
-continued
(179)
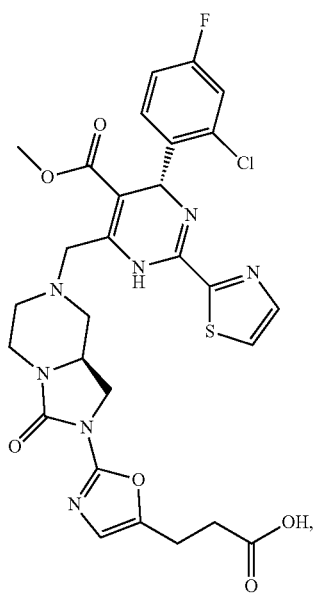
124
-continued
(181)
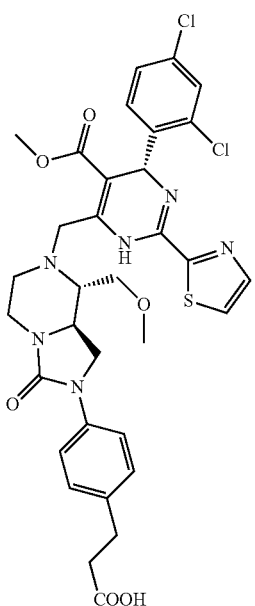
(180)
(182)
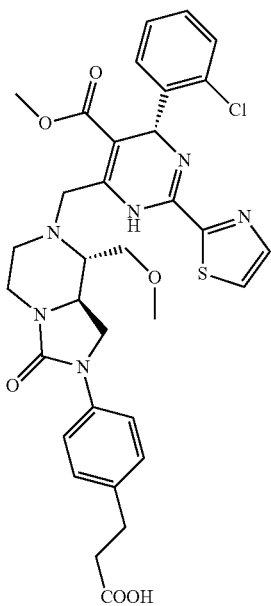

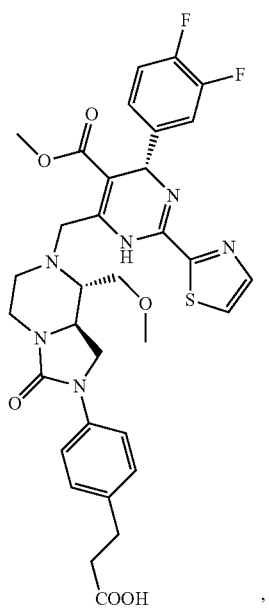
(183)
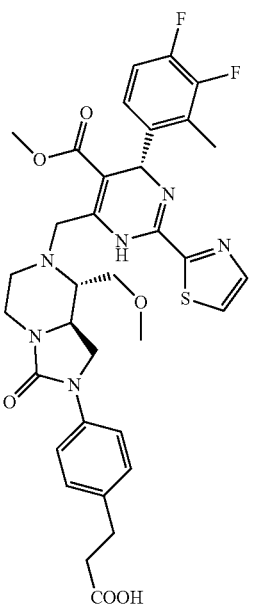
(185)
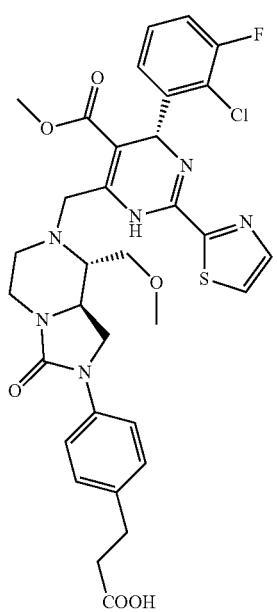
(184)
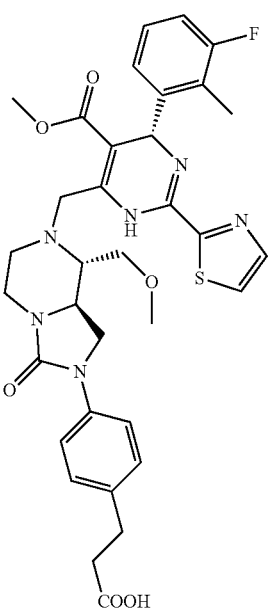
(186)

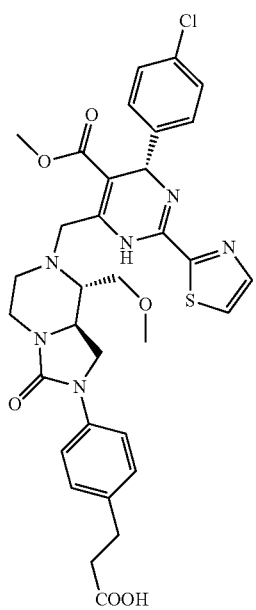
(187)
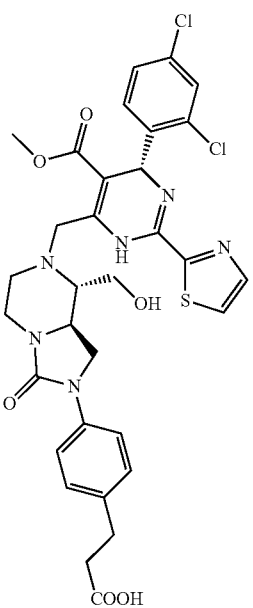
(189)
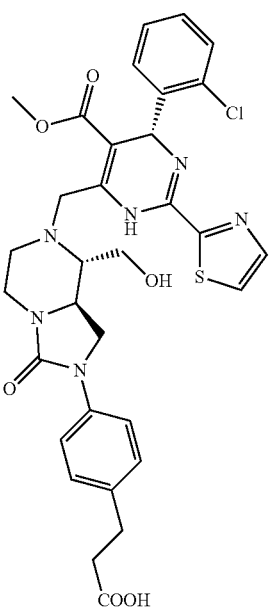
(188)
(190)

(191)
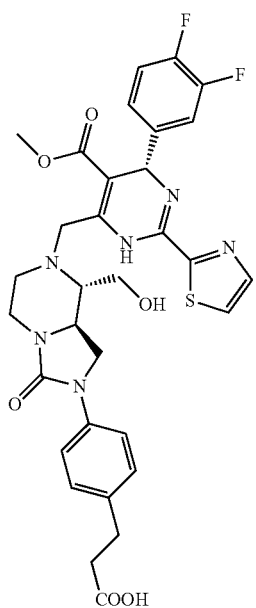
,
(192)
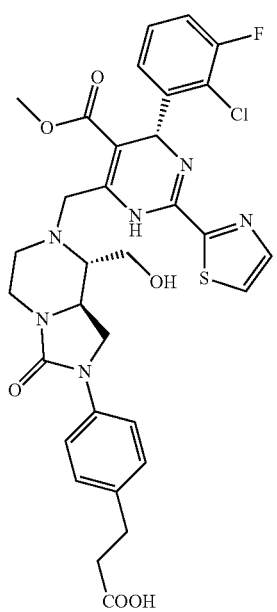
,
(193)
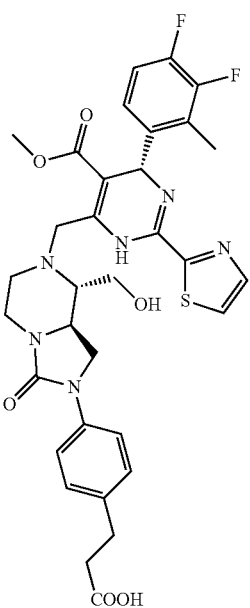
,
(194)
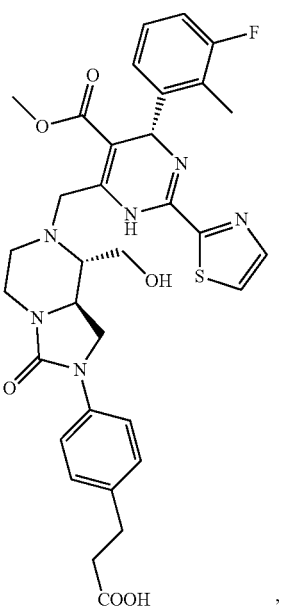
,

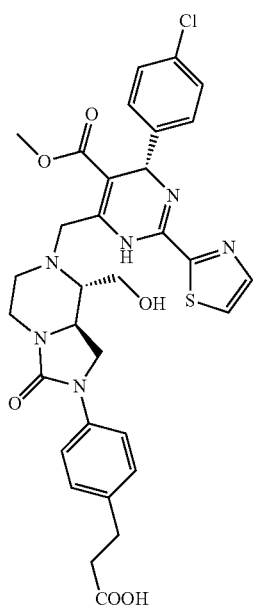
(195)
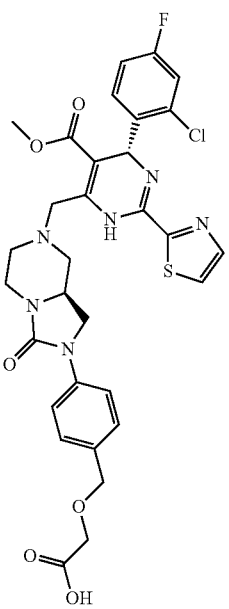
(197)
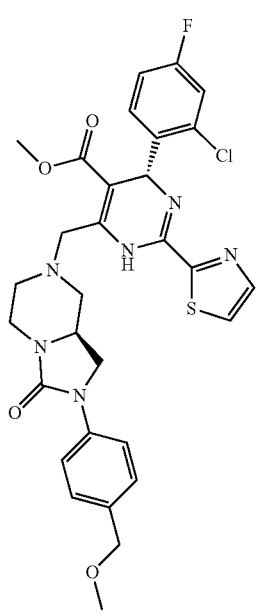
(196)
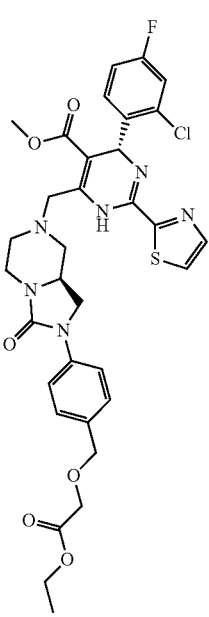
(198)

(199)
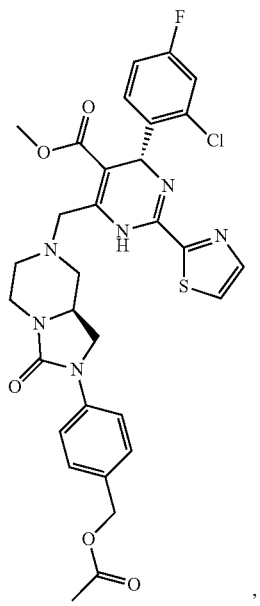
(200)
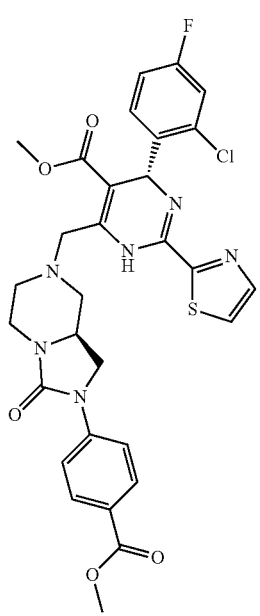
(201)
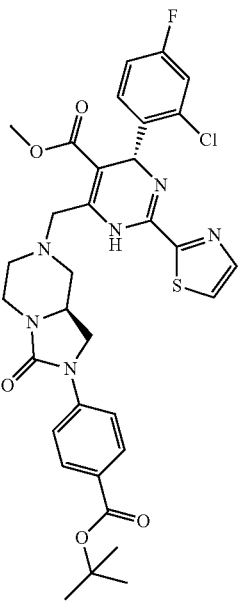
(202)
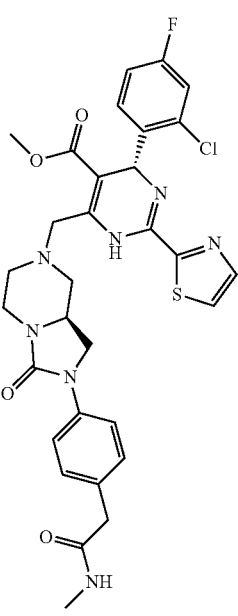

(203)
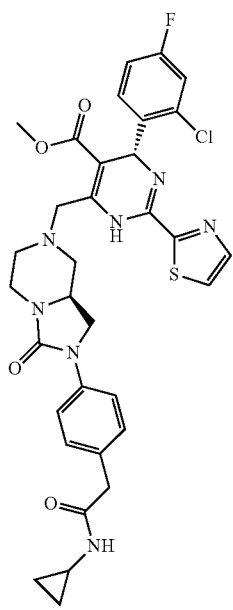
(204)
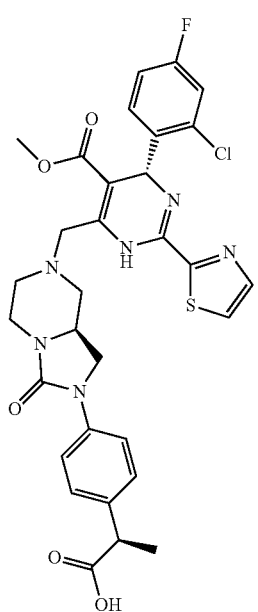
(205)
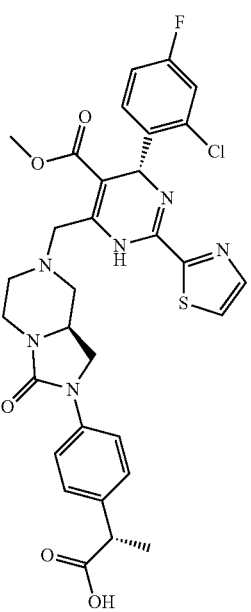
(206)
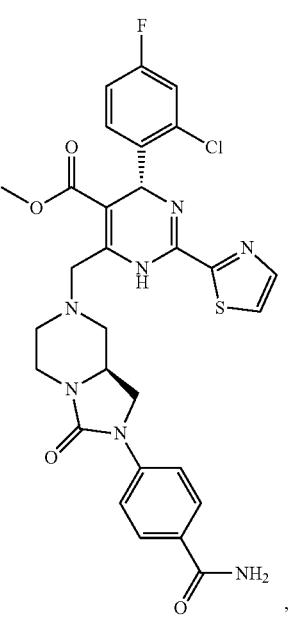

(207)
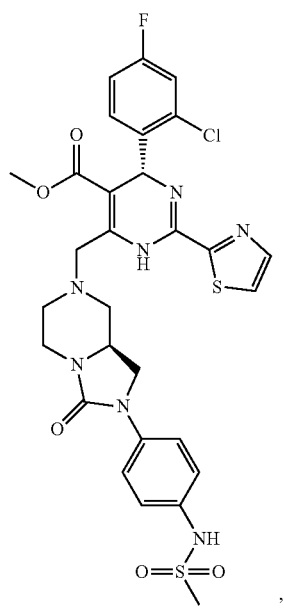
(208)
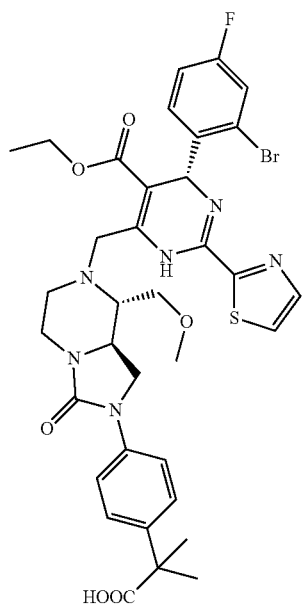
(209)
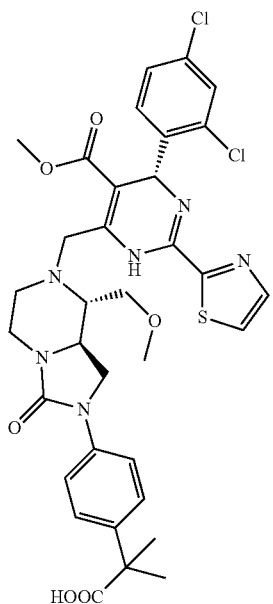
(210)
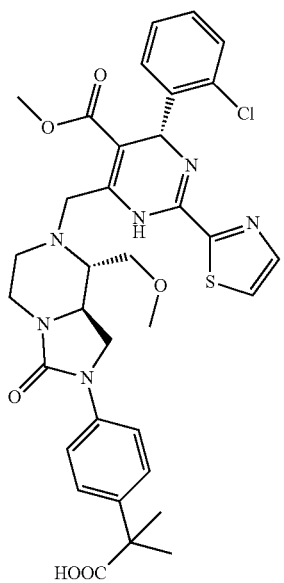

-continued

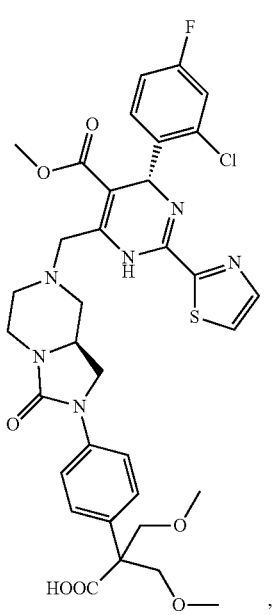
(211)

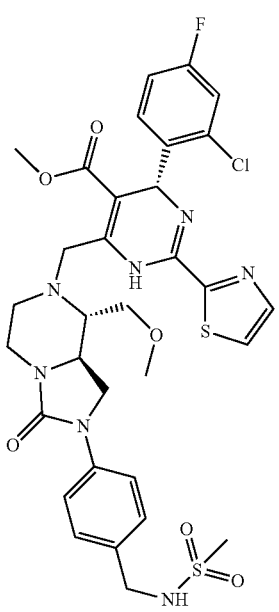
(212)

In other aspect, provided herein is a pharmaceutical composition comprising the compound disclosed herein and a pharmaceutically acceptable adjuvant.

In some embodiments, the pharmaceutical composition disclosed herein further comprises other anti-HBV drug.

In some embodiments of the pharmaceutical composition disclosed herein, wherein the other anti-HBV drug is an HBV polymerase inhibitor, immunomodulator or interferon.

In some embodiments of the pharmaceutical composition, wherein the other anti-HBV drug is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, Euforavac, rintatolimod, Phosphazid, Heplisav, interferon α-2b, levamisole, or propagermanium.

In another aspect, also provided herein is use of the compound or the pharmaceutical composition disclosed herein in the manufacture of a medicament for preventing, treating or lessening a virus disease in a patient.

In some embodiments of the use, wherein the virus disease disclosed herein is hepatitis B infection or a disease caused by hepatitis B infection.

In other embodiments of the use, the disease caused by hepatitis B infection disclosed herein is hepatic cirrhosis or hepatocellular carcinogenesis.

In another aspect, provided herein is use of the compound or the pharmaceutical composition disclosed herein in the manufacture of a medicament for preventing, treating or lessening a virus disease in a patient.

In some embodiments of the use of the compound or the pharmaceutical composition, wherein the virus disease disclosed herein is hepatitis B infection or a disease caused by hepatitis B infection.

In other embodiments of the use of the compound or the pharmaceutical composition, the disease caused by hepatitis B infection disclosed herein is hepatic cirrhosis or hepatocellular carcinogenesis.

In other embodiments, the present invention relates to a method of preventing, treating or lessening a virus disease in a patient, comprising administering a therapeutically effective amount of a pharmaceutically acceptable effective amount of the compound or pharmaceutical composition to a patient.

In some embodiments of the method, wherein the virus disease disclosed herein is hepatitis B infection or a disease caused by hepatitis B infection.

In other embodiments of the method, the disease caused by hepatitis B infection disclosed herein is hepatic cirrhosis or hepatocellular carcinogenesis.

In another aspect, also provided herein is use of the compound or the pharmaceutical composition disclosed herein in the manufacture of a medicament for preventing, treating or lessening a HBV disease in a patient.

In other embodiments, the present invention relates to a method of preventing, treating or lessening an HBV disease in a patient, comprising administering a therapeutically effective amount of a pharmaceutically acceptable effective amount of the compound to a patient.

In other embodiments, the present invention relates to a method of preventing, treating or lessening an HBV disease in a patient, comprising administering a therapeutically effective amount of a pharmaceutically acceptable effective amount of the compound to a patient.

In other aspect, provided herein is use of the compound disclosed herein in the manufacture of a medicament for preventing or treating an HBV disease in a patient, and lessening the severity thereof.

In other aspect, provided herein is use of the composition containing the compound disclosed herein in the manufacture of a medicament for preventing, managing or treating an HBV disease in a patient, and lessening the severity thereof.

In some embodiments, the patient is a mammal, in other embodiments, the patient is human. In other some embodiments, the use further comprises contacting cells with other anti-HBV therapeutic agent.

In other embodiments, provided herein is a method of inhibiting HBV infection, comprising contacting cells with a therapeutically effective amount of the compound or the composition to HBV. In other some embodiments, the method further comprises contacting cells with other anti-HBV therapeutic agent.

In other aspect, the present invention relates to a method of treating an HBV disease in a patient, comprising administrating a therapeutically effective amount of the compound or composition thereof to a patient in need.

In other some embodiments, the method further comprises administering other anti-HBV therapeutic agent or pharmaceutical composition with a therapeutically effective amount.

In other aspect, the present invention relates to a method of inhibiting an HBV infection in a patient, comprising administrating a therapeutically effective amount of the compound or composition thereof to a patient in need. In other some embodiments, the method further comprises administrating a therapeutically effective amount of other anti-HBV therapeutic agent.

In other aspect, provided herein is a method of preparing, separating or purifying the compound of Formula (I) or Formula (Ia).

The present invention also relates to application of the compound and pharmaceutically acceptable salts thereof for effectively inhibiting HBV infection. Use of the compound disclosed herein in the manufacture of a medicament for effectively inhibiting HBV infection. The compound disclosed herein also can be used in the manufacture of a medicament for lessening, preventing, managing or treating a HBV disease in a patient.

Unless otherwise stated, all stereoisomers, geometric isomers, tautomers, N-oxides, hydrates, solvates, metabolites, salts and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The compounds disclosed herein also include salts of the compounds which are not necessarily pharmaceutically acceptable salts, and which may be useful as intermediates for preparing and/or purifying compounds of Formula (I) or (Ia), and/or for separating enantiomers of compounds of Formula (I) or (Ia).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, malic acid, 2-hydroxypropionic acid, citric acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, benzenesulfonic acid, methanesulfonic acid, ethanesulfonic acid, trifluoromethanesulfonic acid, and the like; or the combination thereof.

If the compound disclosed here in is an acid, the desired salt may be prepared by any suitable method, for example, treatment of the free acid with an inorganic or organic base, such as an amine (primary, secondary or tertiary), an alkali metal hydroxide, ammonium, $N^+(R^{14})_4$ salt or alkaline earth metal hydroxide, and the like. Some non-limiting examples of suitable salts include organic salts derived from amino acids, such as glycine and arginine; ammonia, such as primary, secondary and tertiary amine, $N^+(R^{14})_4$ salt, wherein $R^{14}$ is H, $C_{1-4}$ alkyl, $C_{6-10}$ aryl, $C_{6-10}$ aryl-$C_{1-4}$ alkyl, and the like; and cyclic amines, such as piperidine, morpholine and piperazine, and inorganic salts derived from sodium, calcium, potassium, magnesium, manganese, iron, copper, zinc, aluminum, lithium, and the like, and further include, when appropriate, nontoxic ammonium, quaternary ammonium and amine cations formed using counterions such as halide, hydroxide, carboxylate, sulfate, phosphate, nitrate, $C_{1-8}$ sulfonate or aryl sulfonate.

Pharmaceutical Composition, Formulation, Administration and Use of the Compound and Pharmaceutical Composition According to other aspect, the characteristic of the pharmaceutical composition disclosed herein is, the pharmaceutical composition comprises the compound having Formula (I) or (Ia), the compound listed in the invention, or any compound of examples, and a pharmaceutically acceptable adjuvant. The compound of the composition disclosed herein can inhibit hepatitis B virus effectively, and suitable for the treatment of diseases induced by viruses in a patient, especially acute and chronic persistent HBV infections. Chronic viral diseases induced by HBV can worsen the morbidity and the chronic HBV infection can cause liver cirrhosis and/or hepatocellular carcinogenesis in many cases.

Areas of indication which may be mentioned for the compounds of the invention are, for example: the treatment of acute and chronic viral infections which may lead to infectious hepatitis, for example infections with hepatitis B viruses. The compounds of the invention are particularly suitable for the treatment of chronic hepatitis B infections and the treatment of acute and chronic hepatitis B viral infections.

The present invention includes pharmaceutical formulation which, besides nontoxic, inert pharmaceutically suitable carriers, comprise one or more compounds of Formula (I) or (Ia) or a pharmaceutical composition thereof or which consist of one or more active ingredients of Formula (I) or (Ia) or of a pharmaceutical composition thereof.

The pharmaceutical formulations mentioned above may also comprise other active pharmaceutical ingredients apart from the compounds of Formula (I) and (Ia).

It will also be appreciated that certain of the compounds disclosed herein can exist in free form for treatment, or where appropriate, as a pharmaceutically acceptable derivative thereof. According to the invention, the pharmaceutically acceptable derivatives include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutical compositions disclosed herein comprises any one of the compound of formula (I) or (Ia), and further comprise a pharmaceutically acceptable an adjuvant, such adjuvant, which, as used herein, includes any and all solvents, solid excipients, diluents, binders, disintegrants, or other liquid excipients, dispersion, corrigents or suspension aids, surface active agents, isotonic agents, thickening or emulsifying agents, preservatives, solid binders, glidants, lubricants and the like, as suited to the particular dosage form desired. As the following described: Troy et al., Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, both of which are herein incorporated by reference in their entireties, discloses various excipients used in formulating pharmaceutically acceptable compositions and known techniques for the preparation thereof. Except insofar as any conventional adjuvant incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable adjuvants include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The pharmaceutical composition of the compound disclosed herein may be administered in any of the following routes: orally, inhaled by spray, locally, rectally, nasally, locally, vaginally, parenterally such as subcutaneous, intravenous, intramuscular, intraperitoneal, intrathecal, intraventricular, intrasternal, or intracranial injection or infusion, or administered with the aid of an explanted reservoir. Administration routes by orally, intramuscular, intraperitoneal or intravenous injection are preferred.

The compound and pharmaceutically composition thereof may be administered in a unit dosage form. The dosage form may be in a liquid form, or a solid form. The liquid form includes true solutions, colloids, particulates, suspensions. Other dosage forms include tablets, capsules, dropping pills, aerosols, pills, powders, solutions, suspensions, emulsions, granules, suppositories, freeze-dried powder injection, clathrates, implants, patches, liniments, and the like.

Oral tablets and capsules may comprise excipients, e.g., binders, such as syrup, Arabic gum, sorbitol, tragacanth or polyvinylpyrrolidone; fillers, such as lactose, sucrose, corn starch, calcium phosphate, sorbitol, glycine; lubricants such as magnesium stearate, talc, polyethylene glycol, silica; disintegrating agents, such as potato starch, or acceptable moisturizing agents such as sodium lauryl sulfate. Tablets may be coated by using known methods in pharmaceutics.

Oral solution may be made as a suspension of water and oil, a solution, an emulsion, syrup or an elixir, or made as a dried product to which water or other suitable medium is added before use. This liquid preparation may comprise conventional additives, e.g., suspending agents such sorbitol, cellulose methyl ether, glucose syrup, gel, hydroxyethyl cellulose, carboxymethyl cellulose, aluminum stearate gel, hydrogenated edible greases; emulsifying agents such as lecithin, sorbitan monoleate, Arabic gum; or non-aqueous carriers (possibly including edible oil), such as almond oil, grease such as glycerin, ethylene glycol, or ethanol; antiseptics such as methyl or propyl p-hydroxybenzoate, sorbic acid. If desired, a flavoring agent or a colorant may be added.

Suppositories may comprise a conventional suppository base, such as cocoa butter or other glyceride.

For parenteral administration, the liquid dosage form is usually made from the compound and a sterilized adjuvant. Water is the preferred adjuvant. According to the difference of selected adjuvant and drug concentration, the compound can be either dissolved in the adjuvant or made into a supernatant solution. When being made into a solution for injection, the compound is firstly dissolved in water, and then filtered and sterilized before being packaged into a sealed bottle or an ampoule.

For application topically to the skin, the compound disclosed herein may be made into a suitable form of ointments, lotions or creams, wherein the active ingredient is suspended or dissolved in one or more adjuvant(s). Wherein adjuvants used for an ointment preparation include, but are not limited to: mineral oil, liquid vaseline, white vaseline, propylene glycol, polyoxyethylene, polyoxypropylene, emulsified wax and water; adjuvants used for a lotion and a cream include, but are not limited to: mineral oil, sorbitan monostearate, Tween 60, cetyl ester wax, hexadecylene aromatic alcohol, 2-octyl dodecanol, benzyl alcohol and water.

In general, it has proved to be advantageous in either human medicine or veterinary medicine, the total administrated dose of the active compound disclosed herein is about 0.5 to −500 mg every 24 hours, preferably 1 to −100 mg/kg body weight. If appropriate, the drug is administrated in single dose for multiple times, to achieve the desired effect. The amount of the active compound in a single dose is preferably about 1 to −80 mg, more preferably 1 to −50 mg/kg body weight. Nevertheless, the dose may also be varied according to the kind and the body weight of treatment objects, the nature and the severity of diseases, the type of preparations and the method of administration of drugs, and administration period or time interval.

The pharmaceutical composition provided herein further comprises anti-HBV drugs. Wherein the other anti-HBV drug is an HBV polymerase inhibitor, immunomodulator or interferon.

The HBV agent is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, euforavac, veldona, rintatolimod, phosphazid, heplisav, interferon α-2b, levamisole, or propagermanium, and the like.

In another aspect, provided herein is a use of the compound disclosed herein or pharmaceutical compositions thereof in the manufacture of a medicament for preventing, treating or lessening HBV diseases in a patient, comprising administering a pharmaceutically acceptable effective amount to a patient. The HBV disease is a hepatic disease caused by hepatitis B virus infection or hepatitis B infection, including acute hepatitis, chronic hepatitis, cirrhosis and hepatocellular carcinoma. The symptoms of acute hepatitis B virus infection may be asymptomatic or manifested as acute hepatitis symptoms. A patient with chronic virus infection suffers an active disease, which can progress to cirrhosis and liver cancer.

Those HBV drugs may be administered separately from the composition disclosed herein as part of a multiple dosage regimen. Alternatively, those drugs may be part of a single dosage form, mixed together with the compound disclosed herein in a single composition. If administered as part of a multiple dosage regimen, the two active agents may be submitted simultaneously, sequentially or within a period of time from one another which would result in the desired activity of the agents.

The amount of both the compound and the composition (in those compositions which comprise one composition as described above) that may be combined with the adjuvant materials to produce a single dosage form will vary depending upon the host treated and the particular mode of administration Normally, the amount of the composition disclosed herein will be no more than the amount that would normally be administered in a composition comprising that therapeutic agent as the only active agent. In other embodiments, the amount of the presently disclosed compositions will range from about 50% to 100% of the amount normally present in a composition comprising that agent as the only therapeutically active agent. In those compositions which comprise an composition, that composition and the compound disclosed herein may act synergistically.

The compounds disclosed herein show a strong antiviral activity. These compounds have unexpected antiviral activity for HBV, therefore which are suitable for the treatment of various diseases caused by virus, especially for the disease caused by acute and chronic persistent HBV virus infection. Chronic viral diseases caused by HBV may lead to a variety of symptoms with different severity, as everyone knows, the chronic HBV infection may lead to liver cirrhosis and/or hepatocellular carcinoma.

Some examples of indications treated with the compounds of the invention include acute and chronic viral infections which may lead to infectious hepatitis, for example HBV infection. More preferably, chronic hepatitis B infection and acute hepatitis B virus infection.

The present invention also relates to use of the compound and composition disclosed herein in the manufacture of a medicament for treating and preventing viral diseases, especially hepatitis B.

General Synthetic Procedures

Generally, the compounds disclosed herein may be prepared by methods described herein, wherein the substituents are as defined for Formula (I) or (Ia) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua. Reagent Chemical Factory Co. Ltd., Guangzhou Re agent Chemical Factory, Tianjin YuYu Fine Chemical Ltd., Qingdao Tenglong Reagent Chemical Ltd., and Qingdao Ocean Chemical Factory.

Column chromatography was conducted using a silica gel column. Silica gel (200-300 mesh) was purchased from Qingdao Ocean Chemical Factory. 1H NMR spectra were obtained by using $CDCl_3$, $DMSO-d_6$, $CD_3OD$ or $acetone-d_6$ solutions (reported in ppm), with TMS (0 ppm) or chloroform (7.25 ppm) as the reference standard. When peak multiplicities were reported, the following abbreviations were used: s (singlet), d (doublet), t (triplet), m (multiplet), br (broadened), dd (doublet of doublets), dt (doublet of triplets), and br.s (broadened singlet). Coupling constants J, when given, were reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Low-resolution mass spectral (MS) data were also determined on an Agilent 6120 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were showed in Table 1: The gradient elution conditions were showed in Table 1:

TABLE 1

The gradient elution conditions

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
MeCN, CH₃CN acetonitrile
MTBE tert-Butyl methyl ether
MeOH methanol
MeOH-d₄ Deuterated methanol
DCM, CH₂Cl₂ dichloromethane
CHCl₃ chloroform, trichloromethane
CDCl₃ chloroform-d
CbzCl Carbobenzoxy Chloride
CBZ, Cbz carbobenzoxy
Ph₃P triphenylphosphine
LiOH.H₂O Lithium hydroxide monohydrate
LiHDMS Lithium bis(trimethylsilyl)amide
tBuXPhos 2-di-t-butylphosphino-2',4',6'-tri-propyl-1,1'-biphenyl
ILA triethylamine
TFA trifluoroacetic acid
Pd(dppf)Cl₂ [1,1'-bis(diphenylphosphino)ferrocene]dichloropalladium(11)
X—PHO S, X-Phos 2-(dicyclohexylphosphino)-2',4',6'-tri-propyl-1,1'-biphenyl
Xantphos dimethylbisdiphenylphosphinoxanthene
CCl₄ tetrachloromethane
Pd/C Palladium on activated carbon
Boc tert-butoxycarbonyl
(Boc)₂O di-tert-butyl dicarbonate
Pd₂(dba)₃ tris(dibenzylideneacetone)dipalladium
CH₃I iodomethane
SOCl₂ thionyl chloride
NaH sodium hydride
PE petroleum ether
EA, EtOAc ethyl acetate
EtOH ethyl alcohol
HCl hydrochloric acid
K₂CO₃ potassium carbonate
NaHCO₃ sodium bicarbonate
NaOH sodium hydroxide
NaCl sodium chloride
Na₂SO₄ sodium sulfate
Et₃N, ILA triethylamine
NBS N-bromosuccinimide
D₂O heavy water
H₂O water
mL, ml milliliter
RT rt room temperature
Rt retention time
1 atm 101.325 kPa
h hour, hours
H₂ hydrogen
HCl/EA, HCl/EtOAc a hydrogen chloride solution in ethyl acetate
HOAt 1-hydroxy-7-azabenzotriazole
HATU 2-(7-aza-1H-benzotriazole-1-yl)-1,1,3,3-tetramethyluronium hexafluorophosphate
DIPEA ethyldiisopropylamine
DCC dicyclohexylcarbodiimide
DMF N,N-dimethylformamide
THF tetrahydrofuran
DMSO dimethylsulfoxide
CuCN cuprous cyanide
CH₃OH methanol
N₂ nitrogen
NH₄Cl ammonium chloride
Ac₂O acetic anhydride
t₁/₂ half-life period
AUC area under the curve
Vss apparent volume of distribution
CL, clearance clearance rat
F, absolute bioavailability bioavailability
Dose dosage
T$_{max}$ time to peak
C$_{max}$ maximum concentration
hr*ng/mL blood concentration*time Synthetic Methods The following schemes list the synthetic steps of the compounds of the invention, wherein each $R^1$, $R^2$, $R^4$, $R^9$, $X^1$, m and f is as defined herein.

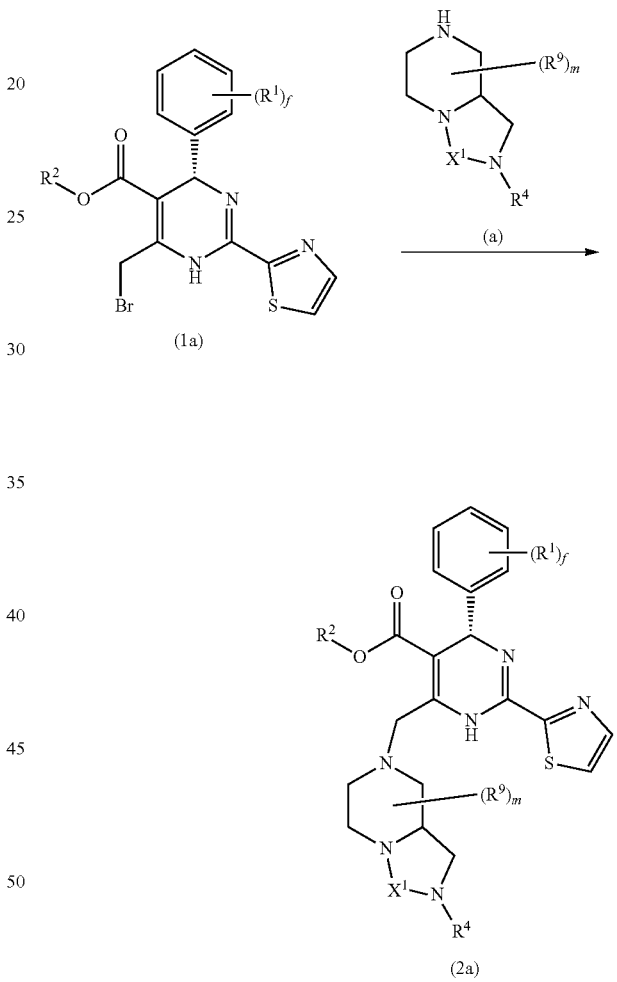

Compound (2a) can be prepared by the method as illustrated in Scheme 1, compound (1a) (compound (1a) can be prepared by methods as shown in scheme 1 of WO2015074546 and specific examples therein) and a suitable solvent (e.g. ethanol, etc) can react to get compound (2a).

EXAMPLES

The structures of the compounds prepared according to the example of the application were listed in table 2.

TABLE 2
| No. | Structure |
|---|---|
| 1 | 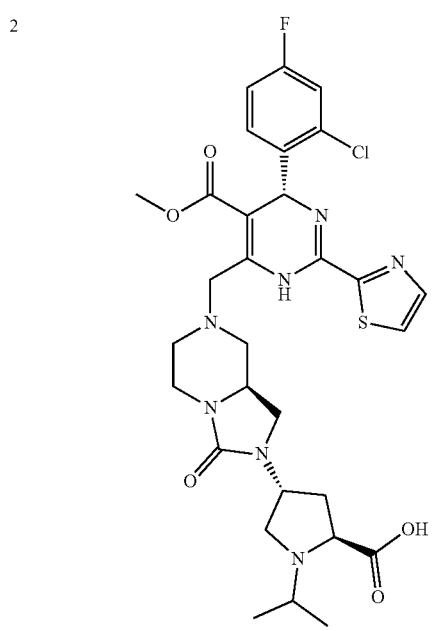 |
| 2 | 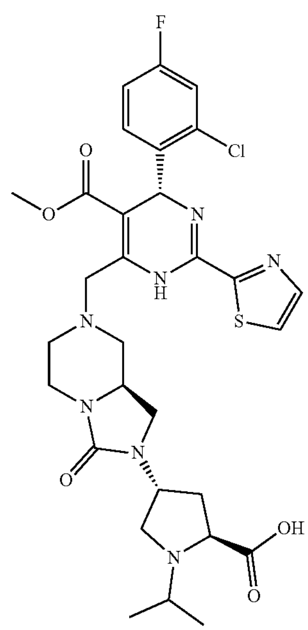 [SMILES: COC(=O)C1=C(CN2CCN3C(=O)N([C@@H]4C[C@@H](C(=O)O)N(C(C)C)C4)C[C@@H]3C2)NC(c2nccs2)=N[C@H]1c1ccc(F)cc1Cl] |
TABLE 2-continued
| No. | Structure |
|---|---|
| 3 | 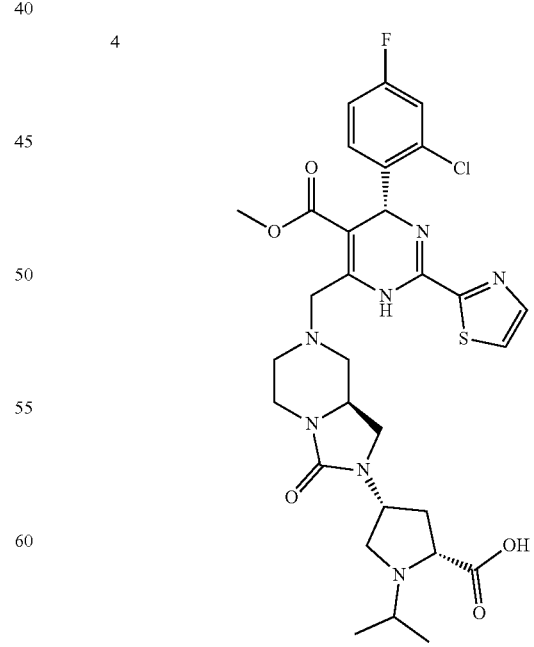 |
| 4 | 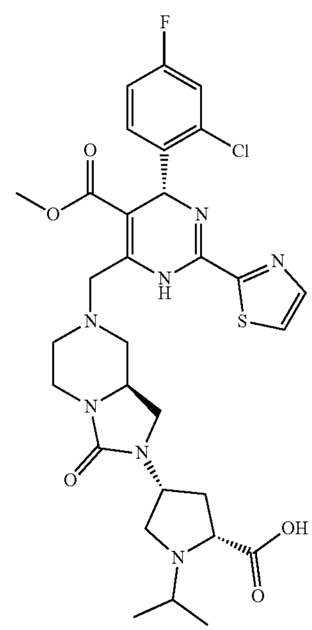 [SMILES: COC(=O)C1=C(CN2CCN3C(=O)N([C@@H]4C[C@H](C(=O)O)N(C(C)C)C4)C[C@@H]3C2)NC(c2nccs2)=N[C@H]1c1ccc(F)cc1Cl] |

TABLE 2-continued
the number of the example and structure thereof
| No. | Structure |
|---|---|
| 5 | 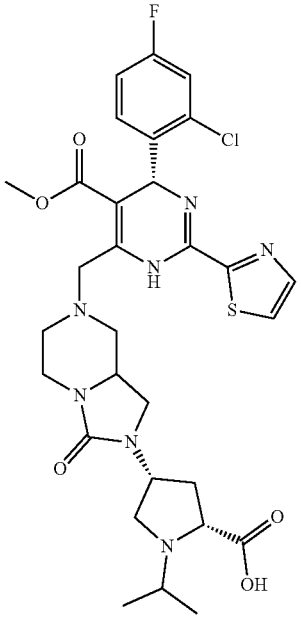 [SMILES: COC(=O)C1=C(CN2CCN3C(=O)N([C@@H]4C[C@H](C(=O)O)N(C(C)C)C4)CC3C2)NC(c2nccs2)=N[C@H]1c1ccc(F)cc1Cl] |
| 6 | 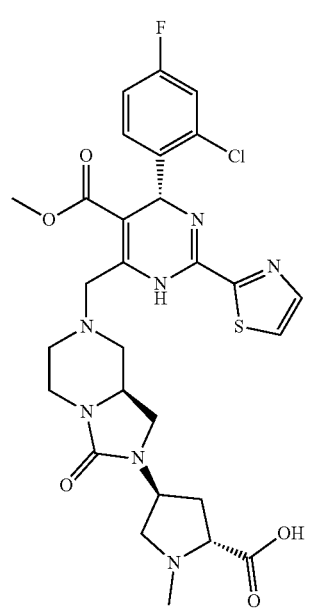 [SMILES: COC(=O)C1=C(CN2CCN3C(=O)N([C@H]4C[C@H](C(=O)O)N(C)C4)C[C@@H]3C2)NC(c2nccs2)=N[C@H]1c1ccc(F)cc1Cl] |
TABLE 2-continued
the number of the example and structure thereof
| No. | Structure |
|---|---|
| 7 | 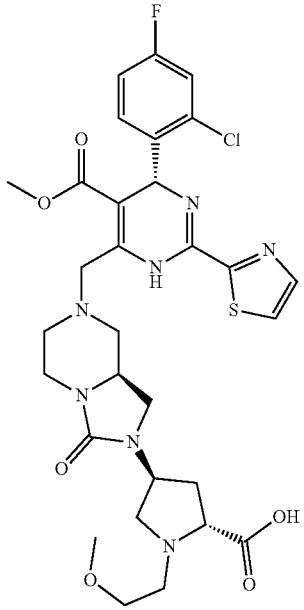 [SMILES: COCCN1C[C@@H](N2C[C@@H]3CN(CC4=C(C(=O)OC)[C@H](c5ccc(F)cc5Cl)N=C(c5nccs5)N4)CCN3C2=O)C[C@@H]1C(=O)O] |
| 8 | 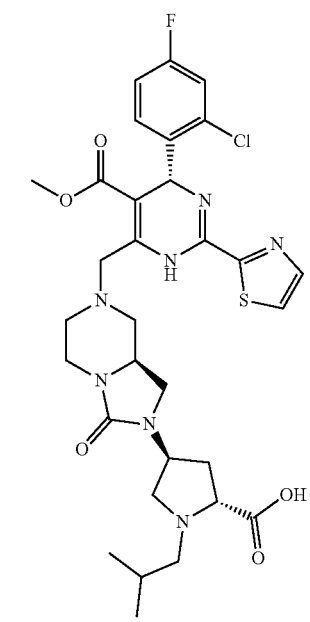 [SMILES: COC(=O)C1=C(CN2CCN3C(=O)N([C@H]4C[C@H](C(=O)O)N(CC(C)C)C4)C[C@@H]3C2)NC(c2nccs2)=N[C@H]1c1ccc(F)cc1Cl] |

TABLE 2-continued
the number of the example and structure thereof
| No. | Structure |
|---|---|
| 9 | 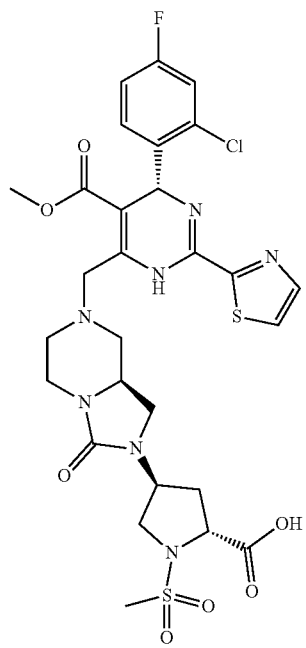 [SMILES: COC(=O)C1=C(CN2CCN3C(=O)N([C@H]4C[C@H](C(=O)O)N(S(C)(=O)=O)C4)C[C@@H]3C2)NC(c2nccs2)=N[C@H]1c1ccc(F)cc1Cl] |
| 10 | 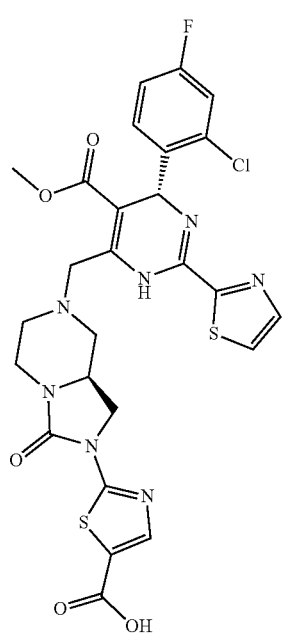 [SMILES: COC(=O)C1=C(CN2CCN3C(=O)N(c4ncc(C(=O)O)s4)C[C@@H]3C2)NC(c2nccs2)=N[C@H]1c1ccc(F)cc1Cl] |
TABLE 2-continued
the number of the example and structure thereof
| No. | Structure |
|---|---|
| 11 | 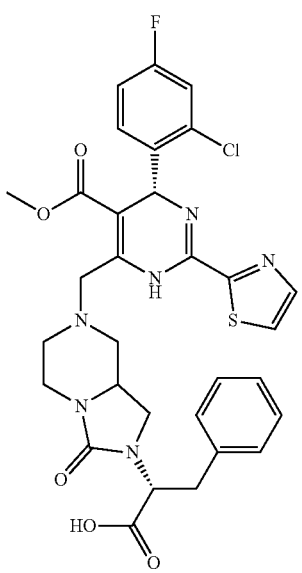 [SMILES: COC(=O)C1=C(CN2CCN3C(=O)N([C@H](Cc4ccccc4)C(=O)O)CC3C2)NC(c2nccs2)=N[C@H]1c1ccc(F)cc1Cl] |
| 12 | 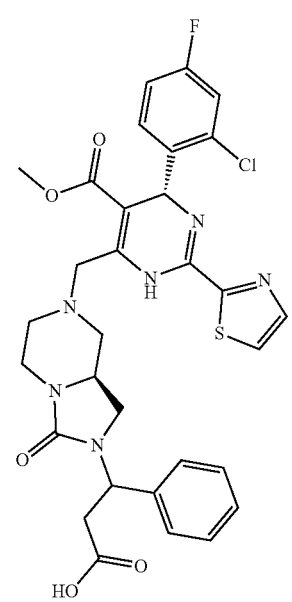 [SMILES: COC(=O)C1=C(CN2CCN3C(=O)N(C(CC(=O)O)c4ccccc4)C[C@@H]3C2)NC(c2nccs2)=N[C@H]1c1ccc(F)cc1Cl] |

TABLE 2-continued
the number of the example and structure thereof
| No. | Structure |
|---|---|
| 13 | 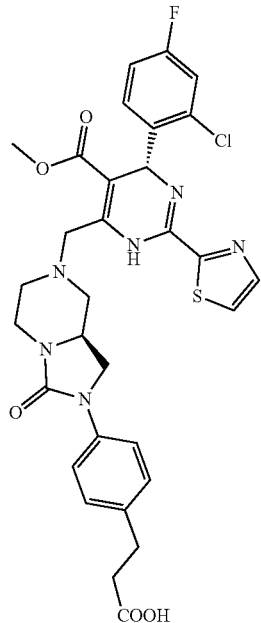 |
| 14 | 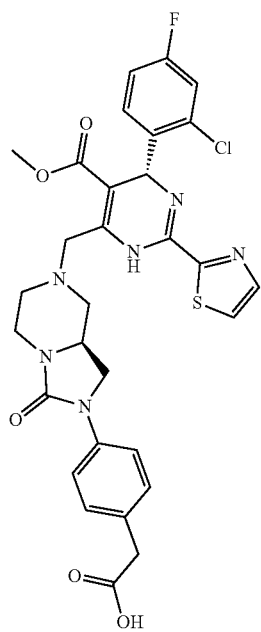 [SMILES: COC(=O)C1=C(CN2CCN3C(=O)N(c4ccc(CC(=O)O)cc4)C[C@@H]3C2)NC(c2nccs2)=N[C@H]1c1ccc(F)cc1Cl] |
| 15 | 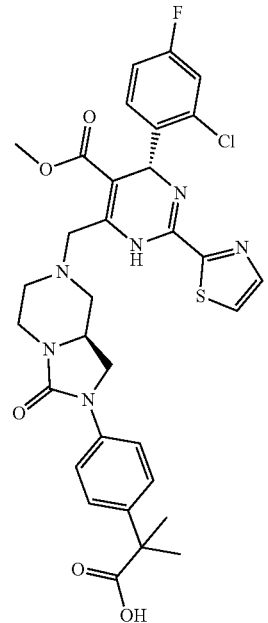 [SMILES: COC(=O)C1=C(CN2CCN3C(=O)N(c4ccc(C(C)(C)C(=O)O)cc4)C[C@@H]3C2)NC(c2nccs2)=N[C@H]1c1ccc(F)cc1Cl] |
| 16 | 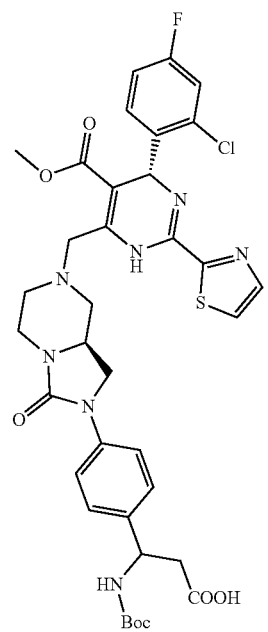 [SMILES: COC(=O)C1=C(CN2CCN3C(=O)N(c4ccc(C(CC(=O)O)NC(=O)OC(C)(C)C)cc4)C[C@@H]3C2)NC(c2nccs2)=N[C@H]1c1ccc(F)cc1Cl] |

TABLE 2-continued
the number of the example and structure thereof
| No. | Structure |
|---|---|
| 17 | 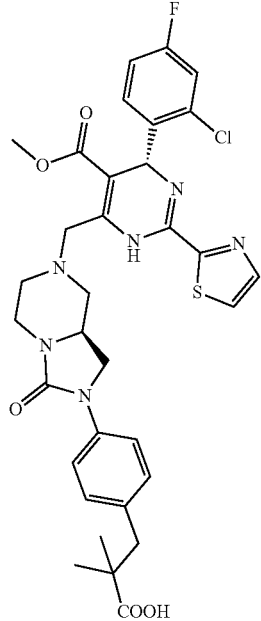 [SMILES: COC(=O)C1=C(CN2CCN3C(=O)N(c4ccc(CC(C)(C)C(=O)O)cc4)C[C@@H]3C2)NC(c2nccs2)=N[C@H]1c1ccc(F)cc1Cl] |
| 18 | 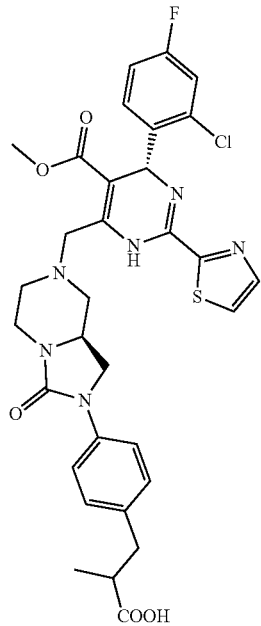 [SMILES: COC(=O)C1=C(CN2CCN3C(=O)N(c4ccc(CC(C)C(=O)O)cc4)C[C@@H]3C2)NC(c2nccs2)=N[C@H]1c1ccc(F)cc1Cl] |
TABLE 2-continued
the number of the example and structure thereof
| No. | Structure |
|---|---|
| 19 | 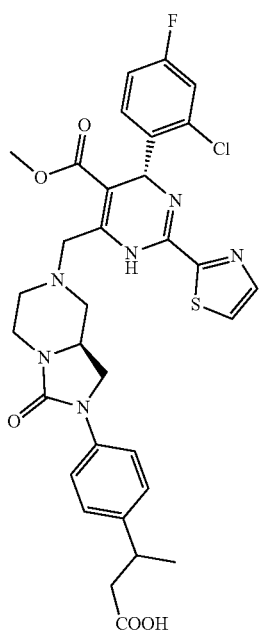 [SMILES: COC(=O)C1=C(CN2CCN3C(=O)N(c4ccc(C(C)CC(=O)O)cc4)C[C@@H]3C2)NC(c2nccs2)=N[C@H]1c1ccc(F)cc1Cl] |
| 20 | 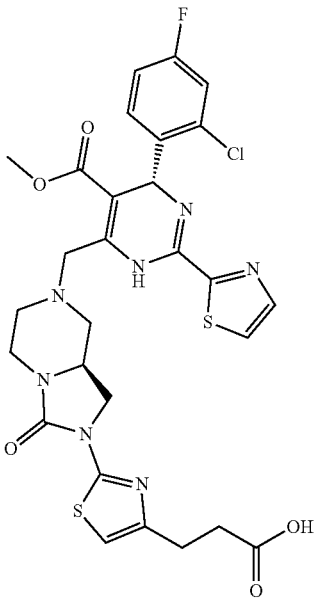 [SMILES: COC(=O)C1=C(CN2CCN3C(=O)N(c4nc(CCC(=O)O)cs4)C[C@@H]3C2)NC(c2nccs2)=N[C@H]1c1ccc(F)cc1Cl] |

TABLE 2-continued
the number of the example and structure thereof
| No. | Structure |
|---|---|
| 21 | 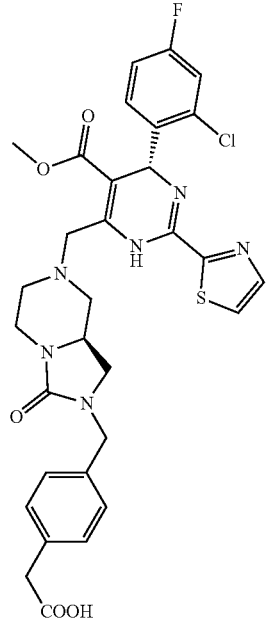 [SMILES: COC(=O)C1=C(CN2CCN3C(=O)N(Cc4ccc(CC(=O)O)cc4)C[C@@H]3C2)NC(c2nccs2)=N[C@H]1c1ccc(F)cc1Cl] |
| 22 | 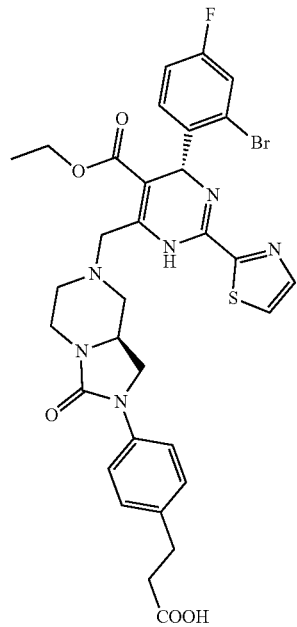 |
TABLE 2-continued
the number of the example and structure thereof
| No. | Structure |
|---|---|
| 23 | 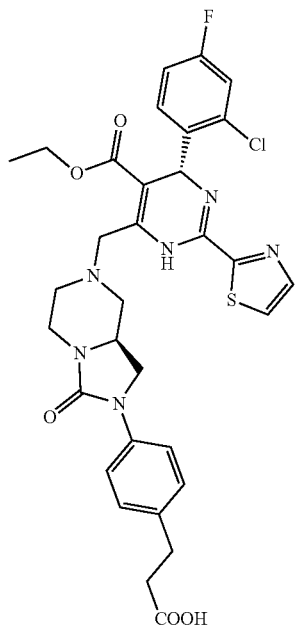 [SMILES: CCOC(=O)C1=C(CN2CCN3C(=O)N(c4ccc(CCC(=O)O)cc4)C[C@@H]3C2)NC(c2nccs2)=N[C@H]1c1ccc(F)cc1Cl] |
| 24 | 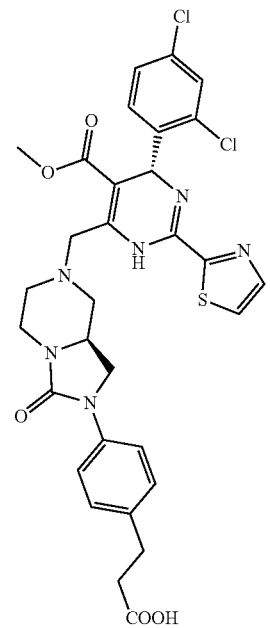 [SMILES: COC(=O)C1=C(CN2CCN3C(=O)N(c4ccc(CCC(=O)O)cc4)C[C@@H]3C2)NC(c2nccs2)=N[C@H]1c1ccc(Cl)cc1Cl] |

TABLE 2-continued
the number of the example and structure thereof
| No. | Structure |
|---|---|
| 25 | 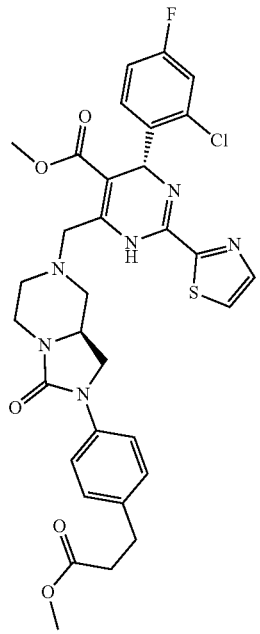 [SMILES: COC(=O)CCc1ccc(N2C[C@@H]3CN(CC4=C(C(=O)OC)[C@H](c5ccc(F)cc5Cl)N=C(c5nccs5)N4)CCN3C2=O)cc1] |
| 26 | 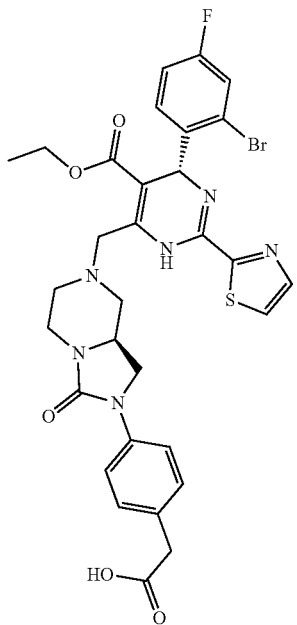 [SMILES: CCOC(=O)C1=C(CN2CCN3C(=O)N(c4ccc(CC(=O)O)cc4)C[C@@H]3C2)NC(c2nccs2)=N[C@H]1c1ccc(F)cc1Br] |
TABLE 2-continued
the number of the example and structure thereof
| No. | Structure |
|---|---|
| 27 | 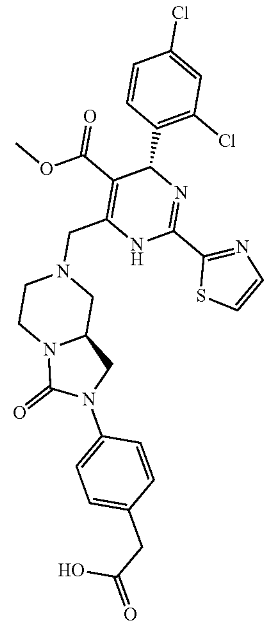 [SMILES: COC(=O)C1=C(CN2CCN3C(=O)N(c4ccc(CC(=O)O)cc4)C[C@@H]3C2)NC(c2nccs2)=N[C@H]1c1ccc(Cl)cc1Cl] |
| 28 | 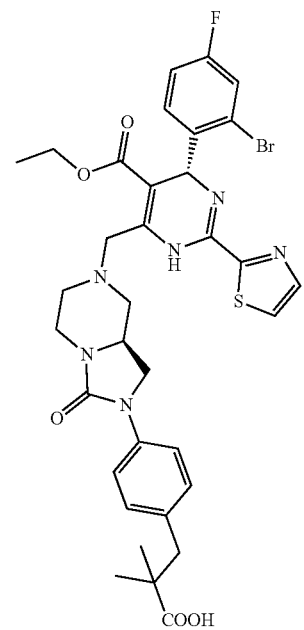 [SMILES: CCOC(=O)C1=C(CN2CCN3C(=O)N(c4ccc(CC(C)(C)C(=O)O)cc4)C[C@@H]3C2)NC(c2nccs2)=N[C@H]1c1ccc(F)cc1Br] |

TABLE 2-continued
the number of the example and structure thereof
| No. | Structure |
|---|---|
| 29 | 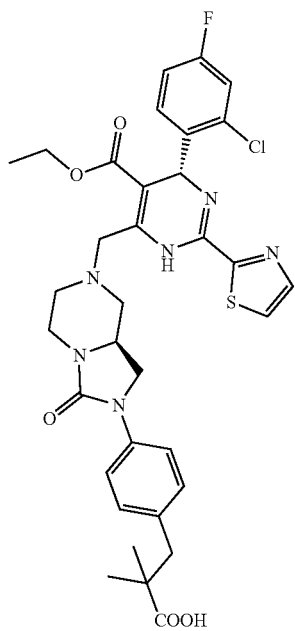 [SMILES: CCOC(=O)C1=C(CN2CCN3C(=O)N(c4ccc(CC(C)(C)C(=O)O)cc4)C[C@@H]3C2)NC(c2nccs2)=N[C@H]1c1ccc(F)cc1Cl] |
| 30 | 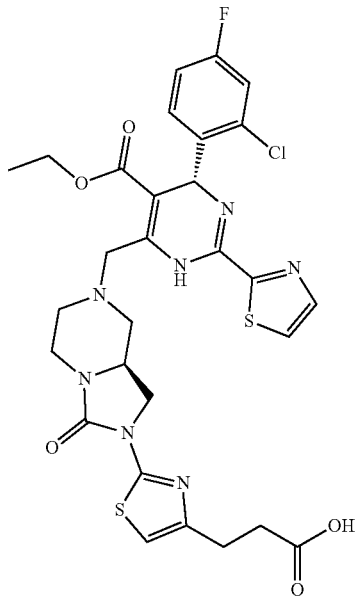 [SMILES: CCOC(=O)C1=C(CN2CCN3C(=O)N(c4nc(CCC(=O)O)cs4)C[C@@H]3C2)NC(c2nccs2)=N[C@H]1c1ccc(F)cc1Cl] |
TABLE 2-continued
the number of the example and structure thereof
| No. | Structure |
|---|---|
| 31 | 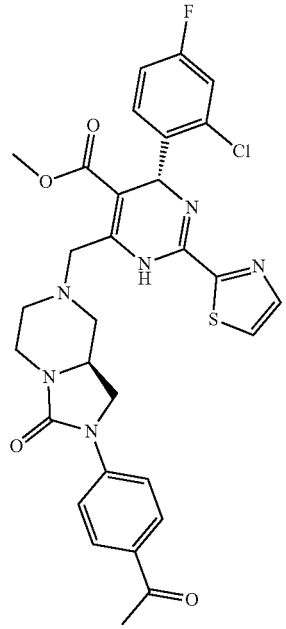 [SMILES: COC(=O)C1=C(CN2CCN3C(=O)N(c4ccc(C(C)=O)cc4)C[C@@H]3C2)NC(c2nccs2)=N[C@H]1c1ccc(F)cc1Cl] |
| 32 | 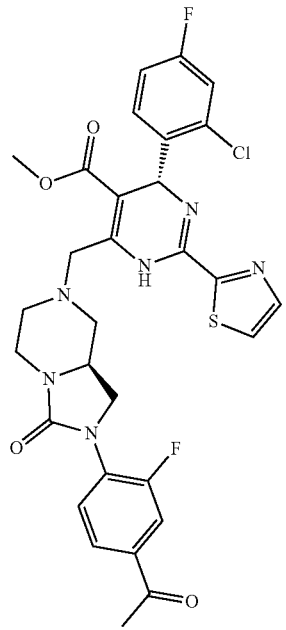 [SMILES: COC(=O)C1=C(CN2CCN3C(=O)N(c4ccc(C(C)=O)cc4F)C[C@@H]3C2)NC(c2nccs2)=N[C@H]1c1ccc(F)cc1Cl] |

TABLE 2-continued
the number of the example and structure thereof
| No. | Structure |
|---|---|
| 33 | 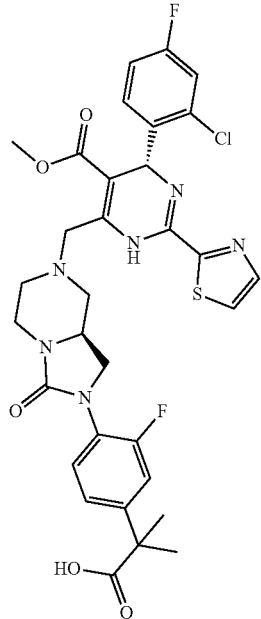 [SMILES: COC(=O)C1=C(CN2CCN3C(=O)N(c4ccc(C(C)(C)C(=O)O)cc4F)C[C@@H]3C2)NC(c2nccs2)=N[C@H]1c1ccc(F)cc1Cl] |
| 34 | 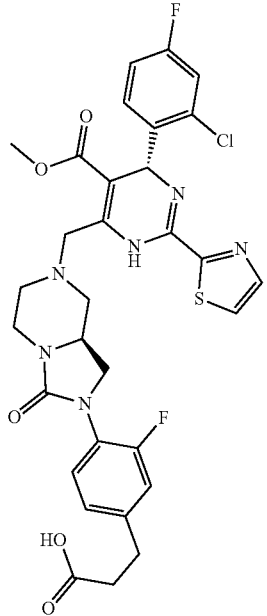 [SMILES: COC(=O)C1=C(CN2CCN3C(=O)N(c4ccc(CCC(=O)O)cc4F)C[C@@H]3C2)NC(c2nccs2)=N[C@H]1c1ccc(F)cc1Cl] |
TABLE 2-continued
the number of the example and structure thereof
| No. | Structure |
|---|---|
| 35 | |
| 36 | |

TABLE 2-continued
the number of the example and structure thereof
| No. | Structure |
|---|---|
| 37 | 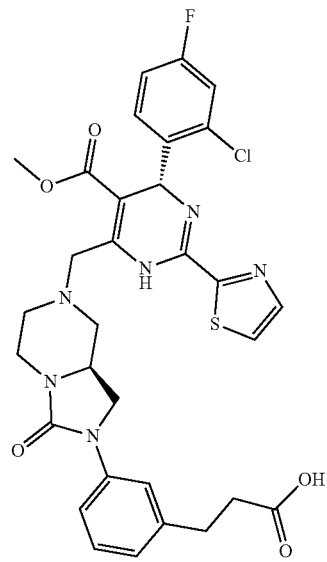 [SMILES: COC(=O)C1=C(CN2CCN3C(=O)N(c4cccc(CCC(=O)O)c4)C[C@@H]3C2)NC(c2nccs2)=N[C@H]1c1ccc(F)cc1Cl] |
| 39 | 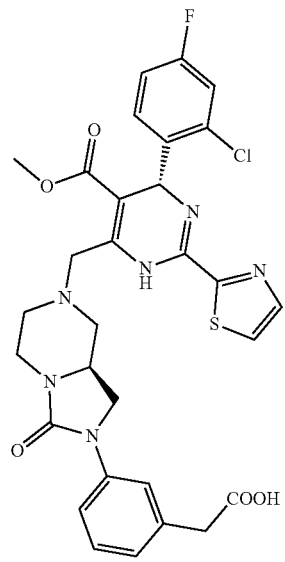 |
| 38 | 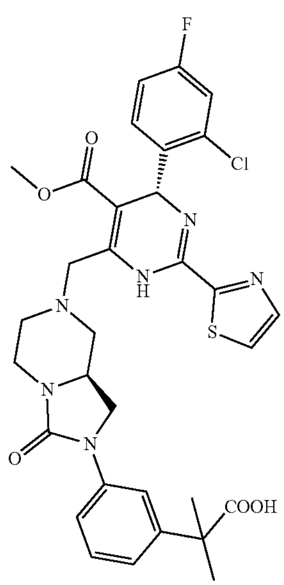 [SMILES: COC(=O)C1=C(CN2CCN3C(=O)N(c4cccc(C(C)(C)C(=O)O)c4)C[C@@H]3C2)NC(c2nccs2)=N[C@H]1c1ccc(F)cc1Cl] |
| 40 | 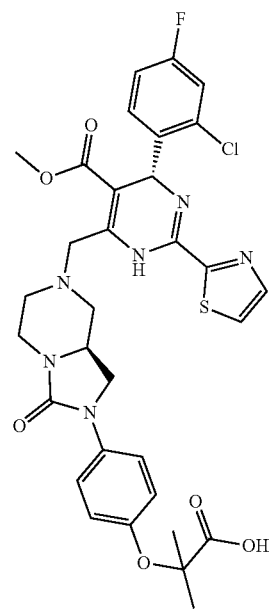 [SMILES: COC(=O)C1=C(CN2CCN3C(=O)N(c4ccc(OC(C)(C)C(=O)O)cc4)C[C@@H]3C2)NC(c2nccs2)=N[C@H]1c1ccc(F)cc1Cl] |

TABLE 2-continued
the number of the example and structure thereof
| No. | Structure |
|---|---|
| 41 | 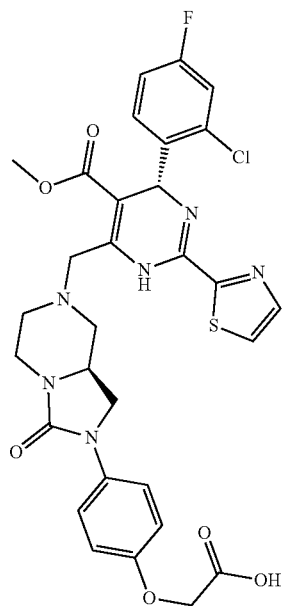 [SMILES: COC(=O)C1=C(CN2CCN3C(=O)N(c4ccc(OCC(=O)O)cc4)C[C@@H]3C2)NC(c2nccs2)=N[C@H]1c1ccc(F)cc1Cl] |
| 42 | 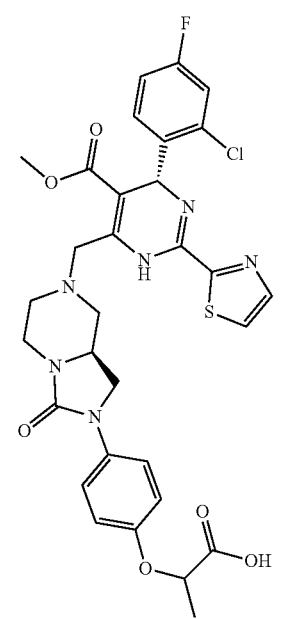 [SMILES: COC(=O)C1=C(CN2CCN3C(=O)N(c4ccc(OC(C)C(=O)O)cc4)C[C@@H]3C2)NC(c2nccs2)=N[C@H]1c1ccc(F)cc1Cl] |
TABLE 2-continued
the number of the example and structure thereof
| No. | Structure |
|---|---|
| 43 | 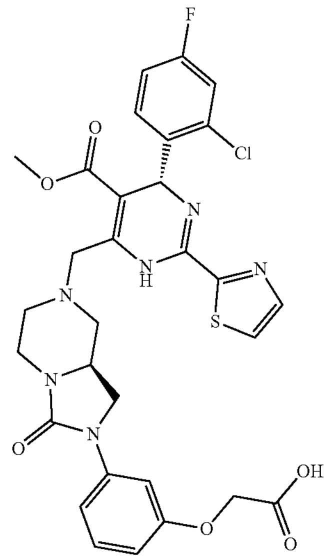 [SMILES: COC(=O)C1=C(CN2CCN3C(=O)N(c4cccc(OCC(=O)O)c4)C[C@@H]3C2)NC(c2nccs2)=N[C@H]1c1ccc(F)cc1Cl] |
| 44 | 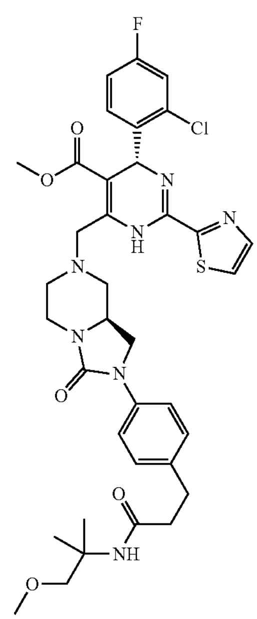 [SMILES: COCC(C)(C)NC(=O)CCc1ccc(N2C[C@@H]3CN(CC4=C(C(=O)OC)[C@H](c5ccc(F)cc5Cl)N=C(c5nccs5)N4)CCN3C2=O)cc1] |

TABLE 2-continued
the number of the example and structure thereof
| No. | Structure |
|---|---|
| 45 | 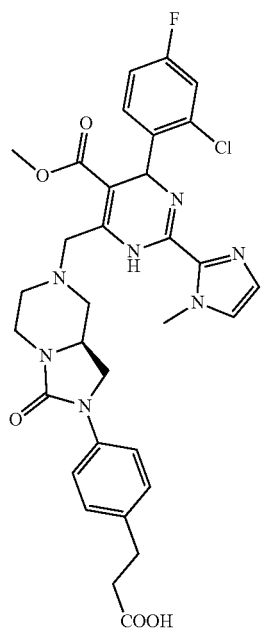 [SMILES: COC(=O)C1=C(CN2CCN3C(=O)N(c4ccc(CCC(=O)O)cc4)C[C@@H]3C2)NC(c2nccn2C)=NC1c1ccc(F)cc1Cl] |
| 46 | 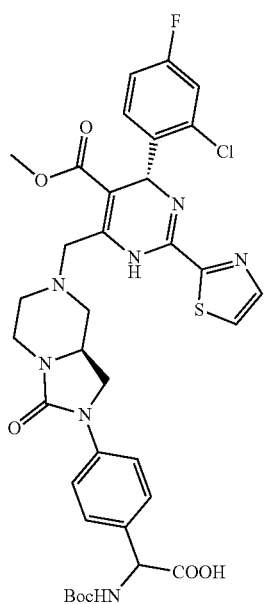 [SMILES: COC(=O)C1=C(CN2CCN3C(=O)N(c4ccc(C(NC(=O)OC(C)(C)C)C(=O)O)cc4)C[C@@H]3C2)NC(c2nccs2)=N[C@H]1c1ccc(F)cc1Cl] |
TABLE 2-continued
the number of the example and structure thereof
| No. | Structure |
|---|---|
| 47 | 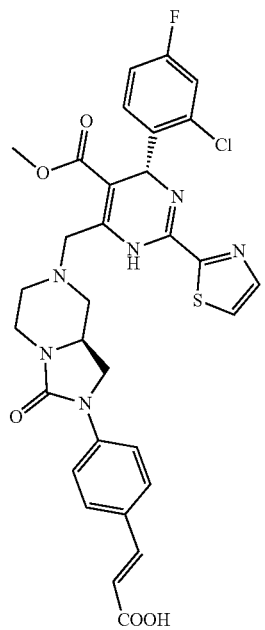 |
| 48 | 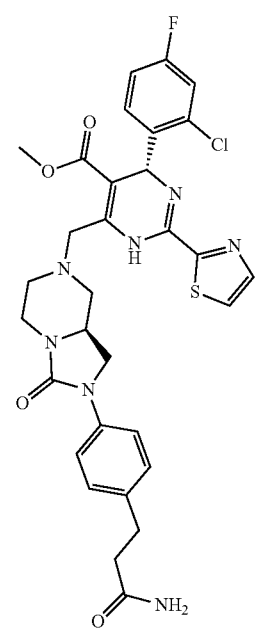 [SMILES: COC(=O)C1=C(CN2CCN3C(=O)N(c4ccc(CCC(N)=O)cc4)C[C@@H]3C2)NC(c2nccs2)=N[C@H]1c1ccc(F)cc1Cl] |

TABLE 2-continued
the number of the example and structure thereof
| No. | Structure |
|---|---|
| 49 | 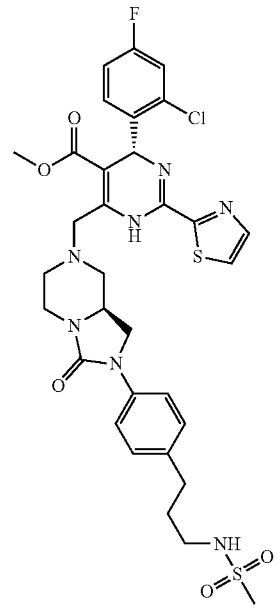 [SMILES: COC(=O)C1=C(CN2CCN3C(=O)N(c4ccc(CCCNS(C)(=O)=O)cc4)C[C@@H]3C2)NC(c2nccs2)=N[C@H]1c1ccc(F)cc1Cl] |
| 50A | 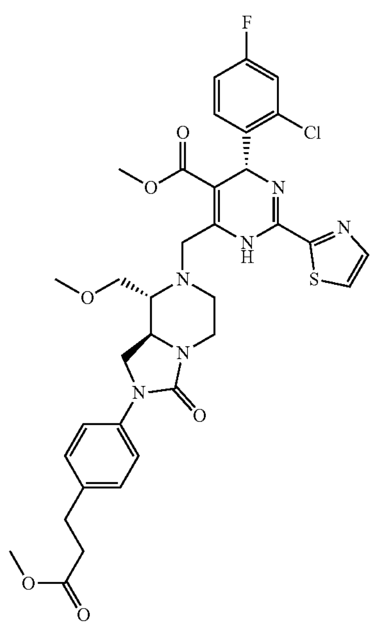 [SMILES: COC[C@H]1[C@@H]2CN(c3ccc(CCC(=O)OC)cc3)C(=O)N2CCN1CC1=C(C(=O)OC)[C@H](c2ccc(F)cc2Cl)N=C(c2nccs2)N1] |
| 50B | |
| 51A | |
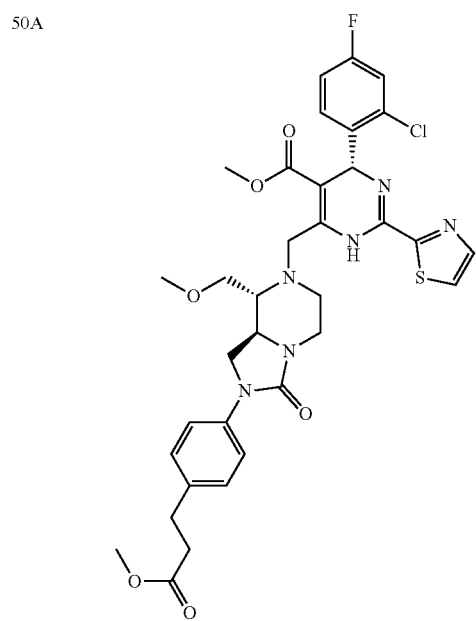
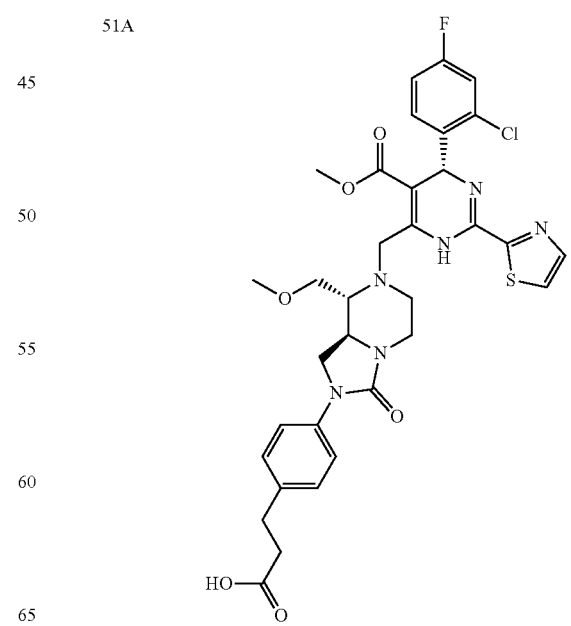

TABLE 2-continued
the number of the example and structure thereof
| No. | Structure |
|---|---|
| 51B | 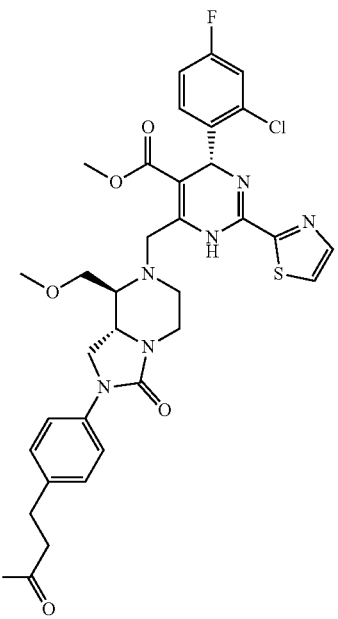 |
| 52 | 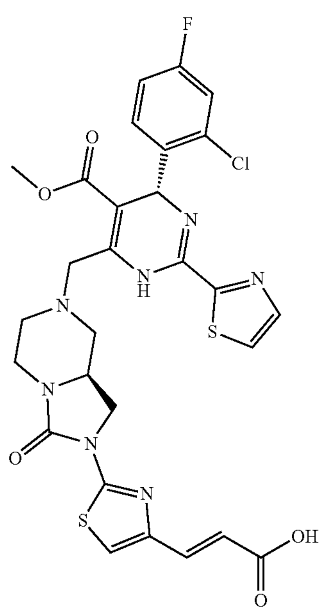 |
| 53 | |
| 54 | |

TABLE 2-continued
the number of the example and structure thereof
| No. | Structure |
|---|---|
| 55 | 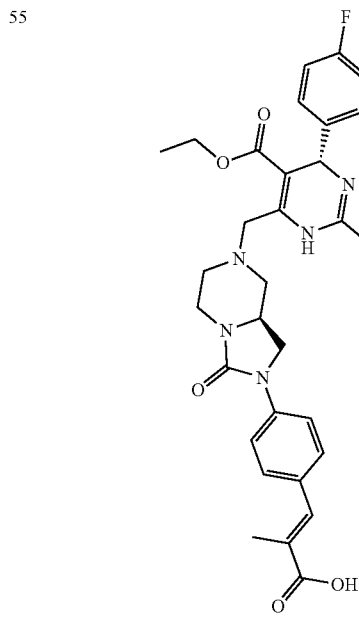 |
| 57 | 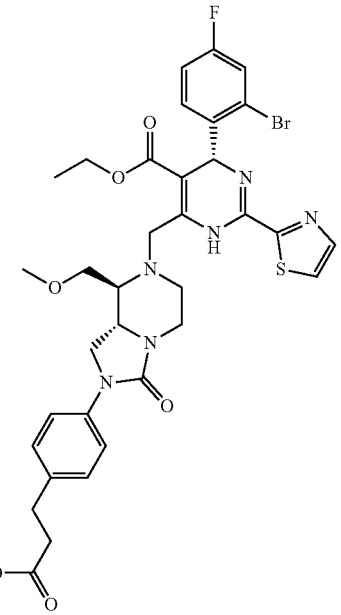 |
| 56 | 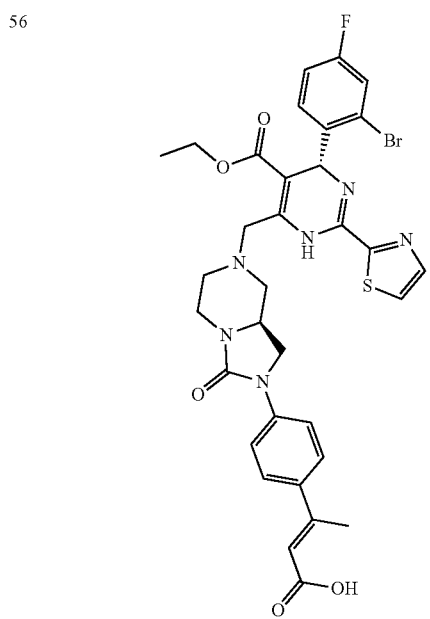 |
| 58A | 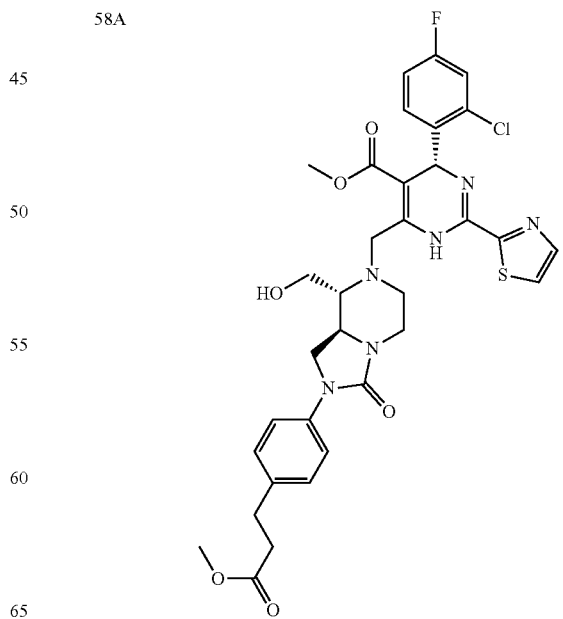 |

TABLE 2-continued
the number of the example and structure thereof
| No. | Structure |
|---|---|
| 58B | 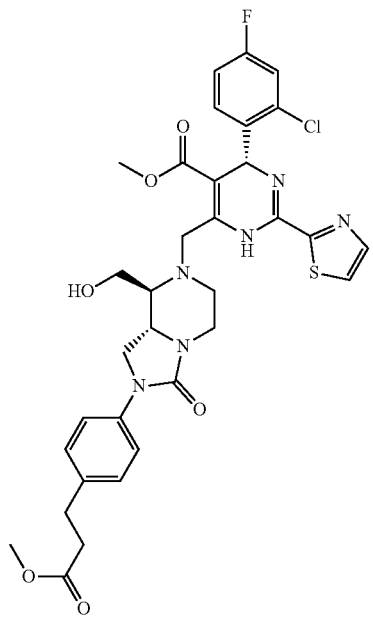 [SMILES: COC[C@@H]1[C@H]2CN(c3ccc(CCC(=O)OC)cc3)C(=O)N2CCN1CC1=C(C(=O)OC)[C@H](c2ccc(F)cc2Cl)N=C(c2nccs2)N1] |
| 59A | 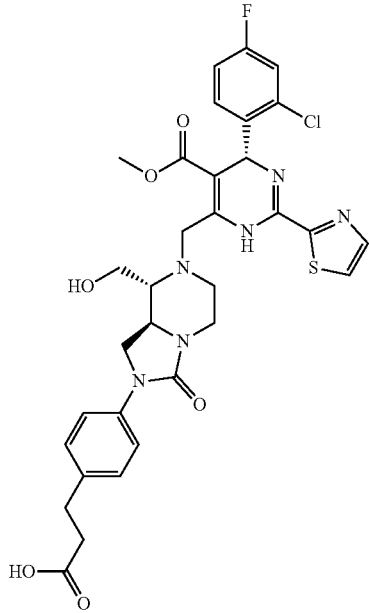 [SMILES: COC(=O)CCc1ccc(N2C[C@H]3[C@H](CO)N(CC4=C(C(=O)OC)[C@H](c5ccc(F)cc5Cl)N=C(c5nccs5)N4)CCN3C2=O)cc1] |
TABLE 2-continued
the number of the example and structure thereof
| No. | Structure |
|---|---|
| 59B | 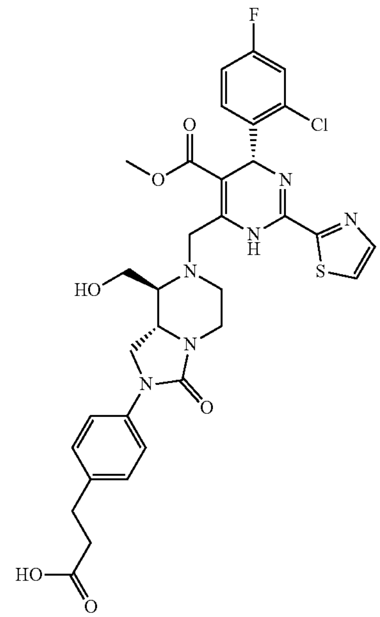 [SMILES: COC(=O)C1=C(CN2CCN3C(=O)N(c4ccc(CCC(=O)O)cc4)C[C@@H]3[C@H]2CO)NC(c2nccs2)=N[C@H]1c1ccc(F)cc1Cl] |
| 60A | 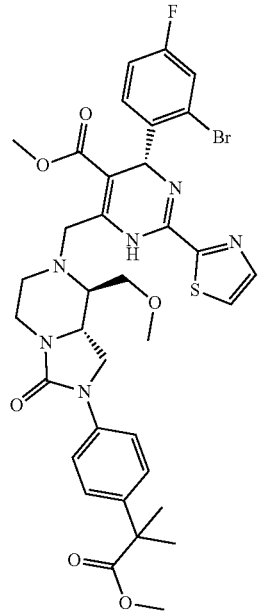 [SMILES: COC[C@H]1[C@@H]2CN(c3ccc(C(C)(C)C(=O)OC)cc3)C(=O)N2CCN1CC1=C(C(=O)OC)[C@H](c2ccc(F)cc2Br)N=C(c2nccs2)N1] |

TABLE 2-continued
the number of the example and structure thereof
| No. | Structure |
|---|---|
| 60B | 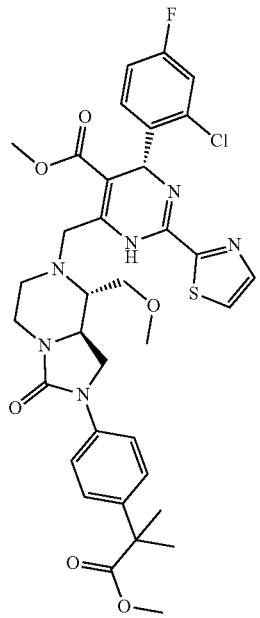 [SMILES: COC[C@@H]1[C@H]2CN(c3ccc(C(C)(C)C(=O)OC)cc3)C(=O)N2CCN1CC1=C(C(=O)OC)[C@H](c2ccc(F)cc2Cl)N=C(c2nccs2)N1] |
| 61A | 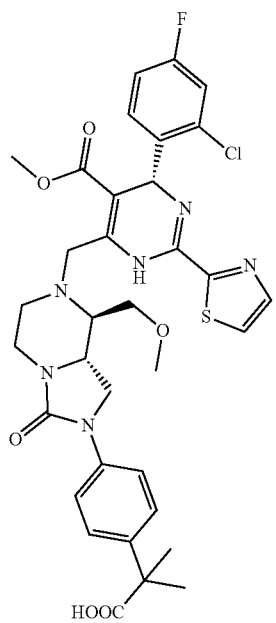 [SMILES: COC[C@H]1[C@@H]2CN(c3ccc(C(C)(C)C(=O)O)cc3)C(=O)N2CCN1CC1=C(C(=O)OC)[C@H](c2ccc(F)cc2Cl)N=C(c2nccs2)N1] |
TABLE 2-continued
the number of the example and structure thereof
| No. | Structure |
|---|---|
| 61B | 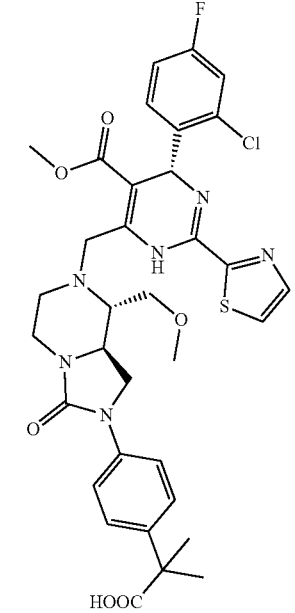 [SMILES: COC[C@@H]1[C@H]2CN(c3ccc(C(C)(C)C(=O)O)cc3)C(=O)N2CCN1CC1=C(C(=O)OC)[C@H](c2ccc(F)cc2Cl)N=C(c2nccs2)N1] |
| 62 | 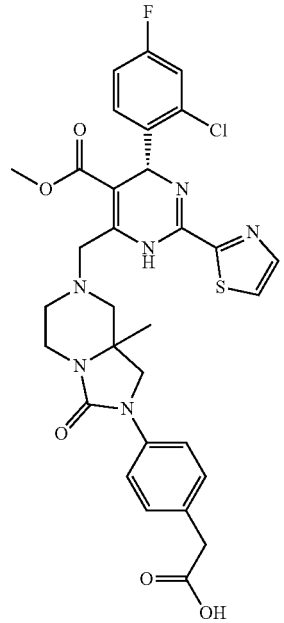 [SMILES: COC(=O)C1=C(CN2CCN3C(=O)N(c4ccc(CC(=O)O)cc4)CC3(C)C2)NC(c2nccs2)=N[C@H]1c1ccc(F)cc1Cl] |

Example 1: (2S,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydro-imidazo[1,5-a]pyrazin-2(3H)-yl)-1-isopropylpyrrolidine-2-carboxylic Acid Step 1: (2S,4R)-1-benzyl 2-methyl 4-hydroxypyrrolidine-1,2-dicarboxylate

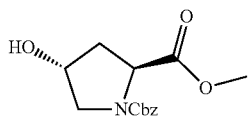 [SMILES: COC(=O)[C@@H]1C[C@@H](O)CN1C(=O)OCc1ccccc1]

A solution of (2S,4R)-methyl 4-hydroxypyrrolidine-2-carboxylate hydrochloride (5.5 g, 30 mmol) in 1,4-dioxane (17 mL) was cooled to 0° C., and then a solution of sodium carbonate (3.5 g, 33 mmol) in H₂O (17 mL) was added in portions, after that, CbzCl (4.8 mL, 34 mmol) was added over 30 min. The obtaining reaction mixture was stirred at 0° C. for 2 hours. The mixture was concentrated in vacuo to remove 1,4-dioxane, the residue was extracted with ethyl acetate (3×100 mL). The combined organic phases were dried over anhydrous sodium sulfate, filtered and the filtrate was concentrated in vacuo. The residue was purified by silica gel chromatograph (PE/EtOAc (V/V)=1/1) to give the title compound as a colorless oil (6.7 g 79%).

Step 2: (2S,4S)-1-benzyl 2-methyl 4-aminopyrrolidine-1,2-dicarboxylate

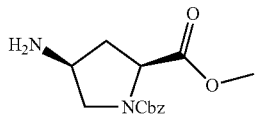 [SMILES: COC(=O)[C@@H]1C[C@H](N)CN1C(=O)OCc1ccccc1]

A solution of (2S,4R)-1-benzyl 2-methyl 4-hydroxypyrrolidine-1,2-dicarboxylate (6.7 g, 24 mmol) and DIPEA (13 mL, 74.6 mmol) in dichloromethane (67 mL) was cooled to 0° C., and then methylsulfonyl chloride (3.7 mL, 21 mmol) was added dropwise, after the addition, the mixture was stirred for 30 min and quenched with saturated sodium bicarbonate solution (100 mL), the organic layer separated from the obtained mixture was washed with saturated sodium chloride solution, and dried over anhydrous sodium sulfate, filtered and the filtrate was concentrated in vacuo.

The above concentrate was dissolved in DMF (18 mL), and sodium azide (7.8 g, 120 mmol) was added. The reaction mixture was heated to 85° C. and stirred overnight. And then, to the reaction mixture was added water (100 mL), the resulting mixture was extracted with ethyl acetate (100 mL). The organic layer was washed with saturated sodium chloride solution twice and dried over anhydrous sodium sulfate, filtered and the filtrate was concentrated in vacuo.

The second concentrate above was dissolved in THF (20 mL), to the solution was added a solution of Ph₃P (13 g, 49.6 mmol) in THF (40 mL) at room temperature. After the addition, the reaction mixture was stirred at rt for 1 hour, and then H₂O (0.9 g, 48 mmol) was added, the resulting mixture was refluxed and stirred for 4 hours. The reaction mixture was concentrated in vacuo, the residue was diluted with ethyl acetate (100 mL) and water (100 mL). The resulting mixture was adjusted with hydrochloric acid (1 M) to pH 4, and stood to separate into layers. The water phase was adjusted with saturated aqueous sodium bicarbonate solution to pH 8, and extracted with ethyl acetate (3×100 mL). The combined organic layers was dried over anhydrous sodium sulfate and filtered, the filtrate was concentrated in vacuo to get the title compound as a colorless oil (4.5 g, 67%). MS (ESI, pos.ion) m/z: 279.2 [M+H]⁺.

Step 3: (S)-di-tert-butyl 2-(((((3S,5S)-1-((benzyloxy)carbonyl)-5-(methoxycarbonyl)pyrrolidin-3-yl)amino)methyl)piperazine-1,4-dicarboxylate

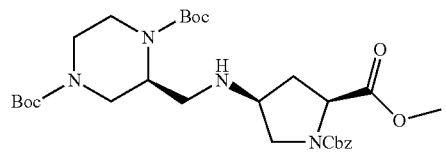 [SMILES: COC(=O)[C@@H]1C[C@H](NC[C@H]2CN(C(=O)OC(C)(C)C)CCN2C(=O)OC(C)(C)C)CN1C(=O)OCc1ccccc1]

To a solution of (2S)-di-tert-butyl 2-formylpiperazine-1,4-dicarboxylate (3 g, 9.5 mmol) and (2S,4S)-1-benzyl 2-methyl 4-aminopyrrolidine-1,2-dicarboxylate (2.6 g, 9.3 mmol) in method (16 mL) was added acetic acid (0.16 mL, 2.8 mmol) at rt, the mixture was stirred for 1 hour and cooled to 0° C., then sodium cyanoborohydride (3 g, 47.0 mmol) was added. After the addition, the mixture was warmed to room temperature and stirred for 2 hours. The reaction was quenched with saturated aqueous sodium bicarbonate solution (100 mL), the resulting mixture was extracted with ethyl acetate (100 mL). The organic layer was concentrated in vacuo. The residue was purified by silica gel column chromatography (PE/EtOAc (v/v)=1/1) to give the title compound as a colorless oil (4.78 g, 78%). MS (ESI, pos.ion) m/z: 577.3 [M+H]⁺.

Step 4: (S)-di-tert-butyl 2-(((((3S,5S)-1-((benzyloxy)carbonyl)-5-(methoxycarbonyl)pyrrolidin-3-yl)((4-nitrophenoxy)carbonyl)amino)methyl)piperazine-1,4-dicarboxylate

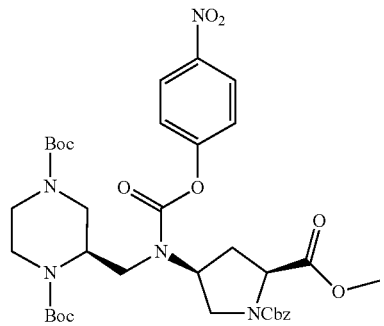 [SMILES: COC(=O)[C@@H]1C[C@H](N(C[C@@H]2CN(C(=O)OC(C)(C)C)CCN2C(=O)OC(C)(C)C)C(=O)Oc2ccc([N+](=O)[O-])cc2)CN1C(=O)OCc1ccccc1]

To a solution of (S)-di-tert-butyl 2-(((((3S,5S)-1-((benzyloxy)carbonyl)-5-(methoxycarbonyl)pyrrolidin-3-yl)amino)methyl)piperazine-1,4-dicarboxylate (4.78 g, 8.29 mmol) and DIPEA (4.3 mL, 25 mmol) in DCM (26 mL) was added p-nitrophenyl chloroformate (3.34 g, 16.6 mmol), the mixture was stirred at rt until the raw materials were consumed. The reaction was quenched with hydrochloric acid (1 M, 50 mL), the resulting mixture was extracted with DCM (3×50 mL). The combined organic layers were concentrated in vacuo. The residue was purified by silica gel column chromatography (PE/EtOAc (v/v)=1/1) to give the title compound as a white foam (4.3 g, 90%). MS (ESI, pos.ion) m/z: 764.3 [M+Na]⁺.

Step 5: (2S,4S)-1-benzyl 2-methyl 4-((R)-7-(tert-butoxycarbonyl)-3-oxohexahydroimidazo[1,5-a]pyrazin-2 (3H)-yl)pyrrolidine-1,2-dicarboxylate

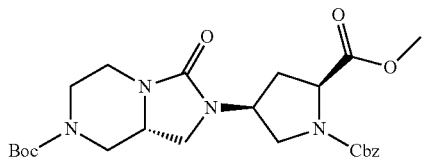 [SMILES: COC(=O)[C@@H]1C[C@H](N2C[C@@H]3CN(C(=O)OC(C)(C)C)CCN3C2=O)CN1C(=O)OCc1ccccc1]

To a solution of (S)-di-tert-butyl 2-((((3S,5S)-1-((benzyloxy)carbonyl)-5-(methoxycarbonyl)pyrrolidin-3-yl)((4-nitrophenoxy)carbonyl)amino)methyl)piperazine-1,4-dicarboxylate (4.3 g, 5.8 mmol) in DCM (6 mL) was added TFA (18 mL) at room temperature, the mixture was stirred at room temperature until the reaction was completed and concentrated in vacuo.

The above concentrate was dissolved in DCM (40 mL), and DIPEA (5.1 mL, 29 mmol) was added to the solution, the resulting solution was heated and refluxed for 4 hours. The reaction mixture was cooled to room temperature, and (Boc)₂O (2.6 g 29 mmol) was added, and then stirred at rt. After the reaction was completed, the reaction was quenched with hydrochloric acid (1 M, 50 mL), the resulting mixture was extracted with DCM (3×50 mL). The combined organic layers were washed with saturated sodium chloride solution and concentrated in vacuo. The residue was purified by silica gel column chromatography (PE/EtOAc (v/v)=1/1) to give the title compound as a white solid (2.64 g, 90%). MS (ESI, pos.ion) m/z: 525.25 [M+Na]⁺.

Step 6: (R)-tert-butyl 2-((3 S,5 S)-5-(methoxycarbonyl)pyrrolidin-3-yl)-3-oxohexahydroimidazo[1,5-a]pyrazine-7(1H)-carboxylate

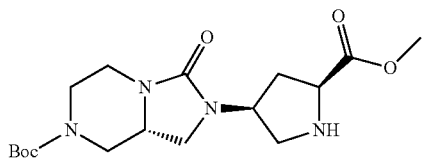 [SMILES: COC(=O)[C@@H]1C[C@H](N2C[C@@H]3CN(C(=O)OC(C)(C)C)CCN3C2=O)CN1]

To a solution of (2S,4S)-1-benzyl 2-methyl 4-((R)-7-(tert-butoxycarbonyl)-3-oxohexahydroimidazo[1,5-a]pyrazin-2 (3H)-yl)pyrrolidine-1,2-dicarboxylate (2.6 g 5.2 mmol) in method (40 mL) was added Pd/C (1.1 g, 1.0 mmol), the mixture was degassed and filled with H₂ three time. The mixture was stirred under 1 atm H₂ at room temperature until the raw materials were consumed. The mixture was filtered through Celite pad. The filtrate was concentrated in vacuo to get the title compound as a colorless oil (1.9 g, 99%).

Step 7: (R)-tert-butyl 2-((3 S,5 S)-1-isopropyl-5-(methoxycarbonyl)pyrrolidin-3-yl)-3-oxohexahydroimidazo[1,5-a]pyrazine-7(1H)-carboxylate

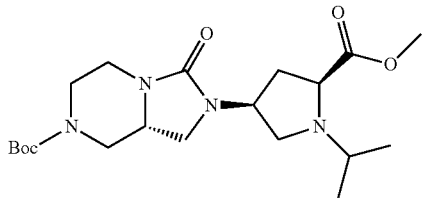 [SMILES: COC(=O)[C@@H]1C[C@H](N2C[C@@H]3CN(C(=O)OC(C)(C)C)CCN3C2=O)CN1C(C)C]

A solution of (R)-tert-butyl 2-((3S,5S)-5-(methoxycarbonyl)pyrrolidin-3-yl)-3-oxohexahydroimidazo[1,5-a]pyrazine-7(1H)-carboxylate (1.9 g 5.2 mmol), K₂CO₃ (1.4 g 10 mmol) and DMF (9 mL) in isopropyl iodide (1.8 g 11 mmol) was heated to 80° C. and stirred overnight. The reaction mixture was diluted with water (100 mL), and extracted with ethyl acetate (100 mL). The resulting mixture was adjusted with hydrochloric acid (1 M, 20 mL), and stood to separate into layers. The organic layer was discarded. The water phase was adjusted with saturated aqueous sodium bicarbonate solution to pH 8, and extracted with ethyl acetate (3×50 mL). The combined organic layers was dried over anhydrous sodium sulfate and filtered, the filtrate was concentrated in vacuo to get the title compound as a colorless oil (1.35 g 40%). MS (ESI, pos.ion) m/z: 411.4[M+H]⁺.

Step 8: (2S,4S)-methyl 1-isopropyl-4-((S)-3-oxohexahydroimidazo[1,5-a]pyrazin-2(3H)-) pyrrolidine-2-carboxylate hydrochloride

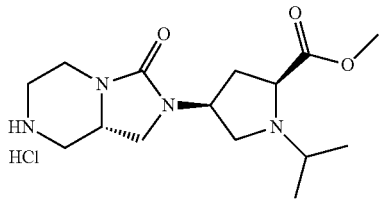 [SMILES: Cl ; COC(=O)[C@@H]1C[C@H](N2C[C@@H]3CNCCN3C2=O)CN1C(C)C]

(R)-tert-Butyl 2-((3S,5S)-1-isopropyl-5-(methoxycarbonyl)pyrrolidin-3-yl)-3-oxohexahydroimidazo[1,5-a]pyrazine-7(1H)-carboxylate (1.35 g 3.29 mmol) was added into a solution of hydrogen chloride in isopropanol (5 mL, 4 mol/L), the mixture was stirred at rt. After the reaction was completed, the mixture was concentrated in vacuo to get the title compound as a white solid (1.1 g 3.3 mmol). MS (ESI, pos.ion) m/z: 311.5 [M+H]⁺.

Step 9: (R)-methyl 4-(2-chloro-4-fluorophenyl)-6-(((S)-2-((3S,5S)-1-isopropyl-5-(methoxycarbonyl)pyrrolidin-3-yl)-3-oxohexahydroimidazo[1,5-a]pyrazin-7(1H)-yl)methyl)-2-(thiazol-2-yl)-1,4-dihydropyrimidine-5-carboxylate

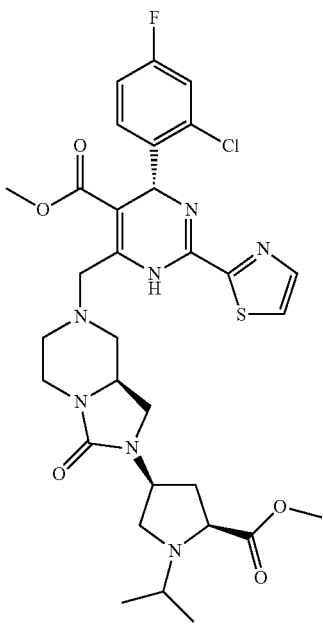

To a 25 mL single flask were added (R)-methyl 6-(bromomethyl)-4-(2-chloro-4-fluorophenyl)-2-(thiazol-2-yl)-1,4-dihydropyrimidine-5-carboxylate (1.56 g 3.5 mmol)(prepared by reference scheme 7 and examples of WO2015144093), (2S,4S)-methyl 1-isopropyl-4-((S)-3-oxohexahydroimidazo[1,5-a]pyrazin-2(3H)-)pyrrolidine-2-carboxylate hydrochloride (1.1 g 3.18 mmol), $K_2CO_3$ (2.3 g, 16.4 mmol) and ethanol (15 mL) in turn, the reaction mixture was stirred at rt for 12 hours and filtered, the filtrate was concentrated in vacuo.

The residue was purified by silica gel column chromatography (DCM/$CH_3OH$ (V/V)=30/1) to give the title compound as a pale yellow solid (1.35 g, 63%).

Step 10: (2S,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-isopropylpyrrolidine-2-carboxylic Acid To a 25 mL single flask were added (R)-methyl 4-(2-chloro-4-fluorophenyl)-6-(((S)-2-((3S,5S)-1-isopropyl-5-(methoxycarbonyl)pyrrolidin-3-yl)-3-oxohexahydroimidazo[1,5-a]pyrazin-7(1H)-yl)methyl)-2-(thiazol-2-yl)-1,4-dihydropyrimidine-5-carboxylate (450 mg, 0.67 mmol), lithium hydroxide monohydrate (56 mg, 1.33 mmol), methanol (4 mL) and water (1.3 mL) in turn, the reaction mixture was stirred at rt for 8 hours and concentrated. The residue was purified by silica gel column chromatography (PE/EtOAc (V/V)=50/1) to give the title compound as a yellow solid (100 mg, 23%). MS (ESI, pos.ion) m/z: 660.2[M+H]$^+$; $^1$H NMR (400 MHz, $CDCl_3$) δ 9.59 (s, 1H), 7.85 (s, 1H), 7.46 (d, J=2.4 Hz, 1H), 7.34-7.25 (m, 1H), 7.14 (d, J=8.0 Hz, 1H), 6.99-6.90 (m, 1H), 6.20 (s, 1H), 4.52-4.42 (m, 1H), 4.13-3.67 (m, 9H), 3.61 (s, 3H), 3.41 (t, J=8.5 Hz, 1H), 3.33-3.09 (m, 2H), 2.78 (d, J=10.6 Hz, 1H), 2.50-2.36 (m, 2H), 2.35-2.18 (m, 2H), 1.46-1.25 (m, 6H).

Example 2: (2S,4R)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydro-imidazo[1,5-a]pyrazin-2(3H)-yl)-1-iso propylpyrrolidine-2-carboxylic Acid Step 1: (2S,4S)-methyl 4-hydroxypyrrolidine-2-carboxylate hydrochloride

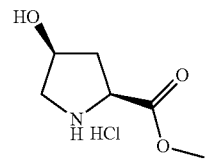

(2S,4S)-4-Hydroxypyrrolidine-2-carboxylic acid hydrochloride (6.36 g, 38.1 mmol) was dissolved in methanol (50 mL), to the solution was added thionyl chloride (3.76 mL, 45.7 mmol) dropwise slowly under an ice-bath. The reaction mixture was further stirred for 30 min, and then warmed to rt and stirred until the reaction was completed. The mixture was concentrated to get the tile compound as a white solid (6.8 g 98%). MS (ESI, pos.ion) m/z: 146.2 [M+H]$^+$.

Step 2: (2S,4S)-methyl 4-hydroxy-1-isopropylpyrrolidine-2-carboxylate

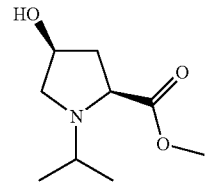

To a mixture of (2S,4S)-methyl 4-hydroxypyrrolidine-2-carboxylate hydrochloride (5.3 g 29 mmol) and potassium carbonate (12 g 86.8 mmol) in N,N-dimethylformamide (60 mL) was added 2-iodopropane (3.5 mL, 35 mmol), the mixture was stirred at 85° C. until the reaction was completed. The mixture was cooled to rt and diluted with water (100 mL), the resulting mixture was extracted with dichloromethane (50 mL×4). The organic layers were combined. The combined organic layers were washed with water (100 mL×3) and saturated brine (100 mL), dried over anhydrous sodium sulfate, filtered, and concentrated under vacuum to give the title compound as a colorless oil (4.1 g 75%). MS (ESI, pos.ion) m/z: 188.2 [M+H]$^+$.

Step 3: (2S,4R)-methyl 4-amino-1-isopropylpyrrolidine-2-carboxylate

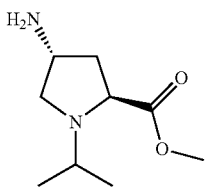

To a solution of (2S,4S)-methyl 4-hydroxy-1-isopropylpyrrolidine-2-carboxylate (4 g 21.4 mmol) and triethylamine (6.0 mL, 42.8 mmol) in dichloromethane (40 mL) was added methylsufonyl chloride (2.8 g 23.5 mmol) under an ice bath, the mixture was stirred until the reaction was completed. The mixture was diluted with water (40 mL), the resulting mixture was extracted with dichloromethane (40 mL×3). The organic layers were combined. The combined organic layers were washed with saturated brine (100 mL), dried over anhydrous sodium sulfate, filtered, and concentrated under vacuum.

To the above concentrate were added N,N-dimethylformamide (40 mL) and sodium azide (1.8 g 27 mmol), the reaction mixture was heated to 85° C. and stirred until the reaction was completed. After the reaction was completed, the mixture was concentrated in vacuo.

The above residue was added to methanol (15 mL), and then Pd/C (526 mg 0.5 mmol, wt. % is 10%) was added. The resulting mixture was degassed and filled with $H_2$ three times, and then the mixture was stirred at rt under 1 atm $H_2$. After the reaction was completed, the mixture was filtered. The filtrate was concentrated in vacuo to get the title compound as a colorless oil (0.71 g 18%). MS (ESI, pos.ion) m/z: 187.2 $[M+H]^+$.

Step 4: (R)-di-tert-butyl 2-((((3R,5S)-1-isopropyl-5-(methoxycarbonyl)pyrrolidin-3-yl)amino)methyl) piperazine-1,4-dicarboxylate

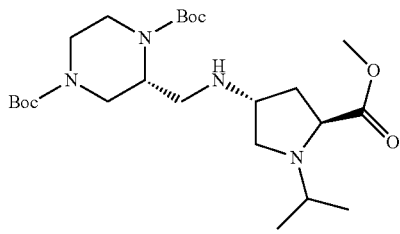 [SMILES: COC(=O)[C@@H]1C[C@@H](NC[C@@H]2CN(C(=O)OC(C)(C)C)CCN2C(=O)OC(C)(C)C)CN1C(C)C]

To a solution of (2S,4R)-methyl 4-amino-1-isopropylpyrrolidine-2-carboxylate (0.71 g 3.8 mmol) and (S)-di-tert-butyl 2-formylpiperazine-1,4-dicarboxylate (1.2 g 3.8 mmol) in methanol (10 mL) was added two drops of acetic acid at rt, the mixture was stirred for 1 hour. After that, sodium cyanoborohydride (0.5 g 8 mmol) was added, the mixture further stirred at rt monitored by TLC until the reaction was completed. The most of solvent was removed by vacuum distillation, then added water (20 mL), the resulting mixture was extracted with ethyl acetate (20 mL×3), the combined organic layers were washed with saturated aqueous NaCl (60 mL) and dried over anhydrous sodium sulfate, and then concentrated in vacuo. The residue was purified by silica gel column chromatography (EtOAc) to give the title compound as a colorless (0.94 g 51%). MS (ESI, pos.ion) m/z: 485.4 $[M+H]^+$.

Step 5: (S)-di-tert-butyl 2-((((3R,5S)-1-isopropyl-5-(methoxycarbonyl)pyrrolidin-3-yl) ((4-nitrophenoxy)carbonyl)amino)methyl)piperazine-1,4-dicarboxylate

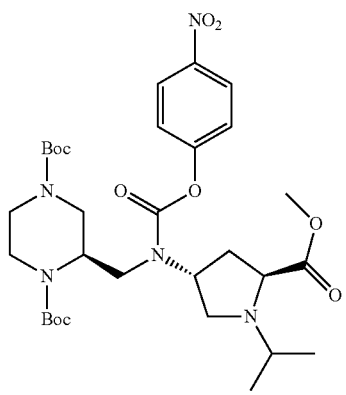 [SMILES: COC(=O)[C@@H]1C[C@@H](N(C[C@@H]2CN(C(=O)OC(C)(C)C)CCN2C(=O)OC(C)(C)C)C(=O)Oc2ccc([N+](=O)[O-])cc2)CN1C(C)C]

To a solution of (R)-di-tert-butyl 2-((((3R,5S)-1-isopropyl-5-(methoxycarbonyl) pyrrolidin-3-yl)amino)methyl) piperazine-1,4-dicarboxylate (0.95 g 2.0 mmol) and DIPEA (0.76 g 5.9 mmol) in dichloromethane (20 mL) was added 4-nitrophenyl chloroformate (0.79 g 3.9 mmol) slowly under an ice bath, the mixture was warmed to 40° C. and stirred. The reaction was monitored by TLC until the reaction was completed. The mixture was concentrated in vacuo. The residue was purified by silica gel column chromatography (PE/EtOAc (v/v)=2/1) to give the title compound as a colorless oil (0.85 g 67%). MS (ESI, pos.ion) m/z: 650.3 $[M+H]^+$.

Step 6: (R)-tert-butyl 2-((3R,5S)-1-isopropyl-5-(methoxycarbonyl)pyrrolidin-3-yl)-3-oxohexahydroimidazo[1,5-a]pyrazine-7(1H)-carboxylate

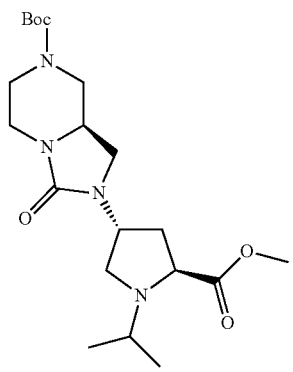 [SMILES: COC(=O)[C@@H]1C[C@@H](N2C[C@@H]3CN(C(=O)OC(C)(C)C)CCN3C2=O)CN1C(C)C]

To a solution of (S)-di-tert-butyl 2-((((3R,5S)-1-isopropyl-5-(methoxycarbonyl) pyrrolidin-3-yl)((4-nitrophenoxy) carbonyl)amino)methyl)piperazine-1,4-dicarboxylate (0.85 g 1.3 mmol) in dichloromethane (10 mL) was added trifluoroacetic acid (20 mL), the mixture was stirred at rt until the reaction was completed. The reaction mixture was concentrated in vacuo to remove the solvent.

The above residue was dissolved in dichloromethane (20 mL) and N,N-diisopropylethylamine (0.9 g 7 mmol), the mixture was heated to 40° C. and stirred for 3 hours, and then (Boc)$_2$O (0.9 g 4 mmol) was added, the resulting mixture was stirred overnight.

The mixture was concentrated in vacuo to remove the solvent. The residue was purified by silica gel column chromatography (PE/EtOAc (v/v)=5/1) to give the title compound as a colorless liquid (298 mg 50%). MS (ESI, pos.ion) m/z: 411.2 [M+H]$^+$.

Step 7: (2S,4R)-methyl 1-isopropyl-4-((S)-3-oxo-hexahydroimidazo[1,5-a]pyrazin-2(3H)-yl) pyrrolidine-2-carboxylate trifluoroacetate

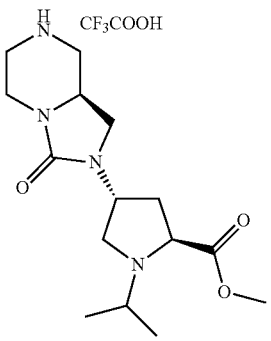 [SMILES: COC(=O)[C@@H]1C[C@@H](N2C[C@@H]3CNCCN3C2=O)CN1C(C)C ; "CF3COOH"]

To a solution of (R)-tert-butyl 2-((3R,5S)-1-isopropyl-5-(methoxycarbonyl)pyrrolidin-3-yl)-3-oxohexahydroimidazo[1,5-a]pyrazine-7(1H)-carboxylate (298 mg, 0.72 mmol) in dichloromethane (6 mL) was added trifluoroacetic acid (6 mL, 77.5 mmol), the mixture was stirred at rt until the reaction was completed. The reaction mixture was concentrated in vacuo to get the title compound as a white solid (300 mg 0.70 mmol, 97%).

Step 8: (R)-methyl 4-(2-chloro-4-fluorophenyl)-6-(((S)-2-((3R,5S)-1-isopropyl-5-(methoxycarbonyl)pyrrolidin-3-yl)-3-oxohexahydroimidazo[1,5-a]pyrazin-7(1H)-yl)methyl)-2-(thiazol-2-yl)-1,4-dihydropyrimidine-5-carboxylate

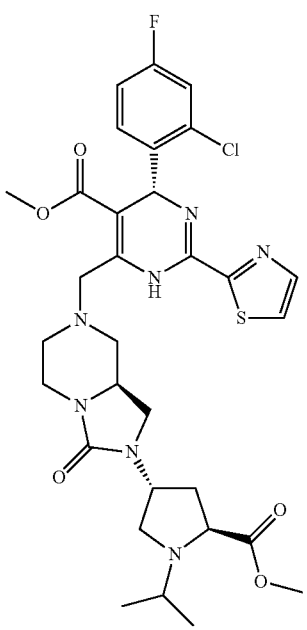

(2S,4R)-Methyl 1-isopropyl-4-((S)-3-oxohexahydroimidazo[1,5-a]pyrazin-2(3H)-yl) pyrrolidine-2-carboxylate trifluoroacetate (266 mg 0.6268 mmol) and potassium carbonate (260 mg 1.88 mmol) were dissolved in ethanol (6 mL), and (R)-methyl 6-(bromomethyl)-4-(2-chloro-4-fluorophenyl)-2-(thiazol-2-yl)-1,4-dihydropyrimidine-5-carboxy late (278 mg, 0.62 mmol) was added, the reaction mixture was stirred at rt until the reaction was completed. The mixture was concentrated in vacuo. The residue was purified by silica gel column chromatography (PE/EtOAc (v/v)=1/1) to give the title compound as a yellow solid (306 mg 72%). MS (ESI, pos.ion) m/z: 674.1 [M+H]$^+$.

Step 9: (2S,4R)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-iso propylpyrrolidine-2-carboxylic Acid (R)-Methyl 4-(2-chloro-4-fluorophenyl)-6-(((S)-2-((3R,5S)-1-isopropyl-5-(methoxy carbonyl)pyrrolidin-3-yl)-3-oxohexahydroimidazo[1,5-a]pyrazin-7(1H)-yl)methyl)-2-(thiazol-2-yl)-1,4-dihydropyrimidine-5-carboxylate (270 mg, 0.40 mmol) was dissolved in methanol (6 mL), and then lsodium hydroxide (110 mg 2.75 mmol) and water (2 mL) were added, the reaction mixture was stirred at rt monitored by TLC, after the reaction was completed, the mixture was concentrated in vacuo. The residue was purified by silica gel column chromatography (DCM/MeOH (V/V)=8/1) to give the title compound as a yellow solid (168 mg 63%). MS (ESI, pos.ion) m/z: 660.1 [M+H]$^+$; $^1$H NMR (600 MHz, CDCl$_3$) δ 9.59 (s, 1H), 7.84 (d, J=3.0 Hz, 1H), 7.45 (d, J=2.9 Hz, 1H), 7.30-7.28 (m, 1H), 7.14 (dd, J=8.5, 2.1 Hz, 1H), 6.95-6.87 (m, 1H), 6.20 (s, 1H), 4.45-4.40 (m, 2H), 4.06 (d, J=17.2 Hz, 1H), 3.99 (s, 1H), 3.94-3.86 (m, 3H), 3.84 (d, J=17.3 Hz, 1H), 3.79-3.69 (m, 1H), 3.61 (s, 3H), 3.41 (t, 1H), 3.30-3.22 (m, 2H), 3.20-3.14 (m, 1H), 2.78 (d, J=10.1 Hz, 2H), 2.48-2.37 (m, 2H), 2.34-2.27 (m, 1H), 2.24 (t, J=10.9 Hz, 1H), 1.39 (d, 3H), 1.33 (d, 3H).

Example 3: (2R,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-iso propylpyrrolidine-2-carboxylic Acid Step 1: (2R,4R)-1-benzyl 2-methyl 4-hydroxypyrrolidine-1,2-dicarboxylate

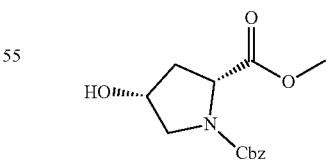

The title compound was prepared as a colorless oil (12.1 g 98%) according to step 1 of example 1 by using (2R,4R)-methyl 4-hydroxypyrrolidine-2-carboxylate hydrochloride (8 g 44.0 mmol), 1,4-dioxane (80 mL), water (80 mL), sodium bicarbonate (7.4 g, 88 mmol) and benzyl chloroformate (8.0 mL, 53 mmol) as materials. MS (ESI, pos.ion) m/z: 280.2 [M+H]$^+$.

Step 2: (2R,4S)-1-benzyl 2-methyl 4-aminopyrrolidine-1,2-dicarboxylate

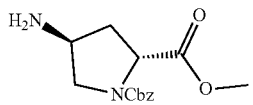 [SMILES: COC(=O)[C@H]1C[C@H](N)CN1C(=O)OCc1ccccc1]

The title compound was prepared as a pale yellow oil (8.2 g 75%) according to step 2 of example 1 by using (2R,4R)-1-benzyl 2-methyl 4-hydroxypyrrolidine-1,2-dicarboxylate (12 g 42.96 mmol), triethylamine (9.1 mL, 65 mmol), dichloromethane (120 mL), methylsufonyl chloride (6.1 g 52 mmol), N,N-dimethylformamide (80 mL), sodium azide (4.4 g 67 mmol), tetrahydrofuran (120 mL), triphenylphosphine (31.4 g 119 mmol) and water (2.5 mL) as materials. MS (ESI, pos.ion) m/z: 279.3[M+H]$^+$.

Step 3: (R)-di-tert-butyl 2-((((3S,5R)-1-((benzyloxy)carbonyl)-5-(methoxycarbonyl)pyrrolidin-3-yl)amino)methyl)piperazine-1,4-dicarboxylate

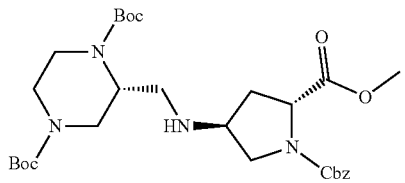 [SMILES: COC(=O)[C@H]1C[C@H](NC[C@@H]2CN(C(=O)OC(C)(C)C)CCN2C(=O)OC(C)(C)C)CN1C(=O)OCc1ccccc1]

The title compound was prepared as a pale yellow oil (5.2 g 77%) according to step 3 of example 1 by using (2S)-di-tert-butyl 2-formylpiperazine-1,4-dicarboxylate (3.7 g 12 mmol), (2R,4S)-1-benzyl 2-methyl 4-aminopyrrolidine-1,2-dicarboxylate, methanol (40 mL) and sodium cyanoborohydride (1.2 g 18 mmol) as materials. MS (ESI, pos.ion) m/z: 577.3 [M+H]$^+$.

Step 4: (S)-di-tert-butyl 2-((((3S,5R)-1-((benzyloxy)carbonyl)-5-(methoxycarbonyl)pyrrolidin-3-yl)((4-nitrophenoxy)carbonyl)amino)methyl)piperazine-1,4-dicarboxylate

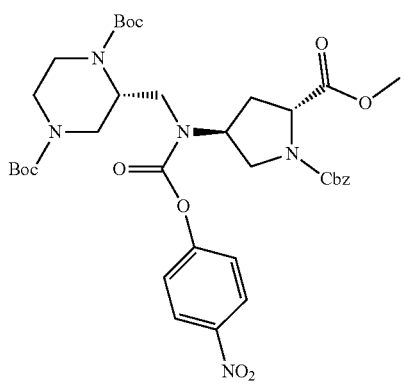 [SMILES: COC(=O)[C@H]1C[C@H](N(C[C@@H]2CN(C(=O)OC(C)(C)C)CCN2C(=O)OC(C)(C)C)C(=O)Oc2ccc([N+](=O)[O-])cc2)CN1C(=O)OCc1ccccc1]

The title compound was prepared as a colorless oil (5.2 g 78%) according to step 3 of example 1 by using (R)-di-tert-butyl 2-((((3S,5R)-1-((benzyloxy)carbonyl)-5-(methoxycarbonyl) pyrrolidin-3-yl)amino)methyl)piperazine-1,4-dicarboxylate (5.2 g 9.0 mmol), N,N-diisopropylethylamine (3 mL, 17.8 mmol), dichloromethane (50 mL) and p-nitrophenyl chloroformate (2.8 g 13 mmol) as materials. MS (ESI, pos.ion) m/z: 764.3[M+Na]$^+$.

Step 5: (2R,4S)-1-benzyl 2-methyl 4-((R)-7-(tert-butoxycarbonyl)-3-oxohexahydroimidazo[1,5-a]pyrazin-2(3H)-yl)pyrrolidine-1,2-dicarboxylate

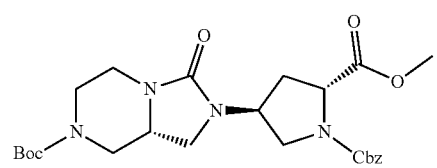 [SMILES: COC(=O)[C@H]1C[C@H](N2C[C@@H]3CN(C(=O)OC(C)(C)C)CCN3C2=O)CN1C(=O)OCc1ccccc1]

The title compound was prepared as a pale yellow oil (2.1 g 77%) according to step 5 of example 1 by using (S)-di-tert-butyl 2-((((3S,5R)-1-((benzyloxy)carbonyl)-5-(methoxycarbonyl) pyrrolidin-3-yl)((4-nitrophenoxy)carbonyl)amino)methyl)piperazine-1,4-dicarboxylate (4.3 g 5.8 mmol), trifluoroacetic acid (20 mL), N,N-diisopropylethylamine (3.5 g 27 mmol), (Boc)$_2$O (2.5 mL, 11 mmol) and dichloromethane (30 mL) as materials. MS (ESI, pos.ion) m/z: 525.2 [M+Na]$^+$.

Step 6) (R)-tert-butyl 2-((3S,5R)-5-(methoxycarbonyl)pyrrolidin-3-yl)-3-oxohexahydroimidazo[1,5-a]pyrazine-7(1H)-carboxylate

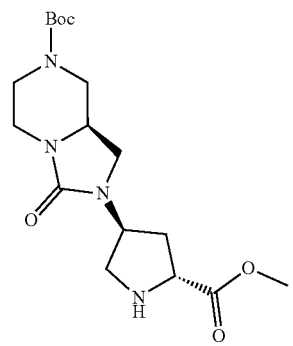 [SMILES: COC(=O)[C@H]1C[C@H](N2C[C@@H]3CN(C(=O)OC(C)(C)C)CCN3C2=O)CN1]

The title compound was prepared (1.8 g 88%) according to step 6 of example 1 by using (2R,4S)-1-benzyl 2-methyl 4-((R)-7-(tert-butoxycarbonyl)-3-oxohexahydroimidazo[1,5-a]pyrazin-2(3H)-yl)pyrrolidine-1,2-dicarboxylate (2.8 g 5.6 mmol), methanol (60 mL), Pd/C (0.59 g 0.55 mmol, wt. % is 10%) as materials. MS (ESI, pos.ion) m/z: 369.5 [M+H]$^+$.

Step 7) (R)-tert-butyl 2-((3S,5R)-1-isopropyl-5-(methoxycarbonyl)pyrrolidine-3-yl)-3-oxohexahydroimidazo[1,5-a]pyrazin-7(1H)-carboxylate

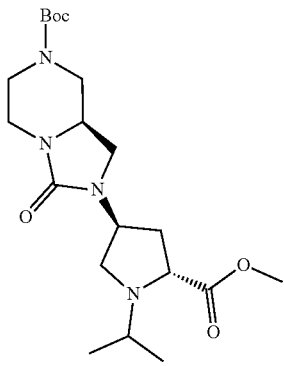 [SMILES: COC(=O)[C@H]1C[C@H](N2C[C@@H]3CN(C(=O)OC(C)(C)C)CCN3C2=O)CN1C(C)C]

The title compound was prepared as a light yellow solid (610 mg 32%) according to step 7 of example 1 by using (R)-tert-butyl 2-((3S,5R)-5-(methoxycarbonyl)pyrrolidin-3-yl)-3-oxohexahydroimidazo[1,5-a]pyrazin-7(1H)-carboxylate (1.7 g 4.6 mmol), potassium carbonate (1.6 g 12 mmol), N,N-dimethylformamide (20 mL), isopropane iodide (1 mL, 9.9 mmol) as materials. MS: (ESI, pos.ion) m/z: 411.3 [M+H]⁺.

Step 8: (2R,4S)-methyl 1-isopropyl-4-((S)-3-oxohexahydroimidazo[1,5-a]pyrazin-2(3H)-yl)pyrrolidine-2-carboxylate trifluoroacetate

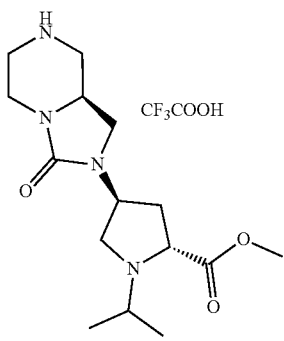 [SMILES: COC(=O)[C@H]1C[C@H](N2C[C@@H]3CNCCN3C2=O)CN1C(C)C ; "CF3COOH"]

The title compound was prepared as a brown oil (523 mg 97%) according to step 8 of example 1 by using (R)-tert-butyl 2-((3S,5R)-1-isopropyl-5-(methoxycarbonyl)pyrrolidin-3-yl)-3-oxohexahydroimidazo[1,5-a]pyrazin-7(1H)-carboxylate (520 mg, 1.27 mmol), dichloromethane (5 mL) and trifluoroacetic acid (5 mL) as materials. MS: (ESI, pos.ion) m/z: 311.2 [M+H]⁺.

Step 9: (R)-methyl 4-(2-chloro-4-fluorophenyl)-6-(((S)-2-((3S,5R)-1-isopropyl-5-(methoxy carbonyl)pyrrolidine-3-yl)-3-oxohexahydroimidazo[1,5-a]pyrazin-7(1H)-yl)methyl)-2-(thiazol-2-yl)-1,4-dihydropyrimidine-5-carboxylate

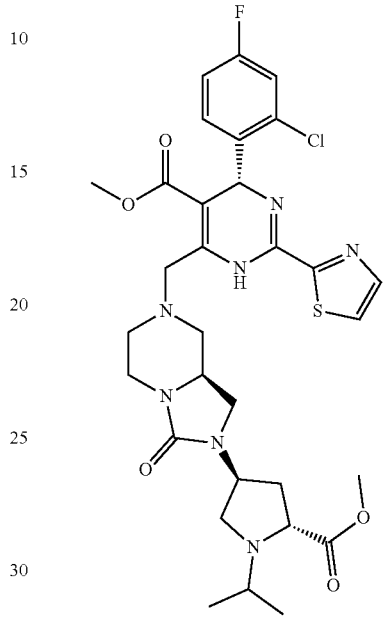

The title compound was obtained as a yellow solid (61 mg, 38%) according to step 9 of example 1 by using (2R,4S)-methyl 1-isopropyl-4-((S)-3-oxohexahydroimidazo[1,5-a]pyrazin-2(3H)-yl)pyrrolidine-2-carboxylate trifluoroacetate (100 mg, 0.23 mmol), potassium carbonate (97 mg, 0.70 mmol), ethanol (10 mL) and (R)-methyl 6-(bromomethyl)-4-(2-chloro-4-fluorophenyl)-2-(thiazol-2-yl)-1,4-dihydropyrimidine-5-carboxylate (105 mg, 0.24 mmol) as materials. MS (ESI, pos.ion) m/z: 674.1 [M+H]⁺.

Step 10) (2R,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-isopropylpyrrolidine-2-carboxylic Acid The title compound was prepared as a yellow oil (113 mg, 73%) according to step 10 of example 1 by using (R)-methyl 4-(2-chloro-4-fluorophenyl)-6-(((S)-2-((3S,5R)-1-isopropyl-5-(methoxycarbonyl)pyrrolidine-3-yl)-3-oxohexahydroimidazo[1,5-a]pyrazin-7(1H)-yl)methyl)-2-(thiazol-2-yl)-1,4-dihydropyrimidine-5-carboxylate (158 mg, 0.23 mmol), sodium hydroxide (94 mg, 2.35 mmol), methanol (6 mL) and water (2 mL) as materials. MS (ESI, pos.ion) m/z: 660.3 [M+H]⁺. ¹H NMR (600 MHz, CDCl₃) δ 9.57 (s, 1H), 7.85 (s, 1H), 7.46 (s, 1H), 7.30-7.24 (m, 1H), 7.13 (d, J=7.3 Hz, 1H), 6.90-6.89 (m, 1H), 6.19 (s, 1H), 4.15-4.05 (m, 2H), 4.02 (s, 1H), 3.98-3.92 (m, 1H), 3.90-3.80 (m, 3H), 3.67-3.62 (m, 1H), 3.60 (s, 3H), 3.51-3.40 (m, 2H), 3.14 (t, J=10.9 Hz, 1H), 3.02 (s, 1H), 2.79 (dd, J=28.0, 9.6 Hz, 2H), 2.50 (s, 2H), 2.44-2.35 (m, 1H), 2.24-2.14 (m, 1H), 1.37 (s, 6H).

Example 4: (2R,4R)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-isopropylpyrrolidine-2-carboxylic Acid Step 1: (2R,4S)-1-benzyl 2-methyl 4-hydroxypyrrolidine-1,2-dicarboxylate

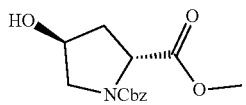

The title compound was prepared as a colorless oil (2.8 g 55%) according to step 1 of example 1 by using (2R,4S)-methyl 4-hydroxypyrrolidine-2-carboxylate hydrochloride (3.3 g 18 mmol), H₂O (17 mL), 1,4-dioxane (17 mL), sodium carbonate (2.1 g, 20 mmol) and CbzCl (2.9 mL, 20 mmol) as materials.

Step 2: (2R,4R)-1-benzyl 2-methyl 4-aminopyrrolidine-1,2-dicarboxylate

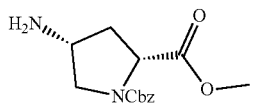

The title compound was prepared as a colorless oil (1.66 g 59%) according to step 2 of example 1 by using (2R,4S)-1-benzyl 2-methyl 4-hydroxypyrrolidine-1,2-dicarboxylate (2.8 g 10 mmol), DIPEA (5.2 mL, 30 mmol), dichloromethane (28 mL), methylsufonyl chloride (1.6 mL, 21 mmol), DMF (18 mL), sodium azide (1.3 g 20 mmol), Ph₃P (5.3 g 20 mmol) and THF (10 mL) as materials. MS (ESI, pos.ion) m/z: 279.1 [M+H]⁺.

Step 3: (S)-di-tert-butyl 2-((((3R,5R)-1-((benzyloxy)carbonyl)-5-(methoxycarbonyl) pyrrolidin-3-yl)amino)methyl)piperazine-1,4-dicarboxylate

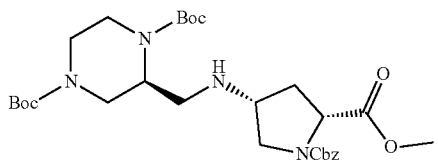 [SMILES: COC(=O)[C@H]1C[C@@H](NC[C@H]2CN(C(=O)OC(C)(C)C)CCN2C(=O)OC(C)(C)C)CN1C(=O)OCc1ccccc1]

The title compound was prepared as a colorless oil (2.6 g 78%) according to step 3 of example 1 by using (2S)-di-tert-butyl 2-formylpiperazine-1,4-dicarboxylate (1.9 g 6.0 mmol), (2R,4R)-1-benzyl 2-methyl 4-aminopyrrolidine-1,2-dicarboxylate (1.6 g 5.7 mmol), acetic Acid (0.16 mL, 2.8 mmol), methanol (16 mL) and sodium cyanoborohydride (1.1 g 18 mmol) as materials. MS (ESI, pos.ion) m/z: 577.3 [M+H]⁺.

Step 4: (S)-di-tert-butyl 2-((((3R,5R)-1-((benzyloxy)carbonyl)-5-(methoxycarbonyl)pyrrolidin-3-yl)((4-nitrophenoxy)carbonyl)amino)methyl)piperazine-1,4-dicarboxylate

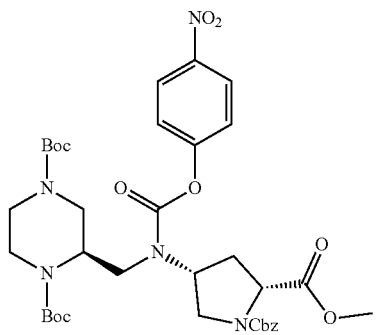 [SMILES: COC(=O)[C@H]1C[C@@H](N(C[C@@H]2CN(C(=O)OC(C)(C)C)CCN2C(=O)OC(C)(C)C)C(=O)Oc2ccc([N+](=O)[O-])cc2)CN1C(=O)OCc1ccccc1]

The title compound was prepared as a white solid (3.0 g 90%) according to step 4 of example 1 by using p-nitrobenzyl chloroformate (1.8 g 8.9 mmol), (S)-di-tert-butyl 2-((((3R,5R)-1-((benzyloxy)carbonyl)-5-(methoxycarbonyl)pyrrolidin-3-yl)amino)methyl)piperazine-1,4-dicarboxylate (2.6 g 4.5 mmol), DIPEA (1.7 mL, 9.7 mmol) and DCM (26 mL) as materials. MS (ESI, pos.ion) m/z: 764.3 [M+Na]⁺.

Step 5: (2R,4R)-1-benzyl 2-methyl 4-((R)-7-(tert-butoxycarbonyl)-3-oxohexahydroimidazo[1,5-a]pyrazin-2(3H)-yl)pyrrolidine-1,2-dicarboxylate

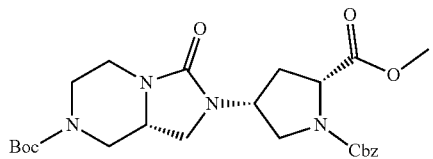 [SMILES: COC(=O)[C@H]1C[C@@H](N2C[C@@H]3CN(C(=O)OC(C)(C)C)CCN3C2=O)CN1C(=O)OCc1ccccc1]

The title compound was prepared as a white solid (1.82 g 90%) according to step 5 of example 1 by using (S)-di-tert-butyl 2-((((3R,5R)-1-((benzyloxy)carbonyl)-5-(methoxycarbonyl) pyrrolidin-3-yl)((4-nitrophenoxy)carbonyl)amino)methyl)piperazine-1,4-dicarboxylate (3 g 4.0 mmol), DCM (6 mL), TFA (18 mL), DIPEA (35 mL, 201 mmol) and (Boc)₂O (1.8 g 8.2 mmol) as materials. MS (ESI, pos.ion) m/z: 525.2 [M+Na]⁺.

Step 6: (R)-tert-butyl 2-((3R,5R)-5-(methoxycarbonyl)pyrrolidin-3-yl)-3-oxohexahydroimidazo[1,5-a]pyrazine-7(1H)-carboxylate

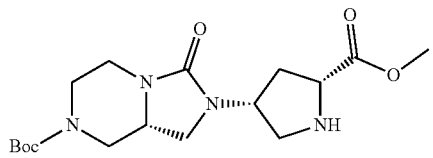 [SMILES: COC(=O)[C@H]1C[C@@H](N2C[C@@H]3CN(C(=O)OC(C)(C)C)CCN3C2=O)CN1]

The title compound was prepared as a colorless oil (1.3 g 99%) according to step 6 of example 1 by using (2R,4R)-

1-benzyl 2-methyl 4-((R)-7-(tert-butoxycarbonyl)-3-oxo-hexahydroimidazo[1,5-a]pyrazin-2(3H)-yl)pyrrolidine-1,2-dicarboxylate (1.8 g 3.6 mmol), Pd/C (0.76 g 0.71 mmol) and methanol (40 mL) as materials. MS (ESI, pos.ion) m/z: 269.2 [M+H].

Step 7: (R)-tert-butyl 2-((3R,5R)-1-isopropyl-5-(methoxycarbonyl)pyrrolidin-3-yl)-3-oxohexahydro-imidazo[1,5-a]pyrazin-7(1H)-carboxylate

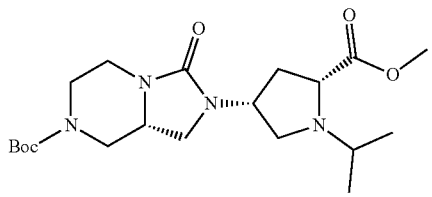 [SMILES: COC(=O)[C@H]1C[C@@H](N2C[C@@H]3CN(C(=O)OC(C)(C)C)CCN3C2=O)CN1C(C)C]

The title compound was prepared as a colorless oil (329 mg 36.91%) according to step 7 of example 1 by using (R)-tert-butyl 2-((3R,5R)-5-(methoxycarbonyl)pyrrolidin-3-yl)-3-oxohexahydroimidazo[1,5-a]pyrazine-7(1H)-carboxylate (800 mg, 2.2 mmol), K$_2$CO$_3$ (600 mg 4.3 mmol), DMF (8 mL), isopropane iodide (738 mg, 4.3 mmol) as materials. MS (ESI, pos.ion) m/z: 411.6 [M+H]$^+$.

Step 8: (2R,4R)-methyl 1-isopropyl-4-((S)-3-oxo-hexahydroimidazo[1,5-a]pyrazin-2(3H)-yl)pyrrolidine-2-carboxylate hydrochloride

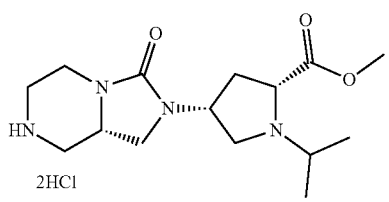 [SMILES: COC(=O)[C@H]1C[C@@H](N2C[C@@H]3CNCCN3C2=O)CN1C(C)C]

The title compound was prepared as a colorless oil (307 mg 100%) according to step 8 of example 1 by using (R)-tert-butyl 2-((3R,5R)-1-isopropyl-5-(methoxycarbonyl)pyrrolidin-3-yl)-3-oxohexahydroimidazo[1,5-a]pyrazin-7(1H)-carboxylate (329 mg 0.80 mmol), hydrogen chloride solution in isopropanol (4 mol/L, 5 mL) as materials. MS (ESI, pos.ion) m/z: 311.2[M+H]$^+$.

Step 9: (R)-methyl 4-(2-chloro-4-fluorophenyl)-6-(((S)-2-((3R,5R)-1-isopropyl-5-(methoxy carbonyl) pyrrolidin-3-yl)-3-oxohexahydroimidazo[1,5-a] pyrazin-7(1H)-yl)methyl)-2-(thiazol-2-yl)-1,4-dihydropyrimidine-5-carboxylate

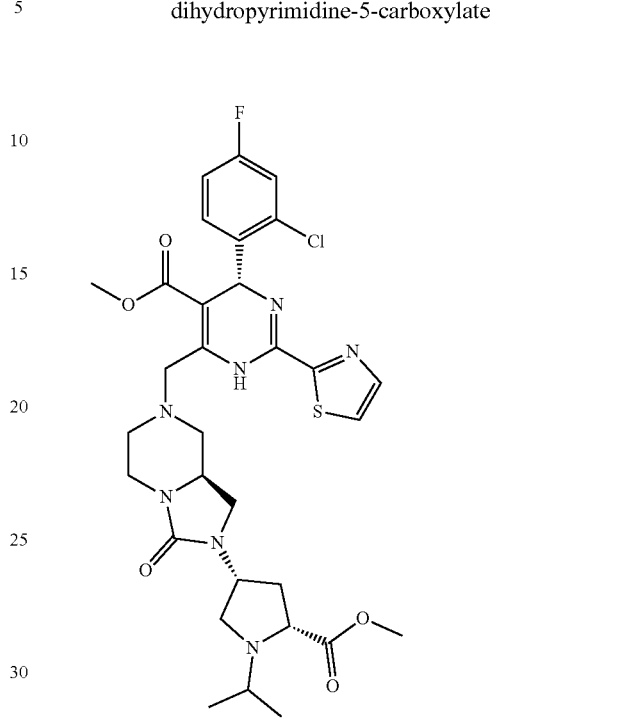

The title compound was prepared as a yellow solid (340 mg 63%) according to step 9 of example 1 by using (R)-methyl 6-(bromomethyl)-4-(2-chloro-4-fluorophenyl)-2-(thiazol-2-yl)-1,4-dihydropyrimidine-5-carboxylate (0.36 g 0.8 mmol), (2R,4R)-methyl 1-isopropyl-4-((S)-3-oxo-hexahydroimidazo[1,5-a]pyrazin-2(3H)-yl)pyrrolidine-2-carboxylate hydrochloride (307 mg 0.80 mmol), K$_2$CO$_3$ (552 mg 4 mmol) and ethanol (5 mL) as materials. MS (ESI, pos.ion) m/z: 674.2 [M+H]$^+$.

Step 10: (2R,4R)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-isopropylpyrrolidine-2-carboxylic Acid The title compound was prepared as a yellow solid (100 mg 30%) according to step 10 of example 1 by using (R)-methyl 4-(2-chloro-4-fluorophenyl)-6-(((S)-2-((3R,5R)-1-isopropyl-5-(methoxycarbonyl)pyrrolidine-3-yl)-3-oxo-hexahydroimidazo[1,5-a]pyrazin-7(1H)-yl)methyl)-2-(thiazol-2-yl)-1,4-dihydropyrimidine-5-carboxylate (340 mg 0.50 mmol), lithium hydroxide monohydrate (42 mg 1.00 mmol), methanol (3 mL) and water (1 mL) as materials. MS (ESI, pos.ion) m/z: 674.2[M+H]$^+$; $^1$H NMR (400 MHz, CDCl$_3$) δ 9.57 (s, 1H), 7.85 (d, J=3.0 Hz, 1H), 7.47 (d, J=2.8 Hz, H), 7.34-7.23 (m, 1H), 7.14 (dd, J=8.6, 2.4 Hz, 1H), 6.92 (td, J=8.3, 2.2 Hz, 1H), 6.20 (s, 1H), 4.15-4.05 (m, 3H), 3.94-3.80 (m, 4H), 3.76-3.65 (m, 2H), 3.61 (s, 3H), 3.56-3.44 (m, 2H), 3.20-3.11 (m, 1H), 3.08-3.00 (m, 1H), 2.86-2.75 (m, 2H), 2.58-2.48 (m, 1H), 2.47-2.39 (m, 1H), 2.20 (t, J=10.8 Hz, 1H), 1.45-1.37 (m, 6H).

Example 5: (2R,4R)-4-(7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-isopropylpyrrolidine-2-carboxylic Acid

Step 1: 1-benzyl 4-tert-butyl 2-((((3R,5R)-1-isopropyl-5-(methoxycarbonyl)pyrrolidin-3-yl)amino)methyl)piperazine-1,4-dicarboxylate

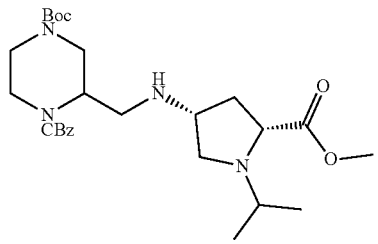

A solution of (2R,4R)-methyl 4-amino-1-isopropylpyrrolidine-2-carboxylate (800 mg, 4.29 mmol) and 1-benzyl 4-tert-butyl 2-formylpiperazine-1,4-dicarboxylate (1.65 g 4.74 mmol) in dichloromethane (15 mL) was stirred at rt for 2 hours. And then to the reaction mixture was added sodium triacetoxyborohydride (1.88 g 8.60 mmol), the mixture was stirred at rt until the reaction was completed. After the reaction was completed. The mixture was concentrated in vacuo. The residue was purified by silica gel column chromatography (EtOAc) to give the title compound as a colorless oil (1.08 g 49%). MS (ESI, pos.ion) m/z: 519.3 [M+H]$^+$.

Step 2: (2R,4R)-1-isopropyl-4-(3-oxohexahydroimidazo[1,5-a]pyrazin-2(3H)-yl)pyrrolidine-2-carboxylic acid hydrochloride

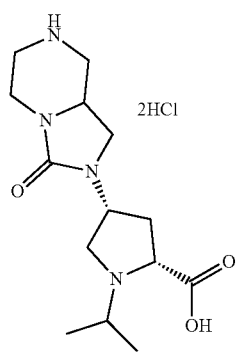 [SMILES: CC(C)N1C[C@H](N2CC3CNCCN3C2=O)C[C@@H]1C(=O)O]

To a dry flask were added sodium hydride (386 mg, 9.65 mmol, wt. % is 60%), and tetrahydrofuran (20 mL) in turn under N$_2$. After mixing uniformly, 1-benzyl 4-tert-butyl 2-((((3R,5R)-1-isopropyl-5-(methoxycarbonyl)pyrrolidin-3-yl)amino)methyl)piperazine-1,4-dicarboxylate (1 g 1.93 mmol) was added. The mixture was heated to 65° C. and stirred. After the reaction was completed, the reaction was quenched with water (30 mL) under an ice bath, and the mixture was adjusted with hydrochloric acid (1 M) to pH about 3 and concentrated in vacuo. To the residue was added HCl/EtOAc (5 mL, 20 mmol, 4.0 mol/L), the resulting mixture was stirred at rt until the reaction was completed. After the reaction was complete, the reaction mixture was concentrated in vacuo to get the title compound as a white solid (0.64 g 90%).

Step 3: (2R,4R)-4-(7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)-1-isopropylpyrrolidine-2-carboxylic Acid To a dry flask were added (2R,4R)-1-isopropyl-4-(3-oxohexahydroimidazo[1,5-a]pyrazin-2(3H)-yl)pyrrolidine-2-carboxyli c acid hydrochloride (0.17 g 0.46 mmol), ethanol (5 mL), potassium carbonate (374 mg 1.35 mmol) and (R)-methyl 6-(bromomethyl)-4-(2-chloro-4-fluorophenyl)-2-(thiazol-2-yl)-1,4-dihydropyrimidine-5-carboxylate (200 mg, 0.45 mmol) in turn. The mixture was stirred at rt for 24 hours. After the reaction was completed, the mixture was filtered, the filtrate was concentrated in vacuo. The residue was purified by silica gel column chromatography (PE/EtOAc (v/v)=8/1) to give the title compound as a yellow solid (110 mg 36.97%). MS (ESI, pos.ion) m/z: 660.3 [M+H]$^+$; H NMR (400 MHz, CD$_3$OD) δ 7.96 (dd, J=4.8, 3.2 Hz, 1H), 7.78 (d, J=3.1 Hz, 1H), 7.50-7.39 (m, 1H), 7.25 (dd, J=8.7, 1.9 Hz, 1H), 7.06 (td, J=8.4, 2.6 Hz, 1H), 6.18 (s, 1H), 4.40-4.25 (m, 1H), 4.23-4.15 (m, 1H), 4.15-4.07 (m, 2H), 4.05-3.92 (m, 2H), 3.91-3.82 (m, 1H), 3.81-3.74 (m, 1H), 3.69-3.52 (m, 5H), 3.43-3.35 (m, 1H), 3.26-3.10 (m, 2H), 3.04-2.85 (m, 1H), 2.62-2.43 (m, 2H), 2.41-2.30 (m, 2H), 1.43-1.34 (m, 6H).

Example 6: (2R,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-methylpyrrolidine-2-carboxylic Acid

Step 1: (R)-tert-butyl 2-((3S,5R)-5-(methoxycarbonyl)-1-methylpyrrolidin-3-yl)-3-oxohexahydroimidazo[1,5-a]pyrazine-7(1H)-carboxylate

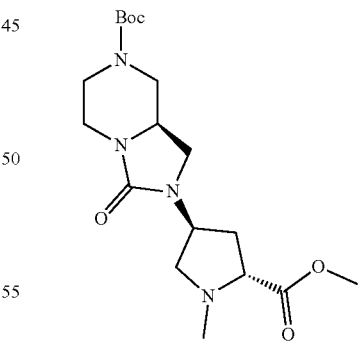

To a solution of (R)-tert-butyl 2-((3S,5R)-5-(methoxycarbonyl)pyrrolidin-3-yl)-3-oxohexahydroimidazo[1,5-a]pyrazine-7(1H)-carboxylate (300 mg 0.81 mmol) in methanol (10 mL) was added aqueous formaldehyde solution (37%, 0.61 mL, 8.1 mmol), the mixture was stirred at rt for 1 hour, and sodium cyanoborohydride (107 mg, 1.62 mmol) was added, the reaction mixture was stirred until the reaction was completed. The mixture was concentrated in vacuo. The residue was purified by silica gel column chromatography (PE/EtOAc (v/v)=1/1) to give the title compound as a pale yellow oil (101 mg, 32%). MS (ESI, pos.ion) m/z: 383.2 [M+H]+.

Step 2: (2R,4S)-methyl 1-methyl-4-((S)-3-oxohexahydroimidazo[1,5-a]pyrazin-2(3H)-yl) pyrrolidine-2-carboxylate trifluoroacetate

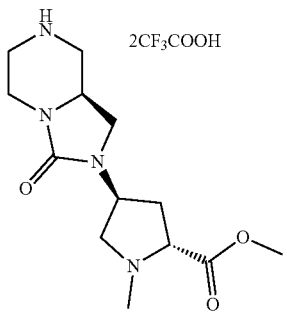 [SMILES: COC(=O)[C@H]1C[C@H](N2C[C@@H]3CNCCN3C2=O)CN1C]

To a solution of (R)-tert-butyl 2-((3S,5R)-5-(methoxycarbonyl)-1-methylpyrrolidin-3-yl)-3-oxohexahydroimidazo[1,5-a]pyrazine-7(1H)-carboxylate (268 mg 0.70 mmol) in dichloromethane (10 mL) was added trifluoroacetic acid (10 mL), the mixture was stirred at rt until the reaction was completed. The reaction mixture was concentrated in vacuo to get the title compound (300 mg, 84.23%). This product was used in next step without further purification. MS: (ESI, pos.ion) m/z: 283.2 [M+H]+.

Step 3: (R)-methyl 4-(2-chloro-4-fluorophenyl)-6-(((S)-2-((3S,5R)-5-(methoxycarbonyl)-1-methylpyrrolidine-3-yl)-3-oxohexahydroimidazo[1,5-a]pyrazin-7(1H)-yl)methyl)-2-(thiazol-2-yl)-1,4-dihydropyrimidine-5-carboxylate

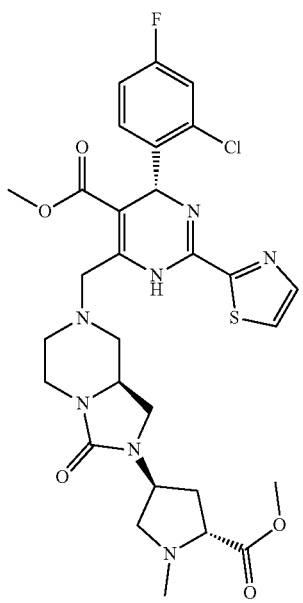 [SMILES: COC(=O)C1=C(CN2CCN3C(=O)N([C@H]4C[C@H](C(=O)OC)N(C)C4)C[C@@H]3C2)NC(c2nccs2)=N[C@H]1c1ccc(F)cc1Cl]

(2R,4S)-Methyl 1-methyl-4-((S)-3-oxohexahydroimidazo[1,5-a]pyrazin-2(3H)-yl) pyrrolidine-2-carboxylate trifluoroacetate (300 mg 0.59 mmol) were dissolved in ethanol (10 mL), and potassium carbonate (245 mg, 1.77 mmol) was added, after stirring for 5 min, (R)-methyl 6-(bromomethyl)-4-(2-chloro-4-fluorophenyl)-2-(thiazol-2-yl)-1,4-dihydro pyrimidine-5-carboxylate (262 mg, 0.59 mmol) was added, the reaction mixture was stirred at rt until the reaction was completed. The mixture was monitored by TLC until the reaction was completed, the mixture was concentrated in vacuo. The residue was purified by silica gel column chromatography (DCM/MeOH (v/v)=15/1) to give the title compound as a yellow solid (280 mg 73%). MS: (ESI, pos.ion) m/z: 646.2 [M+H]+.

Step 4: (2R,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-methylpyrrolidine-2-carboxylic Acid (R)-Methyl 4-(2-chloro-4-fluorophenyl)-6-(((S)-2-((3S,5R)-5-(methoxycarbonyl)-1-methylpyrrolidine-3-yl)-3-oxohexahydroimidazo[1,5-a]pyrazin-7(1H)-yl)methyl)-2-(thiazol-2-yl)-1,4-dihydropyrimidine-5-carboxylate (200 mg 0.31 mmol) was dissolved in methanol (6 mL), and then lithium hydroxide monohydrate (65 mg, 1.55 mmol) and water (2 mL) were added, the reaction mixture was stirred at rt. The mixture was monitored by TLC until the reaction was completed, the mixture was concentrated in vacuo. The residue was purified by silica gel column chromatography (DCM/MeOH (v/v)=10/1) to give the title compound as a yellow solid (180 mg 92%). MS: (ESI, pos.ion) m/z: 632.8 [M+H]+; 1H NMR (400 MHz, DMSO-d6) δ 8.13-8.00 (m, 2H), 7.52-7.40 (m, 2H), 7.27-7.17 (m, 1H), 6.02 (s, 1H), 4.52-4.38 (m, 5H), 4.18-4.00 (m, 1H), 3.90-3.82 (m, 1H), 3.76-3.69 (m, 1H), 3.62-3.58 (m, 1H), 3.57 (s, 3H), 3.52-3.42 (m, 2H), 3.39-3.25 (m, 2H), 3.24-3.15 (m, 1H), 3.09-2.89 (m, 4H), 2.57-2.50 (m, 1H), 2.35-2.18 (m, 1H).

Example 7: (2R,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-(2-2-methoxyethyl)pyrrolidine-2-carboxylic Acid Step 1: (R)-tert-butyl 2-((3S,5R)-5-(methoxycarbonyl)-1-(2-methoxyethyl)pyrrolidine-3-yl)-3-oxohexahydroimidazo[1,5-a]pyrazine-7(1H)-carboxylate

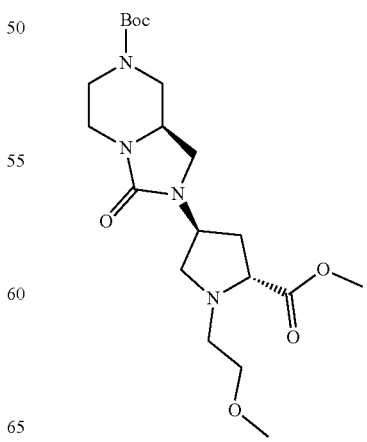

The title compound was prepared as a colorless oil (181 mg 78%) according to step 1 of example 6 by using (R)-tert-butyl 2-((3S,5R)-5-(methoxycarbonyl)pyrrolidin-3-yl)-3-oxohexahydroimidazo[1,5-a]pyrazine-7(1H)-carboxylate (200 mg 0.54 mmol), methoxyethanal (62 mg 0.82 mmol), methanol (10 mL), sodium cyanoborohydride (72 mg 1.09 mmol) as materials. MS (ESI, pos.ion) m/z: 427.7 [M+H]$^+$.

Step 2: (2R,4S)-methyl 1-(2-methoxyethyl)-4-((S)-3-oxohexahydroimidazo[1,5-a]pyrazin-2(3H)-yl)pyrrolidine-2-carboxylate trifluoroacetate

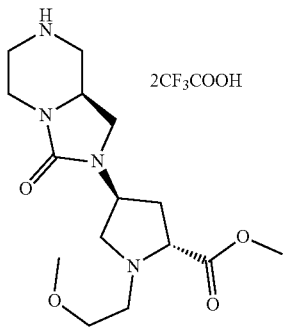 [SMILES: COCCN1C[C@@H](N2C[C@@H]3CNCCN3C2=O)C[C@@H]1C(=O)OC]

The title compound was prepared as a grayish brown oil (100 mg 97%) according to step 2 of example 6 by using (R)-tert-butyl 2-((3S,5R)-5-isopropyl-1-(methoxycarbonyl)pyrrolidine-3-yl)-3-oxohexahydroimidazo[1,5-a]pyrazin-7(1H)-carboxylate (100 mg, 0.23 mmol), dichloromethane (10 mL) and trifluoroacetic acid (10 mL) as materials.

Step 3: (R)-methyl 4-(2-chloro-4-fluorophenyl)-6-(((S)-2-((3S,5R)-5-(methoxycarbonyl)-1-(2-methoxyethyl)pyrrolidine-3-yl)-3-oxohexahydroimidazo[1,5-a]pyrazin-7(1H)-yl)methyl)-2-(thiazol-2-yl)-1,4-dihydropyrimidine-5-carboxylate The title compound was obtained as a yellow solid (210 mg 83.75%) according to step 3 of example 6 by using (2R,4S)-methyl 1-(2-methoxyethyl)-4-((S)-3-oxohexahydroimidazo[1,5-a]pyrazin-2(3H)-yl)pyrrolidine-2-carboxylate trifluoroacetate (200 mg 0.36 mmol), ethanol (10 mL), potassium carbonate (151 mg 1.09 mmol) and (R)-methyl 6-(bromomethyl)-4-(2-chloro-4-fluorophenyl)-2-(thiazol-2-yl)-1,4-dihydropyrimidine-5-carboxylate (161 mg 0.36 mmol) as materials. MS (ESI, pos.ion) m/z: 690.1 [M+H]$^+$.

Step 4: (2R,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-(2-methoxyethyl)pyrrolidine-2-carboxylic Acid The title compound was prepared as a yellow solid (230 mg 78%) according to step 4 of example 6 by using (R)-methyl 4-(2-chloro-4-fluorophenyl)-6-(((S)-2-((3S,5R)-5-(methoxycarbonyl)-1-(2-methoxyethyl)pyrrolidine-3-yl)-3-oxohexahydroimidazo[1,5-a]pyrazin-7(1H)-yl)methyl)-2-(thiazol-2-yl)-1,4-dihydropyrimidine-5-carboxylate (300 mg 0.43 mmol), methanol (6 mL) and lithium hydroxide monohydrate (92 mg 2.19 mmol) as materials. MS: (ESI, pos.ion) m/z: 676.1 [M+H]$^+$; $^1$H NMR (400 MHz, CDCl$_3$) δ 9.58 (s, 1H), 7.85 (s, 1H), 7.47 (s, 1H), 7.30-7.25 (m, 1H), 7.14 (d, J=7.2 Hz, 1H), 6.92 (t, J=7.1 Hz, 1H), 6.20 (s, 1H), 4.30-4.20 (m, 1H), 4.15-3.81 (m, 5H), 3.68-3.63 (m, 1H), 3.60 (s, 3H), 3.50-3.40 (m, 1H), 3.37 (s, 3H), 3.32-3.20 (m, 2H), 3.19-3.10 (m, 1H), 3.03-2.96 (m, 1H), 2.90-2.68 (m, 2H), 2.52-2.29 (m, 3H), 2.19 (t, J=10.5 Hz, 1H), 2.05 (s, 3H).

Example 8: (2R,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-iso propylpyrrolidine-2-carboxylic Acid Step 1: (R)-tert-butyl 2-((3S,5R)-1-isobutyl-5-(methoxycarbonyl)pyrrolidin-3-yl)-3-oxohexahydroimidazo[1,5-a]pyrazine-7(1H)-carboxylate

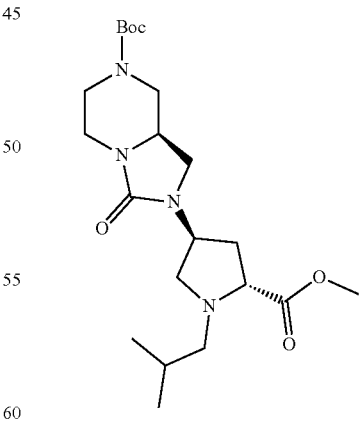

The title compound was prepared as a colorless oil (168 mg, 73%) according to step 1 of example 6 by using (R)-tert-butyl 2-((3S,5R)-5-(methoxycarbonyl)pyrrolidine-3-yl)-3-oxohexahydroimidazo[1,5-a]pyrazine-7(1H)-carboxylate (200 mg 0.5429 mmol), methanol (10 mL), isobutyraldehyde (59 mg 0.814 mmol) and sodium

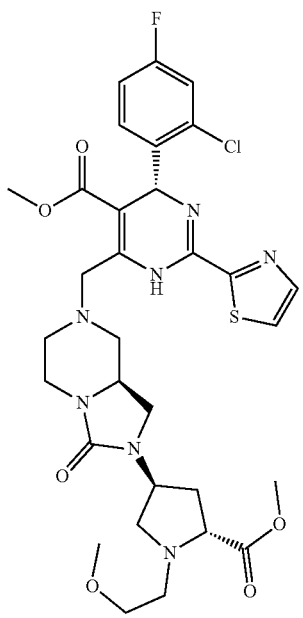 [SMILES: COCCN1C[C@@H](N2C[C@@H]3CN(CC4=C(C(=O)OC)[C@H](c5ccc(F)cc5Cl)N=C(c5nccs5)N4)CCN3C2=O)C[C@@H]1C(=O)OC]

cyanoborohydride (72 mg, 1.09 mmol) as materials. MS: (ESI, pos.ion) m/z: 425.7 [M+H]+.

Step 2: (2R,4S)-methyl 1-isobutyl-4-((S)-3-oxo-hexahydroimidazo[1,5-a]pyrazin-2(3H)-yl) pyrrolidine-2-carboxylate trifluoroacetate

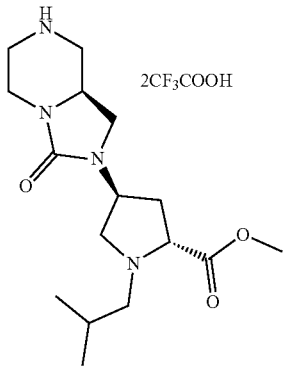 [SMILES: COC(=O)[C@H]1C[C@H](N2C[C@@H]3CNCCN3C2=O)CN1CC(C)C]

The title compound was prepared as a grayish brown oil (200 mg 86%) according to step 2 of example 6 by using (R)-tert-butyl 2-((3S,5R)-1-isobutyl-5-(methoxycarbonyl) pyrrolidin-3-yl)-3-oxohexahydroimidazo[1,5-a]pyrazin-7 (1H)-carboxylate (180 mg 0.42 mmol), dichloromethane (10 mL) and trifluoroacetic acid (10 mL, 129 mmol) as materials.

Step 3: (R)-methyl 4-(2-chloro-4-fluorophenyl)-6-(((S)-2-((3S,5R)-1-isobutyl-5-(methoxy carbonyl) pyrrolidin-3-yl)-3-oxohexahydroimidazo[1,5-a] pyrazin-7(1H)-yl)methyl)-2-(thiazol-2-yl)-1,4-dihydropyrimidine-5-carboxylate

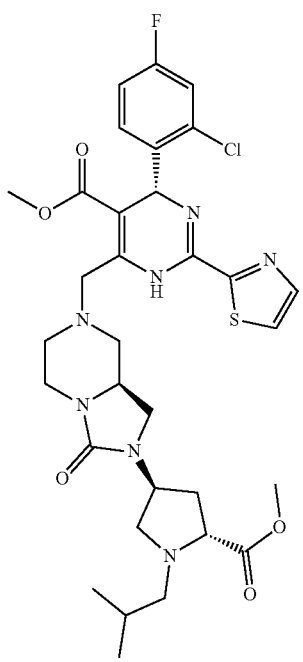 [SMILES: COC(=O)C1=C(CN2CCN3C(=O)N([C@H]4C[C@H](C(=O)OC)N(CC(C)C)C4)C[C@@H]3C2)NC(c2nccs2)=N[C@H]1c1ccc(F)cc1Cl]

The title compound was obtained as a yellow solid (120 mg, 78%) according to step 3 of example 6 by using (2R,4S)-methyl 1-isobutyl-4-((S)-3-oxohexahydroimidazo[1,5-a]pyrazin-2(3H)-yl)pyrrolidine-2-carboxylate trifluoroacetate (121 mg 0.22 mmol), ethanol (10 mL), (R)-methyl 6-(bromomethyl)-4-(2-chloro-4-fluorophenyl)-2-(thiazol-2-yl)-1,4-dihydropyrimidine-5-carboxylate (100 mg 0.22 mmol) and potassium carbonate (61 mg 0.44 mmol) as materials. MS MS (ESI, pos.ion) m/z: 688.2 [M+H]+; 1H NMR (400 MHz, DMSO-$d_6$) δ 9.70 (s, 1H), 8.02 (d, J=2.8 Hz, 1H), 7.96-7.92 (m, 1H), 7.45-7.36 (m, 2H), 7.17 (td, J=8.5, 2.1 Hz, 1H), 6.05 (s, 1H), 4.51-4.39 (m, 1H), 3.97 (d, J=16.9 Hz, 1H), 3.87 (d, J=16.9 Hz, 1H), 3.75-3.68 (m, 1H), 3.68-3.64 (m, 1H), 3.62 (s, 3H), 3.52 (s, 3H), 3.45-3.39 (m, 2H), 3.05-2.98 (m, 1H), 2.97-2.90 (m, 2H), 2.86-2.76 (m, 2H), 2.49-2.44 (m, 1H), 2.32-2.14 (m, 3H), 2.08-1.91 (m, 3H), 1.69-1.57 (m, 1H), 0.86-0.79 (m, 6H).

Step 4: (2R,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-iso butylpyrrolidine-2-carboxylic Acid The title compound was prepared as a yellow solid (160 mg 54%) according to step 4 of example 6 by using (R)-methyl 4-(2-chloro-4-fluorophenyl)-6-(((S)-2-((3S,5R)-5-(methoxycarbonyl)-1-isobutylpyrrolidine-3-yl)-3-oxohexahydroimidazo[1,5-a]pyrazin-7(1H)-yl)methyl)-2-(thiazol-2-yl)-1,4-dihydropyrimidine-5-carboxylate (300 mg, 0.44 mmol), methanol (6 mL) and lithium hydroxide monohydrate (87 mg 2.18 mmol) as materials. MS (ESI, pos.ion) m/z: 674.2[M+H]+; 1H NMR (400 MHz, DMSO-$d_6$) δ 8.11-8.08 (m, 2H), 7.52-7.41 (m, 2H), 7.25-7.15 (m 1H), 6.02 (s, 1H), 4.60-4.43 (m, 4H), 4.15-4.00 (m, 2H), 3.88-3.79 (m, 2H), 3.61-3.58 (m, 1H), 3.56 (s, 3H), 3.50-3.40 (m, 2H), 3.35-3.24 (m, 2H), 3.20-3.18 (m, 1H), 3.15-3.05 (m, 2H), 3.04-2.95 (m, 2H), 2.30-2.20 (m, 1H), 2.00-1.91 (m, 1H), 1.02 (d, J=6.5 Hz, 3H), 0.95 (d, J=6.6 Hz, 3H).

Example 9: (2R,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-(m ethylsulfonyl)pyrrolidine-2-carboxylic Acid Step 1: (R)-tert-butyl 2-((3S,5R)-5-(methoxycarbonyl)-1-(methylsulfonyl)pyrrolidine-3-yl)-3-oxohexahydroimidazo[1,5-a]pyrazin-7(1H)-carboxylate

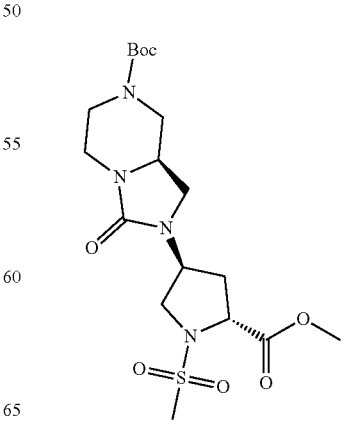

To a solution of (R)-tert-butyl 2-((3S,5R)-5-(methoxycarbonyl)pyrrolidin-3-yl)-3-oxohexahydroimidazo[1,5-a]pyrazine-7(1H)-carboxylate (500 mg, 1.357 mmol) and triethylamine (278 mg, 2.71981 mmol) in dichloromethane (8 mL) was added methylsufonyl chloride (238 mg 2.036 mmol) under an ice bath, the mixture was kept in this temperature and stirred for 30 min, and then warmed to rt and further stirred until the reaction was completed. After the reaction was complete, the mixture was diluted with water (10 mL), and extracted with dichloromethane (10 mL×3), the organic layers were combined and washed with saturated aqueous NaCl (30 mL), concentrated in vacuo to give the title compound as a white solid (400 mg 66%). MS (ESI, pos.ion) m/z: 469.7 [M+Na]$^+$.

Step 2: (2R,4S)-4-((R)-7-(tert-butoxycarbonyl)-3-oxohexahydroimidazo[1,5-a]pyrazin-2(3H)-yl)-1-(methylsulfonyl)pyrrolidine-2-carboxylic Acid

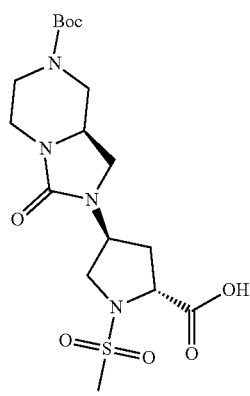 [SMILES: CC(C)(C)OC(=O)N1CCN2C(=O)N([C@H]3C[C@H](C(=O)O)N(S(C)(=O)=O)C3)C[C@@H]2C1]

To a dry flask were added (R)-tert-butyl 2-((3S,5R)-5-(methoxycarbonyl)-1-(methylsulfonyl)pyrrolidine-3-yl)-3-oxohexahydroimidazo[1,5-a]pyrazine-7(1H)-carboxylate (0.4 g 0.89 mmol), methanol (5 mL), water (5 mL) and lithium hydroxide monohydrate (0.37 g 8.9 mmol). The mixture was stirred at rt for 12 hours and concentrated in vacuo, the residue was diluted with water (50 mL) and EtOAc (60 mL), the resulting mixture was adjusted with concentrated hydrochloric acid to pH 5-6 and stood to separate into layers, the organic layer was washed with saturated aqueous NaCl and dried over anhydrous sodium sulfate. The mixture was filtered. The filtrate was concentrated in vacuo to get the title compound as a colorless oil (0.38 g, 100%). MS (ESI, pos.ion) m/z: 433.1 [M+H]$^+$.

Step 3: (2R,4S)-1-(methylsulfonyl)-4-((S)-3-oxohexahydroimidazo[1,5-a]pyrazin-2(3H)-yl) pyrrolidine-2-carboxylic acid trifluoroacetate

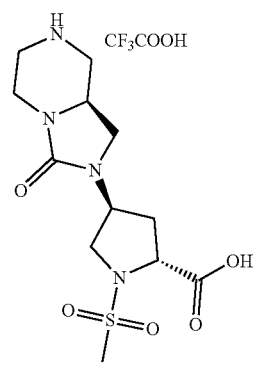 [SMILES: CS(=O)(=O)N1C[C@@H](N2C[C@@H]3CNCCN3C2=O)C[C@@H]1C(=O)O ; "CF3COOH"]

To a dry flask were added (2R,4S)-4-((R)-7-(tert-butoxycarbonyl)-3-oxohexahydroimidazo[1,5-a]pyrazin-2(3H)-yl)-1-(methylsulfonyl)pyrrolidine-2-carboxylic acid (0.38 g 0.88 mmol), DCM (5 mL) and TFA (5 mL), the mixture stirred at rt for 12 hours and concentrated in vacuo to get the title compound as a slightly brown oil (0.39 g 100%). MS (ESI, pos.ion) m/z: 333.1 [M+H]$^+$.

Step 4: (2R,4S)-4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-1-(methylsulfonyl) pyrrolidine-2-carboxylic Acid To a dry flask were added (2R,4S)-1-(methylsulfonyl)-4-((S)-3-oxohexahydroimidazo[1,5-a]pyrazin-2(3H)-yl)pyrrolidine-2-carboxylic acid trifluoroacetate (0.39 g 0.87 mmol), (R)-methyl 6-(bromomethyl)-4-(2-chloro-4-fluorophenyl)-2-(thiazol-2-yl)-1,4-dihydro pyrimidine-5-carboxylate (0.39 g 0.87 mmol), potassium carbonate (0.25 g 1.8 mmol) and anhydrous ethanol (10 mL) in turn. The mixture was stirred at rt for 12 hours, after the reaction was completed, the mixture was filtered, the filtrated was concentrated in vacuo. The residue was purified by silica gel column chromatography (PE/EtOAc (v/v)=10/1) to give the title compound as a yellow solid (242 mg 40%). MS (ESI, pos.ion) m/z: 696.1 [M+H]$^+$; $^1$H NMR (400 MHz, DMSO-$d_6$) δ 8.08 (dd, J=9.2, 3.1 Hz, 2H), 7.50 (dd, J=8.7, 6.2 Hz, 1H), 7.45 (dd, J=8.8, 2.6 Hz, 1H), 7.22 (td, J=8.5, 2.6 Hz, 1H), 6.02 (s, 1H), 4.58 (d, J=16.1 Hz, 1H), 4.52-4.44 (m, 2H), 4.38 (dd, J=9.2, 2.6 Hz, 1H), 4.16-4.08 (m, 1H), 3.91-3.84 (m, 1H), 3.57 (s, 3H), 3.55-3.49 (m, 4H), 3.43-3.32 (m, 2H), 3.20 (dd, J=9.2, 2.3 Hz, 1H), 3.13-2.98 (m, 5H), 2.43-2.32 (m, 1H), 2.05 (ddd, J=12.6, 6.6, 2.6 Hz, 1H).

Example 10: 2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazole-5-carboxylic Acid Step 1: (S)-methyl 2-(7-(tert-butoxycarbonyl)-3-oxohexahydroimidazo[1,5-a]pyrazin-2(3H)-yl)thiazole-5-carboxylate

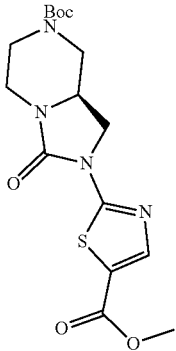 [SMILES: COC(=O)c1cnc(N2C[C@@H]3CN(C(=O)OC(C)(C)C)CCN3C2=O)s1]

To a 25 mL two-neck flask were added (R)-tert-butyl 3-oxohexahydroimidazo[1,5-a]pyrazine-7(1H)-carboxylate (300 mg 1.24 mmol), methyl 2-bromothiazole-5-carboxylate (290 mg 1.31 mmol), Xantphos (72 mg 0.12 mmol), tris(dibenzylideneacetone)dipalladium (68 mg 0.07 mmol), cesium carbonate (810 mg, 2.49 mmol) and dioxane (10 mL). The reaction mixture was stirred at 105° C. for 2 hours under nitrogen. The mixture was filtered by suction filtration, the filter cake was washed with ethyl acetate (20 mL). The organic phase was washed with saturated brine (10 mL×3), dried over anhydrous sodium sulfate, filtered, and the filtrate was concentrated in vacuo. The residue was purified by silica gel chromatograph (PE/EtOAc (V/V)=2/1) to give the title compound as a earthy yellow solid (359 mg, 76%). MS (ESI, pos.ion) m/z: 383.0[M+H]$^+$.

Step 2: (S)-2-(7-(tert-butoxycarbonyl)-3-oxohexahydroimidazo[1,5-a]pyrazin-2(3H)-yl)thiazole-5-carboxylic Acid

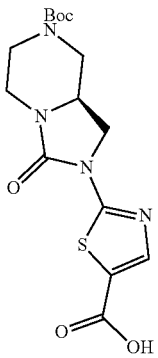 [SMILES: CC(C)(C)OC(=O)N1CCN2C(=O)N(c3ncc(C(=O)O)s3)C[C@@H]2C1]

To a 50 mL single neck flask were added (S)-methyl 2-(7-(tert-butoxycarbonyl)-3-oxohexahydroimidazo[1,5-a]pyrazin-2(3H)-yl)thiazole-5-carboxylate (333 mg 0.87 mmol), THF (5 mL), water (5 mL) and LiOH.H$_2$O (183 mg 4.36 mmol). The reaction mixture was stirred at rt for 1.5 hours and adjusted with hydrochloric acid (6 M) to pH 7 under an ice bath. The resulting mixture was concentrated in vacuo, the residue was diluted with ethyl acetate (10 mL) and water (5 mL) and adjusted with saturated potassium carbonate aqueous solution to pH 9. The mixture was stood to separated into layers. The organic layer was discarded. The water layer was washed with ethyl acetate (10 mL×2), and to the water layer was added ethyl acetate (10 mL) and the resulting mixture was adjusted with hydrochloric acid (6 M) to pH 4-5, and the organic layers was dried over anhydrous sodium sulfate and filtered.

The filtrated was concentrated in vacuo to get the title compound as a brownish yellow solid (232 mg, 72%). MS (ESI, pos.ion) m/z: 369.1 [M+H]$^+$.

Step 3: (S)-2-(3-oxohexahydroimidazo[1,5-a]pyrazin-2(3H)-yl)thiazole-5-carboxylic Acid hydrochloride

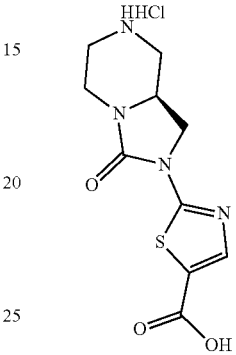

To a 50 mL single neck flask were added (S)-2-(7-(tert-butoxycarbonyl)-3-oxohexahydroimidazo[1,5-a]pyrazin-2(3H)-yl)thiazole-5-carboxylic acid (230 mg, 0.62 mmol), ethyl acetate (5 mL) and HCl ethyl acetate solution (5 mL, 20 mmol, 4 mol/L). The mixture was stirred at rt for 2 hours. The mixture was stood for 5 min, the supernatant was discarded. The solid was washed with ethyl acetate (5 mL×2) to get the tile compound as a beige solid (190 mg 99%). MS (ESI, pos.ion) m/z: 269.1 [M+H]$^+$ Step 4: 2-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)thiazole-5-carboxylic Acid

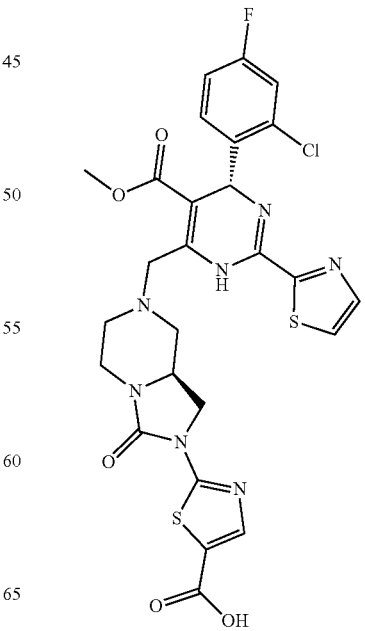

To a 50 mL single flask were added (R)-methyl 6-(bromomethyl)-4-(2-chloro-4-fluorophenyl)-2-(thiazol-2-yl)-1,4-dihydropyrimidine-5-carboxylate (315 mg, 0.56 mmol), (S)-2-(3-oxohexahydroimidazo[1,5-a]pyrazin-2(3H)-yl)thiazole-5-carboxylic acid hydrochloride (190 mg 0.62 mmol), potassium carbonate (174 mg, 1.25 mmol) and ethanol (10 mL) in turn, the reaction mixture was stirred at rt for 24 hours and filtered, the filtrate was concentrated in vacuo. The residue was purified by silica gel column chromatography (DCM/CH$_3$OH (V/V)=25/1) to give the title compound as a pale yellow solid (59 mg, 15%). MS (ESI, pos.ion) m/z: 632.0 [M+H]$^+$; $^1$H NMR (400 MHz, DMSO-d$_6$) δ 9.69 (s, 1H), 8.03 (d, J=2.9 Hz, 1H), 7.94 (d, J=2.9 Hz, 1H), 7.48 (s, 1H), 7.43-7.39 (m, 2H), 7.18 (td, J=8.2, 1.9 Hz, 1H), 6.05 (s, 1H), 4.13-4.03 (m, 1H), 4.01-3.82 (m, 4H), 3.62 (dd, J=10.4, 4.4 Hz, 1H), 3.51 (s, 3H), 3.12 (t, J=11.0 Hz, 1H), 3.01-2.94 (m, 2H), 2.34 (t, J=10.1 Hz, 1H), 2.19 (t, J=10.8 Hz, 1H).

Example 11: (2R)-2-(7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-phenylpropionic Acid Step 1: (R)-2-((tert-butoxycarbonyl)amino)-3-phenylpropionic Acid

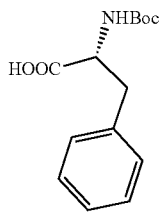

To a dry flask were added (R)-phenylalanine (4.2 g 25 mmol), water (30 mL), 1,4-dioxane (30 mL) and sodium bicarbonate (5.1 g 61 mmol) in turn, After stirring for 10 min, (Boc)$_2$O (10.1 g 45.8 mmol) was added. The resulting mixture was stirred at rt for 24 hours. After the reaction was completed, the mixture was concentrated in vacuo to remove the solvent. The residue was diluted with water (20 mL) and EtOAc (100 mL), and adjusted with HCl (1 M) to pH 6-7. The resulting mixture was stood to separate into layers, the organic layer was washed with saturated aqueous NaCl and dried over anhydrous sodium sulfate, filtered. The filtrate was concentrated in vacuo to remove the solvent to get the title compound as a colorless oil (6.0 g 91%). MS (ESI, pos.ion) m/z: 288.2 [M+Na]$^+$.

Step 2: (R)-benzyl 2-((tert-butoxycarbonyl)amino)-3-phenylpropionate

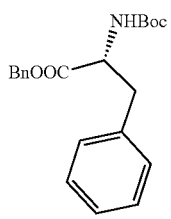

To a dry flask were added (R)-2-((tert-butoxycarbonyl)amino)-3-phenylpropionic acid (6.0 g 23 mmol), benzyl bromide (4.0 mL, 37 mmol), potassium carbonate (6.3 g 45 mmol) and acetonitrile (90 mL) in turn, the mixture was stirred at rt for 1.5 hours and filtered. The filtrate was concentrated in vacuo to remove the solvent. To the residue was added ethyl acetate (90 mL), the organic layer was washed with saturated aqueous NaCl (60 mL×2) and dried over anhydrous sodium sulfate, filtered. The filtrate was concentrated in vacuo to get the title compound as a pale yellow oil (5.72 g 70%). MS (ESI, pos.ion) m/z: 378.2 [M+Na]$^+$.

Step 3: (R)-benzyl 2-amino-3-phenylpropionate hydrochloride

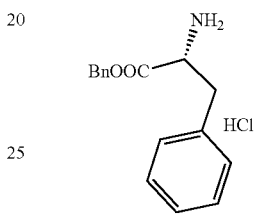

To a 250 mL single neck were added (R)-benzyl 2-((tert-butoxycarbonyl)amino)-3-phenylpropionate (4.0 g 11 mmol) and HCl ethyl acetate solution (4 mol/L, 50 mL). The mixture was stirred at rt for 6 h, and then filtered. The filter cake was washed with ethyl acetate (20 mL) to get the title compound as a white solid (2.1 g 64%).

Step 4: di-tert-butyl 2-((((R)-1-(benzyloxy)-1-oxo-3-phenylpropan-2-yl)amino)methyl) piperazine-1,4-dicarboxylate

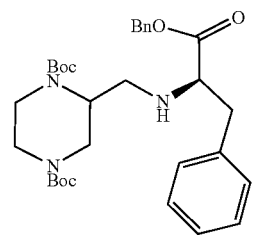 [SMILES: CC(C)(C)OC(=O)N1CCN(C(=O)OC(C)(C)C)C(CN[C@H](Cc2ccccc2)C(=O)OCc2ccccc2)C1]

To a 100 mL single neck flask were added di-tert-butyl 2-formylpiperazine-1,4-dicarboxylate (2.1 g 6.7 mmol), (R)-benzyl 2-amino-3-phenylpropionate hydrochloride (2.1 g 7.2 mmol), dichloromethane (40 mL) and triethylamine (2.0 mL, 14.35 mmol). The mixture was stirred at rt for 3 hours, and subsequently, sodium cyanoborohydride (0.88 g 13 mmol) was added, the resulting mixture was stirred at rt for 12 h and concentrated in vacuo. The residue was purified by silica gel column chromatography (PE/EtOAc (V/V)=1/10) to get the title compound as a colorless oil (2.2 g 59%). MS (ESI, pos.ion) m/z: 554.3 [M+H]$^+$.

Step 5: di-tert-butyl 2-((((R)-1-(benzyloxy)-1-oxo-3-phenylpropan-2-yl)((4-nitrophenoxy) carbonyl)amino)methyl)piperazine-1,4-dicarboxylate

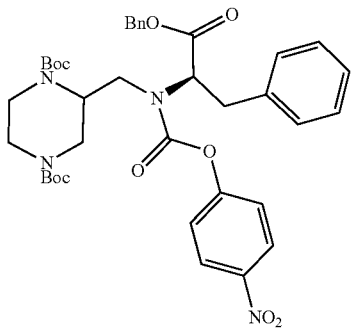 [SMILES: CC(C)(C)OC(=O)N1CCN(C(=O)OC(C)(C)C)C(CN(C(=O)Oc2ccc([N+](=O)[O-])cc2)[C@H](Cc2ccccc2)C(=O)OCc2ccccc2)C1]

To a 100 mL single neck flask were added di-tert-butyl 2-((((R)-1-(benzyloxy)-1-oxo-3-phenylpropan-2-yl)amino)methyl)piperazine-1,4-dicarboxylate (2.2 g 4.0 mmol), dichloromethane (40 mL) and DIPEA (1.5 mL, 8.6 mmol), the mixture was mixed uniformly, p-nitrophenyl chloroformate (0.88 g 4.4 mmol) was added. The resulting mixture was stirred at 40° C. for 2 h and concentrated in vacuo. The residue was purified by silica gel column chromatography (PE/EtOAc (v/v)=10/1) to give the title compound as a colorless oil (2.9 g 100%). MS (ESI, pos.ion) m/z: 741.2 [M+Na]$^+$.

Step 6: tert-butyl 2-((R)-1-(benzyloxy)-1-oxo-3-phenylpropan-2-yl)-3-oxohexahydroimidazo[1,5-a]pyrazine-7(1H)-carboxylate

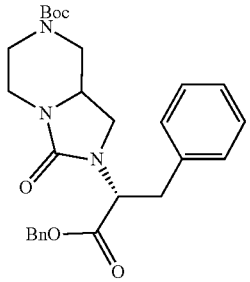 [SMILES: CC(C)(C)OC(=O)N1CCN2C(=O)N([C@H](Cc3ccccc3)C(=O)OCc3ccccc3)CC2C1]

To a 50 mL single neck flask were added di-tert-butyl 2-((((R)-1-(benzyloxy)-1-oxo-3-phenylpropan-2-yl)((4-nitrophenoxy)carbonyl)amino)methyl)piperazine-1,4-dicarboxylate (1.3 g 1.8 mmol), dichloromethane (4 mL) and trifluoroacetic acid (8 mL). The mixture was stirred at rt for 30 min and concentrated in vacuo. To the residue was added dichloromethane (20 mL) and DIPEA (1.6 mL, 9 mmol). The mixture was stirred at 40° C. for 1 hour, and then (Boc)$_2$O (0.84 mL, 4 mmol) was added, the resulting mixture was further stirred at 40° C. for 2 hours. After the reaction was completed, the mixture was diluted with dichloromethane (20 mL) and washed with saturated aqueous NaCl. The organic layer was dried over anhydrous sodium sulfate and filtered. The filtrate was concentrated in vacuo. The residue was purified by silica gel column chromatography (PE/EtOAc (v/v)=4/1) to give the title compound as a colorless oil (0.36 g 42%). MS (ESI, pos.ion) m/z: 480.2 [M+H]$^+$;

Step 7: (2R)-2-(7-(tert-butoxycarbonyl)-3-oxohexahydroimidazo[1,5-a]pyrazine-2(3H)-yl)-3-phenylpropionic Acid

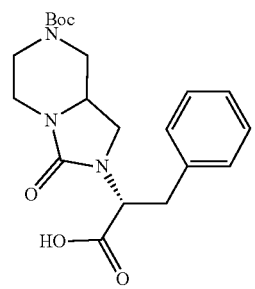 [SMILES: CC(C)(C)OC(=O)N1CCN2C(=O)N([C@H](Cc3ccccc3)C(=O)O)CC2C1]

To a 50 mL single neck flask were added tert-butyl 2-((R)-1-(benzyloxy)-1-oxo-3-phenylpropan-2-yl)-3-oxohexahydroimidazo[1,5-a]pyrazine-7(1H)-carboxylate (0.36 g, 0.75 mmol), ethyl acetate (8 mL) and Pd/C (10%, 0.45 g). The mixture was stirred at rt under H$_2$ for 2 hours and filtered. The filtrate was concentrated in vacuo to get the title compound as a white solid (0.27 g 92%). MS (ESI, pos.ion) m/z: 390.1 [M+H]$^+$.

Step 8: (2R)-2-(3-oxohexahydroimidazo[1,5-a]pyrazin-2(3H)-yl)-3-phenylpropionic Acid hydrochloride

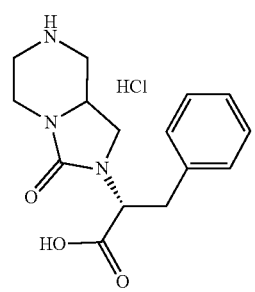 [SMILES: O=C(O)[C@@H](Cc1ccccc1)N1CC2CNCCN2C1=O ; Cl]

To a 25 mL single neck flask were added (2R)-2-(7-(tert-butoxycarbonyl)-3-oxohexahydroimidazo[1,5-a]pyrazin-2(3H)-yl)-3-phenylpropionic acid (0.27 g 0.69 mmol) and a solution of hydrogen chloride in EtOAc (6 mL). The reaction mixture was stirred at rt for 1 hours and concentrated in vacuo. The residue was diluted with toluene and then concentrated in vacuo, the process was repeated twice. The title compound was obtained as a grayish white solid (0.2 g 91%). MS (ESI, pos.ion) m z: 290.1 [M+H]$^+$.

Step 9: (2R)-2-(7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-phenylpropionic Acid To a 50 mL flask were added (2R)-2-(3-oxohexahydroimidazo[1,5-a]pyrazin-2(3H)-yl)-3-phenylpropionic acid hydrochloride (200 mg 0.61 mmol), (R)-methyl 4-(2-chloro- 4-fluorophenyl)-6-(bromomethyl)-2-(thiazol-2-yl)-1,4-dihydropyrimidine-5-carboxy late (0.39 g 0.61 mmol), potassium carbonate (0.24 g 1.7 mmol) and ethanol (15 mL), the mixture was stirred at rt for 12 hours. The mixture was filtered, the filter cake was washed with ethyl acetate (5 mL). The combined filtrates were concentrated and diluted with water (30 mL) and ethyl acetate (10 mL), the mixture was stood to separate into layers, the organic layer was discarded. The water layer was washed with ethyl acetate (10 mL×3), the organic layer was discarded. The water phase was diluted with ethyl acetate (40 mL) and adjusted with hydrochloric acid to pH 5, the water layer was discarded, the organic layer was washed with saturated aqueous NaCl and dried over anhydrous sodium sulfate and filtered. The filtrate was concentrated in vacuo to get the title compound as a yellow solid (0.27 g 67%). MS (ESI, pos.ion) m/z: 653.1 [M+1]$^+$; $^1$H NMR (400 MHz, CD$_3$OD) δ 7.94 (d, J=3.2 Hz, 1H), 7.74 (d, J=2.0 Hz, 1H), 7.38 (dd, J=8.8, 2.0 Hz, 1H), 7.26-7.34 (m, 5H), 7.24-7.21 (dd, J=8.8, 2.4 Hz, 1H), 7.05-7.01 (m, 1H), 6.16 (s, 1H), 3.87 (d, J=16.8 Hz, 1H), 3.82-3.68 (m, 3H), 3.64 (s, 3H), 3.62-3.61 (m, 1H), 3.43 (dd, J=14.8, 4.8 Hz, 1H), 3.15-3.09 (m, 1H), 3.05-2.93 (m, 2H), 2.76 (d, J=10.8 Hz, 1H), 2.48 (d, J=8.5 Hz, 1H).

Example 12: 3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-phenylpropionic Acid Step 1: (2R)-di-tert-butyl 2-(((3-(benzyloxy)-3-oxo-1-phenylpropyl)amino)methyl)piperazine-1,4-dicarboxylate

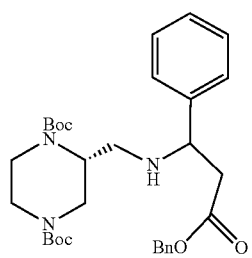 [SMILES: CC(C)(C)OC(=O)N1CCN(C(=O)OC(C)(C)C)[C@H](CNC(CC(=O)OCc2ccccc2)c2ccccc2)C1]

To a 100 mL single neck flask were added (S)-di-tert-butyl 2-formylpiperazine-1,4-dicarboxylate (2.0 g 6.4 mmol), benzyl 3-amino-3-phenylpropionate hydrochloride (1.8 g 7.0 mmol), dichloromethane (40 mL) and triethylamine (1.8 mL). The mixture was stirred at rt for 3 hours, and subsequently, sodium cyanoborohydride (0.8 g 10 mmol) was added, the resulting mixture was stirred at rt for 5 h. After the reaction was completed. The mixture was concentrated in vacuo. The residue was purified by silica gel column chromatography (PE/EtOAc (v/v)=10/1) to give the title compound as a colorless oil (1.4 g 40%). MS (ESI, pos.ion) m/z: 554.8 [M+H]$^+$.

Step 2: (2S)-di-tert-butyl 2-(((3-(benzyloxy)-3-oxo-1-phenylpropyl)((4-nitrophenyloxy) carbonyl)amino)methyl)piperazine-1,4-dicarboxylate

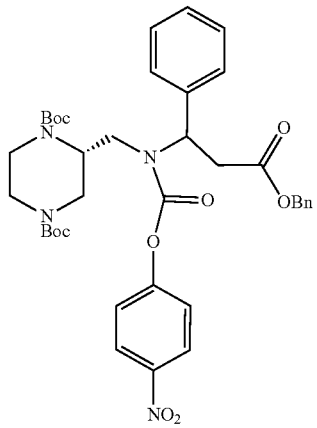 [SMILES: CC(C)(C)OC(=O)N1CCN(C(=O)OC(C)(C)C)[C@H](CN(C(=O)Oc2ccc([N+](=O)[O-])cc2)C(CC(=O)OCc2ccccc2)c2ccccc2)C1]

To a 100 mL single neck flask were added (2R)-di-tert-butyl 2-(((3-(benzyloxy)-3-oxo-1-phenylpropyl)amino)methyl)piperazine-1,4-dicarboxylate (1.2 g 2.17 mmol), dichloromethane (15 mL), p-nitrophenyl chloroformate (0.66 g 3.3 mmol) and DIPEA (0.5 mL, 3 mmol). The resulting mixture was stirred at rt for 3 h. After the reaction was completed. The mixture was concentrated in vacuo. The residue was purified by silica gel column chromatography (PE/EtOAc (v/v)=10/1) to give the title compound as a colorless oil (1.4 g 90%).

Step 3: (8aR)-tert-butyl 2-(3-(benzyloxy)-3-oxo-1-phenylpropyl)-3-oxohexahydroimidazo[1,5-a]pyrazine-7(1H)-carboxylate

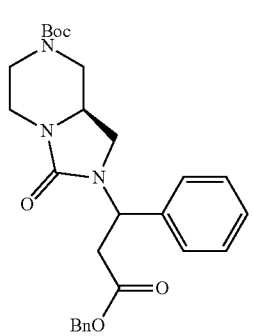 [SMILES: CC(C)(C)OC(=O)N1CCN2C(=O)N(C(CC(=O)OCc3ccccc3)c3ccccc3)C[C@@H]2C1]

To a 100 mL single neck flask were added (2S)-di-tert-butyl 2-(((3-(benzyloxy)-3-oxo-1-phenylpropyl)((4-nitrophenyloxy)carbonyl)amino)methyl)piperazine-1,4-dicarboxylate (1.0 g 1.4 mmol), dichloromethane (10 mL) and trifluoroacetic acid (10 mL). The mixture was stirred at rt for 30 min and concentrated in vacuo. The residue was diluted with toluene (10 mL) and concentrated again, the process was repeated twice. The residue was diluted with dichloromethane (20 mL) and DIPEA (2.0 mL), the mixture was stirred at 40° C. for 4 hour, and then (Boc)$_2$O (1.4 mL, 5.9 mmol) was added, the resulting mixture was further stirred at 40° C. for 2 hours. After the reaction was completed, the mixture was diluted with dichloromethane (20 mL), and the organic phase was washed with saturated aqueous NaCl and dried over anhydrous sodium sulfate and filtered. The filtrate was concentrated in vacuo. The residue was purified by silica gel column chromatography (PE/EtOAc (v/v)=5/1) to give the title compound as a colorless oil (0.6 g 90%). MS (ESI, pos.ion) m/z: 480.7 [M+H]+.

Step 4: 3-((R)-7-(7-tert-butoxycarbonyl)-3-oxohexahydroimidazo[1,5-a]pyrazin-2(3H)-yl)-3-phenylpropionic Acid

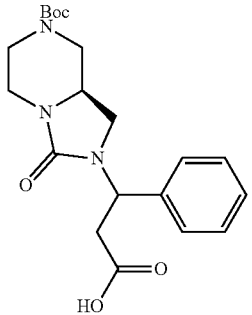 [SMILES: CC(C)(C)OC(=O)N1CCN2C(=O)N(C(CC(=O)O)c3ccccc3)C[C@@H]2C1]

To a 50 mL single neck flask were added (8aR)-tert-butyl 2-(3-(benzyloxy)-3-oxo-1-phenylpropyl)-3-oxohexahydroimidazo[1,5-a]pyrazine-7(1H)-carboxy late (0.33 g 0.69 mmol), ethyl acetate (15 mL) and Pd/C (0.3 g wt. %=10%). The mixture was stirred at rt under $H_2$ for 2 hours. After the reaction was completed, the mixture was filtered and concentrated to get the title compound as a colorless oil (0.27 g 100%). MS (ESI, pos.ion) m/z: 334.5. [M+H−56]+.

Step 5: 3-((S)-3-oxohexahydroimidazo[1,5-a]pyrazin-2(3H)-yl)-3-phenylpropionic Acid trifluoroacetate

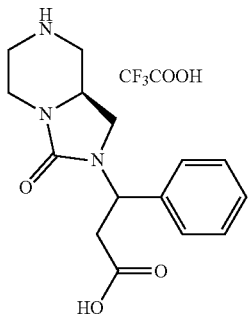 [SMILES: O=C(O)CC(c1ccccc1)N1C[C@@H]2CNCCN2C1=O ; "CF3COOH"]

To a 50 mL flask were added 3-((R)-7-(7-tert-butoxycarbonyl)-3-oxohexahydroimidazo[1,5-a]pyrazin-2(3H)-yl)-3-phenylpropionic acid (0.33 g 0.85 mmol), DCM (5 mL) and TFA (5 mL), the mixture stirred at rt for 6 hours and concentrated in vacuo to get the title compound as a colorless oil (0.3 g 87%).

Step 6: 3-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)-3-phenylpropionic Acid To a 50 mL flask were added 3-((S)-3-oxohexahydroimidazo[1,5-a]pyrazin-2(3H)-yl)-3-phenylpropionic acid trifluoroacetate (300 mg, 0.74 mmol), (R)-methyl 4-(2-chloro-4-fluorophenyl)-6-(bromomethyl)-2-(thiazol-2-yl)-1,4-dihydropyrimidine-5-carboxy late (0.43 g 0.92 mmol), potassium carbonate (0.25 g 1.84 mmol) and ethanol (15 mL). The mixture was stirred at 35° C. for 16 hours. The mixture was filtered, the filter cake was washed with ethyl acetate (5 mL). The filtrate was concentrated in vacuo. The residue was diluted with ethyl acetate (20 mL) and water (10 mL). The mixture was adjusted with concentrated hydrochloric acid to pH 5, the water phase was discarded, the organic phase was washed with saturated brine (10 mL), dried over anhydrous sodium sulfate, filtered, and the filtrate was concentrated in vacuo. The residue was purified by silica gel chromatograph (DCM/$CH_3OH$ (V/V)=10/1) to give the title compound as a yellow solid (150 mg 20%). MS (ESI, pos.ion) m/z: 653.1 [M+H]+; $^1$H NMR (400 MHz, $CD_3OD$) δ 7.92 (d, J=3.1 Hz, 1H), 7.73 (d, J=3.1 Hz, 1H), 7.44-7.41 (m, 1H), 7.40-7.31 (m, 5H), 7.24 (dd, J=8.7, 2.6 Hz, 1H), 7.05 (td, J=8.4, 2.6 Hz, 1H), 6.17 (s, 1H), 5.52 (t, J=7.9 Hz, 1H), 4.07 (d, J=17.0 Hz, 1H), 3.93-3.86 (m, 2H), 3.81 (ddd, J=10.1, 7.4, 4.5 Hz, 1H), 3.61 (s, 3H), 3.20 (d, J=12.3 Hz, 1H), 3.13 (d, J=5.7 Hz, 2H), 2.98 (dd, J=7.9, 2.7 Hz, 2H), 2.88 (d, J=11.1 Hz, 1H), 2.76 (d, J=10.5 Hz, 1H), 2.36 (td, J=11.8, 3.1 Hz, 1H), 2.24 (t, J=11.0 Hz, 1H).

Example 13: 3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)propionic Acid Step 1: methyl 4-bromophenylpropionate

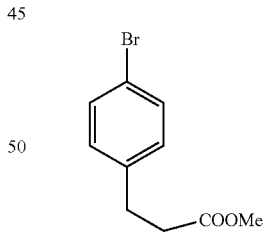

To a 100 mL single neck was added 3-(4-bromophenyl)propionic acid (0.50 g 2.2 mmol), acetonitrile (20 mL), potassium carbonate (0.60 g 4.3 mmol) and iodomethane (0.16 mL, 2.6 mmol), the mixture was stirred at 25° C. for 2 hours and filtered. The filtrate was concentrated. The residue was purified by silica gel column chromatography (PE/EtOAc (v/v)=15/1) to give the title compound as a colorless oil (0.43 g 81%). $^1$H NMR (400 MHz, $CDCl_3$) δ 7.42 (d, J=8.3 Hz, 2H), 7.09 (d, J=8.3 Hz, 2H), 3.68 (s, 3H), 2.92 (t, J=7.7 Hz, 2H), 2.63 (t, J=7.7 Hz, 2H).

Step 2: (R)-tert-butyl 2-(4-(3-methoxy-3-oxopropyl)phenyl)-3-oxohexahydroimidazo[1,5-a]pyrazin-7(1H)-carboxylate

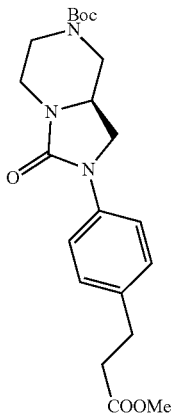 [SMILES: COC(=O)CCc1ccc(N2C[C@@H]3CN(C(=O)OC(C)(C)C)CCN3C2=O)cc1]

To a 100 mL two-neck flask were added (R)-tert-butyl 3-oxohexahydroimidazo[1,5-a]pyrazine-7(1H)-carboxylate (228 mg, 0.95 mmol), methyl 3-(4-bromophenyl)propionate (230 mg 0.95 mmol), tris(dibenzylideneacetone)dipalladium (87 mg 0.095 mmol), 2-di-tert-butylphosphino-2',4',6'-triisopropylbiphenyl (80 mg 0.19 mmol), cesium carbonate (0.62 g 1.89 mmol) and 1,4-dioxane (10 mL). The mixture was stirred at 90° C. for 2 hours, and concentrated in vacuo. The residue was purified by silica gel column chromatography (PE/EtOAc (v/v)=1/1) to give the title compound as a white solid (171 mg 45%). MS (ESI, pos.ion) m/z: 426.1[M+Na]$^+$.

Step 3: (R)-3-(4-(7-(tert-butoxycarbonyl)-3-oxohexahydroimidazo[1,5-a]pyrazin-2(3H)-yl)phenyl)propionic Acid

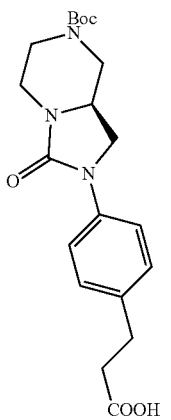 [SMILES: CC(C)(C)OC(=O)N1CCN2C(=O)N(c3ccc(CCC(=O)O)cc3)C[C@@H]2C1]

To a 50 mL single neck flask were added (R)-tert-butyl 2-(4-(3-methoxy-3-oxopropyl)phenyl)-3-oxohexahydroimidazo[1,5-a]pyrazin-7(1H)-carboxylate (161.5 mg 0.40 mmol), methanol (2 mL), water (2 mL) and lithium hydroxide monohydrate (83 mg 2.0 mmol). The reaction mixture was stirred at 25° C. for 6 hours and concentrated, the residue was diluted with water (5 mL) and ethyl acetate (10 mL). The mixture was stood to separate into layers, the water layer was adjusted with dilute hydrochloric acid (1 M) to pH 5, and then extracted with ethyl acetate (10 mL). The organic layer was washed with saturated aqueous NaCl and dried over anhydrous sodium sulfate, filtered. The filtrate was concentrated to get the title compound as a white solid (0.12 g 77%). MS (ESI, pos.ion) m/z: 412.1[M+Na]$^+$.

Step 4: (S)-3-(4-(3-oxohexahydroimidazo[1,5-a]pyrazin-2(3H)-yl)phenyl)propionic Acid hydrochloride

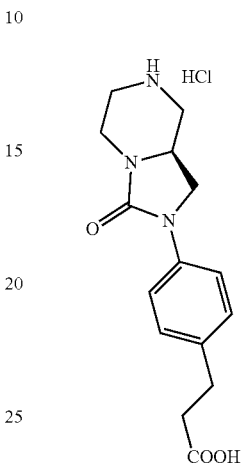

To a 25 mL single neck flask were added (R)-3-(4-(7-(tert-butyloxycarbonyl)-3-oxohexahydroimidazo[1,5-a]pyrazin-2(3H)-yl)phenyl)propionic acid (0.12 g 0.31 mmol) and HCl in 1,4-dioxane solution (4 M, 20 mL). The reaction mixture was stirred at 25° C. for 16 hours, and then the reaction mixture was concentrated in vacuo to get the title compound as a white solid (0.10 g 100%). MS: (ESI, pos.ion) m/z: 290.1 [M+H]$^+$.

Step 5: 3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)propionic Acid

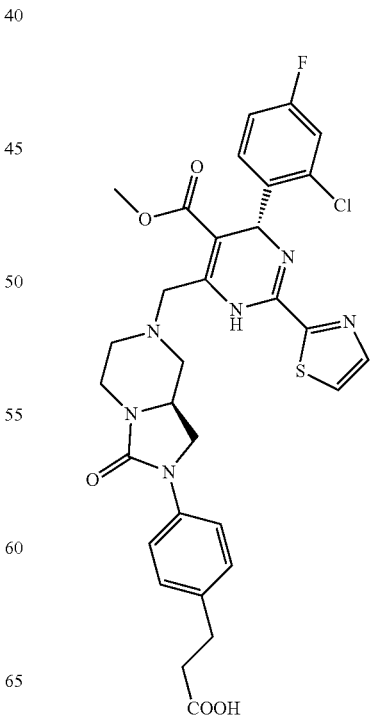

To a 25 mL two neck flask were added (S)-3-(4-(3-oxohexahydroimidazo[1,5-a]pyrazin-2(3H)-yl)phenyl)propionic acid hydrochloride (0.09 g, 0.28 mmol), (R)-methyl 4-(2-chloro-4-fluorophenyl)-6-(bromomethyl)-2-(thiazol-2-yl)-1,4-dihydropyrimidine-5-carboxylate (0.12 g, 0.28 mmol), potassium carbonate (76 mg, 0.55 mmol) and ethanol (10 mL). The reaction mixture was stirred at 35° C. for 5 hours. After the reaction was completed, the reaction mixture was filtered, the filter cake was washed with EA (5 mL), the combined filtrate was concentrated. The residue was diluted with EA (20 mL) and water (5 mL), the resulting mixture was adjusted with dilute hydrochloric acid (1 M) to pH 6, the mixture was stood to separate into layers, the water phase was extracted with EA (10 mL), the water phase was discarded, the combined organic layers were washed with saturated aqueous NaCl (10 mL) and concentrated in vacuo, the residue was purified by silica gel column chromatography (MeOH/DCM (V/V)=1/25) to give the title compound as a yellow solid (85 mg, 47.1%). MS(ESI, pos.ion) m/z: 653.0[M+H]$^+$; $^1$H NMR (400 MHz, MeOH-d$_4$) δ 7.97 (d, J=3.1 Hz, 1H), 7.76 (d, J=3.1 Hz, 1H), 7.49-7.41 (m, 3H), 7.27-7.19 (m, 3H), 7.06 (td, J=8.4, 2.6 Hz, 1H), 6.18 (s, 1H), 4.15 (d, J=17.0 Hz, 1H), 4.06-4.01 (m, 1H), 3.99-3.92 (m, 3H), 3.60 (s, 3H), 3.52 (dd, J=9.2, 4.4 Hz, 1H), 3.30-3.22 (m, 1H), 2.98 (d, J=10.6 Hz, 2H), 2.89 (t, J=7.5 Hz, 2H), 2.59 (t, J=7.6 Hz, 2H), 2.47 (td, J=11.8, 3.1 Hz, 1H), 2.26 (t, J=10.8 Hz, 1H).

Example 14: 2-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)acetic Acid Step 1: methyl 2-(4-bromophenyl)acetate

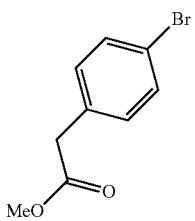

At 0° C., to a solution of 2-(4-bromophenyl)acetic acid (4 g 18.6 mmol) in methanol (22 mL) was added SOCl$_2$ (1.62 mL) dropwise slowly. After the addition, the reaction mixture was stirred at rt for 6 hours. The mixture was concentrated in vacuo, and the residue was diluted with EA (30 mL), the organic layer was washed with saturated aqueous NaCl (30 mL), saturated aqueous NaHCO$_3$ (30 mL) and saturated aqueous NaCl (30 mL) in turn, and then dried over anhydrous sodium sulfate and filtered. The filtrate was concentrated in vacuo. The residue was purified by silica gel column chromatography (EA) to give the title compound as a yellow oil (3.23 g 75.80%).

Step 2: (R)-tert-butyl 2-(4-(2-methoxy-2-oxoethyl)phenyl)-3-oxohexahydroimidazo[1,5-a]pyrazine-7(1H)-carboxylate

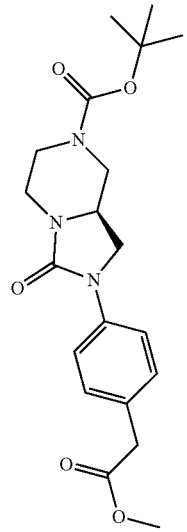 [SMILES: COC(=O)Cc1ccc(N2C[C@@H]3CN(C(=O)OC(C)(C)C)CCN3C2=O)cc1]

To a 50 mL two neck flask were added methyl 2-(4-bromophenyl)acetate (1 g 4.37 mmol), (R)-tert-butyl 3-oxohexahydroimidazo[1,5-a]pyrazine-7(1H)-carboxylate (1.05 g 4.35 mmol), Pd$_2$(dba)$_3$ (300 mg 0.32 mmol), 2-di-tert-butylphosphino-2',4',6'-triisopropylbiphenyl (200 mg 0.46 mmol) and Cs$_2$CO$_3$ (2.82 g 8.65 mmol), the system was degassed and filled with N$_2$ three times, and then 1,4-dioxane (80 mL) was added, the system was degassed and filled with N$_2$ three additional times. The mixture was stirred at 90° C. for 12 hours, and then cooled to rt, filtered by suction filtration, the filter cake was washed with EtOAc (25 mL). The filtrate was diluted with EtOAc (75 mL) and water (50 mL), and the mixture was shaken and stood to separate into layers, the water phase was extracted with EtOAc (50 mL), the combined organic layers was dried over anhydrous Na$_2$SO$_4$ and filtered. The filtrate was concentrated. The residue was purified by silica gel column chromatography (PE/EtOAc (V/V)=1.2/1) to give the title compound as a white solid (400 mg 23.53%). MS (ESI, pos.ion) m/z: 334.30 [M+H−56]$^+$.

Step 3: (S)-methyl 2-(4-(3-oxohexahydroimidazo[1,5-a]pyrazin-2(3H)-yl)phenyl)acetate trifluoroacetate

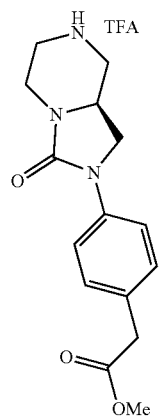 [SMILES: COC(=O)Cc1ccc(N2C[C@@H]3CNCCN3C2=O)cc1 ; "TFA"]

To a solution of (R)-tert-butyl 2-(4-(2-methoxy-2-oxoethyl)phenyl)-3-oxohexahydroimidazo[1,5-a]pyrazine-7(1H)-carboxylate (400 mg 1.03 mmol) in DCM (3.5 mL) was added TFA (1.5 mL). The reaction mixture was stirred at rt for 1.5 hours, and then the reaction mixture was concentrated in vacuo to get the title compound as a yellow oil (413 mg, 99.94%).

Step 4: (R)-methyl 4-(2-chloro-4-fluorophenyl)-6-(((S)-2-(4-(2-methoxy-2-oxoethyl)phenyl)-3-oxohexahydroimidazo[1,5-a]pyrazin-7(1H)-yl)methyl)-2-(thiazol-2-yl)-1,4-dihydropyrimidine-5-carboxylate

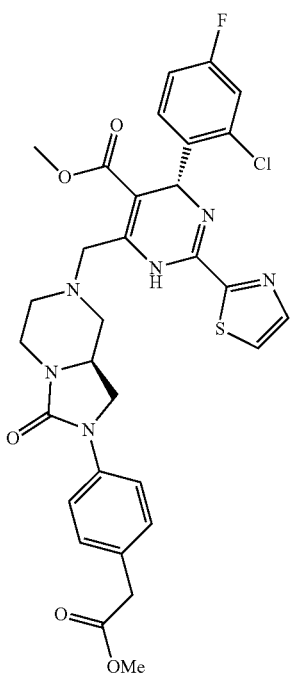 [SMILES: COC(=O)Cc1ccc(N2C[C@@H]3CN(CC4=C(C(=O)OC)[C@H](c5ccc(F)cc5Cl)N=C(c5nccs5)N4)CCN3C2=O)cc1]

(S)-Methyl 2-(4-(3-oxohexahydroimidazo[1,5-a]pyrazin-2(3H)-yl)phenyl)acetate trifluoroacetate (413 mg 1.03 mmol) were dissolved in ethanol (8 mL), and (R)-methyl 6-(bromomethyl)-4-(2-chloro-4-fluorophenyl)-2-(thiazol-2-yl)-1,4-dihydropyrimidine-5-carboxylate (500 mg 1.12 mmol) and K₂CO₃ (566 mg 4.10 mmol) were added. The reaction mixture was stirred at rt under N₂ for 12 hours and concentrated in vacuo to remove the solvent, to the residue was added EA (30 mL) and water (30 mL), the resulting mixture was shaken, and then stood to separate into layers, the organic layers were collected, the water layer was extracted with EA (20 mL), the organic layers were combined, and the combined organic layers were dried over anhydrous sodium sulfate and filtered, the filtrate was concentrated in vacuo. The residue was purified by silica gel column chromatography (PE/EtOAc (v/v)=1/1) to give the title compound as a yellow solid (347 mg 51.75%).

Step 5: 2-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)acetic Acid (R)-methyl 4-(2-chloro-4-fluorophenyl)-6-(((S)-2-(4-(2-methoxy-2-oxoethyl)phenyl)-3-oxohexahydroimidazo[1,5-a]pyrazin-7(1H)-yl)methyl)-2-(thiazol-2-yl)-1,4-dihydropyrimidine-5-carboxylate (347 mg, 0.53 mmol) was dissolved in THF (3 mL), and MeOH (3 mL) and LiOH.H₂O (140 mg) in H₂O (3 mL) were added. The reaction mixture was stirred at rt for 12 hours and adjusted with dilute hydrochloric acid to pH 5-6, the mixture was concentrated. The residue was dissolved in EA (30 mL) and washed with water (30 mL), dried over anhydrous sodium sulfate and concentrated in vacuo. The residue was purified by pre-TLC (DCM/CH₃OH (V/V)=50/1) to give the title compound as a yellow solid (130 mg 38.28%). MS (ESI, pos.ion) m/z: 639.1[M+H]; ¹H NMR (400 MHz, CDCl₃) δ 9.62 (s, 1H), 7.85 (d, J=3.1 Hz, 1H), 7.52 (d, J=8.6 Hz, 2H), 7.46 (d, J=3.1 Hz, 1H), 7.30 (s, 2H), 7.25 (overlap, 3H), 7.14 (dd, J=8.6, 2.5 Hz, 1H), 6.92 (td, J=8.5, 2.6 Hz, 1H), 6.20 (s, 1H), 4.10-4.03 (m, 2H), 3.99-3.94 (m, 1H), 3.92-3.85 (m, 2H), 3.62 (s, 2H), 3.60 (s, 3H), 3.42-3.38 (m, 1H), 3.29-3.19 (m, 1H), 2.86 (d, J=7.6 Hz, 2H), 2.54-2.44 (m, 1H), 2.28-2.17 (m, 1H).

Example 15: 2-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)-2-methylpropionic Acid Step 1: methyl 2-(4-bromophenyl)-2-methylpropionate

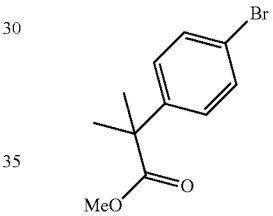

To a solution of methyl 2-(4-bromo)acetate (1.00 g 4.37 mmol) in anhydrous DMF (12.5 mL) was added NaH (700 mg 17.5 mmol, 60%) under N₂ at 0° C., after the mixture was stirred for 15 min and CH₃I (1.62 mL) was added slowly. After the addition, the reaction mixture was further stirred for 15 min at 0° C. and then stirred at rt for 12 hours. After the reaction was completed, the reaction was quenched with saturated aqueous ammonium chloride (20 mL), the resulting mixture was extracted with EA (20 mL), the organic layer was washed with saturated aqueous NaCl (30 mL) and concentrated in vacuo to get the title compound as a yellow oil (1.12 g 99.8%). H NMR (400 MHz, CDCl₃) δ 7.44 (d, J=8.7 Hz, 2H), 7.21 (d, J=8.7 Hz, 2H), 3.65 (s, 3H), 1.56 (s, 3H), 1.55 (s, 3H).

Step 2: (R)-tert-butyl 2-(4-(1-methoxy-2-methyl-1-oxoprop-2-yl)phenyl)-3-oxohexahydro imidazo[1,5-a]pyrazin-7(1H)-carboxylate

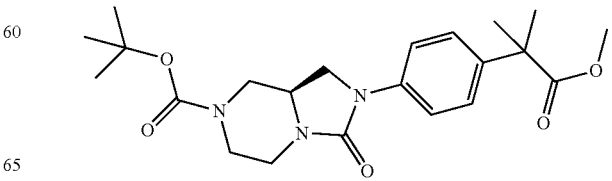

To a 50 mL two neck flask were added methyl 2-(4-bromophenyl)-2-methylpropionate (689 mg 2.68 mmol), (R)-tert-butyl 3-oxohexahydroimidazo[1,5-a]pyrazine-7(1H)-carboxylate (630 mg 2.61 mmol), Pd$_2$(dba)$_3$ (180 mg 0.19 mmol), 2-di-tert-butylphosphino-2',4',6'-triisopropylbiphenyl (550 mg, 1.26 mmol), Cs$_2$CO$_3$ (173 mg 0.53 mmol) and 1,4-dioxane (25 mL), the mixture was stirred at 90° C. for 12 hours. After the reaction was completed, the mixture was cooled to rt and filtered. The filter cake was washed with EtOAc (25 mL). To the filtrate were added EtOAc (75 mL) and water (50 mL), the mixture was shaken and separated into layers. The water layer was extracted with ethyl acetate (50 mL). The combined organic phases were dried over anhydrous sodium sulfate, filtered and the filtrate was concentrated in vacuo. The residue was purified by silica gel chromatograph (PE/EtOAc (V/V)=1.2/1) to give the title compound as a white solid (200 mg 17.88%). MS (ESI, pos.ion) m/z: 440.1 [M+Na]$^+$.

Step 3: (R)-2-(4-(7-(tert-butoxycarbonyl)-3-oxo-hexahydroimidazo[1,5-a]pyrazin-2(3H)-yl)phenyl)-2-methylpropionic Acid

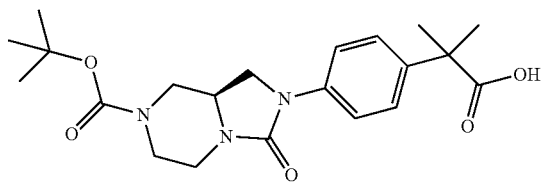 [SMILES: CC(C)(C)OC(=O)N1CCN2C(=O)N(c3ccc(C(C)(C)C(=O)O)cc3)C[C@@H]2C1]

(R)-tert-Butyl 2-(4-(1-methoxy-2-methyl-1-oxoprop-2-yl)phenyl)-3-oxohexahydro imidazo[1,5-a]pyrazine-7(1H)-carboxylate (200 mg 0.48 mmol) was dissolved in THF (6 mL), and then MeOH (2 mL) and LiOH.H$_2$O (85 mg) in H$_2$O (2 mL) were added. The reaction mixture was stirred at rt for 12 hours. After the reaction was complete, the reaction mixture was concentrated in vacuo, the residue was diluted with water (30 mL), and the resulting mixture was extracted with EtOAc (20 mL). The organic layer was discarded. The water phase was adjusted with dilute hydrochloric acid to pH 5-6, and the resulting mixture was extracted with EtOAc (30 mL) and then EtOAc (10 mL). The combined EtOAc layers were dried over anhydrous sodium sulfate. The mixture was filtered and the filtrate was concentrated in vacuo to give the title compound as a yellow solid (155 mg, 80.19%). MS (ESI, pos.ion) m/z: 426.3 [M+Na]$^+$.

Step 4: (S)-2-methyl-2-(4-(3-oxohexahydroimidazo[1,5-a]pyrazin-2(3H)-yl)phenyl)propionic acid-trifluoroacetate

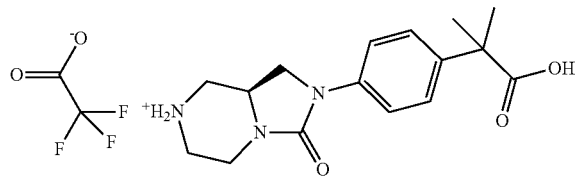

To a solution of (R)-2-(4-(7-(tert-butoxycarbonyl)-3-oxo-hexahydroimidazo[1,5-a]pyrazin-2(3H)-yl)phenyl)-2-methylpropionic acid (155 mg, 0.38 mmol) in DCM (8 mL) was added TFA (4 mL). The reaction mixture was stirred at rt for 2 hours. The reaction mixture was concentrated in vacuo to get the title compound as a yellow oil (160 mg 99.79%).

Step 5: 2-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)-2-methylpropionic Acid (S)-2-Methyl-2-(4-(3-oxohexahydroimidazo[1,5-a]pyrazin-2(3H)-yl)phenyl)propionic acid trifluoroacetate (160 mg 0.38 mmol) were dissolved in ethanol (8 mL), and (R)-methyl 6-(bromomethyl)-4-(2-chloro-4-fluorophenyl)-2-(thiazol-2-yl)-1,4-dihydropyrimidine-5-carboxylate (205 mg 0.46 mmol) and K$_2$CO$_3$ (210 mg 1.53 mmol) were added. The reaction mixture was stirred at rt for 12 hours. After the reaction was completed, the mixture was diluted with EA (30 mL) and H$_2$O (30 mL), and then adjusted with dilute hydrochloric acid (1 M) to pH 5-6. The organic layers were collected. The water layer was extracted with ethyl acetate (10 mL). The organic phases were combined, and the combined organic layers were dried over anhydrous sodium sulfate, filtered and the filtrate was concentrated in vacuo. The residue was purified by silica gel chromatograph (PE/EtOAc (V/V)=1/4) to give the title compound as a yellow solid (30 mg 11.73%). MS (ESI, pos.ion) m/z: 667.1 [M+H]$^+$. $^1$H NMR (400 MHz, CDCl$_3$) δ 9.62 (s, 1H), 7.85 (d, J=3.1 Hz, 1H), 7.52 (d, J=8.8 Hz, 2H), 7.46 (d, J=3.1 Hz, 1H), 7.37 (d, J=8.8 Hz, 2H), 7.30-7.27 (m, 1H), 7.14 (dd, J=8.6, 2.5 Hz, 1H), 6.94-6.88 (m, 1H), 6.20 (s, 1H), 4.12-3.85 (m, 5H), 3.60 (s, 3H), 3.44-3.38 (m, 1H), 3.30-3.19 (m, 1H), 2.86 (d, J=11.1 Hz, 2H), 2.55-2.44 (m, 1H), 2.24 (t, J=10.6 Hz, 1H), 1.60 (s, 6H).

Example 16: 3-((tert-butoxycarbonyl)amino)-3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2 (3H)-yl)phenyl)propanoic Acid Step 1: 3-(4-bromophenyl)-3-((tert-butoxycarbonyl)amino)propionic Acid To a solution of 3-amino-3-(4-bromophenyl)propionic acid (200 mg, 0.82 mmol) in THF (5 mL) were added NaOH (32 mg 0.8 mmol) in H$_2$O (1 mL) and Boc$_2$O (0.30 mL, 1.30 mmol), the reaction mixture was stirred at rt for 12 hours and concentrated in vacuo. The residue was diluted with EA (20 mL) and H$_2$O (10 mL), and then dilute hydrochloric acid (1 M) was added with stirring to adjust pH 6-7. The organic layers were collected. The water layer was extracted with ethyl acetate (20 mL). The combined organic layers were dried over anhydrous sodium sulfate and concentrated in vacuo to give the title compound as a white solid (282 mg, 99.99%). MS (ESI, pos.ion) m/z: 365.9 [M+Na]$^+$.

Step 2: methyl 3-(4-bromophenyl)-3-((tert-butoxycarbonyl)amino)propionate

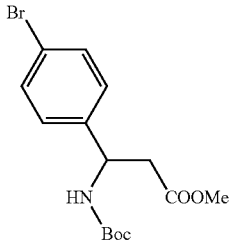 [SMILES: COC(=O)CC(NC(=O)OC(C)(C)C)c1ccc(Br)cc1]

3-(4-Bromophenyl)-3-((tert-butoxycarbonyl)amino)propionic acid (200 mg 0.58 mmol) was dissolved in DCM (5 mL), and HATU (230 mg 0.57 mmol) and DIPEA (75 mg 0.58 mmol) were added in turn. The reaction was stirred at 0° C. for 10 min, and then MeOH (10 mL) was added, then the mixture was remove to rt and stirred for 12 hours. After the reaction was completed, the mixture was concentrated, the residue was diluted with DCM (20 mL), the resulting mixture was washed with saturated aqueous NaCl (30 mL), dried over anhydrous sodium sulfate, and concentrated in vacuo to get the title compound as a yellow oil (208 mg, 99.94%). MS (ESI, pos.ion) m/z: 302.1 [M+H−56]+.

Step 3: (8aR)-benzyl 2-(4-(1-((tert-butoxycarbonyl)amino)-3-methoxy-3-oxopropyl)phenyl)-3-oxohexahydroimidazo[1,5-a]pyrazine-7(1H)-carboxylate

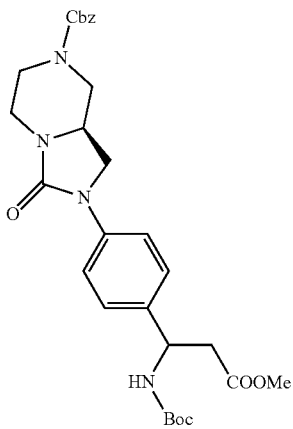 [SMILES: COC(=O)CC(NC(=O)OC(C)(C)C)c1ccc(N2C[C@@H]3CN(C(=O)OCc4ccccc4)CCN3C2=O)cc1]

To a dry flask were added (R)-benzyl 3-oxohexahydroimidazo[1,5-a]pyrazine-7(1H)-carboxylate (326 mg 1.18 mmol), methyl 3-(4-bromophenyl)-3-((tert-butoxycarbonyl)amino)propionate (433 mg 1.21 mmol), Pd$_2$(dba)$_3$ (80 mg, 0.08 mmol), tBu-Xantphos (50 mg 0.11 mmol), Cs$_2$CO$_3$ (780 mg 2.39 mmol) and 1,4-dioxane (35 mL) in turn. The mixture was degassed and filled with N$_2$ four times, and stirred at 90° C. for 12 hours, and concentrated in vacuo. The residue was purified by silica gel column chromatography (PE/EtOAc (v/v)=2/1) to give the title compound as a yellow oil (500 mg 74.85%). MS (ESI, pos.ion) m/z: 575.2 [M+Na]+.

Step 4: 3-(4-((R)-7-((benzyloxy)carbonyl)-3-oxohexahydroimidazo[1,5-a]pyrazin-2(3H)-1)phenyl)-3-((tert-butoxycarbonyl)amino)propionic Acid

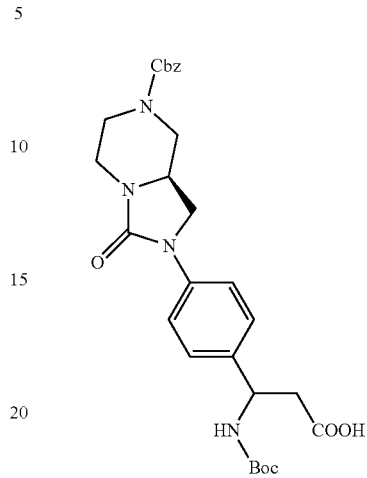

(8aR)-Benzyl 2-(4-(1-((tert-butoxycarbonyl)amino)-3-methoxy-3-oxopropyl)phenyl)-3-oxohexahydroimidazo[1,5-a]pyrazine-7(1H)-carboxylate (495 mg, 0.90 mmol) was dissolved in THF (8 mL), and then LiOH.H$_2$O (260 mg 10.83 mmol) in H$_2$O (8 mL) was added. The reaction mixture was stirred at rt for 12 hours, and then concentrated in vacuo to get a white solid. The white solid was dissolved in water (60 mL) and extracted with EA (30 mL), the organic layer was discarded. The water phase was adjusted with dilute hydrochloric acid to pH 5-6, and then extracted with EA (3×40 mL), the organic layers were combined. The combined organic layers were concentrated in vacuo to get the title compound as a white foam solid (364 mg, 0.70 mmol, 75.45%).

Step 5: 3-((tert-butoxycarbonyl)amino)-3-(4-((S)-3-oxohexahydroimidazo[1,5-a]pyrazin-2(3H)-yl)phenyl)propionic Acid

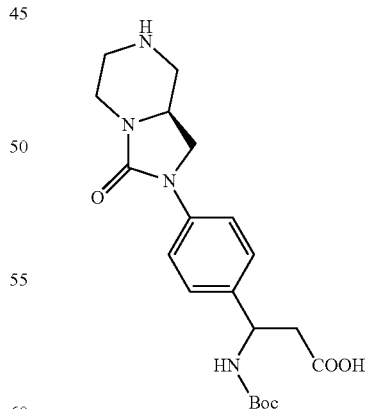

3-(4-((R)-7-((Benzyloxy)carbonyl)-3-oxohexahydroimidazo[1,5-a]pyrazin-2 (3H)-yl)phenyl)-3-((tert-butoxycarbonyl)amino)propionic acid (273.4 mg 0.51 mmol) was dissolved in MeOH (8 mL), and then Pd/C (180 mg) was added. The mixture was stirred at rt under H$_2$ for 2.5 hours. After the reaction was completed, the mixture was filtered through a Celite pad, and the filter cake was rinsed with MeOH (15 mL), and then the filtrate was concentrated to get the title compound as a white solid (130 mg 47.55%).

Step 6: 3-((tert-butoxycarbonyl)amino)-3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)propanoic Acid 3-((tert-Butoxycarbonyl)amino)-3-(4-((S)-3-oxohexahydroimidazo[1,5-a]pyrazin-2(3H)-yl)phenyl)propionic acid (130 mg, 0.32 mmol) were dissolved in ethanol (10 mL), and (R)-methyl 6-(bromomethyl)-4-(2-chloro-4-fluorophenyl)-2-(thiazol-2-yl)-1,4-dihydropyrimidine-5-carboxy late (270 mg 0.60 mmol) and K₂CO₃ (175 mg 1.28 mmol) were added. The reaction mixture was stirred at rt for 12 hours and diluted with (30 mL) and water (30 mL), and then adjusted with dilute hydrochloric acid to pH 5-6, the organic layer was collected, and the water phase was extracted with EA (20 mL), the organic layers were combined. The combined organic layers were dried over anhydrous sodium sulfate and concentrated in vacuo. The residue was purified by pre-TLC (EA) to give the title compound as a yellow solid (83 mg, 33.62%). MS (ESI, pos.ion) m/z: 768.4 [M+H]⁺; MS (ESI, pos.ion) m/z: 768.4 [M+H]⁺; ¹H NMR (600 MHz, CDCl₃) δ 9.61 (s, 1H), 7.85 (d, J=3.1 Hz, 1H), 7.51-7.44 (m, 3H), 7.29-7.26 (m, 3H), 7.14 (dd, J=8.5, 2.6 Hz, 1H), 6.94-6.88 (m, 1H), 6.20 (s, 1H), 5.47 (s, 1H), 5.05 (s, 1H), 4.15-4.07 (m, 1H), 4.06-3.95 (m, 2H), 3.91-3.84 (m, 2H), 3.59 (s, 3H), 3.43-3.38 (m, 1H), 3.27-3.19 (m, 1H), 2.96-2.77 (m, 4H), 2.49-2.44 (m, 1H), 2.25-2.19 (m, 1H), 1.39 (s, 9H).

Example 17: 3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)-2,2-dimethylpropionic Acid Step 1: methyl 3-(4-bromophenyl)-2,2-dimethylpropionate

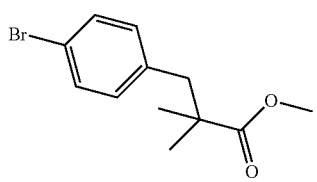

To a 50 mL two neck flask was added LDA (1.3 mL, 2.6 mmol, 2 mol/L) under N₂ at −78° C., after about 10 min, methyl isobutyrate (220 mg 2.15 mmol) in anhydrous THF (1 mL) was added slowly, the mixture was further stirred at −78° C. for about 1 hour, and then p-bromobenzyl bromide (646 mg 2.58 mmol) in anhydrous THF (2 mL) was added slowly by syringe to the about system. The mixture was warm to rt slowly and stirred for about 15 hours, and then the mixture was cooled to 0° C. and quenched with water (2 mL). The reaction mixture was extracted with Et₂O (15 mL), the organic phase was concentrated in vacuo. The residue was purified by silica gel column chromatography (PE/EtOAc (v/v)=20/1) to give the title compound as a pale yellow liquid (463 mg 79.3%). ¹H NMR (400 MHz, CDCl₃) δ 7.40 (d, J=8.3 Hz, 2H), 6.99 (d, J=8.3 Hz, 2H), 3.67 (s, 3H), 2.82 (s, 2H), 1.19 (s, 6H).

Step 2: (R)-tert-butyl 2-(4-(3-methoxy-2,2-dimethyl-3-oxopropyl)phenyl)-3-oxohexahydroimidazo[1,5-a]pyrazin-7(1H)-carboxylate

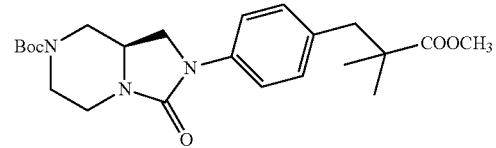 [SMILES: COC(=O)C(C)(C)Cc1ccc(N2C[C@@H]3CN(C(=O)OC(C)(C)C)CCN3C2=O)cc1]

To a 50 mL single neck flask were added (R)-tert-butyl 3-oxohexahydroimidazo[1,5-a]pyrazine-7(1H)-carboxylate (346 mg, 1.43 mmol), methyl 3-(4-bromophenyl)-2,2-dimethylpropionate (389 mg, 1.43 mmol), tris(dibenzylideneacetone)dipalladium (79 mg, 0.09 mmol), Xantphos (83 mg 0.14 mmol), cesium carbonate (935 mg 2.87 mmol) and 1,4-dioxane (15 mL). The reaction mixture was warmed to 90° C. under N₂ and stirred for 3 hours, the mixture was cooled to rt and filtered by suction filtration. To the filtrate was added EtOAc (10 mL), and the mixture was washed with saturated aqueous sodium chloride (10 mL), the organic phase was concentrated in vacuo, and the residue was purified by silica gel column chromatography (PE/EA (v/v)= 3/1) to give the title compound as a white solid (500 mg 80.77%). MS (ESI, pos.ion) m/z: 376.2 [M−56+H]+; 454.3 [M+Na]+; 863.4 [2M+H]⁺.

Step 3: (R)-3-(4-(7-(tert-butoxycarbonyl)-3-oxohexahydroimidazo[1,5-a]pyrazin-2(3H)-yl)phenyl)-2,2-dimethylpropionic Acid

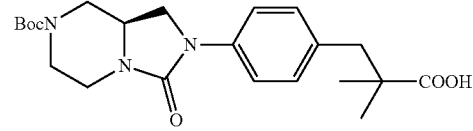 [SMILES: CC(C)(C)OC(=O)N1CCN2C(=O)N(c3ccc(CC(C)(C)C(=O)O)cc3)C[C@@H]2C1]

To a 50 mL single neck flask were added (R)-tert-butyl 2-(4-(3-methoxy-2,2-dimethyl-3-oxoprop yl)phenyl)-3-oxohexahydroimidazo[1,5-a]pyrazin-7(1H)-carboxylate (500 mg 1.16 mmol), MeOH (5 mL), THF (5 mL) and NaOH (83 mg, 2.0 mmol) in water (5 mL). The reaction mixture was stirred at 50° C. for 2 hours and cooled to rt, and then acidified with hydrochloric acid (6 M) to pH 5-6, and then concentrated to remove the most of THF and MeOH, a white solid precipitated, and the mixture was filtered by suction filtration, the filter cake was washed with H₂O (15 mL) and dried at 45° C. in vacuo for 1 hour to get the title compound as a white powder (462 mg, 95.50%). MS (ESI, pos.ion) m/z: 362.1 [M−56+H]; 440.1 [M+Na]+.

Step 4: (S)-2,2-dimethyl-3-(4-(3-oxohexahydroimidazo[1,5-a]pyrazin-2(3H)-yl)phenyl)propionic acid hydrochloride

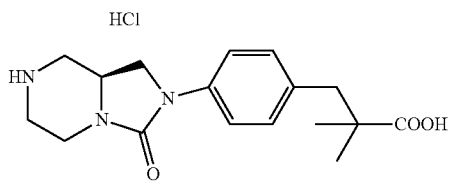 [SMILES: Cl ; CC(C)(Cc1ccc(N2C[C@@H]3CNCCN3C2=O)cc1)C(=O)O]

To a single neck flask were added (R)-3-(4-(7-(tert-butoxycarbonyl)-3-oxohexahydroimidazo[1,5-a]pyrazin-2(3H)-yl)phenyl)-2,2-dimethylpropionic acid (496 mg, 1.19 mmol) and HCl in 1,4-dioxane (10 mL, 40 mmol, 4 mol/L). The reaction mixture was stirred at rt for 2 hours and filtered by suction filtration, the filter cake was washed with 1,4-dioxane (5 mL) and dried at rt in vacuo for 2 hours to get the title compound as an off-white solid (345 mg, 82.08%). MS (ESI, pos.ion) m/z: 318.2 [M+H]$^+$.

Step 5: 3-(4-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)phenyl)-2,2-dimethylpropionic Acid To a single neck flask were added (S)-2,2-dimethyl-3-(4-(3-oxohexahydroimidazo[1,5-a]pyrazin-2(3H)-yl)phenyl)propionic Acid hydrochloride (345 mg 0.98 mmol), (R)-methyl 4-(2-chloro-4-fluorophenyl)-6-(bromomethyl)-2-(thiazol-2-yl)-1,4-dihydropyrimidine-5-carboxylate (434 mg 0.98 mmol), potassium carbonate (272 mg 1.95 mmol) and ethanol (20 mL). The mixture was stirred at 25° C. for 16 hours and filtered, the filter cake was washed with EtOAc (10 mL), the filtrate was concentrated and diluted with EtOAc (30 mL) and water (15 mL), the resulting mixture was adjusted with hydrochloric acid (6 M) to pH 5, the water phase was extracted with EtOAc (15 mL), the organic phases were combined and concentrated in vacuo. The residue was purified by silica gel column chromatography (CH$_2$Cl$_2$/MeOH (V/V)=30/1) to give the title compound as a yellow solid (479 mg 72.11%). MS (ESI, pos.ion) m/z: 681.1 [M+H]$^+$; $^1$H NMR (400 MHz, DMSO-d$_6$) δ 12.20 (s, 1H), 9.72 (s, 1H), 8.04 (d, J=3.1 Hz, 1H), 7.95 (d, J=3.1 Hz, 1H), 7.50-7.38 (m, 4H), 7.19 (td, J=8.5, 2.6 Hz, 1H), 7.09 (d, J=8.6 Hz, 2H), 6.06 (s, 1H), 4.05-3.80 (m, 5H), 3.52 (s, 3H), 3.46 (dd, J=8.4, 3.0 Hz, 1H), 3.12-3.00 (m, 1H), 2.92 (d, J=9.4 Hz, 2H), 2.73 (s, 2H), 2.34-2.25 (m, 1H), 2.15 (t, J=10.6 Hz, 1H), 1.06 (s, 6H).

Example 18: 3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)-2-methylpropionic Acid

Step 1: (R)-tert-butyl 2-(4-formylphenyl)-3-oxohexahydroimidazo[1,5-a]pyrazine-7(1H)-carboxylate

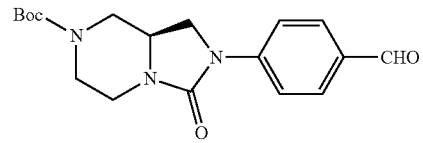 [SMILES: CC(C)(C)OC(=O)N1CCN2C(=O)N(c3ccc(C=O)cc3)C[C@@H]2C1]

To a two-neck flask were added 4-bromobenzaldehyde (1.00 g 5.40 mmol), (R)-tert-butyl 3-oxohexahydroimidazo[1,5-a]pyrazine-7(1H)-carboxylate (1.43 g 5.93 mmol), Pd$_2$(dba)$_3$ (255 mg 0.27 mmol), Xantphos (332 mg 0.56 mmol) and Cs$_2$CO$_3$ (3.27 g 9.73 mmol), and then 1,4-dioxane (60 mL) was added under N$_2$, the mixture was stirred at 80° C. for 1 h and concentrated in vacuo, the residue was dissolved with EA (100 mL), and washed with water (100 mL), saturated NaCl aqueous solution (100 mL×2). The organic phases were collected and concentrated in vacuo. The residue was purified by silica gel column chromatography (PE/EA (v/v)=1/1) to give the title compound as a yellow solid (1.62 g 86.80%). MS (ESI, pos.ion) m/z: 290.2 [M−56+H]$^+$.

Step 2: (R)-tert-butyl 2-(4-(3-ethoxy-2-methyl-3-oxoprop-1-en-1-yl)phenyl)-3-oxohexahydroimidazo[1,5-a]pyrazine-7(1H)-carboxylate

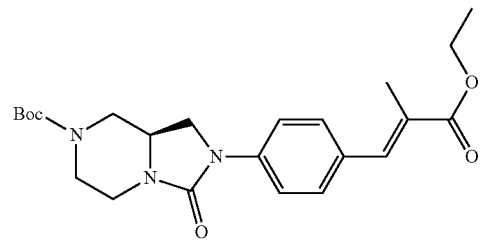 [SMILES: CCOC(=O)/C(C)=C/c1ccc(N2C[C@@H]3CN(C(=O)OC(C)(C)C)CCN3C2=O)cc1]

(R)-tert-Butyl 2-(4-formylphenyl)-3-oxohexahydroimidazo[1,5-a]pyrazine-7(1H)-carboxylate (200 mg, 0.58 mmol) was dissolved in DCM (10 mL), and ethyl 2-(triphenylphosphoranylidene)propionate (230 mg, 0.63 mmol) was added portionwise, after the addition, the mixture was moved to rt and stirred for 12 hours, and then concentrated in vacuo. The residue was purified by silica gel column chromatography (PE/EA (v/v)=1/1) to give the title compound as a white solid (100 mg 40.21%). MS (ESI, pos.ion) m/z: 374.3 [M−56+H].

Step 3: (8aR)-tert-butyl 2-(4-(3-ethoxy-2-methyl-3-oxopropyl)phenyl)-3-oxohexahydroimidazo[1,5-a]pyrazine-7(1H)-carboxylate

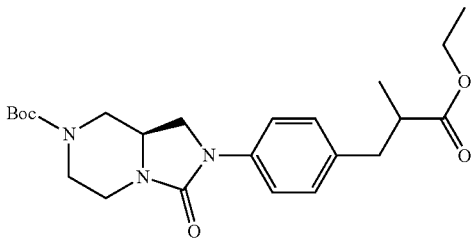 [SMILES: CCOC(=O)C(C)Cc1ccc(N2C[C@@H]3CN(C(=O)OC(C)(C)C)CCN3C2=O)cc1]

To a solution of (R)-tert-butyl 2-(4-(3-ethoxy-2-methyl-3-oxoprop-1-en-1-yl)phenyl)-3-oxohexahydroimidazo[1,5-a]pyrazine-7(1H)-carboxylate (100 mg, 0.23 mmol) in MeOH (10 mL) was added Pd/C (10%, 20 mg). The mixture was stirred under $H_2$ for 12 hours and filtered through Celite pad. The filtrate was concentrated in vacuo to get the title compound as a white solid (100 mg 99.50%). MS (ESI, pos.ion) m/z: 454.2 [M+Na]+.

Step 4: 3-(4-((R)-7-(tert-butoxycarbonyl)-3-oxohexahydroimidazo[1,5-a]pyrazin-2(3H)-yl)phenyl)-2-methylpropionic Acid

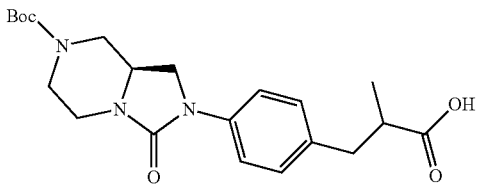 [SMILES: CC(Cc1ccc(N2C[C@@H]3CN(C(=O)OC(C)(C)C)CCN3C2=O)cc1)C(=O)O]

(8aR)-tert-Butyl 2-(4-(3-ethoxy-2-methyl-3-oxopropyl)phenyl)-3-oxohexahydroimidazo[1,5-a]pyrazine-7(1H)-carboxylate (321 mg 0.74 mmol) was dissolved in THF (8 mL), and then lithium hydroxide monohydrate (247 mg 10.3 mmol) in $H_2O$ (8 mL) was added. The mixture was stirred at rt for 6 hours, and adjusted with dilute hydrochloric acid to pH 5-6, and the resulting mixture was extracted with EtOAc (30 mL×2). The combined organic layers were dried over anhydrous sodium sulfate and concentrated in vacuo to give the title compound as a white solid (300 mg 99.94%).

Step 5: 2-methyl-3-(4-((S)-3-oxohexahydroimidazo[1,5-a]pyrazin-2(3H)-yl)phenyl)propionic acid trifluoroacetate

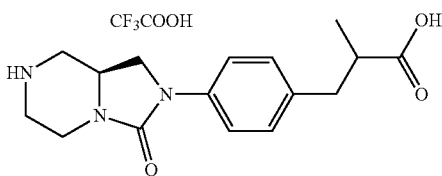 [SMILES: CC(Cc1ccc(N2C[C@@H]3CNCCN3C2=O)cc1)C(=O)O ; "CF3COOH"]

To a solution of 3-(4-((R)-7-(tert-butoxycarbonyl)-3-oxohexahydroimidazo[1,5-a]pyrazin-2(3H)-yl)phenyl)-2-meth-ylpropionic acid (300 mg 0.74 mmol) in DCM (10 mL) was added TFA (5 mL). The reaction mixture was stirred at rt for 1 hour, and then the reaction mixture was concentrated in vacuo to get the title compound as a yellow oil (225 mg 99.74%).

Step 6: 3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)-2-methylpropionic Acid 2-Methyl-3-(4-((S)-3-oxohexahydroimidazo[1,5-a]pyrazin-2(3H)-yl)phenyl)propionic acid trifluoroacetate (225 mg 0.7416 mmol) were dissolved in ethanol (10 mL), and (R)-methyl 6-(bromomethyl)-4-(2-chloro-4-fluorophenyl)-2-(thiazol-2-yl)-1,4-dihydropyrimidine-5-carboxy late (362 mg, 0.81 mmol) and $K_2CO_3$ (410 mg, 2.97 mmol) were added. The mixture was stirred at rt for 12 hours and EA (30 mL) was added, the resulting mixture was washed with water (30 mL), the water layer was extracted with EA (30 mL), the organic layers were combined and concentrated in vacuo. The residue was purified by silica gel column chromatography (DCM/$CH_3OH$ (V/V)=50/1) to give the title compound as a yellow solid (240 mg 48.51%). MS (ESI, pos.ion) m/z: 667.4 [M+H]; $^1$H NMR (400 MHz, $CDCl_3$) δ 9.62 (s, 1H), 7.85 (d, J=3.1 Hz, 1H), 7.50-7.42 (m, 3H), 7.31-7.26 (m, 1H), 7.19-7.10 (m, 3H), 6.95-6.88 (m, 1H), 6.20 (s, 1H), 4.11 (d, 17.4 Hz, 1H),4.07-4.03 (m, 1H), 4.01-3.94 (m, 1H), 3.92-3.84 (m, 2H), 3.59 (s, 3H), 3.43-3.38 (m, 1H), 3.29-3.18 (m, 1H), 3.02 (dd, J=13.4, 6.5 Hz, 1H), 2.86 (d, J=11.0 Hz, 2H), 2.78-2.70 (m, 1H), 2.68-2.59 (m, 1H), 2.53-2.43 (m, 1H), 2.25 (t, J=10.8 Hz, 1H), 1.17 (d, J=6.9 Hz, 3H).

Example 19: 3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl) butanoic Acid Step 1: methyl 3-(4-bromophenyl)but-2-enoate

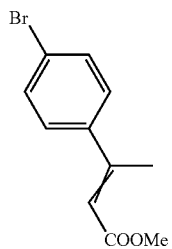

NaH (240 mg 10 mmol, 60%) was added into a 50 mL two-neck flask, at 0° C., anhydrous THF (20 mL) was added under $N_2$, and then ethyl 2-(dimethoxyphosphoryl)acetate (1.62 mL, 10 mmol) was added slowly, after the addition, the mixture was further stirred for 30 min, and then p-bromoacetophenone (1.59 g 7.99 mmol) in THF (5 mL) was added dropwise. The mixture was warmed to rt, and then stirred at 65° C. for 12 hours. After the reaction was completed. The mixture was concentrated in vacuo. The residue was purified by silica gel column chromatography (PE/EtOAc (v/v)=50/1) and dried in vacuo to give the title compound as a white solid (764 mg 37.50%). MS (ESI, pos.ion) m/z: 255.0 [M+H]$^+$.

Step 2: (R)-tert-butyl 2-(4-(4-methoxy-4-oxobut-2-en-2-yl)phenyl)-3-oxohexahydroimidazo[1,5-a]pyrazine-7(1H)-carboxylate

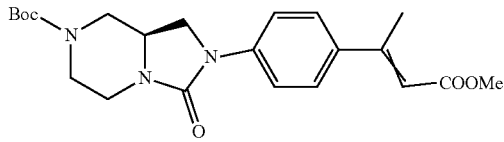 [SMILES: COC(=O)C=C(C)c1ccc(N2C[C@@H]3CN(C(=O)OC(C)(C)C)CCN3C2=O)cc1]

Methyl 3-(4-bromophenyl)but-2-enoate (260 mg, 1.02 mmol) was dissolved in 1,4-dioxane (12 mL), and (R)-tert-butyl 3-oxohexahydroimidazo[1,5-a]pyrazine-7(1H)-carboxylate (270 mg 1.12 mmol), Pd$_2$(dba)$_3$ (111 mg 0.12 mmol), Xantphos (30 mg 0.05 mmol) and Cs$_2$CO$_3$ (598 mg 1.83 mmol) were added in turn. The mixture was stirred at 85° C. under N$_2$ for 12 hours and concentrated in vacuo. The residue was dissolved in EA (20 mL) and washed with water (20 mL) saturated aqueous NaCl (20 mL×2) in turn. The organic phases were collected and concentrated in vacuo. The residue was purified by silica gel column chromatography (PE/EA (v/v)=2/1) to give the title compound as a white solid (185 mg, 43.69%). MS (ESI, pos.ion) m/z: 360.1 [M−56+H]$^+$.

Step 3: (8aR)-tert-butyl 2-(4-(4-methoxy-4-oxobut-2-yl)phenyl)-3-oxohexahydroimidazo[1,5-a]pyrazin-7(1H)-carboxylate

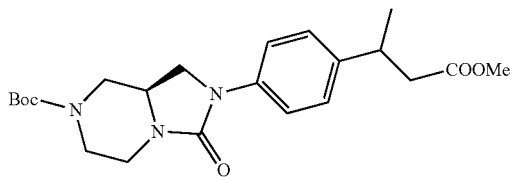 [SMILES: COC(=O)CC(C)c1ccc(N2C[C@@H]3CN(C(=O)OC(C)(C)C)CCN3C2=O)cc1]

To a solution of (R)-tert-butyl 2-(4-(4-methoxy-4-oxobut-2-yl)phenyl)-3-oxohexahydroimidazo[1,5-a]pyrazine-7(1H)-carboxylate (185 mg, 0.45 mmol) in MeOH (5 mL) and THF (10 mL) was added Pd/C (10%, 40 mg). The mixture was stirred at rt under H$_2$ for 12 hours and filtered through Celite pad. The filter cake was rinsed with MeOH (10 mL). The filtrate was concentrated in vacuo to get the title compound as a white solid (185 mg, 99.52%). MS (ESI, pos.ion) m/z: 440.1[M+Na]$^+$.

Step 4: 3-(4-((R)-7-(tert-butoxycarbonyl)-3-oxohexahydroimidazo[1,5-a]pyrazin-2(3H)-yl)phenyl)butanoic Acid

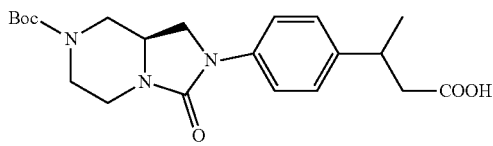 [SMILES: CC(CC(=O)O)c1ccc(N2C[C@@H]3CN(C(=O)OC(C)(C)C)CCN3C2=O)cc1]

(8aR)-tert-Butyl 2-(4-(4-methoxy-4-oxobut-2-yl)phenyl)-3-oxohexahydroimidazo[1,5-a]pyrazin-7(1H)-carboxylate (185 mg, 0.44 mmol) was dissolved in THF (4 mL), and MeOH (4 mL) and NaOH (141 mg, 3.54 mmol) in H$_2$O (4 mL) were added in turn, the mixture was stirred at rt for 3.5 hours, and then adjusted with dilute hydrochloric acid (1 M) to pH 5-6, the resulting mixture was extracted with EA (20 mL), the water layer was extracted with EA (10 mL), the organic layers were combined and dried over anhydrous sodium sulfate, and then concentrated in vacuo to get the title compound as a pale yellow solid (178 mg, 99.55%).

Step 5: 3-(4-((S)-3-oxohexahydroimidazo[1,5-a]pyrazin-2(3H)-yl)phenyl)butanoic Acid trifluoroacetate

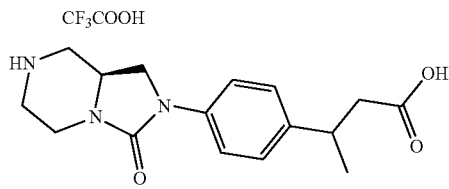 [SMILES: "CF3COOH" ; CC(CC(=O)O)c1ccc(N2C[C@@H]3CNCCN3C2=O)cc1]

3-(4-((R)-7-(tert-Butoxycarbonyl)-3-oxohexahydroimidazo[1,5-a]pyrazin-2(3H)-yl)phenyl)butanoic acid (178 mg, 0.44 mmol) was dissolved in DCM (8 mL) and TFA (4 mL) was added, the mixture stirred at rt for 1 hour and concentrated in vacuo to get the title compound as a yellow oil (133 mg, 99.37%).

Step 6: 3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)butanoic Acid 3-(4-((S)-3-Oxohexahydroimidazo[1,5-a]pyrazin-2(3H)-yl)phenyl)butanoic acid trifluoroacetate (133 mg, 0.44 mmol) was dissolved in EtOH (10 mL), and then (R)-methyl 6-(bromomethyl)-4-(2-chloro-4-fluorophenyl)-2-(thiazol-2-yl)-1,4-dihydropyrimidine-5-carboxy late (192 mg, 0.52 mmol) and K$_2$CO$_3$ (242 mg 1.75 mmol) were added. The mixture was stirred at rt for 12 hours, then EA (30 mL) and water (30 mL) were added in turn, the resulting mixture was adjusted with dilute hydrochloric acid (1 M) to pH 5-6, the organic phase was collected, the water phase was extracted with EA (30 mL), the organic phases were combined and dried over anhydrous sodium sulfate, then concentrated in vacuo. The residue was purified by silica gel column chromatography (DCM/CH$_3$OH (V/V)=15/1) to give the title compound as a yellow solid (130 mg, 44.45%). MS (ESI, pos.ion) m/z: 667.1[M+H]$^+$; $^1$H NMR (600 MHz, CDCl$_3$) δ 9.62 (s, 1H), 7.85 (d, J=3.1 Hz, 1H), 7.50-7.44 (m, 3H), 7.30-7.27 (m, 1H), 7.20 (d, J=8.6 Hz, 2H), 7.14 (dd, J=8.6, 2.6 Hz, 1H), 6.94-6.89 (m, 1H), 6.20 (s, 1H), 4.10 (d, J=17.3 Hz, 1H), 4.07-4.03 (m, 1H), 4.01-3.95 (m, 1H), 3.91-3.85 (m, 2H), 3.59 (s, 3H), 3.41 (dd, J=9.0, 4.7 Hz, 1H), 3.29-3.20 (m, 2H), 2.89-2.82 (m, 2H), 2.64 (dd, J=15.5, 7.1 Hz, 1H), 2.59-2.54 (m, 1H), 2.51-2.44 (m, 1H), 2.24 (t, J=10.8 Hz, 1H), 1.30 (d, J=7.0 Hz, 3H).

Example 20: 3-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)propionic Acid

Step 1: methyl 3-(2-bromothiazol-4-yl)acrylate

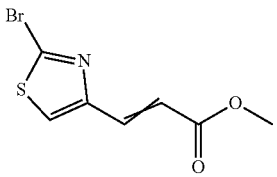

2-Bromothiazole-4-carbaldehyde (500 mg, 2.60 mmol) and methyl (triphenylphosphoranylidene)acetate (968 mg, 2.87 mmol) were dissolved in dichloromethane (10 mL) under $N_2$. The mixture was stirred at rt for 12 hours and concentrated in vacuo. The residue was purified by silica gel column chromatography (PE/EtOAc (v/v)=50/1) to give the title compound as a white solid (530 mg, 82%). $^1$H NMR (400 MHz, CDCl$_3$) δ 7.53 (d, J=15.5 Hz, 1H), 7.37 (s, 1H), 6.77 (d, J=15.5 Hz, 1H), 3.82 (s, 3H).

Step 2: (S)-tert-butyl 2-(4-(3-methoxy-3-oxoprop-1-en-1-yl)thiazol-2-yl)-3-oxohexahydro imidazo[1,5-a]pyrazine-7(1H)-carboxylate

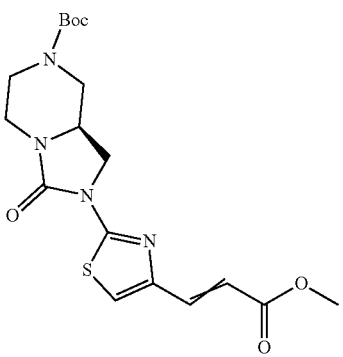 [SMILES: COC(=O)C=Cc1csc(N2C[C@@H]3CN(C(=O)OC(C)(C)C)CCN3C2=O)n1]

(R)-tert-Butyl 3-oxohexahydroimidazo[1,5-a]pyrazine-7(1H)-carboxylate (200 mg, 0.83 mmol), methyl 3-(2-bromothiazol-4-yl)acrylate (226 mg, 0.91 mmol), tris(dibenzylideneacetone)dipalladium (77 mg, 0.08 mmol), 4,5-bis (diphenylphosphino)-9,9-dimethyxanthene (99 mg 0.16 mmol), cesium carbonate (540 mg, 1.66 mmol) were dissolved in 1,4-dioxane (20 mL) under $N_2$, the mixture was heated to 90° C. for 6 hours and concentrated in vacuo. The residue was purified by silica gel column chromatography (PE/EA (v/v)=1/1) to give the title compound as a white solid (230 mg 68%). MS (ESI, pos. ion): m/z 409.1 [M+H]$^+$.

Step 3: (S)-tert-butyl 2-(4-(3-methoxy-3-oxopropyl)thiazol-2-yl)-3-oxohexahydroimidazo[1,5-a]pyrazine-7(1H)-carboxylate

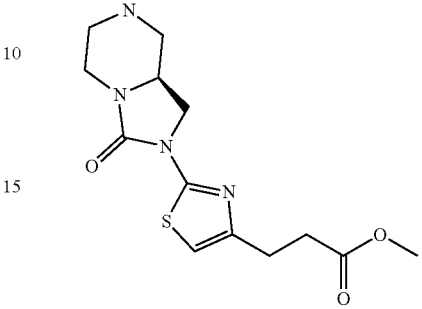

(S)-tert-Butyl 2-(4-(3-methoxy-3-oxoprop-1-en-1-yl)thiazol-2-yl)-3-oxohexahydro imidazo[1,5-a]pyrazine-7(1H)-carboxylate (200 mg 0.49 mmol) and Pd/C (52 mg, 0.05 mmol, wt. % is 10%) were dissolved in ethyl acetate (10 mL), the mixture was stirred at rt under $H_2$ for 12 hours and filtered by suction filtration, the filtrate was concentrated in vacuo to get the title compound as a white solid (180 mg 90%). MS (ESI, pos. ion): m/z 411.3 [M+H]$^+$.

Step 4: (S)-3-(2-(7-(tert-butoxycarbonyl)-3-oxohexahydroimidazo[1,5-a]pyrazin-2(3H)-yl) thiazol-4-yl)propionic Acid

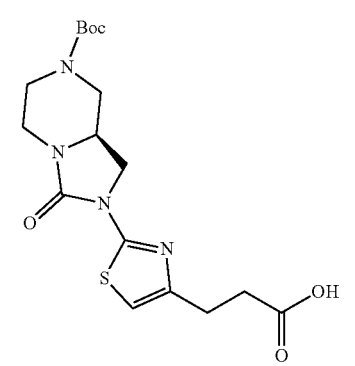 [SMILES: CC(C)(C)OC(=O)N1CCN2C(=O)N(c3nc(CCC(=O)O)cs3)C[C@@H]2C1]

(S)-tert-Butyl 2-(4-(3-methoxy-3-oxopropyl)thiazol-2-yl)-3-oxohexahydro imidazo[1,5-a]pyrazine-7(1H)-carboxylate (150 mg 0.37 mmol) was dissolved in methanol (10 mL), and then lithium hydroxide monohydrate (31 mg 0.74 mmol) in $H_2O$ (1 mL) was added. The mixture was stirred at rt for 5 hours and adjusted with hydrochloric acid (1 M) to pH 3-4, and then extracted with ethyl acetate (20 mL×3). The organic layers were combined and dried over anhydrous sodium sulfate, and then concentrated in vacuo to give the title compound as a white solid (130 mg 90%). MS (ESI, pos. ion): m/z 397.2 [M+H]$^+$.

Step 5: (S)-3-(2-(3-oxohexahydroimidazo[1,5-a]pyrazin-2(3H)-yl)thiazol-4-yl)propionic Acid trifluoroacetate

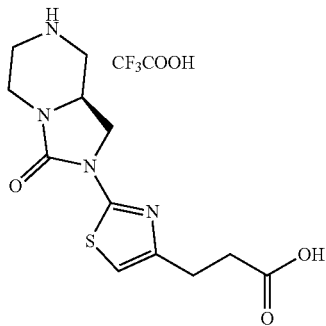 [SMILES: O=C(O)CCc1csc(N2C[C@@H]3CNCCN3C2=O)n1 ; "CF3COOH"]

To a solution of (S)-3-(2-(7-(tert-butoxycarbonyl)-3-oxohexahydroimidazo[1,5-a]pyrazin-2(3H)-yl)thiazol-4-yl)propionic acid (150 mg 0.38 mmol) in dichloromethane (5 mL) was added trifluoroacetic acid (5 mL). The mixture was stirred at rt for 1 hour and concentrated in vacuo to remove the most of solvent, and toluene (10 mL) was added, the resulting mixture was concentrated again to get the title compound as a brown oil (116 mg 99%).

Step 6: 3-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)propionic Acid (S)-3-(2-(3-Oxohexahydroimidazo[1,5-a]pyrazin-2(3H)-yl)thiazol-4-yl)propionic acid trifluoroacetate (150 mg, 0.51 mmol) and potassium carbonate (209 mg 1.51 mmol) were dissolved in ethanol (10 mL), and (R)-methyl 6-(bromomethyl)-4-(2-chloro-4-fluorophenyl)-2-(thiazol-2-yl)-1,4-dihydropyrimidine-5-carboxylate (247 mg 0.55 mmol) was added. The mixture was stirred at rt for 12 hours, and concentrated in vacuo. The residue was purified by silica gel column chromatography (DCM/MeOH (V/V)=8/1) to give the title compound as a yellow solid (150 mg 45%). MS (ESI, pos. ion): m/z 660.0 [M+H]; $^1$H NMR (400 MHz, CDCl$_3$) δ 9.57 (s, 1H), 7.86 (d, J=3.1 Hz, 1H), 7.48 (d, J=3.1 Hz, 1H), 7.31-7.28 (m, 1H), 7.15 (dd, J=8.6, 2.5 Hz, 1H), 6.93 (td, J=8.3, 2.5 Hz, 1H), 6.54 (s, 1H), 6.22 (s, 1H), 4.22-4.12 (m, 2H), 4.11-4.09 (m, 1H), 4.08-4.03 (m, 1H), 3.92 (d, J=17.1 Hz, 1H), 3.71 (dd, J=10.3, 4.3 Hz, 1H), 3.61 (s, 3H), 3.32 (td, J=13.0, 3.2 Hz, 1H), 3.01-2.88 (m, 4H), 2.73 (t, J=6.9 Hz, 2H), 2.51 (td, J=11.6, 3.2 Hz, 1H), 2.28 (t, J=10.8 Hz, 1H).

Example 21: 2-(4-(((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)methyl)phenyl)acetic Acid

Step 1: (R)-2-(4-((7-(tert-butoxycarbonyl)-3-oxohexahydroimidazo[1,5-a]pyrazin-2(3H)-yl)methyl)phenyl)acetic Acid

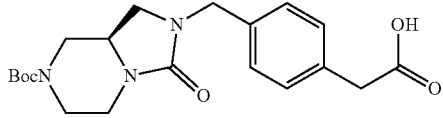 [SMILES: CC(C)(C)OC(=O)N1CCN2C(=O)N(Cc3ccc(CC(=O)O)cc3)C[C@@H]2C1]

To a dry flask was added DMF (10 mL), and then NaH (174 mg, 4.35 mmol, wt. % is 60%) was added slowly, after the mixture was cooled to 0° C., (R)-tert-butyl 3-oxohexahydroimidazo[1,5-a]pyrazin-7(1H)-carboxylate (300 mg, 1.24 mmol) was added, after the addition, the mixture was warmed to rt and stirred for 30 min, then 2-(4-(bromomethyl)phenyl)acetatic acid (428 mg 1.87 mmol) was added, the resulting mixture was kept at rt and stirred for 12 hours. The mixture was stopped stirring and water (20 mL) was added, and adjusted with hydrochloric acid (1 M) to pH 5-6, the resulting mixture was extracted with ethyl acetate (20 mL), the water phase was extracted with ethyl acetate (20 mL×2), the organic phases were combined and washed with saturated NaCl aqueous solution, dried over anhydrous sodium sulfate, then filtered, the filtrate was concentrated in a rotary evaporator. The residue was purified by silica gel column chromatography (DCM/MeOH (V/V)=10/1) to give the title compound as a white solid (390 mg 80.55%). MS (ESI, pos.ion) m/z: 412.4 [M+Na]+.

Step 2: (S)-2-(4-((3-oxohexahydroimidazo[1,5-a]pyrazin-2(3H)-yl)methyl)phenyl)acetic Acid trifluoroacetate

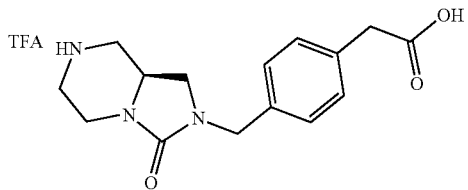 [SMILES: O=C(O)Cc1ccc(CN2C[C@@H]3CNCCN3C2=O)cc1]

To a flask were added (R)-2-(4-((7-(tert-butoxycarbonyl)-3-oxohexahydroimidazo[1,5-a]pyrazin-2(3H)-yl)methyl)phenyl)acetic acid (290 mg 0.74 mmol), dichloromethane (15 mL) and trifluoroacetic acid (5 mL), the mixture was stirred at rt for 6 hours. The mixture was concentrated in a rotary evaporator, and toluene (5 mL) was added, the mixture was concentrated in a rotary evaporator again to give the title compound as a deep-brown solid (300 mg 99.86%).

Step 3: 2-(4-(((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)methyl)phenyl)acetic Acid The title compound was prepared as a pale yellow solid (226 mg 46.5%) according to step 5 of example 13 by replacing (S)-3-(4-(3-oxohexahydroimidazo[1,5-a]pyrazin-2(3H)-yl)phenyl)propanoic acid hydrochloride with (S)-2-(4-((3-oxohexahydroimidazo[1,5-a]pyrazin-2(3H)-yl)methyl)phenyl)acetic acid trifluoroacetate (406 mg, 0.85 mmol). MS (ESI, pos.ion) m/z: 653.2[M+H]$^+$; $^1$H NMR (400 MHz, CDCl$_3$) δ 7.84 (d, J=3.1 Hz, 1H), 7.45 (d, J=3.1 Hz, 1H), 7.31-7.24 (m, 3H), 7.20 (d, J=8.0 Hz, 2H), 7.14 (dd, J=8.6, 2.5 Hz, 1H), 6.92 (td, J=8.3, 2.5 Hz, 1H), 6.20 (s, 1H), 4.37 (s, 2H), 4.06 (d, J=17.2 Hz, 1H), 4.01 (dd, J=13.6, 2.1 Hz, 1H), 3.85 (d, J=17.1 Hz, 2H), 3.63 (s, 2H), 3.60 (s, 3H), 3.30 (t, J=8.8 Hz, 1H), 3.22 (td, J=13.1, 3.2 Hz 1H), 2.82 (dd, J=9.0, 4.3 Hz, 2H), 2.70 (d, J=9.4 Hz, 1H), 2.46 (td, J=11.5, 3.1 Hz, 1H), 2.17 (t, J=10.8 Hz, 1H).

Example 22: 3-(4-((S)-7-(((R)-6-(2-bromo-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)phenyl)prop ionic Acid The title compound was prepared as a yellow solid (214 mg, 65.3%) according to step 5 of example 13 by replacing (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5-carboxylate (232 mg, 0.46 mmol). MS (ESI, pos.ion) m/z: 711.3[M+H]$^+$; $^1$H NMR (600 MHz, CDCl$_3$) δ 7.87 (d, J=3.1 Hz, 1H), 7.50-7.46 (m, 3H), 7.34 (dd, J=8.3, 2.6 Hz, 1H), 7.31 (dd, J=8.6, 6.0 Hz, 1H), 7.20 (d, J=8.6 Hz, 2H), 6.99 (td, J=8.3, 2.5 Hz, 1H), 6.22 (s, 1H), 4.15 (d, J=17.2 Hz, 1H), 4.11-4.02 (m, 3H), 4.02-3.97 (m, 1H), 3.95-3.87 (m, 2H), 3.43 (q, J=4.7 Hz, 1H), 3.27 (td, J=12.9, 3.0 Hz, 1H), 2.94 (t, J=7.7 Hz, 2H), 2.89 (s, 2H), 2.67 (t, J=7.7 Hz, 2H), 2.51 (td, J=11.5, 3.2 Hz, 1H), 2.27 (t, J=10.5 Hz, 1H), 1.15 (t, J=7.1 Hz, 3H).

Example 23: 3-(4-((S)-7-(((R)-6-(2-chloro-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)phenyl)prop ionic Acid The title compound was prepared as a yellow solid (278 mg, 71.45%) according to step 5 of example 13 by replacing (R)-methyl 6-(bromomethyl)-4-(2-chloro-4-fluorophenyl)-2-(thiazol-2-yl)-1,4-dihydropyrimidine-5-carboxylate with (R)-ethyl 4-(2-chloro-4-fluorophenyl)-6-(bromomethyl)-2-(thiazol-2-yl)-1,4-dihydropyrimidine-5-carboxylate (300 mg, 0.59 mmol). MS (ESI, pos.ion) m/z: 667.2[M+H]$^+$; $^1$H NMR (600 MHz, CDCl$_3$) δ 7.87 (d, J=3.1 Hz, 1H), 7.49-7.47 (m, 2H), 7.46 (s, 1H), 7.33 (dd, J=8.6, 6.1 Hz, 1H), 7.19 (d, J=8.5 Hz, 2H), 7.15 (dd, J=8.5, 2.5 Hz, 1H), 6.94 (td, J=8.3, 2.5 Hz, 1H), 6.24 (s, 1H), 4.14 (d, J=17.1 Hz, 1H), 4.09-4.02 (m, 3H), 4.02-3.96 (m, 1H), 3.94-3.86 (m, 2H), 3.43 (q, J=4.7 Hz, 1H), 3.26 (td, J=12.3, 2.4 Hz, 1H), 2.93 (t, J=7.7 Hz, 2H), 2.90 (d, J=10.8 Hz, 2H), 2.66 (t, J=7.7 Hz, 2H), 2.50 (td, J=11.9, 3.0 Hz, 1H), 2.27 (t, J=10.2 Hz, 1H), 1.14 (t, J=7.1 Hz, 3H).

Example 24: 3-(4-((S)-7-(((R)-6-(2,4-dichlorophenyl)-5-(methoxycarbonyl)-2-(thiazol-2-yl)-3,6-dihydropyrimidin-4-yl)methyl)-3-oxohexahydroimidazo[1,5-a]pyrazin-2 (3H)-yl)phenyl)propionic Acid The title compound was prepared as a yellow solid (290 mg 73.7%) according to step 5 of example 13 by replacing (R)-methyl 6-(bromomethyl)-4-(2,4-chloro-4-fluorophenyl)-2-(thiazol-2-yl)-1,4-dihydropyrimidine-5-carboxylate with (R)-methyl 4-(2,4-dichlorophenyl)-6-(bromomethyl)-2-(thiazol-2-yl)-1,4-dihydropyrimidine-5-carboxylate (2, 301 mg, 0.587 mmol). MS (ESI, pos.ion) m/z: 669.1 [M+H]$^+$; $^1$H NMR (400 MHz, CDCl$_3$) δ 7.87 (d, J=3.1 Hz, 1H), 7.49 (d, J=3.1 Hz, 1H), 7.46 (d, J=8.5 Hz, 2H), 7.42 (d, J=1.9 Hz, 1H), 7.27 (d, J=8.4 Hz, 1H), 7.23-7.16 (m, 3H), 6.22 (s, 1H), 4.13 (d, J=17.2 Hz, 1H), 4.05 (d, J=13.5 Hz, 1H), 4.01-3.96 (m, 1H), 3.92 (s, 1H), 3.89 (d, J=9.6 Hz, 1H), 3.61 (s, 3H), 3.42 (q, J=4.6 Hz, 1H), 3.26 (td, J=12.7, 2.9 Hz, 1H), 3.00-2.84 (m, 4H), 2.66 (t, J=7.6 Hz, 2H), 2.50 (td, J=11.9, 3.1 Hz, 1H), 2.27 (t, J=10.6 Hz, 1H).

Example 25: (R)-methyl 4-(2-chloro-4-fluorophenyl)-6-(((S)-2-(4-(3-methoxy-3-oxopropyl)phenyl)-3-oxohexahydroimidazo[1,5-a]pyrazin-7(1H)-yl)methyl)-2-(thiazol-2-yl)-1,4-dihydropyrimidine-5-carboxylate To a dry flask were added 3-(4-((S)-7-(((R)-6-(2-chloro-4-fluorophenyl)-5-(methoxy carbonyl)-2-(thiazol-2-yl)-3,6-dihydropyrimidin-4-yl)methyl-3-oxohexahydroimidazo[1,5-a]pyrazin-2(3H)-yl)phenyl)propanoic acid (653 mg 1 mmol), acetonitrile (20 mL) and anhydrous potassium carbonate (0.277 g 2 mmol) in turn. After the mixture was stirred uniformly, iodomethane (0.16 g 1.1 mol) was added, then the resulting mixture was stirred at 60° C. for 8 hours and cooled to rt, and filtered. The filtrate was concentrated in vacuo to remove the solvent. The residue was purified by silica gel column chromatography (PE/EA (V/V)=3/1) to give the title compound as a yellow solid (0.48 g 72%). MS (ESI, pos.ion) m/z: 667.1 [M+H]$^+$; $^1$H NMR (400 MHz, CDCl$_3$) δ 9.62 (s, 1H), 7.84 (d, J=3.1 Hz, 1H), 7.45 (dd, J=5.8, 2.6 Hz, 3H), 7.30-7.26 (m, 1H), 7.16 (d, J=8.6 Hz, 2H), 7.14-7.11 (m, 1H), 6.91 (td, J=8.3, 2.5 Hz, 1H), 6.20 (s, 1H), 4.14-4.08 (m, 1H), 4.07-4.02 (m, 1H), 4.01-3.93 (m, 1H), 3.91-3.82 (m, 2H), 3.66 (s, 3H), 3.59 (s, 3H), 3.40 (dd, J=9.0, 4.6 Hz, 1H), 3.24 (td, J=13.0, 3.1 Hz, 1H), 2.96-2.80 (m, 4H), 2.60 (t, J=7.7 Hz, 2H), 2.49 (td, J=11.5, 3.1 Hz, 1H), 2.24 (t, J=10.8 Hz, 1H).

Example 26: 2-(4-((S)-7-(((R)-6-(2-bromo-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)phenyl)acetic Acid The title compound was prepared as a yellow solid (321 mg 46.1%) according to example 14 by replacing (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluoro phenyl)-6-(bromomethyl)-2-(thiazol-2-yl)-1,4-dihydropyrimidine-5-acetate (503 mg, 1 mmol). MS (ESI, pos.ion) m/z: 697.1 [M+H]$^+$; $^1$H NMR (400 MHz, CDCl$_3$) δ 7.86 (d, J=3.1 Hz, 1H), 7.50 (d, J=8.5 Hz, 2H), 7.47 (d, J=3.1 Hz, 1H), 7.37-7.30 (m, 2H), 7.25 (d, J=8.5 Hz, 2H), 6.99 (td, J=8.3, 2.5 Hz, 1H), 6.21 (s, 1H), 4.21-4.10 (m, 1H), 4.11-4.01 (m, 3H), 4.01-3.95 (m, 1H), 3.94-3.85 (m, 2H), 3.60 (s, 2H), 3.41 (dd, J=9.0, 4.7 Hz, 1H), 3.26 (dd, J=18.4, 6.5 Hz, 1H), 2.90 (d, J=10.0 Hz, 2H), 2.50 (m, 1H), 2.26 (t, J=10.7 Hz, 1H), 1.14 (t, J=7.1 Hz, 3H).

Example 27: 2-(4-((S)-7-(((R)-6-(2,4-dichlorophenyl)-5-(methoxycarbonyl)-2-(thiazol-2-yl)-3,6-dihydropyrimidin-4-yl)methyl)-3-oxohexahydroimidazo[,5-a]pyrazin-2(3H)-yl)phenyl)acetic Acid The title compound was prepared as a yellow solid (306 mg 46.7%) according to example 14 by replacing (R)-methyl 6-(bromomethyl)-4-(2-chloro-4-fluorophenyl)-2-

(thiazol-2-yl)-1,4-dihydropyrimidine-5-carboxylate with (R)-methyl 4-(2,4-dichlorophenyl)-6-(bromomethyl)-2-(thiazol-2-yl)-1,4-dihydropyrimidine-5-carboxylate (2, 461 mg 1 mmol). MS (ESI, pos.ion) m/z: 655.1 [M+H]⁺; ¹H NMR (400 MHz, CDCl₃) δ 7.87 (d, J=3.1 Hz, 1H), 7.51 (d, J=8.6 Hz, 2H), 7.48 (d, J=3.1 Hz, 1H), 7.42 (d, J=1.9 Hz, 1H), 7.26 (dd, J=8.4, 3.0 Hz, 3H), 7.19 (dd, J=8.4, 1.9 Hz 1H), 6.22 (s, 1H), 4.13 (d, J=17.2 Hz, 1H), 4.06 (dd, J=13.1, 1.6 Hz, 1H), 4.03-3.95 (m, 1H), 3.92 (s, 1H), 3.88 (d, J=6.6 Hz, 1H), 3.61 (m, 5H), 3.41 (dd, J=9.0, 4.6 Hz 1H), 3.25 (td, J=13.1, 2.9 Hz, 1H), 2.89 (d, J=9.9 Hz, 2H), 2.50 (td, J=11.3, 2.7 Hz, 1H), 2.26 (t, J=10.8 Hz, 1H).

Example 28: 3-(4-((S)-7-(((R)-6-(2-bromo-4-fluorophenyl)-5-(ethoxycarbonyl)-2-(thiazol-2-yl)-3,6-dihydropyrimidin-4-yl)-3-oxohexahydroimidazo[1,5-a]pyrazin-2(3H)-yl)phenyl)-2,2-dimethylpropionic Acid The title compound was prepared as a yellow solid (130 mg 37.2%) according to example 17 by replacing (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5-carboxylate (250 mg, 0.50 mmol). MS (ESI, pos.ion) m/z: 739.1 [M+H]⁺; 1H NMR (400 MHz, CDCl₃) δ 9.60 (s, 1H), 7.84 (d, J=3.1 Hz, 1H), 7.47-7.40 (m, 3H), 7.33-7.27 (m, 2H), 7.13 (d, J=8.5 Hz, 2H), 6.99-6.91 (m, 1H), 6.19 (s, 1H), 4.11 (d, J=17.3 Hz, 1H), 4.07-3.99 (m, 3H), 3.98-3.92 (m, 1H), 3.91-3.85 (m, 2H), 3.40 (dd, J=9.0, 4.6 Hz, 1H), 3.27-3.18 (m, 1H), 2.88 (overlap, 4H), 2.53-2.42 (m, 1H), 2.23 (t, J=10.7 Hz, 1H), 1.18 (s, 6H), 1.12 (t, J=7.1 Hz, 3H).

Example 29: 3-(4-((S)-7-(((R)-6-(2-chloro-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)phenyl)-2,2-dimethylpropionic Acid The title compound was prepared as a yellow solid (120 mg, 36.52%) according to example 17 by replacing (R)-methyl 6-(bromomethyl)-4-(2-chloro-4-fluorophenyl)-2-(thiazol-2-yl)-1,4-dihydropyrimidine-5-carboxylate with (R)-ethyl 6-(bromomethyl)-4-(2-bromo-4-fluorophenyl)-2-(thiazol-2-yl)-1,4-dihydropyrimidine-5-carboxylate (235 mg, 0.51 mmol). MS (ESI, pos.ion) m/z: 695.3 [M+H]⁺; ¹H NMR (400 MHz, CDCl₃) δ 9.61 (s, 1H), 7.85 (d, J=3.1 Hz, 1H), 7.49-7.38 (m, 3H), 7.30 (dd, J=8.5, 6.2 Hz, 1H), 7.15-7.09 (m, 3H), 6.96-6.87 (m, 1H), 6.22 (s, 1H), 4.10 (d, J=17.8 Hz, 1H), 4.06-3.99 (m, 3H), 3.98-3.93 (m, 1H), 3.91-3.84 (m, 2H), 3.40 (dd, J=9.0, 4.5 Hz, 1H), 3.23 (t, J=11.1 Hz, 1H), 2.84 (overlap, 4H), 2.51-2.39 (m, 1H), 2.23 (t, J=10.6 Hz, 1H), 1.18 (s, 6H), 1.12 (t, J=7.1 Hz, 3H).

Example 30: 3-(2-((S)-7-(((R)-6-(2-bromo-4-fluorophenyl)-5-(ethoxycarbonyl)-2-(thiazol-2-yl)-3,6-dihydropyrimidin-4-yl)-3-oxohexahydroimidazo[1,5-a]pyrazin-2(3H)-yl)thiazol-4-yl)propionic Acid The title compound was prepared as a yellow solid (210 mg, 58%) according to example by replacing (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluoro phenyl)-6-(bromomethyl)-2-(thiazol-2-yl)-1,4-dihydropyrimidine-5-carboxylate (281 mg, 0.56 mmol). MS (ESI, pos. ion): m/z 718.1[M+H]⁺; ¹H NMR (400 MHz, CDCl₃) δ 9.52 (s, 1H), 7.86 (d, J=3.0 Hz, 1H), 7.48 (d, J=2.8 Hz, 1H), 7.37-7.28 (m, 2H), 6.99 (td, J=8.4, 2.2 Hz, 1H), 6.55 (s, 1H), 6.22 (s, 1H), 4.23-4.10 (m, 3H), 4.09-4.00 (m, 3H), 3.94 (d, J=17.1 Hz, 1H), 3.71 (dd, J=10.1, 4.3 Hz, 1H), 3.33 (t, J=11.2 Hz, 1H), 3.02-2.88 (m, 4H), 2.79-2.69 (m, 2H), 2.58-2.46 (m, 1H), 2.28 (t, J=10.7 Hz, 1H), 1.14 (t, J=7.1 Hz, 3H).

Example 31: (R)-methyl 6-(((S)-2-(4-acetylphenyl)-3-oxohexahydroimidazo[1,5-a]pyrazin-7(1H)-yl) methyl)-4-(2-chloro-4-fluorophenyl)-2-(thiazol-2-yl)-1,4-dihydropyrimidine-5-carboxy late Step 1: (R)-tert-butyl 2-(4-acetylphenyl)-3-oxohexahydroimidazo[1,5-a]pyrazine-7(1H)-carboxylate

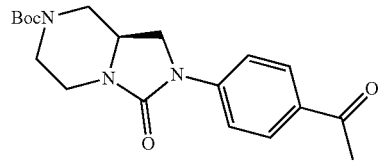 [SMILES: CC(=O)c1ccc(N2C[C@@H]3CN(C(=O)OC(C)(C)C)CCN3C2=O)cc1]

To a two-neck flask were added (R)-tert-butyl 3-oxohexahydroimidazo[1,5-a]pyrazine-7(1H)-carboxylate (2.02 g 8.37 mmol), p-bromoacetophenone (1.82 g 9.14 mmol), tris(dibenzylideneacetone)dipalladium (456 mg 0.50 mmol), Xantphos (480 mg 0.83 mmol), cesium carbonate (5.40 g 16.6 mmol) and dioxane (50 mL), the mixture was stirred at 100° C. under N₂ for 1 hour. The mixture was cooled to rt and filtered by suction filtration, the filter cake was washed with EtOAc (20 mL), the filtrate was washed with saturated aqueous NaCl and dried over anhydrous Na₂SO₄, and then concentrated. The residue was purified by silica gel column chromatography (PE/EA (v/v)=2/1) to give the title compound as a brownish red (1.41 g 46.9%). MS (ESI, pos.ion) m/z: 304.1 [M+H–56]+.

Step 2: (S)-2-(4-acetylphenyl)hexahydroimidazo[1,5-a]pyrazine-3(2H)-one hydrochloride

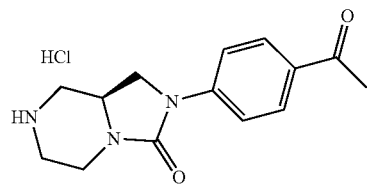 [SMILES: CC(=O)c1ccc(N2C[C@@H]3CNCCN3C2=O)cc1 ; Cl]

To a single neck flask were added (R)-tert-butyl 2-(4-acetylphenyl)-3-oxohexahydro imidazo[1,5-a]pyrazine-7(1H)-carboxylate (160 mg 0.45 mmol), EtOAc (3 mL) and EtOAc/HCl (6 mL, 24 mmol, 4 mol/L), the mixture was stirred at rt for 12 hours. The mixture was filtered by suction filtration, the filter cake was washed with EtOAc (5 mL) to get the title compound as a brown solid (117 mg 88.9%). MS (ESI, pos.ion) m/z: 260.2 [M+H]⁺.

Step 3: (R)-methyl 6-(((S)-2-(4-acetylphenyl)-3-oxohexahydroimidazo[1,5-a]pyrazin-7(1H)-yl) methyl)-4-(2-chloro-4-fluorophenyl)-2-(thiazol-2-yl)-1,4-dihydropyrimidine-5-carboxylate To a 50 mL flask were added (S)-2-(4-acetylphenyl) hexahydroimidazo[1,5-a]pyrazine-3(2H)-one hydrochloride (117 mg 0.40 mmol), (R)-methyl 4-(2-chloro-4-fluorophenyl)-6-(bromomethyl)-2-(thiazol-2-yl)-1,4-dihydropyrimidine-5-carboxylate (176 mg 0.40 mmol), K₂CO₃ (110 mg 0.79 mmol) and EtOH (10 mL), the mixture was stirred at rt for 12 hours. The mixture was filtered by suction filtration, the filtrate was concentrated in vacuo. The residue was purified by silica gel column chromatography (CH₂Cl₂/MeOH (V/V)=30/1) to give the title compound as a pale yellow solid (33 mg 13.39%). MS (ESI, pos.ion) m/z: 623.3 [M+H]⁺; ¹H NMR (400 MHz, CDCl₃) δ 9.60 (s, 1H), 7.97 (d, J=8.6 Hz, 2H), 7.87 (d, J=2.6 Hz, 1H), 7.67 (d, J=8.6 Hz, 2H), 7.48 (d, J=2.6 Hz, 1H), 7.32 (s, 1H), 7.16 (d, J=6.6 Hz, 1H), 6.94 (t, J=7.2 Hz, 1H), 6.23 (s, 1H), 4.21-4.02 (m, 3H), 4.01-3.88 (m, 2H), 3.61 (s, 3H), 3.51-3.48 (m, 1H), 3.30 (t, J=11.2 Hz, 1H), 2.93 (d, J=10.3 Hz, 2H), 2.59 (s, 3H), 2.52 (d, J=11.4 Hz, 1H), 2.28 (t, J=10.7 Hz, 1H).

Example 32: (R)-methyl 6-(((S)-2-(4-acetyl-2fluorophenyl)-3-oxohexahydroimidazo[1,5-a]pyrazin-7(1H)-yl)methyl)-4-(2-chloro-4-fluorophenyl)-2-(thiazol-2-yl)-1,4-dihydropyrimidine-5-carboxylate The title compound was prepared as a brownish yellow solid (552 mg 86.05%) according to example 31 by replacing p-bromoacetophenone with 4-bromo-3-fluoroacetophenone (270 mg, 1.24 mmol). MS (ESI, pos.ion) m/z: 641.0 [M+H]⁺; ¹H NMR (400 MHz, CDCl₃) δ 9.52 (s, 1H), 7.79 (d, J=8.7 Hz, 2H), 7.70-7.57 (m, 2H), 7.39 (s, 1H), 7.25-7.17 (m, 1H), 7.06 (d, J=7.7 Hz, 1H), 6.84 (t, J=7.1 Hz, 1H), 6.13 (s, 1H), 4.04 (t, J=17.0 Hz, 2H), 3.95 (d, J=6.1 Hz, 2H), 3.83 (d, J=17.2 Hz, 1H), 3.56 (s, 1H), 3.52 (s, 3H), 3.21 (t, J=11.2 Hz, 1H), 2.82 (d, J=9.8 Hz, 2H), 2.49 (s, 3H), 2.43 (d, J=10.9 Hz, 1H), 2.25 (t, J=9.7 Hz, 1H).

Example 33: 2-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-fluorophenyl)-2-methylpropionic Acid The title compound was prepared as a yellow solid (600 mg, 43.04%) according to step 1 of example 15 by replacing methyl 2-(4-bromophenyl)acetate with methyl 2-(4-bromo-3-fluorophenyl)acetate (866 mg, 3.51 mmol). MS (ESI, pos.ion) m/z: 685.2 [M+H]⁺; ¹H NMR (400 MHz, CDCl₃) δ 9.63 (s, 1H), 7.86 (d, J=3.1 Hz, 1H), 7.52-7.44 (m, 2H), 7.30-7.27 (m, 1H), 7.18-7.10 (m, 3H), 6.95-6.87 (m, 1H), 6.21 (s, 1H), 4.12 (d, J=17.2 Hz, 1H), 4.02 (s, 2H), 3.92-3.82 (m, 2H), 3.60 (s, 3H), 3.49 (dd, J=8.9, 4.5 Hz, 1H), 3.30-3.22 (m, 1H), 2.85 (t, J=9.4 Hz, 2H), 2.57-2.45 (m, 1H), 2.34 (t, J=10.9 Hz, 1H), 1.58 (s, 6H).

Example 34: 3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-fluorophenyl)propionic Acid The title compound was prepared as a yellow solid (530 mg 75.8%) according to example 18 by replacing 4-bromobenzaldehyde with 4-bromo-3-fluorobenzaldehyde (400 mg, 1.97 mmol). MS (ESI, pos.ion) m/z: 671.4 [M+H]⁺; ¹H NMR (400 MHz, CDCl₃) δ 7.87 (d, J=2.9 Hz, 1H), 7.54 (d, J=3.0 Hz, 1H), 7.42-7.29 (m, 2H), 7.15 (dd, J=8.3, 2.2 Hz, 1H), 7.05-6.93 (m, 3H), 6.17 (s, 1H), 4.66 (d, J=15.1 Hz, 1H), 4.43-4.31 (m, 2H), 3.89 (t, J=8.9 Hz, 2H), 3.61 (s, 3H), 3.49 (s, 4H), 2.93 (t, J=7.1 Hz, 4H), 2.65 (t, J=7.3 Hz, 2H).

Example 35: 3-(6-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-3-yl)propionic Acid The title compound was prepared as a yellow solid (692 mg 74.8%) according to step 1 of example 20 by replacing 2-bromothiazole-4-carbaldehyde with 6-bromopyridine-3-carbaldehyde (500 mg 2.69 mmol). MS (ESI. pos) m/z: 655.20[M+H]⁺; ¹H NMR (600 MHz, CDCl₃) δ 9.65 (s, 1H), 8.25 (d, J=8.6 Hz, 1H), 8.15 (s, 1H), 7.87 (d, J=2.5 Hz, 1H), 7.54 (d, J=8.2 Hz, 1H), 7.48 (d, J=2.5 Hz, 1H), 7.31 (d, J=8.0 Hz, 1H), 7.15 (d, J=6.8 Hz, 1H), 6.94 (t, J=7.1 Hz, 1H), 6.22 (s, 1H), 4.10 (dt, J=22.4, 12.0 Hz, 3H), 4.00 (s, 1H), 3.92 (d, J=17.2 Hz, 1H), 3.70 (dd, J=10.4, 4.7 Hz, 1H), 3.61 (s, 3H), 3.28 (t, J=11.2 Hz, 1H), 3.00-2.84 (m, 4H), 2.66 (t, J=6.7 Hz, 2H), 2.50 (t, J=10.1 Hz, 1H), 2.27 (t, J=10.6 Hz, 1H).

Example 36: 3-(5-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-3-yl)propionic Acid The title compound was prepared as a yellow solid (177 mg 34.8%) according to step 1 of example 20 by replacing 2-bromothiazole-4-carbaldehyde with 5-bromopyridine-3-carbaldehyde (300 mg 1.61 mmol). MS (ESI. pos) m/z: 655.20[M+H]⁺; ¹H NMR (400 MHz, CDCl₃) δ 9.60 (s, 1H), 8.44 (s, 1H), 8.24 (d, J=16.0 Hz, 2H), 7.87 (d, J=3.0 Hz, 1H), 7.48 (d, J=3.0 Hz, 1H), 7.33-7.29 (m, 1H), 7.15 (dd, J=8.5, 2.4 Hz, 1H), 6.93 (td, J=8.4, 2.4 Hz, 1H), 6.22 (s, 1H), 4.19-4.02 (m, 3H), 3.99-3.91 (m, 1H), 3.77 (t, J=6.3 Hz, 2H), 3.61 (s, 3H), 3.48 (dd, J=9.0, 4.8 Hz, 1H), 3.28 (t, J=11.0 Hz, 1H), 3.02-2.90 (m, 3H), 2.69 (t, J=6.8 Hz, 2H), 2.51 (dd, J=11.4, 8.8 Hz, 1H), 2.28 (t, J=10.7 Hz, 1H).

Example 37: 3-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)propionic Acid Step 1: (E)-methyl 3-(3-bromophenyl)acrylate

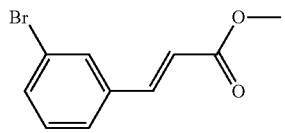

To a dry flask were added 3-bromobenzaldehyde (1.01 g 5.46 mmol) and DCM (15 mL) in turn, the mixture was stirred uniformly and cooled to 0° C. And then methyl (triphenylphosphoranylidene)acetate (3.61 g 10.8 mmol) was added, the mixture was stirred at rt for 8 hours. The mixture was concentrated in a rotary evaporator. The residue was purified by silica gel column chromatography (PE/EA (v/v)=10/1) to give the title compound as a white solid (1.18 g 89.7%). ESI: (ESI, pos.ion) m/z: 241.10 [M+H]⁺.

Step 2: methyl 3-(3-bromophenyl)propionate

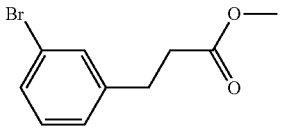

To a dry flask were added (E)-methyl 3-(3-bromophenyl) acrylate (1.18 g, 4.89 mmol), methanol (10 mL) and 10% Pd/C (120 mg) in turn, the mixture was stirred at 40° C. under H₂ for 6 hours. The mixture was filtered and the filtrate was concentrated in a rotary evaporator to get the title compound as a brown liquid (1.2 g 100%). ESI: (ESI, pos.ion) m/z: 243.1 [M+H]⁺.

Step 3: 3-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl) propionic Acid The title compound was prepared as a yellow solid (478 mg 81.4%) according to step 1 of example 13 by replacing methyl 3-(4-bromophenyl)propionate with methyl 3-(3-bromophenyl)propionate (700 mg, 2.88 mmol). MS (ESI, pos.ion) m/z: 653.1 [M+H]⁺; ¹H NMR (400 MHz, CDCl₃) δ 9.65 (s, 1H), 7.87 (d, J=2.7 Hz, 1H), 7.53 (s, 1H), 7.48 (d, J=2.7 Hz, 1H), 7.34-7.22 (m, 3H), 7.18-7.12 (m, 1H), 7.00-6.88 (m, 2H), 6.23 (s, 1H), 4.16-4.09 (m, 1H), 4.09-3.96 (m, 2H), 3.95-3.86 (m, 2H), 3.61 (s, 3H), 3.43 (dd, J=8.5, 4.2 Hz, 1H), 3.25 (t, J=11.2 Hz, 1H), 3.01-2.93 (m, 2H), 2.89 (d, J=10.1 Hz, 2H), 2.73-2.62 (m, 2H), 2.50 (t, J=10.1 Hz, 1H), 2.27 (t, J=10.6 Hz, 1H).

Example 38: 2-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)-2-methylpropionic Acid The title compound was prepared as a yellow solid (420 mg 64%) according to step 1 of example 15 by replacing methyl 2-(4-bromophenyl)acetate with methyl 2-(3-bromophenyl)acetate (4.5 g 20 mmol). MS (ESI, pos.ion) m/z: 667.4 [M+H]⁺; ¹H NMR (600 MHz, CDCl₃) δ 7.88 (d, J=3.0 Hz, 1H), 7.73 (s, 1H), 7.58 (d, J=3.0 Hz, 1H), 7.34 (dd, J=8.7, 5.9 Hz, 1H), 7.31 (t, J=8.0 Hz, 1H), 7.21 (d, J=8.1 Hz, 1H), 7.17 (dd, J=8.2, 2.5 Hz, 1H), 7.14 (d, J=7.9 Hz, 1H), 7.00 (td, J=8.4, 2.4 Hz, 1H), 6.17 (s, 1H), 4.81 (d, J=14.8 Hz, 1H), 4.50 (d, J=14.9 Hz, 1H), 4.45-4.39 (m, 1H), 4.08 (dd, J=14.4, 2.9 Hz, 1H), 3.95 (t, J=9.0 Hz, 1H), 3.79 (d, J=9.3 Hz, 1H), 3.74 (d, J=11.2 Hz, 1H), 3.62 (s, 3H), 3.61-3.53 (m, 1H), 3.46 (dd, J=9.6, 3.0 Hz, 1H), 3.04 (M, 2H), 1.58 (s, 6H).

Example 39: 2-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl) acetic Acid The title compound was prepared as a yellow solid (280 mg 57%) according to step 1 of example 14 by replacing 2-(4-bromophenyl)acetatic acid with 2-(3-bromophenyl)acetatic acid (2 g 9.30 mmol). MS (ESI, pos.ion) m/z: 639.0 [M+H]⁺; ¹H NMR (600 MHz, CDCl₃) δ 9.65 (s, 1H), 7.87 (d, J=3.1 Hz, 1H), 7.55 (s, 1H), 7.48 (d, J=3.1 Hz, 1H), 7.43 (dd, J=8.2, 1.2 Hz, 1H), 7.32-7.29 (m, 2H), 7.16 (dd, J=8.5, 2.5 Hz, 1H), 6.99 (d, J=7.5 Hz, 1H), 6.94 (td, J=8.3, 2.5 Hz, 1H), 6.22 (s, 1H), 4.15-4.10 (m, 1H), 4.06 (dd, J=13.1, 2.0 Hz, 1H), 4.03-3.98 (m, 1H), 3.94-3.89 (m, 2H), 3.65 (s, 2H), 3.62 (s, 3H), 3.44 (dd, J=9.1, 4.8 Hz 1H), 3.26 (td, J=13.1, 3.1 Hz, 1H), 2.89 (d, J=9.8 Hz, 2H), 2.51 (td, J=11.6, 3.2 Hz, 1H), 2.27 (t, J=10.7 Hz, 1H).

Example 40: 2-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)-2-methylpropionic Acid Step 1: (R)-tert-butyl 2-(4-hydroxyphenyl)-3-oxohexahydroimidazo[1,5-a]pyrazin-7(1H)-carboxylate

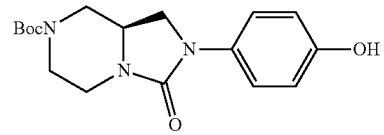 [SMILES: CC(C)(C)OC(=O)N1CCN2C(=O)N(c3ccc(O)cc3)C[C@@H]2C1]

To a 25 mL single-neck flask were added (R)-tert-butyl 3-oxohexahydroimidazo[1,5-a]pyrazine-7(1H)-carboxylate (1.00 g 4.14 mmol), 4-bromophenol (717 mg 4.14 mmol), palladium acetate (93 mg 0.41 mmol), 2-di-tert-butylphosphino-2',4',6'-triisopropylbiphenyl (352 mg 0.83 mmol), cesium carbonate (2.70 g 8.29 mmol) and 1,4-dioxane (20 mL). The mixture was heated to 90° C. under N₂ and stirred for 2 hours. The mixture was cooled to rt and filtered by suction filtration, the filter cake was washed with EtOAc (20 mL), the filtrate was washed with saturated aqueous NaCl and dried over anhydrous Na₂SO₄, and filtered, the filtrated was concentrated in vacuo. The residue was purified by silica gel column chromatography (PE/EA (v/v)=1/1) to give the title compound as an off white solid (507 mg 36.7%). MS (ESI, pos.ion) m/z: 334.3 [M+H]⁺.

Step 2: (R)-tert-butyl 2-(4-((1-ethoxy-2-methyl-1-oxoprop-2-yl)oxy)phenyl)-3-oxohexahydro imidazo[1,5-a]pyrazine-7(1H)-carboxylate

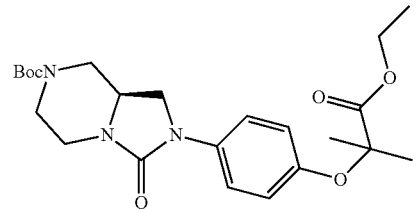 [SMILES: CCOC(=O)C(C)(C)Oc1ccc(N2C[C@@H]3CN(C(=O)OC(C)(C)C)CCN3C2=O)cc1]

To a 25 mL single neck flask were added (R)-tert-butyl 2-(4-hydroxyphenyl)-3-oxohexahydroimidazo[1,5-a]pyrazine-7(1H)-carboxylate (365 mg, 1.10 mmol), DMF (5 mL), cesium carbonate (1.07 g 3.28 mmol) and ethyl 2-bromo-2-methyl-propionate (427 mg 2.19 mmol), the mixture was stirred at rt for 16 hours. The mixture was filtered, the filter cake was washed with EtOAc (20 mL), the filtrate was wash with saturated aqueous NaCl (20 ml×4), and dried over anhydrous Na₂SO₄ and filtered, the filtrate was concentrated Step 3: (R)-2-(4-(7-(tert-butoxycarbonyl)-3-oxo-hexahydroimidazo[1,5-a]pyrazin-2(3H)-yl) phenoxy)-2-methylpropionic Acid

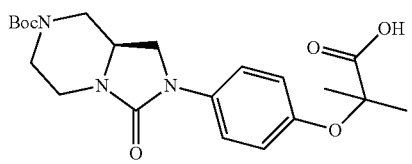 [SMILES: CC(C)(C)OC(=O)N1CCN2C(=O)N(c3ccc(OC(C)(C)C(=O)O)cc3)C[C@@H]2C1]

To a dry flask were added (R)-tert-butyl 2-(4-((1-ethoxy-2-methyl-1-oxoprop-2-yl)oxy)phenyl)-3-oxohexahydroimidazo[1,5-a]pyrazine-7(1H)-carboxylate (490 mg, 1.10 mmol), THF (3 mL) and NaOH (447 mg 11.2 mmol) in water (3 mL), the mixture was stirred at rt for 11.5 hours. Then the mixture was adjusted with hydrochloric acid (6 M) to pH 6, and then EA (100 mL) was added. The organic phase was washed with saturated brine (10 mL), dried over anhydrous sodium sulfate, filtered, and the filtrate was concentrated in vacuo. The residue was purified by silica gel chromatograph (EtOAc) to give the title compound as a white solid (412 mg 89.69%). MS (ESI, pos.ion) m/z: 364.1 [M−56+H]$^+$.

Step 4: (S)-2-methyl-2-(4-(3-oxohexahydroimidazo[1,5-a]pyrazin-2(3H)-yl)phenoxy)propionic acid hydrochloride

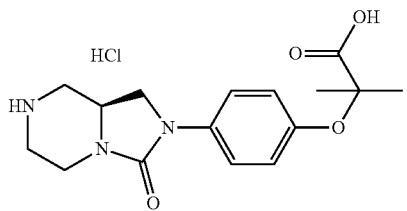 [SMILES: CC(C)(Oc1ccc(N2C[C@@H]3CNCCN3C2=O)cc1)C(=O)O ; Cl]

To a single neck flask were added (R)-2-(4-(7-(tert-butoxycarbonyl)-3-oxohexahydroimidazo[1,5-a]pyrazin-2(3H)-yl)phenoxy)-2-methylpropionic acid (412 mg, 0.98 mmol) and HCl in 1,4-dioxane (5 mL, 20 mmol, 4 mol/L), the mixture was stirred at rt for 1.5 hours and filter by suction filtration, the filter cake was washed with 1,4-dioxane (5 mL) and dried at rt to get the title compound as a white solid (294 mg, 84.13%). MS (ESI, pos.ion) m/z: 320.3 [M+H]$^+$.

Step 5: 2-(4-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)phenoxy)-2-methylpropionic Acid To a 50 mL single neck flask were added (S)-2-methyl-2-(4-(3-oxohexahydroimidazo[1,5-a]pyrazin-2(3H)-yl)phenoxy)propionic acid hydrochloride (294 mg 0.83 mmol), (R)-methyl 6-(bromomethyl)-4-(2-chloro-6-fluorophenyl)-2-(thiazol-2-yl)-1,4-dihydropyrimidine-5-carboxylate (368 mg, 0.83 mmol), potassium carbonate (237 mg 1.70 mmol) and ethanol (15 mL) in turn, the mixture was stirred at rt for 23 hours. After the reaction was completed, the reaction mixture was filtered by suction filtration, the filter cake was washed with EtOAc (10 mL), the filtrated was concentrated in vacuo, the residue was diluted with EtOAc (30 mL) and water (15 mL), the resulting mixture was adjusted with hydrochloric acid (6 M) to pH 5. The water phase was extracted with EtAOc (15 mL) once, the organic phases were combined and concentrated in vacuo. The residue was purified by silica gel column chromatography (CH$_2$Cl$_2$/MeOH (V/V)=50/1) to give the title compound as a yellow solid (469 mg, 83.1%). MS (ESI, pos.ion) m/z: 683.3 [M+H]$^+$; $^1$H NMR (400 MHz, CDCl$_3$) δ 9.65 (s, 1H), 7.87 (d, J=3.1 Hz, 1H), 7.49 (d, J=3.1 Hz, 1H), 7.42 (d, J=9.0 Hz, 2H), 7.33-7.29 (m, 1H), 7.15 (dd, J=8.6, 2.5 Hz, 1H), 6.99-6.90 (m, 3H), 6.23 (s, 1H), 4.14 (d, J=17.2 Hz, 1H), 4.05 (d, J=13.3 Hz, 1H), 4.02-3.95 (m, 1H), 3.94-3.83 (m, 2H), 3.61 (s, 3H), 3.43-3.35 (m, 1H), 3.31-3.20 (m, 1H), 2.90 (d, J=8.8 Hz, 2H), 2.58-2.45 (m, 1H), 2.27 (t, J=10.2 Hz, 1H), 1.58 (s, 6H).

Example 41: 2-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)acetic Acid The title compound was prepared as a yellow solid (172 mg 39.1%) according to step 2 of example 40 by replacing ethyl 2-bromo-2-methylpropionate with ethyl bromoacetate (230 mg, 1.4 mmol). MS (ESI, pos.ion) m/z: 655.0 [M+H]$^+$; $^1$H NMR (400 MHz, CDCl$_3$) δ 7.87 (d, J=3.1 Hz, 1H), 7.49 (d, J=3.1 Hz, 1H), 7.41 (d, J=9.0 Hz, 2H), 7.33-7.29 (m, 1H), 7.15 (dd, J=8.5, 2.5 Hz, 1H), 6.95 (dd, J=8.2, 2.5 Hz, 1H), 6.90 (d, J=9.0 Hz, 2H), 6.21 (s, 1H), 4.61 (s, 2H), 4.21 (d, J=16.7 Hz, 1H), 4.06-3.92 (m, 3H), 3.83 (t, J=8.9 Hz, 1H), 3.61 (s, 3H), 3.38-3.32 (m, 1H), 3.27 (t, J=11.1 Hz, 1H), 2.98 (d, J=9.5 Hz, 2H), 2.61-2.47 (m, 1H), 2.35 (t, J=10.7 Hz, 1H).

Example 42: 2-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)propionic Acid The title compound was prepared as a yellow solid (560 mg 45.6%) according to step 2 of example 40 by replacing ethyl 2-bromo-2-methylpropionate with methyl 2-bromopropionate (0.35 mL, 3.0 mmol). MS (ESI, pos.ion) m/z: 669.0 [M+H]$^+$; $^1$H NMR (600 MHz, CDCl$_3$) δ 7.92 (s, 1H), 7.65 (s, 1H), 7.34 (d, J=25.0 Hz, 3H), 7.17 (d, J=8.0 Hz, 1H), 7.02 (s, 1H), 6.90 (s, 2H), 6.19 (s, 1H), 4.87-4.72 (m, 2H), 4.55 (s, 1H), 4.22 (d, J=28.2 Hz, 1H), 3.98-3.91 (m, 1H), 3.85-3.67 (m, 3H), 3.64 (s, 3H), 3.49-3.34 (m, 1H), 3.24 (s, 1H), 3.15-2.83 (m, 2H), 1.58 (s, 3H).

Example 43: 2-(3-((S)-7-(((R)-6-(2-chloro-4-fluoro-phenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)acetic Acid Step 1: ethyl 2-(3-bromophenoxy)acetate

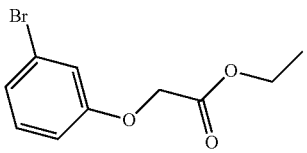

To a dry flask were added 3-bromophenol (1.00 g 5.78 mmol), DMF (5 mL) and K$_2$CO$_3$ (1.99 g 14.4 mmol) in turn, after stirring, ethyl 2-bromoacetate (0.77 mL) was added. The mixture was further stirred at rt for 2 h, then EA (60 mL) was added, the organic layer was washed with saturated aqueous NaCl, dried over anhydrous sodium sulfate and filtered, the filtrate was concentrated in vacuo to get the title compound as a colorless liquid (1.43 g, 95.5%). MS (ESI, pos.ion) m/z: 259.1 [M+H]$^+$.

Step 2: 2-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)acetic Acid The title compound was prepared as a yellow solid (650 mg 51.61%) according to step 2 of example 17 by replacing 3-(4-bromophenyl)-2,2-dimethylpropionate with 2-(3-bromophenoxy)acetate (800 mg 3.09 mmol). MS (ESI, pos.ion) m/z: 655.0 [M+H]$^+$; $^1$H NMR (400 MHz, CDCl$_3$) δ 7.85 (d, J=3.0 Hz, 1H), 7.50 (d, J=3.0 Hz, 1H), 7.44 (s, 1H), 7.33-7.27 (m, 1H), 7.21 (t, J=8.3 Hz, 1H), 7.14 (dd, J=8.5, 2.4 Hz, 1H), 6.98-6.87 (m, 2H), 6.62 (d, J=8.3 Hz, 1H), 6.17 (s, 1H), 4.64 (s, 2H), 4.42 (d, J=15.2 Hz, 1H), 4.03 (d, J=12.8 Hz, 1H), 3.79 (t, J=9.2 Hz, 1H), 3.60 (s, 3H), 3.49 (s, 3H), 3.41-3.20 (m, 5H), 2.73-2.64 (m, 1H), 2.59-2.48 (m, 1H).

Example 44: (R)-methyl 4-(2-chloro-4-fluorophenyl)-6-(((S)-2-(4-(3-((1-methoxy-2-methylpropan-2-yl)amino)-3-oxoprop yl)phenyl)-3-oxohexahydroimidazo[1,5-a]pyrazin-7(1H)-yl)methyl)-2-(thiazol-2-yl)-1,4-dihydropyrimidine-5-carboxylate To a dry single neck flask were added 3-(4-((S)-7-(((R)-6-(2-chloro-4-fluorophenyl)-5-(methoxycarbonyl)-2-thiazol-2-yl)-3,6-dihydropyrimidin-4-yl)methyl)-3-oxohexahydroimidazo[1,5-a]pyrazin-2(3H)-yl)phenyl)propionic acid (900 mg 1.38 mmol), DCM (10 mL), 1-methoxy-2-methylpropane-2-amine (185 mg 1.79 mmol) and DIPEA (1.2 mL, 6.9 mmol), the mixture was stirred uniformly, and HATU (827 mg 2.07 mmol) was added. The reaction mixture was stirred at rt for 4 hours. After the reaction was completed, the mixture was diluted with DCM (30 mL) and water (20 mL), the organic phase was washed with dilute hydrochloric acid (0.5 M) and saturated aqueous NaCl in turn, and then dried over anhydrous sodium sulfate and concentrated in vacuo. The residue was purified by silica gel column chromatography (DCM/MeOH (v/v)=50/1) to give the title compound as a yellow solid (803 mg 78.93%). MS (ESI, pos.ion) m/z: 738.2 [M+H]$^+$; $^1$H NMR (400 MHz, CDCl$_3$) δ 7.83 (d, J=3.0 Hz, 1H), 7.52 (d, J=3.0 Hz, 1H), 7.38 (d, J=8.4 Hz, 2H), 7.30 (dd, J=8.6, 6.1 Hz, 1H), 7.17-7.06 (m, 3H), 7.00-6.89 (m, 1H), 6.15 (s, 1H), 5.64 (s, 1H), 4.31 (d, J=16.5 Hz, 1H), 4.17-4.00 (m, 3H), 3.87 (t, J=9.0 Hz, 1H), 3.58 (s, 3H), 3.41 (dd, J=9.3, 4.1 Hz, 1H), 3.32 (s, 3H), 3.31-3.25 (m, 3H), 3.24-3.10 (m, 2H), 2.84 (t, J=7.6 Hz, 2H), 2.74 (s, 1H), 2.58 (s, 1H), 2.35 (t, J=7.7 Hz, 2H), 1.26 (s, 6H).

Example 45: 3-(4-((8aS)-7-((-6-(2-chloro-4-fluorophenyl)-5-(methoxycarbonyl)-2-(1-methyl-1H-imidazol-2-yl)-3,6-dihydropyrimidin-4-yl)methyl)-3-oxohexahydroimidazo[1,5-a]pyrazin-2(3H)-yl)phenyl)propionic Acid The title compound was prepared as a yellow solid (0.28 g 43%) according to step 5 of example 13 by replacing (R)-methyl 4-(2-chloro-4-fluorophenyl)-6-(bromomethyl)-2-(thiazol-2-yl)-1,4-dihydropyrimidine-5-carboxylate with methyl 6-(bromomethyl)-4-(2-chloro-4-fluorophenyl)-2-(1-methyl-1H-imidazol-2-yl)-1,4-dihydropyrimidine-5-carboxylate (0.44 g 1 mmol). MS (ESI, pos.ion) m/z: 650.1 [M+H]$^+$.

Example 46: 2-((tert-butoxycarbonyl)amino)-2-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)acetic Acid Step 1: 2-(4-bromophenyl)-2-((tert-butoxycarbonyl)amino)acetic Acid

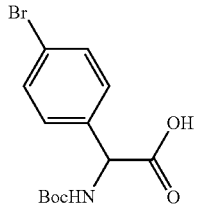 [SMILES: CC(C)(C)OC(=O)NC(C(=O)O)c1ccc(Br)cc1]

To a flask were added 2-amino-2-(4-bromophenyl)acetic acid (0.9 g 4 mmol), THF (9 mL) and H$_2$O (9 mL) in turn, after the mixture was stirred uniformly, triethylamine (1.1 mL, 7.9 mmol) and (Boc)$_2$O (1.3 g 6.0 mmol) were added, the resulting mixture was stirred at rt for 12 h and concentrated in vacuo. The residue was diluted with EA (100 mL) and washed with saturated aqueous NaCl, dried over anhydrous sodium sulfate, filtered. The filtrate was concentrated in vacuo to get the title compound as a white solid (1.1 g 90%). MS (ESI, pos.ion) m/z: 352.00[M+Na]$^+$.

Step 2: methyl 2-(4-bromophenyl)-2-((tert-butoxycarbonyl)amino)acetate

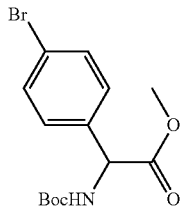

To a dry flask were added 2-(4-bromophenyl)-2-(tert-butoxycarbonylamino)acetic Acid (1.1 g 3.3 mmol) and DMF (15 mL) in turn. After complete dissolution, K$_2$CO$_3$ (921 mg 6.67 mmol) and iodomethane (0.23 mL, 3.7 mmol) were added, the mixture was stirred at 75° C. for 12 h and cooled to rt. To the reaction mixture was added EA (100 mL), the organic layer was washed with saturated aqueous NaCl and dried over anhydrous sodium sulfate. The mixture was filtered and the filtrate was concentrated in a rotary evaporator to get a crude product. The crude product was purified by silica gel column chromatography (PE/EA (V/V)= 20/1) to give the title compound as a colorless oil (0.7 g 60%). MS (ESI, pos.ion) m/z: 288.2 [M+H−56]$^+$.

Step 3: (8aR)-benzyl 2-(4-(1-(((tert-butoxycarbonyl)amino)-2-methoxy-2-oxoethyl)phenyl)-3-oxohexahydroimidazo[1,5-a]pyrazin-7(1H)-carboxylate

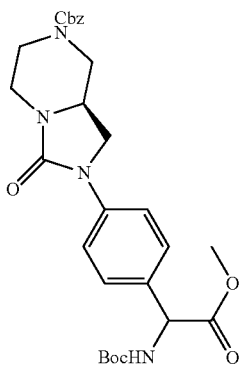 [SMILES: COC(=O)C(NC(=O)OC(C)(C)C)c1ccc(N2C[C@@H]3CN(C(=O)OCc4ccccc4)CCN3C2=O)cc1]

To a dry flask were added (R)-benzyl 3-oxohexahydroimidazo[1,5-a]pyrazine-7(1H)-carboxylate (439 mg, 1.60 mmol), methyl 2-(4-bromophenyl)-2-((tert-butoxycarbonyl)amino)acetate (0.5 g, 1.45 mmol), Pd$_2$(dba)$_3$ (137 mg, 0.15 mmol), tBuXantphos (95 mg, 0.22 mmol, wt. % is 97%), Cs$_2$CO$_3$ (947 mg 2.9 mmol) and 1,4-dioxane (20 mL) in turn, the mixture was stirred at 90° C. under N$_2$ for 12 hours. The mixture was cooled to rt and filtered, the filtrate was washed with EA (100 mL), the organic layer was washed with saturated aqueous NaCl and dried over anhydrous sodium sulfate. The mixture was filtered and the filtrate was concentrated in vacuo. The residue was purified by silica gel column chromatography (PE/EA (v/v)=1/2) to give the title compound as a white solid (0.52 g, 66%). MS (ESI, pos.ion) m/z: 561.2[M+Na]$^+$.

Step 4: methyl 2-((tert-butoxycarbonyl)amino)-2-(4-((S)-3-oxohexahydroimidazo[1,5-a]pyrazin-2(3H)-yl)phenyl)acetate

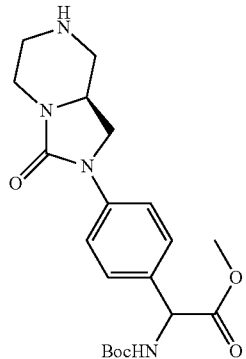 [SMILES: COC(=O)C(NC(=O)OC(C)(C)C)c1ccc(N2C[C@@H]3CNCCN3C2=O)cc1]

To a dry flask were added (8aR)-benzyl 2-(4-(1-(((tert-butoxycarbonyl)amino)-2-methoxy-2-oxopropyl)phenyl)-3-oxohexahydroimidazo[1,5-a]pyrazine-7(1H)-carboxylate (0.26 g 0.48 mmol), Pd/C (10%, 0.1 g) and methanol (10 mL) in turn, the mixture was stirred at rt under H$_2$ for 12 hours. The mixture was filtered. The filtrate was concentrated in vacuo to get the title compound as a slightly brown oil (0.19 g, 96%). MS (ESI, pos.ion) m/z: 349.3 [M+H−56]$^+$.

Step 5: (4R)-methyl 6-(((8 aS)-2-(4-(1-(((tert-butoxycarbonyl)amino)-2-methoxy-2-oxoethyl)phenyl)-3-oxohexahydroimidazo[1,5-a]pyrazin-7(1H)-yl)methyl)-4-(2-chloro-4-fluorophenyl)-2-(thiazol-2-yl)-1,4-dihydropyrimidine-5-carboxylate

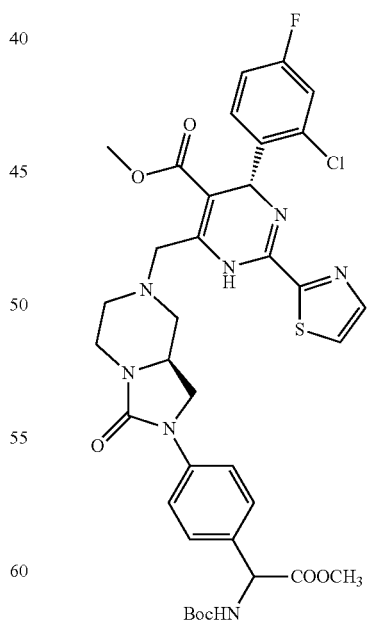

To a dry flask were added methyl 2-((tert-butoxycarbonyl)amino)-2-(4-((S)-3-oxohexahydroimidazo[1,5-a]pyrazin-2 (3H)-yl)phenyl)acetate (75 mg 0.19 mmol), (R)-methyl 4-(2-chloro-4-fluorophenyl)-6-(bromomethyl)-2-(thiazol-2- yl)-1,4-dihydropyrimidine-5-carboxy late (90 mg 0.20 mmol), K$_2$CO$_3$ (51 mg 0.37 mmol) and anhydrous DMF (5 mL) in turn, the mixture was stirred at 70° C. under N$_2$ for 4 hours and cooled to rt. The reaction mixture was diluted with EA (100 mL) and washed with saturated aqueous NaCl and dried over anhydrous sodium sulfate. The mixture was filtered and the filtrate was concentrated in vacuo. The residue was purified by silica gel column chromatography (PE/EA (v/v)=2/1) to give the title compound as a yellow solid (90 mg 63%). MS (ESI, pos.ion) m/z: 768.2[M+H]$^+$.

Step 6: 2-((tert-butoxycarbonyl)amino)-2-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)acetic Acid To a dry flask were added (4R)-methyl 6-(((8aS)-2-(4-(1-((tert-butoxycarbonyl)amino)-2-methoxy-2-oxoethyl)phenyl)-3-oxohexahydroimidazo[1,5-a]pyrazin-7(1H)-yl)methyl)-4-(2-chloro-4-fluorophenyl)-2-(thiazol-2-yl)-1,4-dihydropyrimidine-5-carboxylate (90 mg 0.12 mmol), methanol (4 mL) and THF (2 mL) in turn, the mixture was stirred uniformly, and NaOH (37 mg, 0.93 mmol) in water (1 mL) was added. The mixture was stirred at rt for 2 hours and concentrated in vacuo. The residue was diluted with EA (100 mL) and water (50 mL), the resulting mixture was adjusted with hydrochloric acid (2 M) to pH 6-7 with stirring, and then stood to separate into layers, the organic layer was washed with saturated aqueous NaCl and dried over anhydrous sodium sulfate. The mixture was concentrated in vacuo. The residue was purified by silica gel column chromatography (DCM/CH$_3$OH (V/V)=25/1) to give the title compound as a yellow solid (70 mg, 79.22%). MS (ESI, pos.ion) m/z: 754.1[M+H]$^+$; $^1$H NMR (400 MHz, MeOH-d$_4$) δ 7.97 (d, J=3.1 Hz, 1H), 7.76 (d, J=3.1 Hz, 1H), 7.56 (d, J=8.3 Hz, 2H), 7.44 (dd, J=8.6, 6.1 Hz, 1H), 7.39 (d, J=8.6 Hz, 2H), 7.24 (dd, J=8.7, 2.5 Hz, 1H), 7.06 (td, J=8.4, 2.5 Hz, 1H), 6.19 (s, 1H), 5.14 (s, 1H), 4.17 (d, J=17.0 Hz, 1H), 4.08-4.02 (m, 1H), 4.01-3.91 (m, 3H), 3.61 (s, 3H), 3.57-3.51 (m, 1H), 3.29-3.23 (m, 1H), 3.02 (d, J=10.1 Hz, 2H), 2.53-2.46 (m, 1H), 2.29 (t, J=10.9 Hz, 1H), 1.46 (s, 9H).

Example 47: (E)-3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)acrylic Acid Step 1: (R,E)-tert-butyl 2-(4-(3-methoxy-3-oxoprop-1-en-1-yl)phenyl)-3-oxohexahydroimidazo[1,5-a]pyrazine-7(1H)-carboxylate

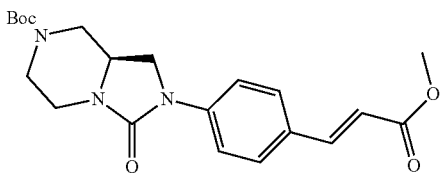 [SMILES: COC(=O)/C=C/c1ccc(N2C[C@@H]3CNCCN3C2=O)cc1]

(R)-tert-Butyl 3-oxohexahydroimidazo[1,5-a]pyrazine-7(1H)-carboxylate (1.80 g 7.46 mmol), methyl 4-bromocinnamate (2.0 g 8.3 mmol), palladium acetate (84 mg 0.37 mmol), 2-di-tert-butylphosphino-2',4',6'-triisopropylbiphenyl (320 mg 0.75 mmol) and cesium carbonate (3.65 g 11.2 mmol) were dissolved in 1,4-dioxane (20 mL). The mixture was stirred at 100° C. for 12 hours under N$_2$. The mixture was cooled to rt and filtered, the filter cake was washed with dichloromethane (100 mL), the filtrate was concentrated in a rotary evaporator. The residue was purified by silica gel column chromatography (PE/EA (v/v)=3/1) to give the title compound as a white solid (1.95 g 65.1%). MS (ESI, pos. ion): m/z 424.3 [M+Na]$^+$.

Step 2: (R,E)-3-(4-(7-(tert-butoxycarbonyl)-3-oxohexahydroimidazo[1,5-a]pyrazin-2(3H)-yl)phenyl)acrylic Acid

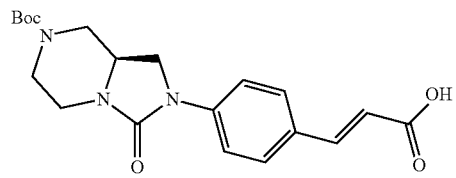 [SMILES: O=C(O)/C=C/c1ccc(N2C[C@@H]3CNCCN3C2=O)cc1]

(R,E)-tert-Butyl 2-(4-(3-methoxy-3-oxoprop-1-en-1-yl)phenyl)-3-oxohexahydroimidazo[1,5-a]pyrazine-7(1H)-carboxylate (700 mg, 1.74 mmol) was dissolved in methanol (2 mL) and tetrahydrofuran (6 mL), and lithium hydroxide monohydrate (146 mg 3.48 mmol) in water (2 mL) was added, the mixture was heated to 50° C. and stirred for 2 hours, then concentrated in a rotary evaporator. To the residue were added water (50 mL) and DCM (100 mL). The mixture was adjusted with hydrochloric acid (1 M) to pH 4-5 with stirring, and then stood to separate into layers, the organic layer was washed with saturated aqueous NaCl and dried over anhydrous sodium sulfate, filtered. The filtrate was concentrated in a rotary evaporator to get the title compound as a white solid (650 mg 96%). MS (ESI, pos. ion): m/z 410.1[M+Na]+.

Step 3: (S,E)-3-(4-(3-oxohexahydroimidazo[1,5-a]pyrazin-2(3H)-yl)phenyl)acrylic Acid trifluoroacetate

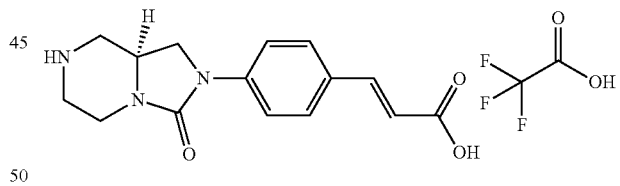

To a solution of (R,E)-3-(4-(7-(tert-butoxycarbonyl)-3-oxohexahydroimidazo[1,5-a]pyrazin-2(3H)-yl)phenyl) acrylic acid (650 mg 1.68 mmol) in dichloromethane (5 mL) was added trifluoroacetic acid (5 mL), the mixture was stirred at rt for 1 hour. The mixture was concentrated in a rotary evaporator to remove the most of solvent, and toluene (10 mL) was added, the mixture was concentrated in a rotary evaporator again to give the title compound as a brown solid (670 mg 99%), which was used in the next step directly.

Step 4: (E)-3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)acrylic Acid (S,E)-3-(4-(3-Oxohexahydroimidazo[1,5-a]pyrazin-2 (3H)-yl)phenyl)acrylic acid trifluoroacetate (300 mg, 0.66 mmol) and potassium carbonate (517 mg 3.74 mmol) were dissolved in ethanol (10 mL), and (R)-methyl 6-(bromomethyl)-4-(2,4-dichlorophenyl)-2-(thiazol-2-yl)-1,4-dihydropyrimidine-5-carboxylate (550 mg 1.24 mmol) was added the mixture was stirred at 40° C. for 6 hours and concentrated in a rotary evaporator. The residue was purified by silica gel column chromatography (DCM/MeOH (V/V)=10/1) to give the title compound as a yellow solid (500 mg, 60%). MS (ESI, pos. ion): m/z 651.2 [M+H]+; $^1$H NMR (600 MHz, CDCl$_3$) δ 9.62 (s, 1H), 7.87 (d, J=3.1 Hz, 1H), 7.74 (d, J=15.8 Hz, 1H), 7.62 (d, J=8.8 Hz, 2H), 7.54 (d, J=8.8 Hz, 2H), 7.49 (d, J=3.1 Hz, 1H), 7.30 (dd, J=8.6, 6.1 Hz, 1H), 7.16 (dd, J=8.5, 2.6 Hz, 1H), 6.94 (td, J=8.3, 2.6 Hz, 1H), 6.38 (d, J=15.9 Hz, 1H), 6.23 (s, 1H), 4.17-4.14 (m, 1H), 4.11-4.07 (m, 1H), 4.07-4.02 (m, 1H), 3.97-3.89 (m, 2H), 3.62 (d, J=5.1 Hz, 3H), 3.47 (dd, J=9.2, 4.9 Hz, 1H), 3.33-3.23 (m, 1H), 2.92 (d, J=4.6 Hz, 2H), 2.57-2.47 (m, 1H), 2.28 (t, J=10.5 Hz, 1H).

Example 48: (R)-methyl 6-(((S)-2-(4-(3-amino-3-oxopropyl)phenyl)-3-oxohexahydroimidazo[1,5-a]pyrazin-7(1H)-yl)methyl)-4-(2-chloro-4-fluorophenyl)-2-(thiazol-2-yl)-1,4-dihydropyrimidine-5-carboxylate To a flask were added 3-(4-((S)-7-(((R)-6-(2-chloro-4-fluorophenyl)-5-(methoxy carbonyl)-2-(thiazol-2-yl)-3,6-dihydropyrimidin-4-yl)methyl)-3-oxohexahydroimidazo[1,5-a]pyrazin-2(3H)-yl)phenylpropionic acid (0.50 g 0.77 mmol), NH$_4$Cl (0.12 g 2.31 mmol), N,N-dimethylformamide (10 mL), 1H-benzotriazol-1-yl-oxytripyrrolidinophosphonium hexafluorophosphate (0.6 g 1.2 mmol), 1-hydroxybenzotriazole (0.16 g 1.2 mmol), DIPEA (0.25 mL, 1.5 mmol) in turn, and the mixture was stirred at 25° C. for 1 h, then water (20 mL) and ethyl acetate (50 mL) were added, the mixture was separated into layers, the organic layer was washed with saturated aqueous NaCl (20 mL) and dried over anhydrous Na$_2$SO$_4$. The mixture was concentrated in vacuo. The residue was purified by silica gel column chromatography (DCM/CH$_3$OH (V/V)=30/1) to give the title compound as a yellow solid (0.26 g 52%). MS (ESI, pos.ion) m/z: 652.2 [M+H]+; $^1$H NMR (400 MHz, MeOH-d$_4$) δ 7.95 (d, J=3.1 Hz, 1H), 7.72 (d, J=3.1 Hz, 1H), 7.43 (t, J=8.8 Hz, 3H), 7.21 (dd, J=12.0, 5.5 Hz, 3H), 7.04 (td, J=8.4, 2.5 Hz, 1H), 6.18 (s, 1H), 4.11 (m, 1H), 3.98 (dd, J=15.3, 9.8 Hz, 2H), 3.90 (dd, J=10.3, 7.6 Hz, 2H), 3.59 (s, 3H), 3.47 (dd, J=9.3, 4.4 Hz, 1H), 3.27-3.18 (m, 1H), 2.95 (d, J=10.8 Hz, 2H), 2.87 (d, J=8.0 Hz, 2H), 2.49 (t, J=7.7 Hz, 2H), 2.45-2.38 (m, 1H), 2.20 (t, J=10.8 Hz, 1H).

Example 49: (R)-methyl 4-(2-chloro-4-fluorophenyl)-6-(((S)-2-(4-(3-(methylsulfonylamino) propyl)phenyl)-3-oxohexahydroimidazo[1,5-a]pyrazin-7(1H)-yl)methyl)-2-(thiazol-2-yl)-1,4-dihydropyrimidin-5-carboxylate Step 1: (R)-tert-butyl 2-(4-(3-(dibenzylamino)-3-oxopropyl)phenyl)-3-oxohexahydroimidazo[1,5-a]pyrazine-7(1H)-carboxylate

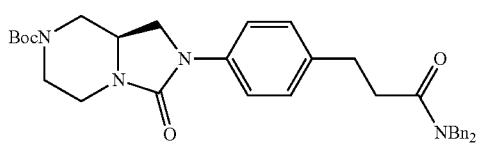

To a flask were added (R)-3-(4-(7-(tert-butoxycarbonyl)-3-oxohexahydroimidazo[1,5-a]pyrazin-2(3H)-yl)phenyl)propionic acid (3.50 g 9.0 mmol), DMF (28 mL), HATU (4.1 g 11 mmol) and DIPEA (3.1 mL, 18 mmol), the mixture was stirred at 25° C. for 10 min, dibenzylamine (2.1 mL, 11 mmol) was added, and then the mixture was stirred at 25° C. for 7 hours, water (100 mL) and ethyl acetate (200 mL) was added. The resulting mixture was separated into layers, the organic layer was washed with water (50 mL×2) and concentrated. The residue was purified by silica gel column chromatography (PE/EA (V/V)=3/1) to get a white solid (3.5 g 68%). MS (ESI, pos.ion) m/z: 513.4 [M+H−56]+.

Step 2: (R)-tert-butyl 2-(4-(3-(dibenzylamino)propyl)phenyl)-3-oxohexahydroimidazo[1,5-a]pyrazine-7(1H)-carboxylate

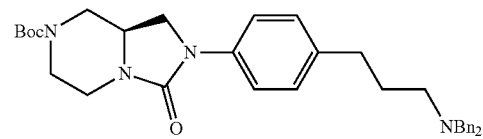

To a flask were added (R)-tert-butyl 2-(4-(3-(dibenzylamino)-3-oxopropyl)phenyl)-3-oxohexahydroimidazo[1,5-a]pyrazine-7(1H)-carboxylate (2.0 g 3.5 mmol) and tetrahydrofuran (40 mL), the mixture was cooled to −15° C., and borane in tetrahydrofuran (8 mL, 8.8 mmol, 1 mol/L) was added dropwise. After the addition, the mixture was warmed to 55° C. and stirred for 16 hours, and then cooled to rt, the reaction was quenched by adding MeOH (10 mL) slowly, after that, the mixture was refluxed to become clear. The mixture was concentrated in a rotary evaporator, the residue was dissolved in ethyl acetate (200 mL), and the mixture was washed with sodium hydroxide aqueous solution (20 mL, wt. % is 1%) and saturated aqueous NaCl once, then dried over anhydrous sodium sulfate. The mixture was concentrated in vacuo, and the residue was purified by silica gel column chromatography (PE/EA (v/v)=5/1) to give the title compound as a colorless oil (1.2 g 62%). MS (ESI, pos.ion) m/z: 555.4 [M+H]+.

Step 3: (R)-tert-butyl 2-(4-(3-aminopropyl)phenyl)-3-oxohexahydroimidazo[1,5-a]pyrazine-7(1H)-carboxylate

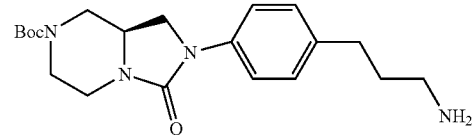 [SMILES: CC(C)(C)OC(=O)N1CCN2C(=O)N(c3ccc(CCCN)cc3)C[C@@H]2C1]

To a flask were added (R)-tert-butyl 2-(4-(3-(dibenzylamino)propyl)phenyl)-3-oxohexahydroimidazo[1,5-a]pyrazine-7(1H)-carboxylate (1.2 g 2.2 mmol), ethyl acetate (20 mL) and Pd/C (0.4 g 10%), the mixture was stirred at 25° C. under a H$_2$ pressure of 1 atm for 12 hours, the mixture was warmed to 55° C. and further stirred for 48 hours. After the reaction was stopped, the mixture was filtered, the filtrate was concentrated, and the residue was purified by silica gel column chromatography (DCM/CH$_3$OH (V/V)=30/1) to get the title compound as a white solid (0.3 g 40%). MS (ESI, pos.ion) m/z: 375.2 [M+H]$^+$.

Step 4: (R)-tert-butyl 2-(4-(3-(methylsulfonylamino)propyl)phenyl)-3-oxohexahydroimidazo[1,5-a]pyrazine-7(1H)-carboxylate

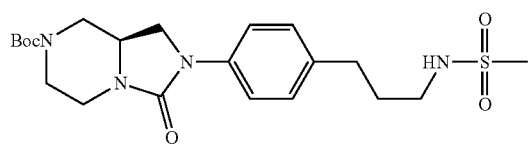 [SMILES: CC(C)(C)OC(=O)N1CCN2C(=O)N(c3ccc(CCCNS(C)(=O)=O)cc3)C[C@@H]2C1]

To a flask were added (R)-tert-butyl 2-(4-(3-aminopropyl)phenyl)-3-oxohexahydroimidazo[1,5-a]pyrazine-7(1H)-carboxylate (0.25 g 0.67 mmol), DCM (10 mL) and triethylamine (0.19 mL, 1.4 mmol), the mixture was stirred until complete dissolution, then methylsulfonyl chloride (0.06 mL, 0.8 mmol) was added, the resulting mixture was stirred at 25° C. for 1 hours and concentrated, and the residue was purified by silica gel column chromatography (DCM/CH$_3$OH (V/V)=30/1) to get the title compound as a white solid (0.30 g 99%). MS (ESI, pos.ion) m/z: 453.2 [M+H]$^+$.

Step 5: (S)—N-(3-(4-(3-oxohexahydroimidazo[1,5-a]pyrazin-2(3H)-yl)phenyl)propyl)methane sulfonamide trifluoroacetate

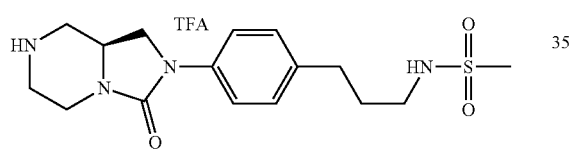

To a flask were added (R)-tert-butyl 2-(4-(3-(methylsulfonylamino)propyl)phenyl)-3-oxohexahydroimidazo[1,5-a]pyrazine-7(1H)-carboxylate (250 mg 0.55 mmol), DCM (2 mL) and trifluoroacetic acid (2 mL), the mixture was stirred at 25° C. for 0.5 hours and concentrated, and the residue was used in the next step without further purification.

Step 6: (R)-methyl 4-(2-chloro-4-fluorophenyl)-6-(((S)-2-(4-(3-(methylsulfonylamino)propyl)phenyl)-3-oxohexahydroimidazo[1,5-a]pyrazin-7(1H)-yl)methyl)-2-(thiazol-2-yl)-1,4-dihydropyrimidine-5-carboxylate To a flask were added (S)—N-(3-(4-(3-oxohexahydroimidazo[1,5-a]pyrazin-2(3H)-yl)phenyl)propyl)methanesulfonamide trifluoroacetate (0.25 g 0.54 mmol), (R)-methyl 4-(2-chloro-4-fluorophenyl)-6-(bromomethyl)-2-(thiazol-2-yl)-1,4-dihydropyrimidine-5-carboxylate (0.24 g 0.54 mmol), 1,2-dichloroethane (10 mL) and DIPEA (0.3 mL, 2 mmol), the mixture was stirred at 50° C. for 12 hours. The mixture was concentrated in vacuo. The residue was purified by silica gel column chromatography (DCM/CH$_3$OH (V/V)= 30/1) to give the title compound as a yellow solid (340 mg 88%). MS (ESI, pos.ion) m/z: 716.2 [M+H]$^+$; $^1$H NMR (400 MHz, MeOH-d$_4$) δ 7.96 (d, J=3.1 Hz, 1H), 7.73 (d, J=3.1 Hz, 1H), 7.43 (t, J=8.6 Hz, 3H), 7.22 (dd, J=8.7, 2.5 Hz, 1H), 7.18 (d, J=8.5 Hz, 2H), 7.05 (td, J=8.4, 2.5 Hz, 1H), 6.18 (s, 1H), 4.12 (d, J=17.0 Hz, 1H), 4.03-3.88 (m, 4H), 3.60 (s, 3H), 3.48 (dd, J=9.3, 4.4 Hz, 1H), 3.28-3.19 (m, 1H), 3.06 (t, J=6.9 Hz, 2H), 2.97 (d, J=6.6 Hz, 2H), 2.92 (s, 3H), 2.66 (t, J=7.6 Hz, 2H), 2.43 (td, J=11.5, 2.7 Hz, 1H), 2.22 (t, J=10.8 Hz, 1H), 1.89-1.80 (m, 2H).

Example 50A and Example 50B

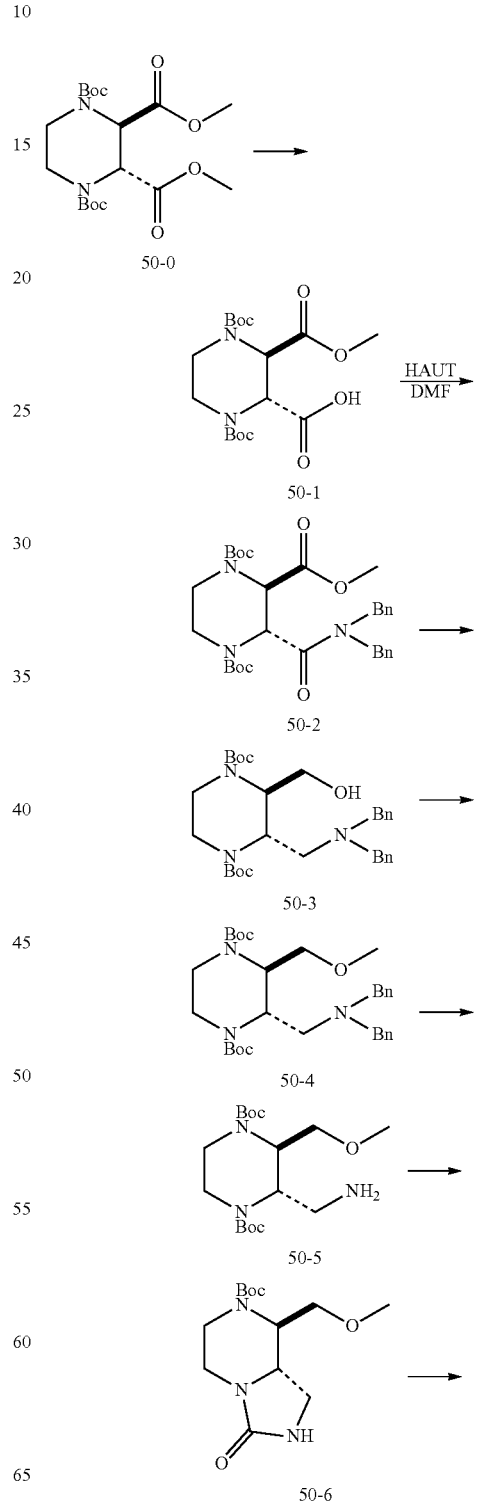

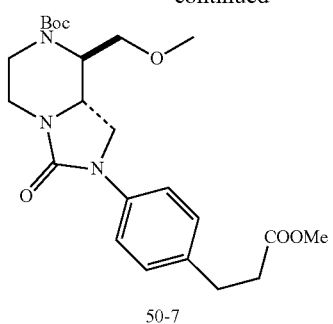

50-7

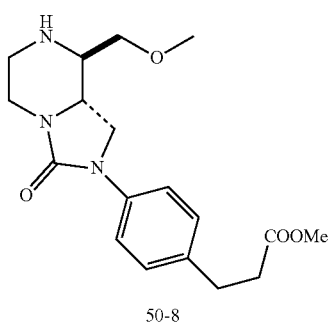

50-8

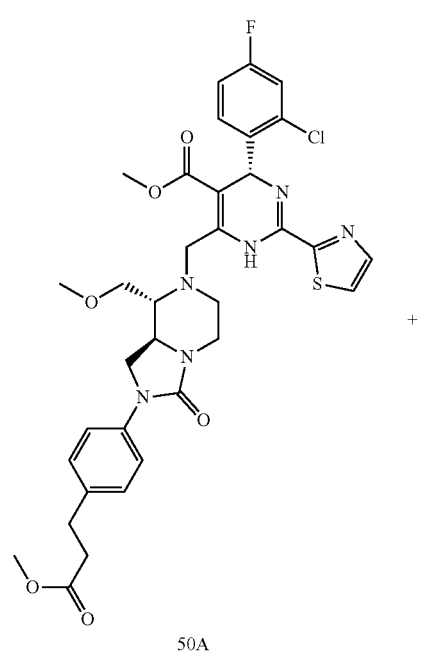

50A

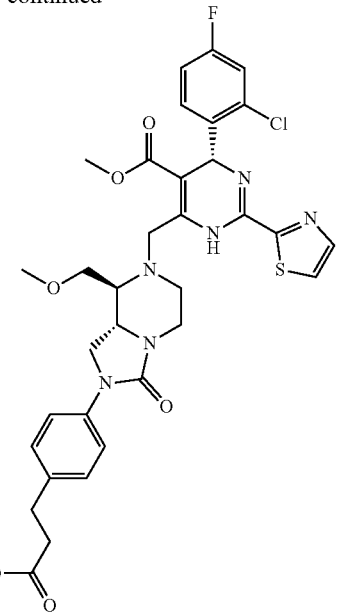

50B

Wherein one structure of compound 50-1 to compound 50-8 with ----- and ▬▬ represents a mixture of two trans isomers, such as compound 50-8, which represents the mixture of two trans isomers.

Step 1: Compound 50-1

To a dry flask were added compound 50-0 (7.6 g 18.9 mmol, the mixture of two trans isomers), methanol (40 mL) and sodium hydroxide (0.98 g 24.5 mmol) in water (10 mL) in turn, the mixture was stirred at 50° C. for 2 hours and cooled to rt, then EA (300 mL) and water (100 mL) were added, the mixture was adjusted to pH 4-5 by adding hydrochloric acid (2 M) with stirring the mixture was separated into layers, the water layer was extracted with EA (100 mL), the organic layers were combined and washed with saturated aqueous NaCl, dried over anhydrous sodium sulfate, and concentrated in vacuo. The residue was purified by silica gel column chromatography (DCM/CH$_3$OH (V/V)= 50/1) to get the title compound as a colorless oil (4.3 g 58.6%). MS (ESI, pos.ion) m/z: 388.4 [M+H]$^+$.

Step 2: Compound 50-2

To a single flask were added compound 50-1 (2.70 g 6.95 mmol, the mixture of two trans isomers), DMF (30 mL), dibenzylamine (1.65 g, 8.36 mmol), HATU (4.0 g 11 mmol) and DIPEA (1.35 g 10.4 mmol), the mixture was stirred at 25° C. for 6 hours, after the reaction was stopped, the mixture was diluted with water (20 mL) and ethyl acetate (100 mL). The resulting mixture was separated into layers, the organic layer was washed with saturated aqueous NaCl (20 mL×2), dried over anhydrous sodium sulfate, and concentrated. The residue was purified by silica gel column chromatography (PE/EA (V/V)=6/1) to get a pale yellow oil (2.5 g 63%). MS (ESI, pos.ion) m/z: 590.3 [M+Na]$^+$.

Step 3: Compound 50-3

To a single flask were added compound 50-2 (2.5 g 4.4 mmol, the mixture of two trans isomers) and THF (15 mL)

at rt, after complete dissolution, borane in tetrahydrofuran (26 mL, 26 mmol, 1 mol/L) was added, the mixture was stirred at 50° C. for 12 hours. The mixture was cooled to 0° C. and quenched with methanol (20 mL), after stirring for 30 min, the mixture was concentrated, and then water (20 mL) and EA (90 mL) was added, the mixture was separated into layers, the organic layer was dried and concentrated. The residue was purified by silica gel column chromatography (PE/EA (V/V)=3/1) to get a colorless oil (2.3 g 99%). MS (ESI, pos.ion) m/z: 526.5 [M+H]$^+$.

Step 4: Compound 50-4

Compound 50-3 (2.3 g 4.38 mmol, the mixture of two trans isomers) was dissolved in THF (10 mL), sodium hydride (350 mg 8.75 mmol, 60%) was added at 0° C., after stirring for 10 min, iodomethane (1.4 g 9.9 mmol) was added, the resulting mixture was stirred at 25° C. for 12 hours. The mixture was filtered, the filtrate was concentrated. The residue was purified by silica gel column chromatography (PE/EA (v/v)=10/1) to give the title compound as a colorless oil (2.3 g 97%). MS (ESI, pos.ion) m/z: 540.5 [M+H]$^+$.

Step 5: Compound 50-5

To a single flask were added compound 50-4 (2.3 g 4.26 mmol, the mixture of two trans isomers), methanol (10 mL) and Pd/C (1.0 g 10%), the mixture was stirred at 50° C. under a H$_2$ pressure of 1 atm for 5 hours and filtered, the filtrate was concentrated to get the title compound as a colorless oil (1.4 g 91%). MS (ESI, pos.ion) m/z: 360.3 [M+H]$^+$.

Step 6: Compound 50-6

To a single flask were added sodium hydride (270 mg, 6.67 mmol, 60%) and tetrahydrofuran (10 mL), after stirring for 5 min, compound 50-5 (600 mg 1.67 mmol, the mixture of two trans isomers) was added, the mixture was stirred at 70° C. for 6 hours. The mixture was concentrated and quenched with water (10 mL), and then concentrated, the residue was diluted with water (10 mL) and EA (50 mL), the mixture was separated into layers, the organic layer was concentrated in vacuo, the obtained residue was purified by silica gel column chromatography (DCM/CH$_3$OH (V/V) =50/1) to give the title compound as a gray solid (0.47 g 100%). MS (ESI, pos.ion) m/z: 308.1 [M+Na]$^+$.

Step 7: Compound 50-7

To a flask were added compound 50-6 (1.0 g 3.5 mmol, the mixture of two trans isomers), methyl 3-(4-bromophenyl)propionate (1.3 g 5.3 mmol), palladium acetate (100 mg, 0.445 mmol), t-BuXPhos (300 mg 0.63 mmol), cesium carbonate (2.0 g 6.1 mmol) and 1,4-dioxane (10 mL), the mixture was stirred at 90° C. for 3 hours and concentrated. The obtained residue was purified by silica gel column chromatography (PE/EA (V/V)=1/1) to give the title compound as a white solid (1.0 g 64%). MS (ESI, pos.ion) m/z: 470.2 [M+Na]+.

Step 8: Compound 50-8

To a flask were added compound 50-7 (0.43 g 0.10 mmol, the mixture of two trans isomers) and HCl in 1,4-dioxane (20 mL, 4 mol/L), the mixture was stirred at 25° C. for 16 hours and concentrated in vacuo to get the title compound as a white solid (0.37 g 100%).

Step 9: Compound 50A (i.e. Example 50A) and compound 50B (i.e. Example 50B)

To a flask were added compound 50-8 (144 mg 0.26 mmol, the mixture of two trans isomers), (R)-methyl 4-(2-chloro-4-fluorophenyl)-6-(bromomethyl)-2-(thiazol-2-yl)-1,4-dihydropyrimidin-5-carboxylate (0.1 g 0.26 mmol), potassium iodide (100 mg, 0.60 mmol), DMF (4 mL) and DIPEA (0.5 mL), the mixture was stirred at 50° C. for 2 hours. To the reaction mixture was added water (20 mL) and EtOAc (20 mL). The resulting mixture was partitioned, and the aqueous layer was extracted with ethyl acetate (10 mL). The combined organic layers were washed with saturated brine (20 mL), dried over anhydrous sodium sulfate and concentrated in vacuo, and the residue was purified by silica gel column chromatography (PE/EtOAc (v/v)=2/1) to give compound 50A as a yellow solid (80 mg, 43%) and compound 50B as a yellow solid (80 mg 43%). MS (ESI, pos.ion) m/z: 711.1[M+H]$^+$.

Example 51A

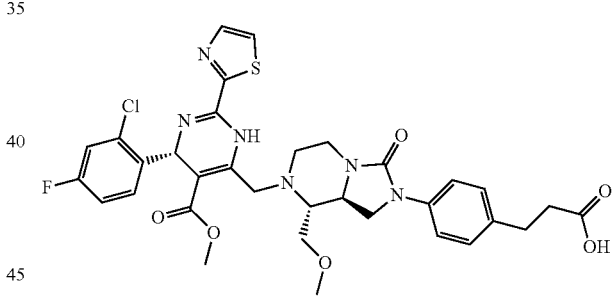

To a flask were added compound 50A (170 mg 0.24 mmol), methanol (5 mL), water (5 mL) and lithium hydroxide monohydrate (50 mg 1.2 mmol), the mixture was stirred at 50° C. for 1 hour and concentrated. To the residue was added water (10 mL) and EtOAc (5 mL), then the organic layer was discarded, and EtOAc (20 mL) was added, the resulting mixture was adjusted with concentrated hydrochloric acid to pH 4. The water phase was extracted with EtOAc (10 mL). The organic layers were combined and washed with saturated aqueous NaCl, and then concentrated. The residue was purified by silica gel column chromatography (DCM/CH$_3$OH (V/V)=10/1) to give title compound as a yellow solid (70 mg 42%). MS (ESI, pos.ion) m/z: 697.5 [M+H]$^+$.

Example 51B

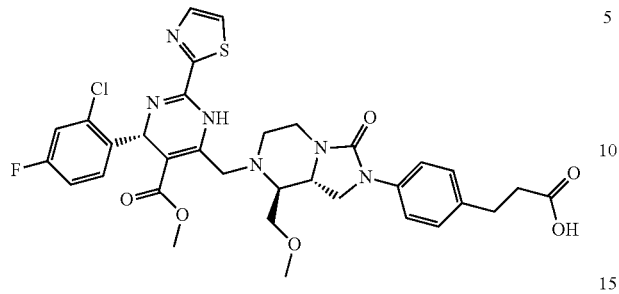

To a flask were added compound 50B (170 mg, 0.24 mmol), methanol (5 mL), water (5 mL) and lithium hydroxide monohydrate (50 mg 1.2 mmol), the mixture was stirred at 50° C. for 1 hour and concentrated. To the residue was added water (10 mL) and EtOAc (5 mL), then the organic layer was discarded, and EtOAc (20 mL) was added, the resulting mixture was adjusted with concentrated hydrochloric acid to pH 4. The water phase was extracted with EtOAc (10 mL). The organic layers were combined and washed with saturated aqueous NaCl, and then concentrated. The residue was purified by silica gel column chromatography (DCM/CH$_3$OH (V/V)=10/1) to give title compound as a yellow solid (70 mg 42%). MS (ESI, pos.ion) m/z: 697.5 [M+H]$^+$.

Example 52: (E)-3-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-thiazol-4-yl)acrylic Acid

Step 1: (S,E)-3-(2-(7-(tert-butoxycarbonyl)-3-oxohexahydroimidazo[1,5-a]pyrazin-2(3H)-yl)-thiazol-4-yl)-acrylic Acid

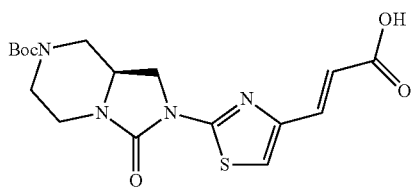 [SMILES: CC(C)(C)OC(=O)N1CCN2C(=O)N(c3nc(/C=C/C(=O)O)cs3)C[C@@H]2C1]

(S,E)-tert-Butyl 2-(4-(3-methoxy-3-oxoprop-1-en-1-yl) thiazol-2-yl)-3-oxohexahydro imidazo[1,5-a]pyrazine-7 (1H)-carboxylate (500 mg 1.22 mmol) was dissolved in methanol (10 mL), and then lithium hydroxide monohydrate (250 mg, 6.10 mmol) in H$_2$O (5 mL) was added. The mixture was stirred at 50° C. for 12 hours. And then the mixture was concentrated in vacuo, the residue was diluted with EA (100 mL) and water (50 mL), the mixture was cooled to 0° C., and adjusted with hydrochloric acid (1 M) to pH 3-4, the mixture was stood to separated into layers, the organic layer was washed with saturated aqueous NaCl and filtered, the filtrate was concentrated in vacuo to get the title compound as a brown solid (480 mg 99%).

Step 2: (S,E)-3-(2-(3-oxohexahydroimidazo[1,5-a] pyrazin-2(3H)-yl)thiazol-4-yl)acrylic Acid hydrochloride

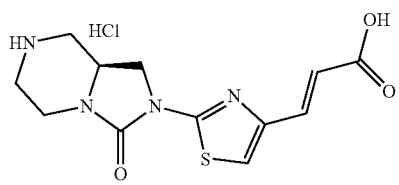 [SMILES: O=C(O)/C=C/c1csc(N2C[C@@H]3CNCCN3C2=O)n1 ; Cl]

(S,E)-3-(2-(7-(tert-Butoxycarbonyl)-3-oxohexahydroimidazo[1,5-a]pyrazin-2(3H)-yl)-thiazol-4-yl)-acrylic acid (480 mg 1.2 mmol) was dissolved in HCl in 1,4-dioxane (10 mL, 4 mol/L), the mixture was stirred at 25° C. for 12 hours and concentrated in vacuo to get the title compound as a white solid (400 mg 99%).

Step 3: (E)-3-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazine-2(3H)-yl)thiazol-4-yl)acrylic Acid (S,E)-3-(2-(3-Oxohexahydroimidazo[1,5-a]pyrazin-2 (3H)-yl)thiazol-4-yl)-acrylic acid hydrochloride (400 mg 1.2 mmol) and potassium carbonate (500 mg 3.6 mmol) were dissolved in ethanol (20 mL), and (R)-methyl 6-(bromomethyl)-4-(2-chloro-4-fluorophenyl)-2-(thiazol-2-yl)-1, 4-dihydropyrimidine-5-carboxylate (700 mg, 1.2 mmol) was added, the mixture was stirred at 40° C. for 3 hours. The mixture was filtered, and the filtrate was concentrated in a rotary evaporator, the residue was diluted with water (30 mL) and ethyl acetate (100 mL). The mixture was adjusted with concentrated hydrochloric acid to pH 4-5, the mixture was stood to separated into layers. The organic phase was washed with saturated brine (20 mL), dried over anhydrous sodium sulfate, and concentrated in vacuo. The residue was purified by silica gel chromatograph (DCM/CH$_3$OH (V/V)= 25/1) to give the title compound as a yellow solid (500 mg 63%). MS(ESI, pos.ion) m/z: 658.5 [M+H]$^+$; $^1$H NMR (600 MHz, MeOH-d$_4$) δ 7.96 (d, J=3.1 Hz, 1H), 7.74 (d, J=3.1 Hz, 1H), 7.48 (d, J=15.4 Hz, 1H), 7.43 (dd, J=8.7, 6.1 Hz, 1H), 7.31 (s, 1H), 7.23 (dd, J=8.7, 2.6 Hz, 1H), 7.05 (td, J=8.4, 2.6 Hz, 1H), 6.53 (d, J=15.4 Hz, 1H), 6.17 (d, J=7.0 Hz, 1H), 4.23 (t, J=9.8 Hz, 1H), 4.18-4.12 (m, 2H), 3.98 (m, 2H), 3.79 (dd, J=10.6, 4.8 Hz, 1H), 3.60 (s, 3H), 3.31 (dd, J=8.2, 4.9 Hz, 1H), 3.13-3.05 (m, 1H), 3.02 (d, J=11.0 Hz, 1H), 2.48 (td, J=11.7, 3.4 Hz, 1H), 2.29 (t, J=11.0 Hz, 1H).

Example 53: (E)-3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)-2-methylacrylic Acid

Step 1: (R,E)-3-(4-(7-(tert-butoxycarbonyl)-3-oxohexahydroimidazo[1,5-a]pyrazin-2(3H)-yl)phenyl)-2-methylacrylic Acid

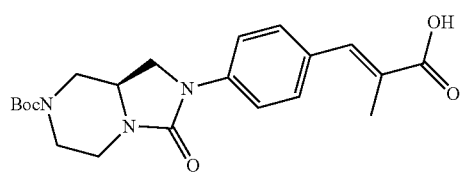 [SMILES: C/C(=C\c1ccc(N2C[C@@H]3CN(C(=O)OC(C)(C)C)CCN3C2=O)cc1)C(=O)O]

(R,E)-tert-Butyl 2-(4-(3-ethoxy-2-methyl-3-oxoprop-1-en-1-yl)phenyl)-3-oxohexahydro imidazo[1,5-a]pyrazine-7(1H)-carboxylate (400 mg 0.93 mmol) was dissolved in tetrahydrofuran (10 mL) and methanol (2 mL), and then sodium hydroxide (111 mg 2.77 mmol) in H₂O (1 mL) was added dropwise. The mixture was stirred at 53° C. for 2 hours. The mixture was concentrated in a rotary evaporator, the residue was diluted with water (20 mL) and EA (60 mL), and then adjusted with hydrochloric acid (1 M) to pH 4-5. The organic layer was washed with saturated sodium chloride aqueous solution, dried over anhydrous sodium sulfate and filtered. The filtrate was concentrated in a rotary evaporator to get the title compound as a white solid (0.36 g 96%). MS(ESI, pos.ion) m/z: 424.2[M+Na]⁺.

Step 2: (S,E)-2-methyl-3-(4-(3-oxohexahydroimidazo[1,5-a]pyrazin-2(3H)-yl)phenyl)acrylic acid trifluoroacetate

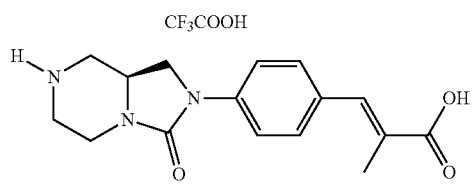 [SMILES: C/C(=C\c1ccc(N2C[C@@H]3CNCCN3C2=O)cc1)C(=O)O ; "CF3COOH"]

To a solution of (R,E)-3-(4-(7-(tert-butoxycarbonyl)-3-oxohexahydroimidazo [1,5-a]pyrazin-2(3H)-yl)phenyl)-2-methylacrylic acid (180 mg 0.45 mmol) in dichloromethane (2 mL) was added trifluoroacetic acid (2 mL), the mixture was stirred for 0.5 hour. The reaction mixture was concentrated in vacuo to get the title compound as a slightly brown oil (0.19 g 100%).

Step 3: (E)-3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)-2-methylacrylic Acid (S,E)-2-Methyl-3-(4-(3-oxohexahydroimidazo[1,5-a]pyrazin-2(3H)-yl)phenyl)acrylic acid trifluoroacetate (0.19 g 0.45 mmol) and (R)-methyl 6-(bromomethyl)-4-(2-chloro-4-fluorophenyl)-2-(thiazol-2-yl)-1,4-dihydropyrimidine-5-carboxylate (195 mg 0.44 mmol) were dissolved in EtOH (10 mL), and potassium carbonate (0.14 g 1 mmol) was added. The mixture was stirred at 25° C. for 12 hours, the mixture was diluted with EA (20 mL) and water (100 mL), the resulting mixture was adjusted with hydrochloric acid (1 M) to pH 5-6 and stood to separate into layers, the organic phases was concentrated. The residue was purified by silica gel column chromatography (DCM/CH₃OH (V/V)=50/1) to give the title compound as a yellow solid (153 mg 51.34%). MS(ESI, pos.ion) m/z: 665.2[M+H]⁺; ¹H NMR (400 MHz, DMSO-d₆) δ 12.37 (s, 1H), 9.72 (s, 1H), 8.04 (d, J=3.0 Hz, 1H), 7.95 (d, J=3.0 Hz, 1H), 7.64 (d, J=8.7 Hz, 2H), 7.55 (s, 1H), 7.47 (d, J=8.7 Hz, 2H), 7.45-7.39 (m, 2H), 7.19 (td, J=8.5, 2.3 Hz, 1H), 6.06 (s, 1H), 4.06-3.99 (m, 1H), 3.99-3.91 (m, 2H), 3.91-3.82 (m, 2H), 3.53-3.49 (m, 4H), 3.13-3.03 (m, 1H), 2.99-2.91 (m, 2H), 2.37-2.27 (m, 1H), 2.16 (t, J=10.8 Hz, 1H), 2.05 (s, 3H).

Example 54: (E)-3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)-2-butenoic Acid

Step 1: (R,E)-3-(4-(7-(tert-butoxycarbonyl)-3-oxohexahydroimidazo[1,5-a]pyrazin-2(3H)-1)phenyl)-2-butenoic Acid

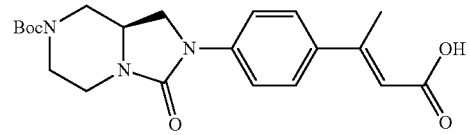 [SMILES: C/C(=C\C(=O)O)c1ccc(N2C[C@@H]3CN(C(=O)OC(C)(C)C)CCN3C2=O)cc1]

(R,E)-tert-Butyl 2-(4-(4-methoxy-4-oxobut-2-en-2-yl)phenyl)-3-oxohexahydroimidazo[1,5-a]pyrazine-7(1H)-carboxylate (400 mg 0.96 mmol) was dissolved in tetrahydrofuran (4 mL) and methanol (10 mL), and then sodium hydroxide (121 mg 2.88 mmol) in H₂O (1 mL) was added dropwise. The mixture was stirred at 53° C. for 2 hours. The mixture was concentrated in vacuo, the residue was diluted with water (20 mL) and EA (100 mL), and then adjusted with hydrochloric acid (1 M) to pH 4-5. The organic layer was washed with saturated sodium chloride aqueous solution, dried over anhydrous sodium sulfate and filtered. The filtrate was concentrated in a rotary evaporator to get the title compound as a white solid (0.37 g 96%). MS(ESI, pos.ion) m/z: 424.2[M+Na]⁺

Step 2: (S,E)-3-(4-(3-oxohexahydroimidazo[1,5-a]pyrazine-2(3H)-yl)phenyl)-2-butenoic Acid trifluoroacetate

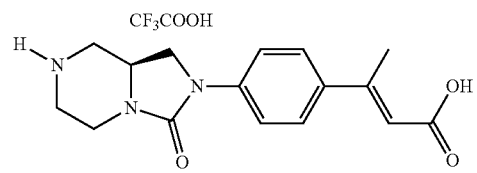 [SMILES: C/C(=C\C(=O)O)c1ccc(N2C[C@@H]3CNCCN3C2=O)cc1 ; "CF3COOH"]

To a solution of (R,E)-3-(4-(7-(tert-butoxycarbonyl)-3-oxohexahydroimidazo[1,5-a]pyrazin-2(3H)-yl)phenyl)-2- butenoic acid (180 mg, 0.45 mmol) in dichloromethane (2 mL) was added trifluoroacetic acid (2 mL), the mixture was stirred for 0.5 hour and concentrated in a rotary evaporator to get the title compound as a slightly brown oil (0.19 g 100%).

Step 3: (E)-3-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazine-2(3H)-yl)phen yl)-2-butenoic Acid (S,E)-3-(4-(3-Oxohexahydroimidazo[1,5-a]pyrazin-2 (3H)-yl)phenyl)-2-butenoic acid trifluoroacetate (0.19 g 0.45 mmol) and (R)-methyl 6-(bromomethyl)-4-(2-chloro-4-fluorophenyl)-2-(thiazol-2-yl)-1,4-dihydropyrimidine-5-carboxylate (195 mg, 0.44 mmol) were dissolved in EtOH (10 mL), and potassium carbonate (0.14 g 1 mmol) was added. The mixture was stirred at rt for 12 hours, the mixture was diluted with water (20 mL) and EA (100 mL), the resulting mixture was adjusted with hydrochloric acid (1 M) to pH 5-6 and stood to separate into layers, the organic phase was concentrated. The residue was purified by silica gel column chromatography (DCM/CH$_3$OH (V/V)=50/1) to give the title compound as a yellow solid (115 mg 39%). MS(ESI, pos.ion) m/z: 665.2[M+H]$^+$; $^1$H NMR (400 MHz, CDCl$_3$) δ 9.63 (s, 1H), 7.88 (d, J=3.1 Hz, 1H), 7.59 (d, J=8.9 Hz, 2H), 7.52 (d, J=8.8 Hz, 2H), 7.49 (d, J=3.1 Hz, 1H), 7.33-7.29 (m, 1H), 7.16 (dd, J=8.6, 2.5 Hz, 1H), 6.94 (td, J=8.3, 2.5 Hz, 1H), 6.23 (s, 1H), 6.20 (s, 1H), 4.13-4.00 (m, 3H), 3.98-3.88 (m, 2H), 3.62 (s, 3H), 3.47 (dd, J=9.1, 4.7 Hz, 1H), 3.29 (td, J=13.0, 2.9 Hz, 1H), 2.92 (d, J=10.5 Hz, 2H), 2.60 (s, 3H), 2.53 (td, J=11.4, 2.9 Hz, 1H), 2.28 (t, J=10.7 Hz, 1H).

Example 55: (E)-3-(4-((S)-7-(((R)-6-(2-bromo-4-fluorophenyl)-5-(ethoxycarbonyl)-2-(thiazol-2-yl)-3,6-dihydropyrimidin-4-yl)methyl)-3-oxohexahydro-imidazo[1,5-a]pyrazin-2(3H)-yl)phenyl)-2-methylacrylic Acid The title compound was prepared as a yellow solid (0.17 g 24%) according to example 53 by replacing (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5-acetate (0.5 g, 1 mmol). MS(ESI, pos.ion) m/z: 723.2[M+H]$^+$; $^1$H NMR (400 MHz, CDCl$_3$) δ 9.59 (s, 1H), 7.87 (d, J=3.0 Hz, 1H), 7.77 (s, 1H), 7.62 (d, J=8.7 Hz, 2H), 7.50-7.43 (m, 3H), 7.37-7.29 (m, 2H), 6.99 (td, J=8.4, 2.3 Hz, 1H), 6.22 (s, 1H), 4.17 (d, J=17.2 Hz, 1H), 4.12-4.01 (m, 4H), 3.98-3.89 (m, 2H), 3.47 (dd, J=9.1, 4.7 Hz, 2H), 3.34-3.24 (m, 1H), 2.93 (d, J=9.9 Hz, 2H), 2.58-2.49 (m, 1H), 2.28 (t, J=10.7 Hz, 1H), 2.18 (s, 3H), 1.14 (t, J=7.1 Hz, 3H).

Example 56: (E)-3-(4-((S)-7-(((R)-6-(2-bromo-4-fluorophenyl)-5-(ethoxycarbonyl)-2-(thiazol-2-yl)-3,6-dihydropyrimidin-4-yl)methyl)-3-oxohexahydro-imidazo[1,5-a]pyrazin-2(3H)-yl)phenyl)-2-butenoic Acid The title compound was prepared as a yellow solid (0.19 g 26%) according to example 54 by replacing (R)-methyl 6-(bromomethyl)-4-(2-chloro-4-fluorophenyl)-2-(thiazol-2-yl)-1,4-dihydropyrimidine-5-carboxylate with (R)-methyl 4-(2-bromo-4-fluoro phenyl)-6-(bromomethyl)-2-(thiazol-2-yl)-1,4-dihydropyrimidine-5-carboxylate (0.5 g 1 mmol). MS(ESI, pos.ion) m/z: 723.2[M+H]$^+$; $^1$H NMR (600 MHz, CDCl$_3$) δ 9.59 (s, 1H), 7.87 (d, J=3.1 Hz, 1H), 7.58 (d, J=8.9 Hz, 2H), 7.52 (d, J=8.8 Hz, 2H), 7.48 (d, J=3.1 Hz, 1H), 7.34 (dd, J=8.3, 2.5 Hz, 1H), 7.31 (dd, J=8.4, 6.2 Hz, 1H), 6.99 (td, J=8.3, 2.5 Hz, 1H), 6.22 (s, 1H), 6.19 (s, 1H), 4.16 (d, J=17.2 Hz, 1H), 4.11-4.01 (m, 4H), 3.96-3.91 (m, 2H), 3.46 (dd, J=9.2, 4.8 Hz, 1H), 3.29 (td, J=13.1, 3.2 Hz, 1H), 2.92 (d, J=10.4 Hz, 2H), 2.59 (s, 3H), 2.53 (td, J=11.5, 3.2 Hz, 1H), 2.28 (t, J=10.7 Hz, 1H), 1.14 (t, J=7.1 Hz, 3H).

Example 57: 3-(4-((8S,8aR)-7-(((R)-6-(2-bromo-4-fluorophenyl)-5-(ethoxycarbonyl)-2-(thiazol-2-yl)-3,6-dihydropyrimidin-4-yl)methyl)-8-(methoxymethyl)-3-oxohexahydroimidazo[1,5-a]pyrazin-2(3H)-yl)phenyl)propionic Acid The title compound was prepared as a yellow solid (0.12 g) according to example 50 by rep lacing (R)-methyl 6-(bromomethyl)-4-(2-chloro-4-fluorophenyl)-2-(thiazol-2-yl)-1,4-dihydropyrimidine-5-carboxylate with (R)-methyl 4-(2-bromo-4-fluorophenyl)-6-(bromomethyl)-2-(thiazol-2-yl)-1,4-dihydropyrimidine-5-carboxylate (0.5 g 1 mmol).

$^1$H NMR (600 MHz, MeOH-d$_6$) δ 7.96 (d, J=3.1 Hz, 1H), 7.75 (dd, J=4.1, 3.2 Hz, 1H), 7.48 (dd, J=8.6, 5.4 Hz, 2H), 7.47-7.41 (m, 2H), 7.23 (dd, J=8.5, 3.9 Hz, 2H), 7.12 (m, 1H), 6.18 (s, 1H), 4.57 (m, 1H), 4.08-4.04 (m, 3H), 4.03-3.95 (m, 1H), 3.91-3.84 (m, 2H), 3.74 (m, 1H), 3.71-3.65 (m, 1H), 3.65-3.61 (m, 1H), 3.53 (dd, J=10.9, 3.4 Hz, 1H), 3.23 (s, 3H), 3.04 (dd, J=11.7, 1.7 Hz, 1H), 2.91 (td, J=7.6, 2.3 Hz, 2H), 2.77-2.70 (m, 1H), 2.60 (td, J=7.6, 2.2 Hz 3H), 1.16 (td, J=7.1, 2.0 Hz, 3H).

Example 58A and Example 58B

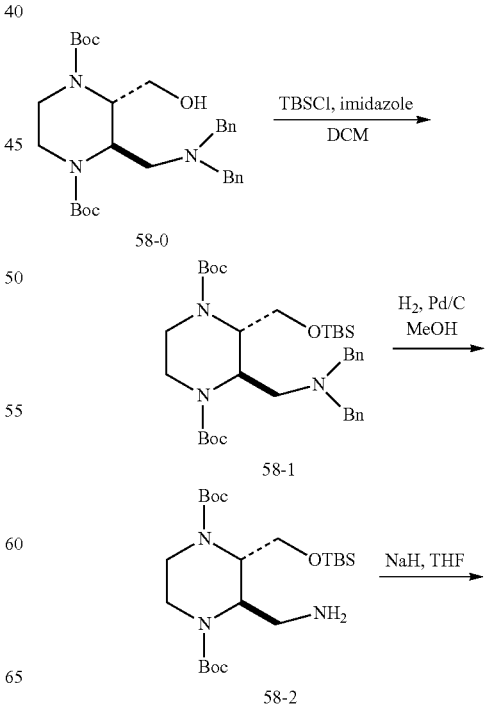

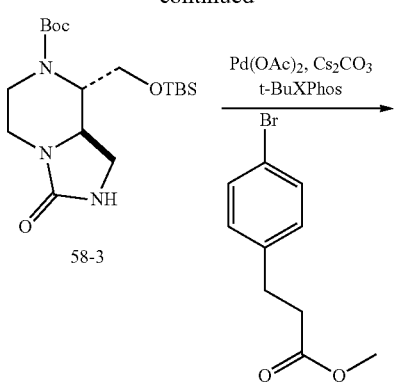

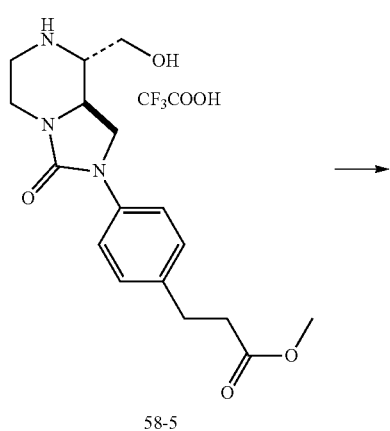

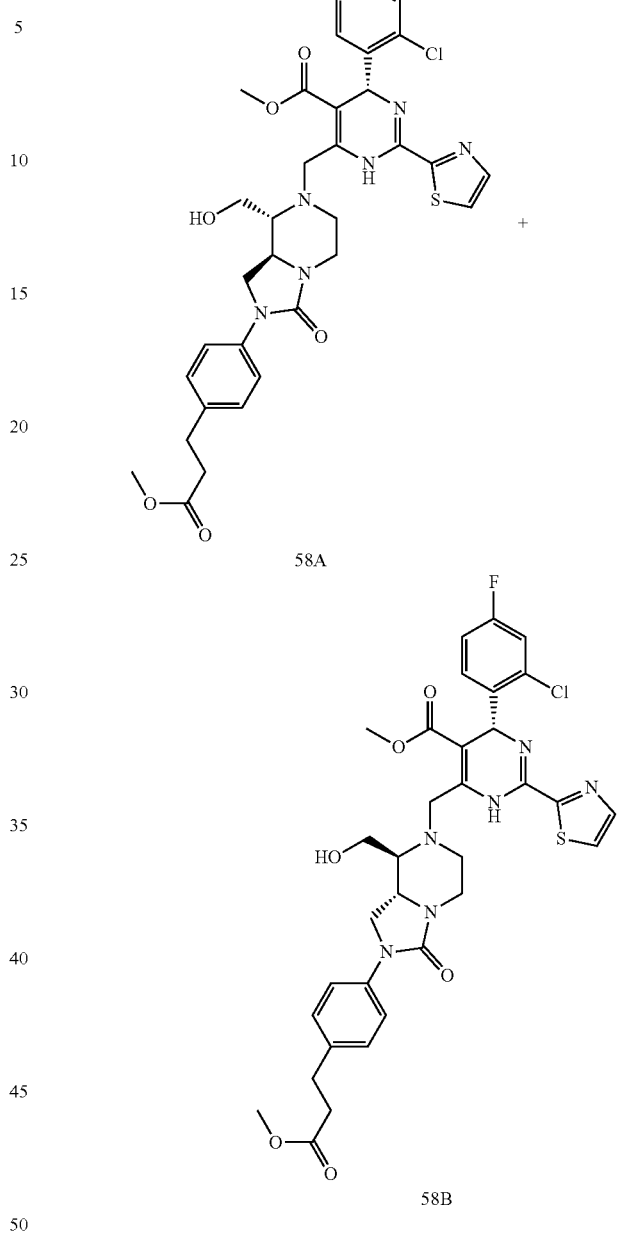

Wherein one structure of compound 58-0 to compound 58-5 with ----- and —— represents a mixture of two trans isomers, such as compound 58-5, which represents the mixture of two trans isomers.

Step 1: Compound 58-1

Compound 58-0 (3.18 g, 6.05 mmol, the mixture of two trans isomers), TBSCl (1.82 g 12.1 mmol) and imidazole (1.24 g, 18.2 mmol) were dissolved in DCM (20 mL), the mixture was stirred at rt for 8 hours. The mixture was quenched with water (20 mL), and diluted with DCM (200 mL), the organic layer was washed with water (100 mL) and saturated aqueous NaCl (100 mL) in turn, then dried over anhydrous sodium sulfate and concentrated. The residue was purified by silica gel column chromatography (PE/EA (V/V)= 20/1) to give the title compound as a slightly yellow oil (3.48 g 89.9%).

Step 2: Compound 58-2

To a dry flask were added compound 58-1 (3.48 g 5.44 mmol, the mixture of two trans isomers), Pd/C (1.74 g 10 mass %) and methanol (50 mL) in turn. The mixture was stirred at 45° C. under $H_2$ for 12 hours. The reaction mixture was filtered and the filtrate was concentrated in vacuo to get the title compound as a brown oil (2.37 g 5.16 mmol).

Step 3: Compound 58-3

To a dry flask were added compound 58-2 (2.37 g, 5.16 mmol, the mixture of two trans isomers) and THF (25 mL). After the mixture was dissolved completely, and sodium hydride (1.65 g 41.3 mmol, wt. % is 60%) was added slowly, the mixture was refluxed for 12 hours and cooled to 0° C., then methanol (20 mL) was added slowly to quench the reaction, the resulting mixture was concentrated in vacuo. The residue was diluted with EtOAc (100 mL), the organic layer was washed with water (100 mL) and saturated aqueous NaCl, dried over anhydrous sodium sulfate. The mixture was concentrated in vacuo. The residue was purified by silica gel column chromatography (EA) to give the title compound as a slightly yellow solid (0.94 g 47%). MS (ESI, pos.ion) m/z: 408.3 [M+Na]$^+$.

Step 4: Compound 58-4

To a dry flask were added methyl 3-(4-bromophenyl) propionate (0.77 g 3.2 mmol), compound 58-3 (0.94 g 2.4 mmol, the mixture of two trans isomers), t-BuXPhos (0.21 g 0.49 mmol), cesium carbonate (1.6 g 4.9 mmol), palladium acetate (54 mg 0.24 mmol) and 1,4-dioxane (10 mL) in turn, the mixture was stirred at 90° C. under $N_2$ for 8 hours. The mixture was cooled to rt and filtered, the filtrate was concentrated in vacuo. The residue was purified by silica gel column chromatography (PE/EA (v/v)=3/1) to give the title compound as a slightly yellow solid (1.17 g, 88%). MS (ESI, pos.ion) m/z: 570.3 [M+Na]+; H NMR (400 MHz, CDCl$_3$) δ 7.44 (d, J=8.6 Hz, 2H), 7.16 (d, J=8.5 Hz, 2H), 4.14 (dd, J=13.7, 5.8 Hz, 1H), 4.08-3.95 (m, 2H), 3.91-3.86 (m, 1H), 3.81-3.60 (m, 7H), 3.29-3.17 (m, 2H), 2.91 (t, J=7.7 Hz, 2H), 2.60 (t, J=7.8 Hz, 2H), 1.46 (s, 9H), 0.92 (s, 9H), 0.08 (s, 3H), 0.07 (s, 3H).

Step 5: Compound 58-5

Compound 58-4 (0.99 g 1.8 mmol, the mixture of two trans isomers) was dissolved in DCM (10 mL), and trifluoroacetic acid (5 mL) was added. The reaction mixture was stirred at rt for 2 hours and concentrated in vacuo to get the title compound as a yellow oil (0.81 g, 100%).

Step 6: Compound 58A (i.e. Example 58A) and Compound 58B (i.e. Example 58B)

To a dry flask were added (R)-methyl 6-(bromomethyl)-4-(2-chloro-4-fluorophenyl)-2-(thiazol-2-yl)-1,4-dihydropyrimidine-5-carboxylate (0.18 g, 0.41 mmol), DMF (10 mL), DIPEA (0.56 mL), potassium iodide (68 mg, 0.41 mmol) and compound 58-5 (153 mg, 0.27 mmol) in turn. The mixture was stirred at 55° C. for 4 hours, and diluted with water (30 mL) and EtOAc (100 mL), the organic layer was washed with saturated aqueous NaCl, dried over anhydrous sodium sulfate, and concentrated. The residue was purified by silica gel column chromatography (PE/EA (V/V)= 1/2) to give compound 58A and 58B (55 mg, 29%). MS (ESI, pos.ion) m/z: 697.3 [M+H]$^+$.

Example 59A

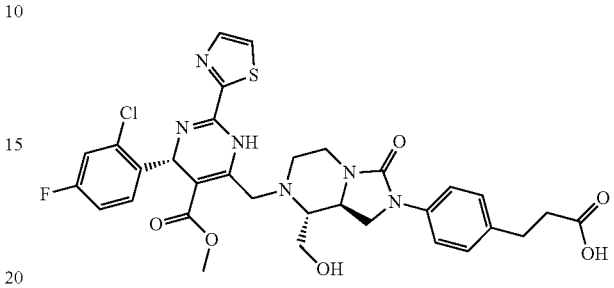

To a dry flask were added compound 58A (80 mg, 0.11 mmol), lithium hydroxide monohydrate (48 mg, 1.144 mmol), THF (1 mL) and water (1 mL) in turn. The mixture was stirred at 35° C. for 1 hour and concentrated in vacuo. The residue was diluted with EA (50 mL) and water (50 mL) and adjusted with hydrochloric acid (1 M) to pH 3-4. The organic phase was washed with saturated brine, dried over anhydrous sodium sulfate, and concentrated. The residue was purified by silica gel chromatograph (EA/MeOH (V/V)= 20/1) to give the title compound as a slightly yellow solid (50 mg, 60%). MS (ESI, pos.ion) m z: 683.1 [M+H]$^+$; $^1$H NMR (600 MHz, CH$_3$OH-d$_4$) δ 7.98 (d, J=3.1 Hz, 1H), 7.81 (d, J=3.2 Hz, 1H), 7.38 (d, J=8.5 Hz, 2H), 7.23-7.16 (m, 4H), 7.01-6.94 (m, 1H), 5.28 (s, 1H), 3.86-3.78 (m, 2H), 3.75 (s, 3H), 3.70-3.66 (m, 2H), 3.62-3.55 (m, 1H), 3.53-3.41 (m, 3H), 3.24-3.17 (m, 1H), 2.86-2.83 (m, 2H), 2.76 (d, J=9.5 Hz, 1H), 2.54 (d, J=11.4 Hz, 1H), 2.50-2.44 (m, 2H), 2.27-2.19 (m, 1H), 2.15-2.08 (m, 1H).

Example 59B

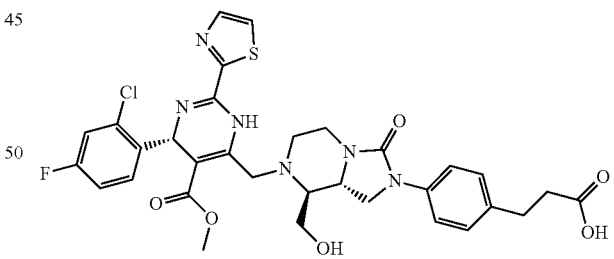

To a dry flask were added compound 58B (100 mg 0.14 mmol), lithium hydroxide monohydrate (60 mg, 1.43 mmol), THF (1 mL) and water (1 mL) in turn. The mixture was stirred at 35° C. for 1 hour and concentrated in vacuo. The residue was diluted with EA (50 mL) and water (50 mL) and adjusted with hydrochloric acid (1 M) to pH 3-4. The organic phase was washed with saturated brine, dried over anhydrous sodium sulfate, and concentrated. The residue was purified by silica gel chromatograph (EA/MeOH (V/V)= 20/1) to give the title compound as a slightly yellow solid (80 mg, 80%). MS (ESI, pos.ion) m/z: 683.1 [M+H]; $^1$H NMR (600 MHz, CH$_3$OH-d$_4$) δ 7.92 (d, J=3.2 Hz, 1H), 7.73 (d, J=3.1 Hz, 1H), 7.45-7.38 (m, 3H), 7.24-7.17 (m, 3H), 7.08 (td, J=8.4, 2.6 Hz 1H), 5.49 (d, J=10.1 Hz, 1H), 3.93-3.86 (m, 3H), 3.84-3.78 (m, 1H), 3.69-3.65 (m, 1H), 3.63 (dd, J=9.4, 5.5 Hz, 1H), 3.60-3.55 (m, 1H), 3.52 (s, 3H), 3.26 (td, J=12.8, 3.3 Hz, 1H), 3.19 (d, J=9.6 Hz, 1H), 3.02 (d, J=11.5 Hz, 1H), 2.89-2.81 (m, 3H), 2.71 (d, J=11.5 Hz, 1H), 2.51 (t, J=7.8 Hz, 2H), 2.30 (td, J=11.7, 3.4 Hz, 1H), 2.21 (td, J=10.0, 3.4 Hz, 1H).

Example 60A (i.e. Compound 60A) and Example 60B (i.e. Compound 60B)

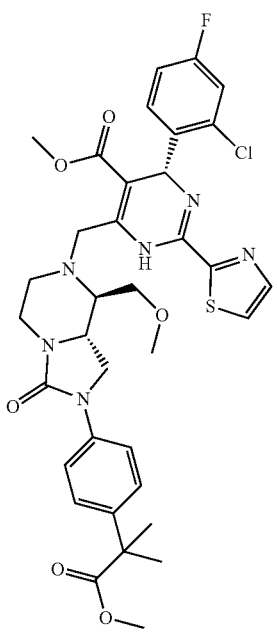 [SMILES: COC[C@H]1[C@@H]2CN(c3ccc(C(C)(C)C(=O)O)cc3)C(=O)N2CCN1CC1=C(C(=O)OC)[C@H](c2ccc(F)cc2Cl)N=C(c2nccs2)N1]

60A

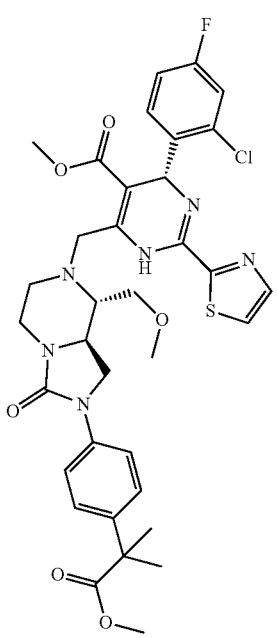

60B

The title compound 60A as a yellow solid (0.2 g, 27%) and compound 60B as a yellow solid (0.17 g 23%) were prepared according to step 7 of example 50A and compound 50B by rep lacing methyl 3-(4-bromophenyl)propionate with methyl 2-(3-bromophenyl)-2-methylpropionate (0.51 g 2 mmol). MS (ESI, pos.ion) m/z: 725.1 [M+H]$^+$.

Example 61A

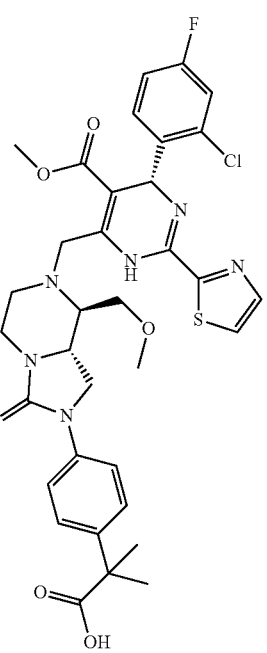

To a dry flask were added compound 60A (0.2 g 0.28 mmol), methanol (3 mL), THF (2 mL), water (1 mL) and lithium hydroxide monohydrate (70 mg 1.68 mmol) in turn, the mixture was stirred at 50° C. for 12 hours and concentrated in vacuo, then EA (100 mL) and water (30 mL) were added, the mixture was adjusted to pH 4-5 with concentrated hydrochloric acid, the mixture was separated into layers, the organic layer was washed with saturated aqueous NaCl, dried over anhydrous sodium sulfate, filtered and the filtrate was concentrated in vacuo. The residue was purified by silica gel column chromatography (DCM/CH$_3$OH (V/V) =25/1) to get the title compound as a yellow solid (80 mg, 40%). MS (ESI, pos.ion) m/z: 711.1 [M+H]$^+$. $^1$H NMR (600 MHz, CH$_3$OH-d$_4$) δ 7.96 (d, J=3.1 Hz, 1H), 7.75 (dd, J=4.9, 3.1 Hz, 1H), 7.48 (dd, J=8.5, 5.6 Hz, 2H), 7.46-7.41 (m, 1H), 7.26-7.21 (m, 3H), 7.09-7.03 (m, 1H), 6.19 (s, 1H), 4.53 (d, J=17.8 Hz, 1H), 4.02-3.95 (m, 2H), 3.90-3.86 (m, 2H), 3.82-3.80 (m, 1H), 3.73-3.70 (m, 2H), 3.69-3.65 (m, 1H), 3.62 (s, 3H), 3.52-3.49 (d, J=10.6 Hz, 1H), 3.41 (s, 3H), 2.75-2.72 (m, 2H), 1.61 (s, 6H).

Example 61B

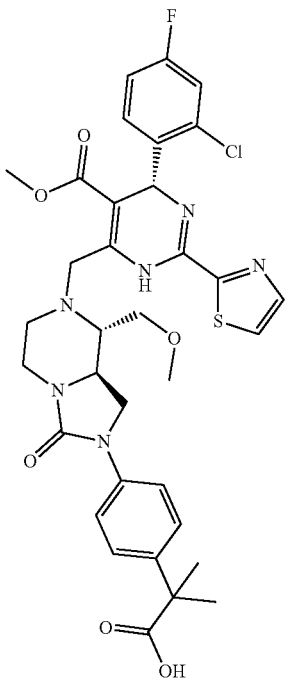 [SMILES: COC[C@@H]1[C@H]2CN(c3ccc(C(C)(C)C(=O)O)cc3)C(=O)N2CCN1CC1=C(C(=O)OC)[C@H](c2ccc(F)cc2Cl)N=C(c2nccs2)N1]

The title compound was prepared as a yellow solid (62 mg 38%) according to example 61A by replacing compound 60A with 60B (0.17 g 0.23 mmol). MS (ESI, pos.ion) m/z: 711.2 [M+H]$^+$. $^1$H NMR (600 MHz, CH$_3$OH-d$_4$) δ 7.95 (d, J=3.1 Hz, 1H), 7.74 (dd, J=4.9, 3.1 Hz 1H), 7.46 (dd, J=8.5, 5.6 Hz, 2H), 7.44-7.39 (m, 1H), 7.25-7.21 (m, 3H), 7.08-7.02 (m, 1H), 6.18 (s, 1H), 4.51 (d, J=17.8 Hz, 1H), 4.01-3.94 (m, 2H), 3.90-3.84 (m, 2H), 3.80-3.79 (m, 1H), 3.72-3.69 (m, 2H), 3.67-3.64 (m, 1H), 3.61 (s, 3H), 3.50-3.47 (m, 1H), 3.40 (s, 3H), 2.73-2.71 (m, 2H), 1.60 (s, 6H).

Example 62: 2-(4-(7-(((R)-6-(2-chloro-4-fluorophenyl)-5-(methoxycarbonyl)-2-(thiazol-2-yl)-3,6-dihydropyrimidin-4-yl)methyl)-8a-methyl-3-oxohexahydroimidazo[1,5-a]pyrazin-2(3H)-yl)phenyl)acetic Acid

Step 1: 1,4-di-tert-butyl 2-methyl piperazine-1,2,4-tricarboxylate

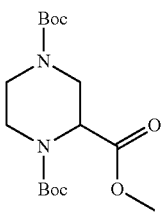

To a dry flask were added 1,4-di(tert-butoxycarbonyl) piperazine-2-carboxylic acid (14 g 42.37 mmol), potassium carbonate (11.7 g 84.7 mmol), acetone (200 mL), iodomethane (5.3 mL, 85 mmol) in turn, the mixture was stirred at rt for 12 hours. The mixture was filtered, the filtrate was concentrated in vacuo and to the residue was added (200 mL) and water (200 mL), the mixture was separated into layers, the organic layer was washed with saturated aqueous NaCl and dried over anhydrous sodium sulfate, then concentrated in vacuo to get the title compound as a white solid (13.55 g 93%). MS (ESI, pos. ion) m/z: 367.2 [M+Na]$^+$.

Step 2: 1,4-di-tert-butyl 2-methyl 2-methylpiperazine-1,2,4-tricarboxylate

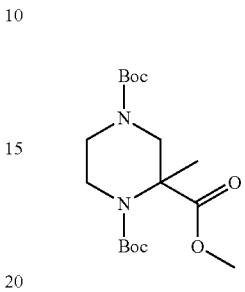

To a dry flask were added 1,4-di-tert-butyl 2-methyl piperazine-1,2,4-tricarboxylate (10 g 29.04 mmol), anhydrous tetrahydrofuran (100 mL) in turn, the mixture was cooled to −78° C. under N$_2$, and then LiHDMS (35 mL, 35 mmol, 1 mol/L) was added dropwise slowly. The mixture was keeped at −78° C. and stirred for 2 hours, then iodomethane (3.7 mL, 59 mmol) was added. The mixture was further stirred for 1 hour, and warmed to rt and stirred for 12 hours. The reaction was quenched with saturated ammonium chloride aqueous solution (50 mL) in an ice bath, and the mixture was extracted with EtOAc (100 mL×2). The combined organic layers were washed with saturated brine (80 mL), dried over anhydrous sodium sulfate, and concentrated in vacuo, and the residue was purified by silica gel column chromatography (PE/EA (V/V)= 10/1) to give the title compound as a colorless oil (8.2 g, 79%). MS (ESI, pos. ion) m/z: 381.2 [M+Na]$^+$.

Step 3: 1,4-di(tert-butoxycarbonyl)-2-methylpiperazine-2-carboxylic Acid

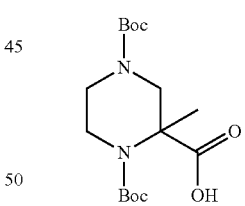

To a dry flask were added 1,4-di-tert-butyl 2-methyl 2-methylpiperazine-1,2,4-tricarboxylate (8 g 22.32 mmol), tetrahydrofuran (60 mL), methanol (10 mL), lithium hydroxide monohydrate (9.35 g 223.2 mmol) in water (10 mL) solution in turn, the mixture was stirred at 50° C. for 12 hours and cooled to rt. The mixture was diluted with water (200 mL) and extracted with PE (200 mL×2), the organic layers were discarded. The water phase was adjusted with hydrochloric acid (1M) to pH 3-4, and the resulting mixture was extracted with DCM (200 mL), and the organic layer was washed with saturated aqueous NaCl and dried over anhydrous sodium sulfate. The mixture was filtered and the filtrate was concentrated in vacuo to give the title compound as a white solid (6.8 g 88%). MS (ESI, pos. ion) m/z: 367.2 [M+Na]$^+$.

Step 4: di-tert-butyl 2-(dibenzylcarbamoyl)-2-methylpiperazine-1,4-dicarboxylate

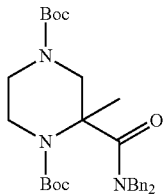

To a dry flask were added 1,4-di(tert-butoxycarbonyl)-2-methylpiperazine-2-carboxylic acid (5 g 14.52 mmol), HATU (7.0 g 17 mmol), DCM (50 mL), DIPEA (4.81 mL, 29.0 mmol) and dibenzylamine (3.35 mL, 17.4 mmol) in turn, the mixture were stirred at rt for 2 hours. The mixture was concentrated in vacuo and the residue was purified by silica gel column chromatography (PE/EA (v/v)=10/1) to give the title compound as a white solid (2.3 g 30%). MS (ESI, pos. ion): m/z 546.5 [M+Na]+.

Step 5: di-tert-butyl 2-((dibenzylamino)methyl)-2-methylpiperazine-1,4-dicarboxylate

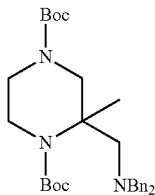

To a dry flask were added di-tert-butyl 2-(dibenzylcarbamoyl)-2-methylpiperazine-1,4-dicarboxylate (1.1 g 2.1 mmol) and tetrahydrofuran (10 mL) under $N_2$ in turn, after stirring uniformly and borane-tetrahydrofuran complex (21 mL, 21 mmol, 1.0 mol/L) was added under an ice bath, then the mixture was warmed to 50° C. and stirred for 20 hours. The mixture was quenched under ice bath by adding methanol (40 mL) dropwise slowly, concentrated in vacuo and the residue was purified by silica gel column chromatography (PE/EA (v/v)=2/1) to give the title compound as a white solid (950 mg 89%). MS (ESI, pos. ion): m/z 510.6 [M+H]+.

Step 6: di-tert-butyl 2-(aminomethyl)-2-methylpiperazine-1,4-dicarboxylate

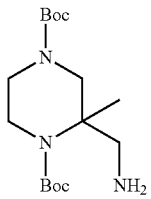

To a hydrogenation reactor were added di-tert-butyl 2-((dibenzylamino)methyl)-2-methylpiperazine-1,4-dicarboxylate (1.0 g 2.0 mmol), methanol (20 mL) and Pd/C (0.5 g 0.5 mmol, 10 mass %) in turn, the mixture was stirred under 3 MPa $H_2$ at 60° C. for 12 hours. The mixture was filtered and the filter cake was washed with methanol (10 mL), the filtrate was concentrated in a rotary evaporator to get the title compound as a yellow solid (600 mg 93%). MS (ESI, pos. ion): m/z 330.3 [M+H]+.

Step 7: tert-butyl 8a-methyl-3-oxohexahydroimidazo[1,5-a]pyrazin-7(1H)-carboxylate

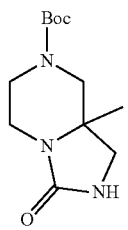

To a dry flask were added di-tert-butyl 2-(aminomethyl)-2-methylpiperazine-1,4-dicarboxylate (500 mg 1.52 mmol), THF (5 mL) and sodium hydride (300 mg, 7.5 mmol, mass % is 60%) in turn, the mixture was stirred at 70° C. for 3 hours. The mixture was concentrated in a rotary evaporator. The residue was purified by silica gel column chromatography (EA) to give the title compound as a white solid (230 mg 59%). MS (ESI, pos. ion): m/z 278.2 [M+Na]+.

Step 8: tert-butyl 2-(4-(2-methoxy-2-oxoethyl)phenyl)-8a-methyl-3-oxohexahydroimidazo[1,5-a]pyrazin-7(1H)-carboxylate

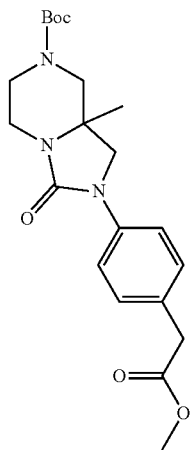 [SMILES: COC(=O)Cc1ccc(N2CC3(C)CN(C(=O)OC(C)(C)C)CCN3C2=O)cc1]

tert-Butyl (8a)-methyl-3-oxohexahydroimidazo[1,5-a]pyrazine-7(1H)-carboxylate (200 mg 0.78 mmol), methyl 2-(4-bromophenyl)acetate (215 mg 0.93 mmol), palladium acetate (9 mg 0.04 mmol), 2-di-tert-butylphosphino-2',4',6'-triisopropylbiphenyl (34 mg 0.08 mmol) and cesium carbonate (383 mg 1.18 mmol) were dissolved in 1,4-dioxane (10 mL). The mixture was stirred at 100° C. for 12 hours under $N_2$. The mixture was concentrated in vacuo and the residue was purified by silica gel column chromatography (PE/EA (v/v)=2/1) to give the title compound as a white solid (200 mg 63%). MS (ESI, pos. ion): m/z 426.2 [M+Na]+.

Step 9: 2-(4-(7-(tert-butoxycarbonyl)-8a-methyl-3-oxohexahydroimidazo[1,5-a]pyrazin-2(3H)-yl)phenyl)acetic Acid

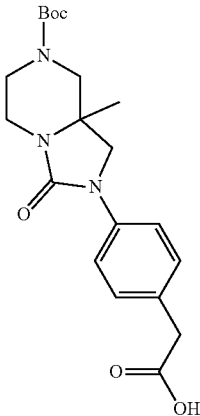 [SMILES: CC(C)(C)OC(=O)N1CCN2C(=O)N(c3ccc(CC(=O)O)cc3)CC2(C)C1]

To a dry flask were added tert-butyl 2-(4-(2-methoxy-2-oxoethyl)phenyl)-8a-methyl-3-oxohexahydroimidazo[1,5-a]pyrazin-7(1H)-carboxylate (200 mg, 0.50 mmol), THF (2 mL) and methanol (2 mL) and lithium hydroxide monohydrate (41 mg, 0.98 mmol) in water (2 mL), the mixture was stirred at rt for 5 hours. The mixture was concentrated in vacuo, the residue was diluted with EA (60 mL) and water (20 mL), and then adjusted with hydrochloric acid (1 M) to pH 4-5. The organic layer was washed with saturated sodium chloride aqueous solution, dried over anhydrous sodium sulfate and filtered. The filtrate was concentrated in a rotary evaporator to get the title compound as a white solid (180 mg, 93%). MS (ESI, pos. ion): m/z 412.2 [M+Na]$^+$.

Step 10: 2-(4-(8a-methyl-3-oxohexahydroimidazo[1,5-a]pyrazin-2(3H)-yl)phenyl)acetic Acid trifluoroacetate

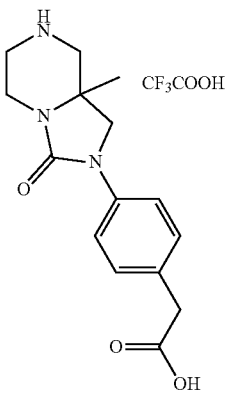 [SMILES: CC12CNCCN1C(=O)N(c1ccc(CC(=O)O)cc1)C2 ; "CF3COOH"]

2-(4-(7-(tert-Butoxycarbonyl)-8a-methyl-3-oxohexahydroimidazo[1,5-a]pyrazin-2(3H)-yl)phenyl)acetic acid (180 mg, 0.46 mmol) was dissolved in DCM (2 mL), and TFA (2 mL) was added, the mixture stirred at rt for 1 hour and concentrated in vacuo to get the title compound as a brown oil (186 mg, 100%).

Step 11: 2-(4-(7-(((R)-6-(2-chloro-4-fluorophenyl)-5-(methoxycarbonyl)-2-(thiazol-2-yl)-3,6-dihydropyrimidin-4-yl)methyl)-8a-methyl-3-oxohexahydroimidazo[1,5-a]pyrazin-2(3H)-yl)phenyl)acetic Acid To a dry flask were added 2-(4-(8a-methyl-3-oxohexahydroimidazo[1,5-a]pyrazin-2(3H)-yl)phenyl)acetic acid trifluoroacetate (210 mg 0.52 mmol), potassium carbonate (215 mg 1.56 mmol), ethanol (5 mL), and (R)-methyl 6-(bromomethyl)-4-(2-chloro-4-fluorophenyl)-2-(thiazol-2-yl)-1, 4-dihydropyrimidine-5-carboxylate (230 mg 0.52 mmol) in turn. The mixture was stirred at rt for 8 hours and concentrated in vacuo. The residue was purified by silica gel column chromatography (DCM/MeOH (V/V)=15/1) to give the title compound as a yellow solid (120 mg 35.44%). MS (ESI, pos. ion): m/z 653.1 [M+H]$^+$; $^1$H NMR (400 MHz, CDCl$_3$) δ 9.73-9.58 (m, 1H), 7.85 (dd, J=7.9, 2.9 Hz, 1H), 7.54 (t, J=8.0 Hz, 2H), 7.48 (t, J=3.3 Hz, 1H), 7.33-7.30 (m, 1H), 7.28-7.24 (m, 2H), 7.17-7.14 (m, 1H), 6.98-6.89 (m, 1H), 6.22 (d, J=3.4 Hz, 1H), 4.05 (d, J=17.1 Hz, 1H), 4.02-3.77 (m, 3H), 3.64-3.62 (m, 2H), 3.60 (d, J=3.5 Hz, 3H), 3.55 (d, J=14.4 Hz, 1H), 3.40-3.28 (m, 1H), 2.89-2.64 (m, 2H), 2.55-2.42 (m, 1H), 2.41-2.30 (m, 1H), 1.75-1.64 (m, 3H).

Biological Test

Test 1: Test Method of EC$_{50}$ of Anti HBV

HBV Cell Line and Culture Conditions

HepG2.2.15 (SELLS, PNAS, 1987 and SELLS, JV, 1988) chromosomes have an integrated complete HBV genome, and stably express viral RNA and viral protein. HepG2.2.15 cells can secrete mature HBV particles, HBsAg and HBeAg to medium. HepG2.2.15 cells were cultured in DMEM containing 10% fetal bovine serum, 100 U/mL penicillin, 100 U/mL streptomycin, 1% non essential amino acid, 1 mM sodium pyruvate and 300 g/mL G418.

Viral particles DNA secreted from HepG2.2.15 cells can be quantified by qPCR, and the effect of the compound on viral replication can be detected.

Test of Anti HBV Activity In Vitro

8000 HepG 2.2.15 cells per well were seeded into a 96-well plate, the plate was cultured at 37° C. and 5% CO2 for 3 days till the cells grew to full wells. Old liquid medium can be removed and replaced with new medium (200 μL) on day 0.

Formulating the compound and treating the cells in the experiment of anti virus: the compound was dissolved in DMSO to a concentration of 30 mM, and then the compound solution was diluted with DMSO to a concentration of 800M, and then eight dilutions at 4 fold were performed, the highest concentration is 800 μM. The serial diluted compound was added to the above plate at 1 μL per well, the highest final concentration in the experiment is 4 μM (200 fold dilution). TDF (tenofovir dipiroxil fumarate, Selleck, Cat S1400) has a highest concentration of 4 μM as a positive control. 1 μL of DMSO was added in to the positive control well at a final concentration of 0.5%, TDF was added in to the positive control well at a final concentration of 1 μM.

Detection of Viral Genomic DNA by qPCR

Primer: HBV-For-202, CAGGCGGGGTTTTTCTTGTTGA; HBV-Rev-315, GTGATTGGAGGTTGGGGACTGC. Copies of virus can be calculated using a standard curve plotted by using plasmid containing HBV genome and using SYBR Premix Ex Taq II Takara DRR081S kit and 1 μL cell culture supernatant as a template. EC50 values of the compound on viral replication were calculated by a four parametric nonlinear regression model using Graphpad Prism 5 software to manage concentration—viral copy number. The results were shown as table 3.

TABLE 3

EC50 values of the compound of the invention against HBV replication

| Example | $EC_{50}$(nM) |
|---|---|
| Example 7 | 56 |
| Example 11 | 32 |
| Example 12 | 37 |
| Example 13 | 4 |
| Example 14 | 7 |
| Example 15 | 5 |
| Example 16 | 14 |
| Example 17 | 4 |
| Example 18 | 4 |
| Example 19 | 3 |
| Example 20 | 5 |
| Example 21 | 22 |
| Example 22 | 5 |
| Example 23 | 7 |
| Example 24 | 4 |
| Example 25 | 5 |
| Example 26 | 8 |
| Example 27 | 7 |
| Example 28 | 5 |
| Example 29 | 6 |
| Example 30 | 12 |
| Example 31 | 4 |
| Example 32 | 6 |
| Example 33 | 25 |
| Example 34 | 16 |
| Example 35 | 8 |
| Example 37 | 5 |
| Example 38 | 15 |
| Example 39 | 29 |
| Example 40 | 71 |
| Example 44 | 10 |
| Example 45 | 8 |
| Example 46 | 22 |
| Example 47 | 3 |
| Example 48 | 10 |
| Example 49 | 12 |
| Example 50B | 8 |
| Example 51B | 9 |
| Example 52 | 13 |
| Example 53 | 14 |
| Example 54 | 11 |
| Example 55 | 9 |
| Example 56 | 12 |
| Example 57 | 12 |
| Example 58B | 14 |
| Example 59B | 15 |
| Example 60B | 4 |
| Example 61B | 5 |

Conclusion: the data of the experiment indicate that the compounds of the invention have better inhibitory activity, and which give a prospect in development and application in the aspect of anti HBV Test 2: Cytotoxicity and Selectivity Index Methods of Testing Cytotoxicity and Selectivity Index The serial diluted compound was added to a 384 wells plate at 50 μL HepG2.2.15 cell per well (3000 cells per well), the highest final concentration in the experiment is 150 μM (200 fold dilution). The plate was cultured at 37° C. in an incubator with C02 for 4 days, and cytotoxicity of the compound was detected using CellTiter Glo agent.

The cytotoxicity of the compound was calculated using the following formulate, cytotoxicity (%)=100−(detection value/mean of DMSO control wells values×100). CC50 values were calculated by a four parametric nonlinear regression model using Graphpad Prism 5 software to manage concentration–cytotoxicity (%). CC50 values more than 50 shows that the cytotoxicity is low. The results were shown as table 4.

TABLE 4

CC50 values of cytotoxicity of the compounds of the invention

| Example | $CC_{50}$(μM) |
|---|---|
| Example 13 | >150 |
| Example 14 | >150 |
| Example 15 | >150 |
| Example 16 | >150 |
| Example 17 | >150 |
| Example 18 | >150 |
| Example 19 | >150 |
| Example 20 | >150 |
| Example 21 | 110 |
| Example 22 | >150 |
| Example 23 | >150 |
| Example 24 | >150 |
| Example 25 | >150 |
| Example 26 | >150 |
| Example 27 | >150 |
| Example 28 | >150 |
| Example 29 | >150 |
| Example 30 | 133 |
| Example 31 | >150 |
| Example 32 | >150 |
| Example 33 | >150 |
| Example 34 | >150 |
| Example 36 | >150 |
| Example 37 | >150 |
| Example 38 | >150 |
| Example 39 | >150 |
| Example 40 | >150 |
| Example 44 | >150 |
| Example 45 | >150 |
| Example 46 | >150 |
| Example 47 | >150 |
| Example 48 | >150 |
| Example 49 | >150 |
| Example 51A | >150 |
| Example 51B | >150 |
| Example 52 | >150 |
| Example 53 | >150 |
| Example 54 | >150 |
| Example 59A | >150 |
| Example 59B | >150 |

Conclusion: the cytotoxicity experimental data indicate that the compounds of the invention have low cytotoxicity.

Pharmacokinetic Activities the Compounds of the Invention on Beagle Dogs, Mice, Rats (1) PK Test on Beagle Dogs The PK test method of the compound in vivo of beagle dogs (purchased from Hunan slack Jing Da laboratory animal Co., Ltd, weight: 10-12 kg male, ages of 10-12 months, 3 per oral group, 3 per intravenous injection group):

The beagle dogs were administered intragastrically with the test compound at doses of 2.5 mg/kg or 5 mg/kg or administered intravenously with the test compound at doses of 1 mg/kg or 2 mg/kg.

Blood samples were taken at 0.083, 0.25, 0.5, 1, 2, 4, 6, 8 and 24 hours from vein after the administration, and collected in anticoagulation tube with EDTA-K2. The test compounds were extracted from plasma samples by liquid-liquid extraction. Then quantitative analysis was performed on a triple-quadrupole tandem mass spectrometer using multiple reactions monitoring (MRM). Pharmacokinetic parameters were calculated using a noncompartmental method by WinNonLin 6.3 software.

Conclusion: the data of the PK experiment indicates that the compounds of the invention have better pharmacokinetics properties in vivo of beagle dogs, and which give a prospect in development and application in the aspect of anti HBV (2) PK Test on Mice The PK test method of the compound in vivo of mice (purchased from Hunan slack Jing Da laboratory animal Co., Ltd, weight: 20-25 g, male, ages of 45-60 days, 3 per oral group, 3 per intravenous injection group):

The ICR mice were administered intragastrically with the test compound at doses of 10 mg/kg or administered intravenously in the tail veins with the test compound at doses of 2 mg/kg or 10 mg/kg. Blood samples were taken at 0.083, 0.25, 0.5, 1, 2, 4, 6, 8 and 24 hours from orbital vein after the administration, and collected in anticoagulation tube with EDTA-K2. The test compounds were extracted from plasma samples by liquid-liquid extraction. Then quantitative analysis was performed on a triple-quadrupole tandem mass spectrometer using multiple reaction monitoring (MRM). Pharmacokinetic parameters were calculated using a noncompartmental method by WinNonLin 6.3 software.

Conclusion: the data of the PK experiment indicates that the compounds of the invention have better pharmacokinetics properties in vivo of mice, and which give a prospect in development and application in the aspect of anti HBV (3) PK Test on SD Rats The PK test method of the compound in vivo of SD rats (purchased from Hunan slack Jing Da laboratory animal Co., Ltd, weight: 200-250 kg male, ages of 2-3 months, 3 per oral group, 3 per intravenous injection group):

The Rats were administered intragastrically with the test compound at doses of 2.5 mg/kg or 5 mg/kg or administered intravenously with the test compound at doses of 1 mg/kg.

Blood samples were taken at 0.083, 0.25, 0.5, 1, 2, 5, 7 and 24 hours from vein after the administration, and collected in anticoagulation tube with EDTA-K2. The test compounds were extracted from plasma samples by liquid-liquid extraction. Then quantitative analysis was performed on a triple-quadrupole tandem mass spectrometer using multiple reaction monitoring (MRM). Pharmacokinetic parameters were calculated using a noncompartmental method by WinNonLin 6.3 software. The results of a part of compounds were shown as table 4.

Test 4: Stability Test of the Compound of the Invention in Liver Microsome of Different Species Stability test method of the compound in liver microsome of different species:

To a 96 wells plate were added 30 μL of blank solution and 30 μL of liver microsomal mixed solution, and to each well was added 15 μL of buffer solution containing the test compound, the sample was prepared in duplicate. The plates were preincubated at 37° C. for 10 min, and 15 μL of NADPH solution (8 mM) was added at points in time, the final concentration of the test compound is 1 μM, the concentration of liver microsome is 0.5 mg/mL, the final concentration of NADPH is 2 mM. The plates were incubated for 0, 15, 30, 60 min respectively, after incubation was complete, 150 μL of acetonitrile containing interior label was added to the mixed system. The samples diluted with acetonitrile were centrifuged at 4000 rpm for 5 min, 150 μL of the supernatant was sampled to be analyzed by LC-MS/MS.

Conclusion: the compounds of the invention in liver microsome of different species have better stability.

Test 5: Solubility Test Method

Solubility Test Method of the Compound

Unless otherwise indicated, the test sample ground to a fine powder was weighed or the liquid sample was measured and added into a certain amount of solvent at 25° C.±2° C., the mixture was shook vigorously for 30 sec every other 5 min, the solubility was observed in 30 min, which was dissolved completely if there was no visible solute particle or liquid drop. According to Chinese pharmacopoeia standards (Ch.P. 2015IV)

Very soluble is that 1 g (mL) of solute can be dissolved completely in a <1 mL of solvent Freely solu is that 1 g (mL) of solute can be dissolved completely in a 1 to <10 mL of solvent Soluble is that 1 g (mL) of solute can be dissolved completely in a 10 to <30 mL of solvent Sparingly soluble is that 1 g (mL) of solute can be dissolved completely in a 30 to <100 mL of solvent

TABLE

PK data of a part of compounds of rats

| Test compound | drug delivery route | Dose mg/kg | $T_{max}$ h | $AUC_{last}$ hr*ng/mL | $AUC_{inf}$ hr*ng/mL | F % |
|---|---|---|---|---|---|---|
| Example 13 | iv | 1 | 0.083 | 1320 | 1320 | N/A |
|  | po | 5 | 0.5 | 3050 | 3080 | 31.2 |
| Example 14 | iv | 1 | 0.083 | 680 | 684 | N/A |
|  | po | 5 | 0.5 | 2250 | 2250 | 44 |
| Example 17 | iv | 1 | 0.083 | 977 | 979 | N/A |
|  | po | 5 | 1.0 | 4710 | 5580 | 114.1 |
| Example 19 | iv | 1 | 0.083 | 5520 | 5520 | N/A |
|  | po | 5 | 0.5 | 20300 | 20300 | 73.4 |

"ND" stands for "not assayed";

Conclusion: the data of the PK experiment indicate that the area under the curve AUClast of the compound of the invention is larger, and the exposure is better, which indicate that the compound of the invention is absorbed well in SD rats. Therefore, the compound of the invention has better pharmacokinetics properties in vivo of SD rats, and which give a prospect in development and application in the aspect of anti HBV Less soluble is that 1 g (mL) of solute can be dissolved completely in a 100 to <1000 mL of solvent Very slightly soluble is that 1 g (mL) of solute can be dissolved completely in a 1000 to <10000 mL of solvent Little or no solubility is that 1 g (mL) of solute can not be dissolved completely in a 10000 000 mL of solvent Conclusion: the results of the stability test indicate that the compounds of the invention have better solubility Test 6: hERG Test Method
Test Method of the Compound to the Heart To a 384 wells plate were added a compound, a positive control, a negative control, membrane-bound fragments containing hERG channel, a tracer with a high affinity to the hERG channel in turn, the plate was incubated at 25° C. and 250 rpm for 4 hours. Fluorescence polarization value of each well can be measured by a multimode reader, the relative inhibition rate and 50% inhibitory concentration (IC50) on hERG channel were calculated.

Conclusion: the hERG test experiment data indicate that the compounds of the invention have a low toxicity on heart.

Test 7: Liver Drug Enzyme Induction Effect Test Incubation of Cells

All of the incubations are carried out at 37° C. in an incubator with 5% C02 and 95% humidity.

After resuscitation of cryopreserved human hepatocytes (Baltimore, Md., USA), cell number and cell viability were measured on a cell counter by a trypan blue staining. After counting, the hepatocytes were diluted with preheated plate culture medium to 700 thousand living cells per ml. The diluted hepatocytes suspension were seeded into the 48 wells plate with pre-laying collagen at 0.2 mL per well, which was incubated in an incubator for at least 4 hours, the seed culture fluid was replaced with incubation medium containing 2% base matrigel while the cells is adherent.

The administration liquid was freshly prepared every day using incubation medium, including the sample (the concentration is not less than 0.1 μM), positive inducers (omeprazole, phenobarbital, rifampicin) of CYP1A2, CYP2B6 and CYP3A4 obtained through diluting with DMSO stock solution to 1000 fold. The administration liquid was listed as following table.

| Positive inducer | Final concentration of positive inducer | Final concentration of organic phase |
|---|---|---|
| Omeprazole | 50 μM | 0.1% DMSO (v/v) |
| Rifampicin | 10 μM | |
| Phenobarbital | 1000 μM | |

After the incubation system was established, the upper culture medium of sandwich culture medium was abandoned, 200 μL of preheated to 37° C. and freshly prepared administration liquid (including sample, positive control, negative control and base control) was added to each cell incubation well, the cell incubation plate was placed in the incubator and further incubated for 24 hours. After 24 hours incubation, the administration liquid was replaced with the freshly prepared administration liquid and further incubated for 24 hours. The whole incubation time is 48 hours. Each compound concentration and control concentration have triplicates.

After 48 hours incubation of the cells and administration liquid, the remainder drug solution of the plate was abandoned, and the cell wells were washed with 0.5 mL of preheated to 37° C. HBSS solution twice, and then to each well was added 100 μL of preheated to 37° C. enzyme labelled substrate liquid, the plate was incubated for 30 min. After 30 min incubation, 75 L of the supernatant sample was sampled from each well and added to a 96 deep well plate containing 150 μL of stop buffer. The plate was shaken for 10 min and centrifuged at 4° C. and 3220 g for 20 min, the supernatant solution was taken and diluted with 0.1% aqueous formic acid solution in the proportion of 1:4. The diluted sample plate was shaken for 10 min, and the amount of the metabolite production was measured by liquid chromatography-tandem mass spectrometry (LC/MS/MS).

After the detection of the enzyme activity, the remainder of the supernatant solution was abandoned, and the cells were washed with 0.5 mL of preheated HBSS. To each well was added 280 μL of 1% RLT lysis solution of 3-mercaptoethanol, the plate was sealed and shaken for 10 min, and then the plate was moved to a refrigerator (−80° C.).

Cytotoxicity Test

The potential toxicity of the sample was evaluated through releases of lactate dehydrogenase (LDH) from hepatocytes. The 100 μL administration liquid incubated with cells for 24 hours and 48 hours was sampled respectively and the concentrating of the lactate dehydrogenase therein was detected using a commercial LDH kit. The cell lysis solution was as the positive control, and the incubation medium was as the blank control.

RNA Analysis Test

The frozen sample plate was at room temperature, all of the samples were removed into a new 48 well cell incubation plate. RNA was extracted by an automatic nucleic acid extraction workstation. The samples more than 10% of total samples were taken out randomly from different position of the sample plate, the OD values at 260 nM and 280 nM were measured by using an ND2000 micro spectrophotometer, the total RNA purify was determined by calculating the ratio of the two. Reverse transcription can get cDNA. The selective gene was real time quantitatively analyzed by a CFX Connect™ realtime qPCR. The reaction conditions were set as follows: 50° C. two minutes; 95° C. ten minutes; the following two steps were repeated in 40 cycles: 95° C. fifteen seconds, 60° C. one minute. Endogenous control 18S rRNA was as the interior label.

Sample Analysis Test

The concentration of metabolites (Acetaminophen, Hydroxybupropion and 1'-Hydroxymidazolam) is detected by liquid chromatography-tandem mass spectrometry (LC/MS/MS), the metabolites are of three CYP enzyme substrates in hepatocytes precipitated by protein. The analysis methods would be described table 6.

TABLE 6

| | Induction test LCMS analysis method |
|---|---|
| Compound name | Acetaminophen, hydroxybupropion and 1'-hydroxymidazolam HPLC conditions |
| Mobile phase A | Water with 0.1% formic acid |
| Mobile phase B | Acetonitrile with 0.1% formic acid |
| Chromatographic column | Acquity UPLC BEH C18 1.7 μm 2.1*50 mm, batch number: 186004044 |
| Interior label | acetaminophen-$d_4$ (interior label of acetaminophen), hydroxybupropion-$d_6$ (interior label of hydroxybupropion) and 1'-hydroxymidazolam-$^{13}C_3$ (interior label of 1'-hydroxymidazolam) |

TABLE 6-continued

Induction test LCMS analysis method

| HPLC system | Waters UPLC | | | |
|---|---|---|---|---|
| Automatic sampler | Waters UPLC | | | |
| Injection volume | 5 μL | | | |

| Gradient | Time (min) | Flow rate (μL/min) | A (%) | B (%) |
|---|---|---|---|---|
| | 0.01 | 600 | 98 | 2 |
| | 0.10 | 600 | 98 | 2 |
| | 1.40 | 600 | 5 | 95 |
| | 1.80 | 600 | 5 | 95 |
| | 1.81 | 600 | 98 | 2 |
| | 2.00 | 600 | 98 | 2 |

Mass Spectroscope

| Mass spectrum | API 4000 |
|---|---|
| Ion source | Electrospray ionization |
| Scan patterns | Multiplereaction monitoring |
| Polarity | Positive ion |

| Compound name | Ion pair | Retention time (min) | Declustering potential (eV) | Collision energy (eV) |
|---|---|---|---|---|
| Acetaminophen | 152.1/110.1 | 0.66 | 39 | 23 |
| Hydroxybupropion | 256.4/238.0 | 0.80 | 70 | 30 |
| 1'-Hydroxymidazolam | 342.1/203.1 | 0.91 | 51 | 35 |
| Acetaminophen-$d_4$ (interior label) | 156.1/114.2 | 0.65 | 55 | 23 |
| Hydroxybupropion-$d_6$ (interior label) | 262.3/139.0 | 0.79 | 31 | 30 |
| 1'-Hydroxymidazolam-$^{13}C_3$ (interior label) | 347.1/208.1 | 0.91 | 53 | 37 |

| Mass spectrum parameters | Collision gas | 20 |
|---|---|---|
| | Curtain Gas | 55 |
| | Atomization gas | 60 |
| | Heating auxiliary gas | 5500 |
| | Ion transmission voltage | 600 |
| | Atomization temperature | ON |
| | Heater interface | 10 |
| | Entrance voltage | 10 |
| | Collision chamber outlet voltage | 15 |

Calculation Gene Expression Data

The differences of gene expression between different treatment groups were compared by using ΔCt relative quantify in this project, 18S rRNA is used as the internal reference gene to correct the gene expression of each sample. The Ct value of the target gene minus the Ct value of the reference gene equal to ΔCt, i.e. Ct target gene−Ct18S=ΔCt. The ΔCt value of the treatment group minus the ΔCt value of the blank control equal to ΔΔCt, i.e. ΔCt treatment group−ΔCt blank control=ΔΔCt. The changes of multiple between the treatment group and the blank control were compared by the statistical analysis by the 2-ΔΔCt method.

Calculation of Enzyme Activity Data

The amount of enzyme metabolite production of CYP1A2, CYP2B6 and CYP3A4 were shown as the data of the experiment. The changes of the enzyme activity were represented by comparison of induction multiples of the corresponding cytochrome enzyme in the presence or absence of a test compound. The calculation method of induction multiple and the calculation method of induction ratio to the control compound were shown as follows:

induction multiple=enzyme activity of the sample treated with the test compound/enzyme activity of the sample treated with control group induction ratio to the control compound=(induction multiple of the sample treated with the test compound−1)/(induction multiple of the sample treated with the control compound−1)×100%

The results of liver drug enzyme induction effect test are shown as table 7:

TABLE 7

The data of liver drug enzyme induction effect test

| | Induction ratio of the control compound (10 μM, rifampicin) | | |
|---|---|---|---|
| Example | CYP1A2 | CYP2B6 | CYP3A4 |
| Example 11 | 2.5% | 2.4% | 17.0% |
| Example 13 | −2.7% | −5.3% | −3.7% |
| Example 14 | −0.8% | −1.6% | −0.9% |
| Example 15 | −0.8% | −2.7% | −1.04% |
| Example 16 | −0.8% | 0.03% | −1.21% |
| Example 17 | −2.0% | −3.9% | −5.1 |
| Example 18 | 1.8% | 1.3% | 0.9% |
| Example 19 | 3.7% | 1.9% | 1.6% |
| Example 20 | −0.8% | −2.1% | 1.4% |
| Example 21 | 0.3% | 1.6% | 10.3% |
| Example 22 | 2.1% | 1.5% | 1.0% |
| Example 23 | −2.5% | −3.9% | −1.6% |
| Example 24 | −2.8% | −5.7% | −3.9% |

TABLE 7-continued

The data of liver drug enzyme induction effect test

| Example | Induction ratio of the control compound (10 μM, rifampicin) | | |
|---|---|---|---|
| | CYP1A2 | CYP2B6 | CYP3A4 |
| Example 25 | −2.9% | −5.6% | −3.2% |
| Example 26 | 1.6% | 1.4% | 0.5% |
| Example 27 | −1.2% | −1.3% | −0.8% |
| Example 28 | 2.3% | 1.2% | 1.4% |
| Example 29 | −1.3% | −2.7% | −4.4 |
| Example 30 | −0.5% | −1.7% | 1.9% |
| Example 33 | 2.9% | 3.2% | 2.1% |
| Example 34 | −2.1% | −4.2% | −2.4% |
| Example 35 | −1.6% | −5.7% | −2.5% |
| Example 37 | −3.2% | −4.6% | −2.2% |
| Example 38 | 3.7% | 4.1% | 2.8% |
| Example 39 | −1.8% | −3.2% | −3.6% |
| Example 44 | −1.7% | −4.2% | −2.9% |
| Example 46 | 2.6% | 1.9% | 5.9% |
| Example 47 | 5.8% | 3.9% | 6.3% |
| Example 48 | −1.9% | −5.7% | −3.9% |
| Example 49 | 1.4% | 5.2% | 4.9% |
| Example 51A | 4.7% | 7.1% | 5.8% |
| Example 51B | 2.6% | −4.8% | 3.5% |
| Example 52 | −2.7% | −4.6% | −2.3% |
| Example 53 | 4.6% | 3.9% | 8.4% |
| Example 54 | 3.7% | 6.5% | 9.1% |
| Example 59A | −3.4% | −1.7% | −8.3% |
| Example 59B | 3.3% | 2.9% | 6.8% |
| Example 61A | 0.5% | 1.5% | 4.8% |
| Example 61B | 0.3% | 3.7% | 2.9% |

Conclusion: the experiment data of the liver drug enzyme induction effect test indicate that the compounds of the invention have no induction effect to liver drug enzyme.

Test 8: Effect of Human Serum on Anti HBV Efficacy of Compounds

Experiment Principle

HepG2.2.15 chromosomes have an integrated complete HBV genome, and stably express viral RNA and viral protein. HepG2.2.15 cells can secrete mature HBV particles, HBsAg and HBeAg to medium. Viral DNA secreted from HepG2.2.15 cells can be quantified by qPCR, human serum with different concentrations were added during the treatment process with the test compound, and the effect of human serum on anti HBV efficacy of compounds was detected.

Test Method

Treatment of HepG2.2.15 with Compounds

Step 1: 15000 per well HepG2.2.15 cells were paved in a 96 wells cell incubation plate, 200 μL cell culture medium per well.

Step 2: the plate was incubated at 37° C. in a cell incubator with 5% C02 for 3 days till the cells grew to full wells.

Step 3: Old liquid medium can be removed and replaced with new medium (200 μL) containing 2% FBS and human serum (HS) with different concentrations (0% HS, 5% HS, 10% HS, 20% HS, 40% HS and 50% HS) on day 0.

Step 4: Formulating the compound and treating the cells in the experiment of anti virus: the compound was dissolved in DMSO to a concentration of 30 mM, and then the compound solution was diluted with DMSO to a concentration of 800 μM, and then eight dilutions at 4 fold were performed, the highest concentration is 800 μM. The serial diluted compound was added to the plate from step 3 at 1 μL per well, the highest final concentration in the experiment is 4 μM (200 fold dilution).

Step 5: the experiment was carried out under the condition of 2% FBS, TDF (tenofovir dipiroxil fumarate, Selleck, Cat S1400) has a highest concentration of 4 μM as a positive control. To the negative control well was added 1 μL of DMSO to an experiment final concentration of 0.5%.

Step 6: the 96 wells cell incubation plate was incubated at 37° C. in an incubator with CO2 for 11 days, the liquid was replaced every other day (at 2, 4, 6, 8, 10 days), and 1 μL of freshly formulated test compound was added, the method was shown in steps 3 to 5.

Step 7: 150 μL of supernatant was sampled from each well at 11 days for detection of viral DNA.

Step 8: formulation of the compound and treatment of the cells in the cytotoxicity experiment: the serial dilute compound was formulated with Bravo liquid handling system, 11 dilutions at 3 fold were performed, the highest concentration is 30 mM. 0.25 μL of the serial dilute compound was removed into each well of a 384 wells cytotoxicity plate (Greiner 781098) by using Echo550. HepG2.2.15 cells were prepared and resuspended in culture medium with different concentrations of human serum (50%, 40%, 20%, 10%, 5% and 0%). 50 μL of the HepG2.2.15 cells (4000 cells) prepared above per well were added into the 384 wells cytotoxicity plate, the highest final concentration in the experiment is 150 μM (200 fold dilution). After 4 days incubation at 37° C. in an incubator with $CO_2$, the cytotoxicity test was carried out.

Detection of Viral Genomic DNA by qPCR

Step 1: the supernatant was diluted with DPBS 2 folds under the experiment condition of 20% HS, the supernatant was diluted with DPBS 4 folds under the experiment condition of 40% HS, the supernatant was diluted with DPBS 5 folds under the experiment condition of 50% HS. After uniformly mixing, 1 μL of which was sampled, and detected by qPCR.

Step 2: 1 μL of the supernatant was sampled directly to be detected by qPCR under the experiment conditions of 0% HS, 5% HS and 10% HS.

Step 3: the qPCR reaction system was formulated as following components:

| | |
|---|---|
| SYBR Premix Ex TaqTM II (2×) | 10 μL |
| HBV-For-202 (10 μM) | 0.8 μL |
| HBV-Rev-315 (10 μM) | 0.8 μL |
| ROX Reference Dye (50×) | 0.4 μL |
| viral supernatant | 1 μL |
| the final volume after adding water | 20 L |

Step 4: the parameters of ABI ViiA7 qPCR instrument were set as follows

Stage 1:
　Reps: 95° C., 30 s, 1 cycle
Stage 2:
　Reps: 95° C., 5 s and 60° C., 34 s, 40 cycles
Adding the curve of dissolution Detection of Cytotoxic Effects of Compounds Step 1: PromegaCelltiter-Glo reagent was balanced to room temperature.

Step 2: culture medium in the cytotoxicity experimental plate was discarded, and 50 μL of DPBS was added into each well.

Step 3: 10 μL of CellTiter-Glo reagent was added into each well.

Step 4: the plate was shaken on a vibrator for 2 min.

Step 5: the plate was balanced at rt away from light for 10 min.

Step 6: the data was read on the Envision reading board (0.1 sec/well)

Analysis of Results

The standard curve was plotted based on the plasmids containing the HBV genome (Virus copy number: 2×10E6, 2×10E5, 2×10E4, 2×10E3), and the virus copy number was calculated by the standard curve. EC50 values were calculated by a four parametric nonlinear regression model using Graphpad Prism 5 software to process the data and plot the concentration-viral copy number curve. cytotoxicity %=100-(detection value/mean of DMSO control wells values×100). CC50 values were calculated by a four parametric nonlinear regression model using Graphpad Prism 5 software to process the cytotoxicity % data and plot the curve.

Conclusion: the experiment data indicate that the effects of human serum on the antiviral efficacy of the compound is small, and the compounds of the invention play good antiviral effects in the human body.

Though the invention is described in detail in the above with reference to general description and detailed embodiments, modifications and variants are possible obvious to a person of ordinary skills in the art may be made based on the invention. Therefore, the modifications and variants all belong to the scopes of the invention without departing from the spirits of the invention.

What is claimed is:

1. A compound having Formula (I) or Formula (Ia), or a stereoisomer, a tautomer, an N-oxide, a solvate, a metabolite, a pharmaceutically acceptable salt or a prodrug thereof,

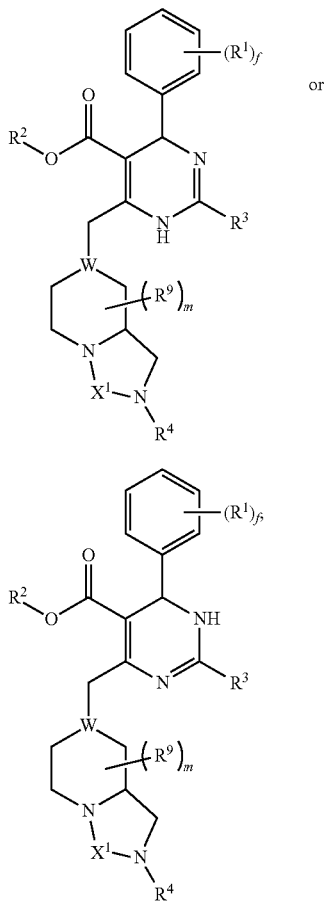

wherein each $R^1$ is independently H, deuterium, F, Cl, Br, I, methyl, or ethyl;

each $R^2$ is independently $C_{1-6}$ alkyl, deuterium substituted $C_{1-6}$ alkyl or $C_{1-6}$ haloalkyl;

each $R^3$ is independently 5 membered heteroaryl, wherein each of 5 membered heteroaryl is independently unsubstituted or substituted with one or two substituents independently selected from deuterium, F, Cl, Br or $C_{1-6}$ alkyl;

each W is N;

each $X^1$ is independently —C(=O) or —$CH_2$;

each $R^7$ and $R^8$ is independently H, deuterium, F, Cl, Br, amino, $C_{1-6}$ alkyl, $NH_2C$(=O)—, $C_{1-6}$ alkyl-OC(=O)—, carboxy, carboxy $C_{1-6}$ alkylene, hydroxy $C_{1-6}$ alkyl, $C_{1-4}$ alkoxy-$C_{1-4}$ alkyl or $C_{1-6}$ haloalkyl, or $R^7$ and $R^8$, together with the carbon atom to which they are attached, form $C_{3-6}$ cycloalkyl or carbonyl;

each $R^9$ is independently H, deuterium, $C_{1-6}$ alkyl, $C_{1-6}$ alkyl-OC(=O)—, carboxy, hydroxy $C_{1-6}$ alkyl or $C_{1-4}$ alkoxy-$C_{1-4}$ alkyl;

$R^4$ is pyridyl, 5 membered monocyclic heteroaryl, phenyl, naphthyl or phenyl-($CR^7R^8$)—, wherein the 5 membered monocyclic heteroaryl and naphthyl are each independently unsubstituted or substituted with one, two or three $R^w$, the pyridyl, phenyl and phenyl of phenyl-($CR^7R^8$)— are each independently substituted with one, two, three or four $R^x$;

each $R^w$ is independently deuterium, F, Cl, Br, OH, CN, $R^aR^bNC$(=O)—, $R^cR^dP$(=O)—, HOOC—($CR^7R^8$)$_k$—, amino, $C_{1-8}$ alkyl, $C_{2-8}$ alkenyl, hydroxy $C_{1-8}$ alkyl, $C_{1-8}$ alkyl-C(=O)—, $C_{1-8}$ alkoxy, $C_{1-8}$ alkyl-OC(=O)— or $C_{1-8}$ alkyl-S(=O)$_2$—, wherein the amino, $C_{1-8}$ alkyl, $C_{2-8}$ alkenyl, hydroxy $C_{1-8}$ alkyl, $C_{1-8}$ alkyl-C(=O)—, $C_{1-8}$ alkoxy, $C_{1-8}$ alkyl-OC(=O)— and $C_{1-8}$ alkyl-S(=O)$_2$— are each independently unsubstituted or substituted with one, two, three, four or five $R^y$;

each $R^x$ is independently deuterium, F, Cl, Br, OH, CN, $R^aR^bNC$(=O)—, $R^cR^dP$(=O)—, HOOC—($CR^7R^8$)$_n$—, amino, $C_{1-8}$ alkyl, $C_{2-8}$ alkenyl, hydroxy $C_{1-8}$ alkyl, $C_{1-8}$ alkyl-C(=O)—, $C_{1-8}$ alkoxy, $C_{1-8}$ alkyl-OC(=O)—, HOOC-methylene-O-methylene-, $C_{1-4}$ alkyl-OC(=O)-methylene-O-methylene, $C_{1-4}$ alkyl-C(=O)O-methylene or $C_{1-8}$ alkyl-S(=O)$_2$—, wherein the amino, $C_{1-8}$ alkyl, $C_{2-8}$ alkenyl, hydroxy $C_{1-8}$ alkyl, $C_{1-8}$ alkyl-C(=O)—, $C_{1-8}$ alkoxy, $C_{1-8}$ alkyl-OC(=O)—, HOOC-methylene-O-methylene-, $C_{1-4}$ alkyl-OC(=O)-methylene-O-methylene, $C_{1-4}$ alkyl-C(=O)O-methylene and $C_{1-8}$ alkyl-S(=O)$_2$— are each independently unsubstituted or substituted with one, two, three, four or five $R^y$;

each $R^y$ is independently deuterium, F, Cl, Br, OH, CN, $R^aR^bNC$(=O)—, $R^cR^dP$(=O)—, HOOC—($CR^7R^8$)$_h$—, amino, $C_{1-6}$ alkyl-S(=O)$_2$—NH—, $C_{1-8}$ alkyl, $C_{1-8}$ alkoxy, $C_{1-8}$ alkyl-S(=O)$_2$—, $C_{1-8}$ alkyl-C(=O)—, $C_{1-8}$ alkyl-OC(=O)—, benzyl-OC(=O) or $C_{1-8}$ alkylamino-S(=O)$_2$—, wherein the amino, $C_{1-6}$ alkyl-S(=O)$_2$—NH—, $C_{1-8}$ alkyl, $C_{1-8}$ alkoxy, $C_{1-8}$ alkyl-S(=O)$_2$—, $C_{1-8}$ alkyl-C(=O)—, $C_{1-8}$ alkyl-OC(=O)—, benzyl-OC(=O)—, phenyl-OC(=O)— and $C_{1-8}$ alkylamino-S(=O)$_2$— are each independently unsubstituted or substituted with one, two, three, four or five substituents selected from deuterium, F, Cl, Br, OH, $C_{1-8}$ alkoxy, $C_{1-8}$ alkyl, HOOC—($CR^7R^8$)$_h$— or $C_{1-8}$ alkoxy-($CR^7R^8$)$_n$—O—;

each $R^a$, $R^b$, $R^c$ and $R^d$ is independently H, deuterium, HOOC—($CR^7R^8$)$_q$—, $C_{1-8}$ alkyl, $C_{1-8}$ alkyl-OC(=O)—, $C_{1-8}$ alkoxy, $C_{3-7}$ cycloalkyl or 3-12 membered heterocyclyl, wherein the $C_{1-8}$ alkyl, $C_{1-8}$ alkyl-OC(=O)—, $C_{1-8}$ alkoxy, $C_{3-7}$ cycloalkyl and 3-12 membered heterocyclyl are each independently unsubstituted or substituted with one, two, three, four or five substituents selected from deuterium, F, Cl, Br, OH, amino, $C_{1-8}$ alkyl, $C_{1-8}$ alkoxy, HOOC—$(CR^7R^8)_q$— or $C_{1-8}$ alkoxy-$(CR^7R^8)_n$—O—;

each f, k, h and q is independently 0, 1, 2, 3 or 4;
each m is independently 0, 1 or 2;
each n is independently 1, 2, 3 or 4;
each j is independently 1, 2 or 3.

2. The compound of claim 1 having Formula (II) or Formula (IIa),

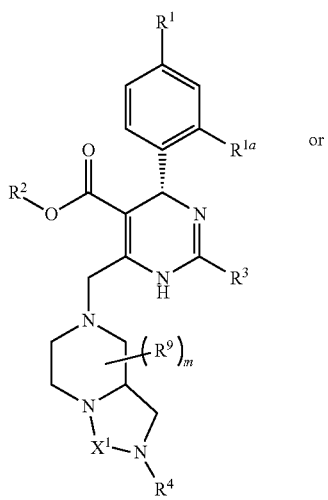

(II)

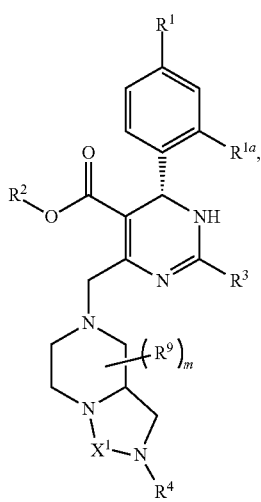

(IIa)

wherein each $R^1$ and $R^{1a}$ is independently H, deuterium, F, Cl, Br, I or methyl or ethyl.

3. The compound of claim 1 having Formula (III) or Formula (IIIa),

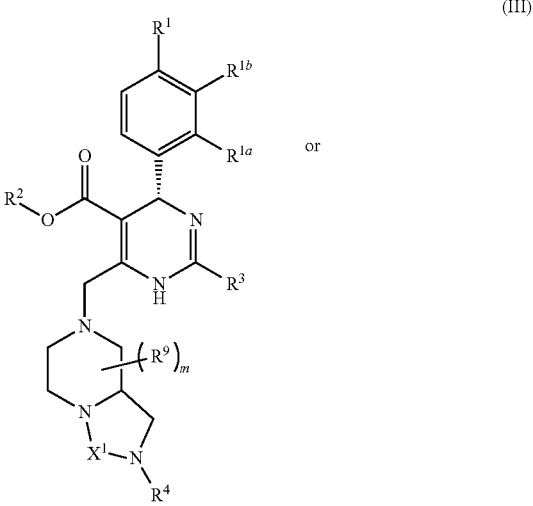

(III)

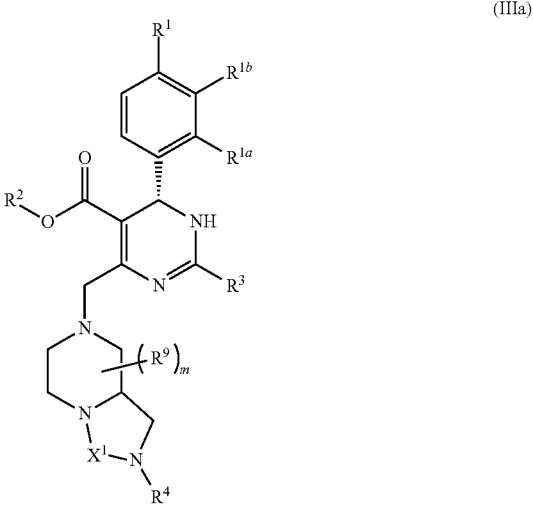

(IIIa)

wherein each $R^1$, $R^{1b}$ and $R^{1a}$ is independently H, deuterium, F, Cl, Br, I, methyl or ethyl.

4. The compound of claim 1 having Formula (IV) or (IVa):

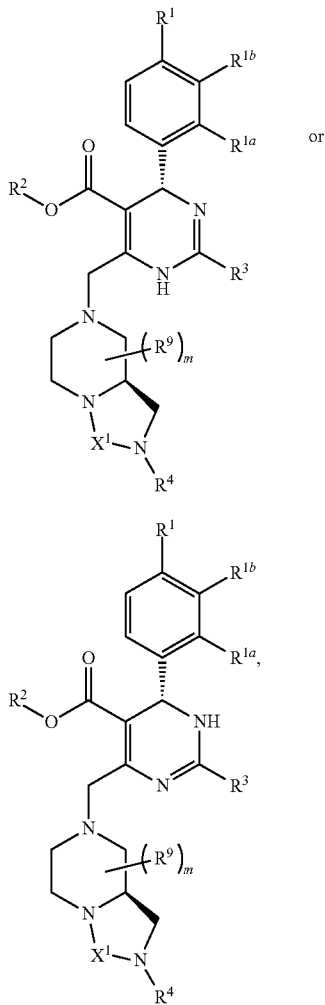

(IV)

(IVa)

wherein each $R^1$, $R^{1b}$ and $R^{1a}$ is independently H, deuterium, F, Cl, Br, I, methyl or ethyl.

5. The compound of claim 1, wherein each $R^2$ is independently methyl, deuterated methyl, ethyl, n-propyl, i-propyl or $C_{1-4}$ haloalkyl;

$R^3$ is furyl, pyrrolyl, pyrazolyl, imidazolyl, triazolyl, tetrazolyl, oxazolyl, oxadiazolyl, thiazolyl, thienyl, wherein each of furyl, pyrrolyl, pyrazolyl, imidazolyl, triazolyl, tetrazolyl, oxazolyl, oxadiazolyl, thiazolyl and thienyl, is independently unsubstituted or substituted with one or two substituents independently selected from deuterium, F, Cl, Br or $C_{1-4}$ alkyl;

each $R^7$ and $R^8$ is independently H, deuterium, F, Cl, Br, methyl, ethyl, n-propyl, i-propyl, $NH_2C(=O)-$, $C_{1-4}$ alkyl-OC(=O)—, carboxy, carboxy $C_{1-3}$ alkylene, hydroxy $C_{1-4}$ alkyl, ethoxyethyl, methoxyethyl, isopropoxymethyl, methoxymethyl or $C_{1-4}$ haloalkyl, or $R^7$ and $R^8$, together with the carbon atom to which they are attached, form cyclopropyl, cyclobutyl, cyclopentyl, cyclohexyl or carbonyl;

each $R^9$ is independently H, deuterium, methyl, ethyl, n-propyl, i-propyl, $C_{1-4}$ alkyl-OC(=O)—, carboxy, hydroxy $C_{1-4}$ alkyl, ethoxyethyl, methoxyethyl, isopropoxymethyl or methoxymethyl.

6. The compound of claim 1, wherein $R^4$ is pyridyl, 5 membered monocyclic heteroaryl, phenyl, naphthyl or phenyl-$(CR^7R^8)-$, wherein the 5 membered monocyclic heteroaryl and naphthyl are each independently unsubstituted or substituted with one two or three $R^w$, the pyridyl, phenyl and phenyl of phenyl-$(CR^7R^8)-$ are each independently substituted with one, two, three or four $R^x$.

7. The compound of claim 1, wherein $R^4$ is pyridyl, furyl, pyrrolyl, pyrazolyl, imidazolyl, triazolyl, tetrazolyl, oxazolyl, isoxazolyl, oxadiazolyl, thiazolyl, thienyl, phenyl, naphthyl or phenyl-$(CR^7R^8)-$, wherein each of furyl, pyrrolyl, pyrazolyl, imidazolyl, triazolyl, tetrazolyl, oxazolyl, isoxazolyl, oxadiazolyl, thiazolyl, thienyl, and naphthyl is independently unsubstituted or substituted with one, two or three $R^w$; the pyridyl, phenyl and phenyl of phenyl-$(CR^7R^8)-$ are each independently substituted with one, two, three or four $R^x$.

8. The compound of claim 1, wherein each $R^w$ is independently deuterium, F, Cl, Br, OH, CN, $R^aR^bNC(=O)-$, $R^cR^dP(=O)-$, $HOOC-(CR^7R^8)_k-$, amino, $C_{1-6}$ alkyl, $C_{2-6}$ alkenyl, hydroxy $C_{1-6}$ alkyl, $C_{1-6}$ alkyl-C(=O)—, $C_{1-6}$ alkoxy, $C_{1-6}$ alkyl-OC(=O)— or $C_{1-6}$ alkyl-S(=O)$_2$—, wherein the amino, $C_{1-6}$ alkyl, $C_{2-6}$ alkenyl, hydroxy $C_{1-6}$ alkyl, $C_{1-6}$ alkyl-C(=O)—, $C_{1-6}$ alkoxy, $C_{1-6}$ alkyl-OC(=O)— and $C_{1-6}$ alkyl-S(=O)$_2$— are each independently unsubstituted or substituted with one, two, three, four or five $R^y$;

each $R^x$ is independently deuterium, F, Cl, Br, OH, CN, $R^aR^bNC(=O)-$, $R^cR^dP(=O)-$, $HOOC-(CR^7R^8)_n-$, amino, $C_{1-6}$ alkyl, $C_{2-6}$ alkenyl, hydroxy $C_{1-6}$ alkyl, $C_{1-6}$ alkyl-C(=O)—, $C_{1-6}$ alkoxy, $C_{1-6}$ alkyl-OC(=O)—, HOOC-methylene-O-methylene-, $C_{1-4}$ alkyl-OC(=O)-methylene-O-methylene, $C_{1-4}$ alkyl-C(=O)O-methylene or $C_{1-6}$ alkyl-S(=O)$_2$—, wherein the amino, $C_{1-6}$ alkyl, $C_{2-6}$ alkenyl, hydroxy $C_{1-6}$ alkyl, $C_{1-6}$ alkyl-C(=O)—, $C_{1-6}$ alkoxy, $C_{1-6}$ alkyl-OC(=O)—, HOOC-methylene-O-methylene-, $C_{1-4}$ alkyl-OC(=O)-methylene-O-methylene, $C_{1-4}$ alkyl-C(=O)O-methylene and $C_{1-6}$ alkyl-S(=O)$_2$— are each independently unsubstituted or substituted with one, two, three, four or five $R^y$.

9. The compound of claim 1, wherein each $R^w$ is independently deuterium, F, Cl, Br, OH, CN, $R^aR^bNC(=O)-$, $R^cR^dP(=O)-$, $HOOC-(CR^7R^8)_k-$, amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)— or $C_{1-4}$ alkyl-S(=O)$_2$—, wherein the amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)— and $C_{1-4}$ alkyl-S(=O)$_2$— are each independently unsubstituted or substituted with one, two, three, four or five $R^y$;

each $R^x$ is independently deuterium, F, Cl, Br, OH, CN, $R^aR^bNC(=O)-$, $R^cR^dP(=O)-$, $HOOC-(CR^7R^8)_n-$, amino, $C_{1-4}$ alkyl, vinyl, propenyl, allyl, hydroxy $C_{1-4}$ alkyl, $C_{1-4}$ alkyl-C(=O)—, $C_{1-4}$ alkoxy, $C_{1-4}$ alkyl-OC(=O)—, HOOC-methylene-O-methylene-, methyl-OC(=O)-methylene-O-methylene, ethyl-OC(=O)-methylene-O-methylene, methyl-C(=O)O-methylene or $C_{1-4}$ alkyl-S(=O)$_2$—, wherein the amino, $C_{1-4}$ alkyl, hydroxy $C_{1-4}$ alkyl, vinyl, propenyl, allyl, $C_{1-4}$ alkyl-C(=O)—, $C_{1-4}$ alkoxy, $C_{1-4}$ alkyl-OC(=O)—, HOOC-methylene-O-methylene-, methyl-OC(=O)-methylene-O-methylene, ethyl-OC(=O)-methylene-O-methylene, methyl-C(=O)O-methylene and $C_{1-4}$ alkyl-S(=O)$_2$— are each independently unsubstituted or substituted with one, two, three, four or five $R^y$.

10. The compound of claim 1, wherein each $R^y$ is independently deuterium, F, Cl, Br, OH, CN, $R^aR^bNC(=O)$—, $R^cR^dP(=O)$—, HOOC—(CR$^7$R$^8$)$_n$—, amino, $C_{1-4}$ alkyl-S(=O)$_2$—NH—, $C_{1-6}$ alkyl, $C_{1-6}$ alkoxy, $C_{1-6}$ alkyl-S(=O)$_2$—, $C_{1-6}$ alkyl-C(=O)—, $C_{1-6}$ alkyl-OC(=O)—, benzyl-OC(=O) or $C_{1-6}$ alkylamino-S(=O)$_2$—, wherein the amino, $C_{1-4}$ alkyl-S(=O)$_2$—NH—, $C_{1-6}$ alkyl, $C_{1-6}$ alkoxy, $C_{1-6}$ alkyl-S(=O)$_2$—, $C_{1-6}$ alkyl-C(=O)—, $C_{1-6}$ alkyl-OC(=O)—, benzyl-OC(=O)—, phenyl-OC(=O)— and $C_{1-6}$ alkylamino-S(=O)$_2$— are each independently unsubstituted or substituted with one, two, three, four or five substituents selected from deuterium, F, Cl, Br, OH, $C_{1-6}$ alkoxy, $C_{1-6}$ alkyl, HOOC—(CR$^7$R$^8$)$_n$— or $C_{1-6}$ alkoxy-(CR$^7$R$^8$)$_n$—O—;

each $R^a$, $R^b$, $R^c$ and $R^d$ is independently H, deuterium, HOOC—(CR$^7$R$^8$)$_q$—, $C_{1-6}$ alkyl, $C_{1-6}$ alkyl-OC(=O)—, $C_{1-6}$ alkoxy, $C_{3-6}$ cycloalkyl or 5-10 membered heterocyclyl, wherein the $C_{1-6}$ alkyl, $C_{1-6}$ alkyl-OC(=O)—, $C_{1-6}$ alkoxy, $C_{3-6}$ cycloalkyl and 5-10 membered heterocyclyl are each independently unsubstituted or substituted with one, two, three, four or five substituents selected from deuterium, F, Cl, Br, OH, amino, $C_{1-6}$ alkyl, $C_{1-6}$ alkoxy, HOOC—(CR$^7$R$^8$)$_q$— or $C_{1-6}$ alkoxy-(CR$^7$R$^8$)$_n$—O—.

11. The compound of claim 1, wherein each $R^y$ is independently deuterium, F, Cl, Br, OH, CN, $R^aR^bNC(=O)$—, $R^cR^dP(=O)$—, HOOC—(CR$^7$R$^8$)$_n$—, amino, methyl-S(=O)$_2$—NH—, ethyl-S(=O)$_2$—NH—, $C_{1-4}$ alkyl, $C_{1-4}$ alkoxy, $C_{1-4}$ alkyl-S(=O)$_2$—, $C_{1-4}$ alkyl-C(=O)—, $C_{1-4}$ alkyl-OC(=O)—, benzyl-OC(=O) or $C_{1-4}$ alkylamino-S(=O)$_2$—, wherein the amino, methyl-S(=O)$_2$—NH—, ethyl-S(=O)$_2$—NH—, $C_{1-4}$ alkyl, $C_{1-4}$ alkoxy, $C_{1-4}$ alkyl-S(=O)$_2$—, $C_{1-4}$ alkyl-C(=O)—, $C_{1-4}$ alkyl-OC(=O)—, benzyl-OC(=O) and $C_{1-4}$ alkylamino-S(=O)$_2$— are each independently unsubstituted or substituted with one, two, three, four or five substituents selected from deuterium, F, Cl, Br, OH, $C_{1-4}$ alkoxy, $C_{1-4}$ alkyl, HOOC—(CR$^7$R$^8$)$_n$— or $C_{1-4}$ alkoxy-(CR$^7$R$^8$)$_n$—O—;

each $R^a$, $R^b$, $R^c$ and $R^d$ is independently H, deuterium, HOOC—(CR$^7$R$^8$)$_q$—, $C_{1-4}$ alkyl, $C_{1-4}$ alkyl-OC(=O)—, $C_{1-4}$ alkoxy, $C_{3-6}$ cycloalkyl or 5-6 membered heterocyclyl, wherein the $C_{1-4}$ alkyl, $C_{1-4}$ alkyl-OC(=O)—, $C_{1-4}$ alkoxy, $C_{3-6}$ cycloalkyl and 5-6 membered heterocyclyl are each independently unsubstituted or substituted with one, two, three, four or five substituents selected from deuterium, F, Cl, Br, OH, amino, $C_{1-4}$ alkyl, $C_{1-4}$ alkoxy, HOOC—(CR$^7$R$^8$)$_q$— or $C_{1-4}$ alkoxy-(CR$^7$R$^8$)$_n$—O—.

12. A compound having one of the following structures:

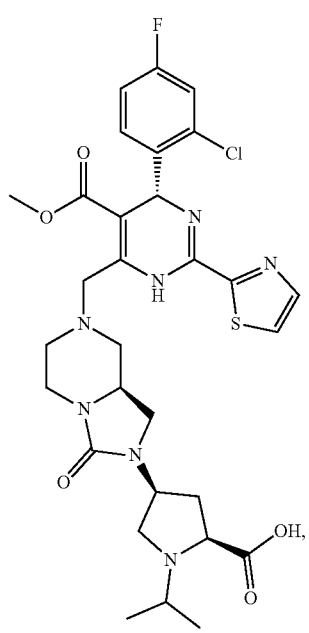

(1)

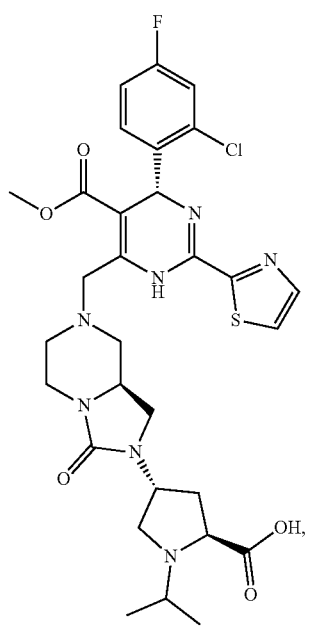

(2)

303
-continued
(3)
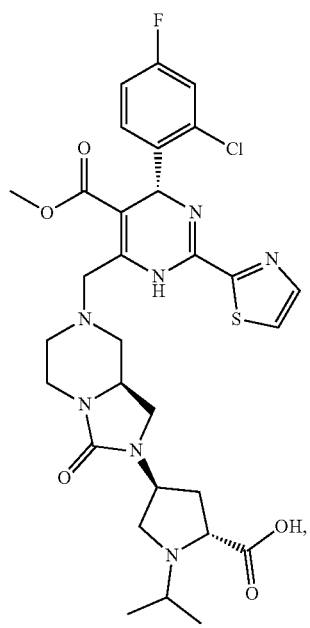
304
-continued
(5)
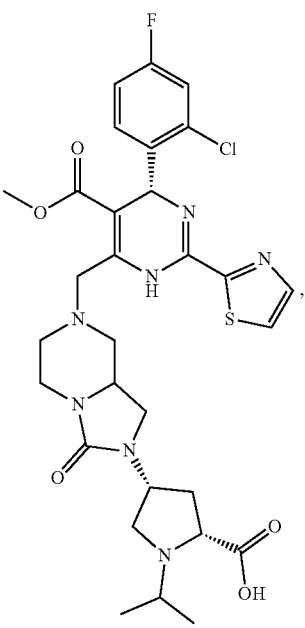
(4)
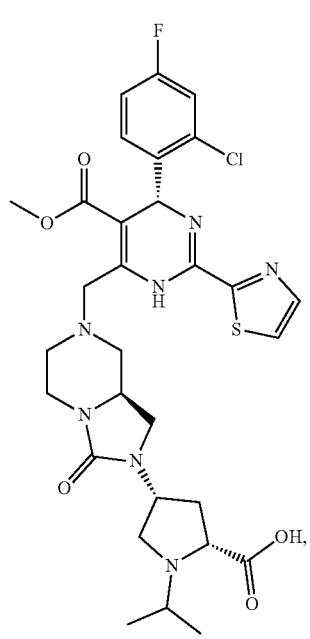
(6)
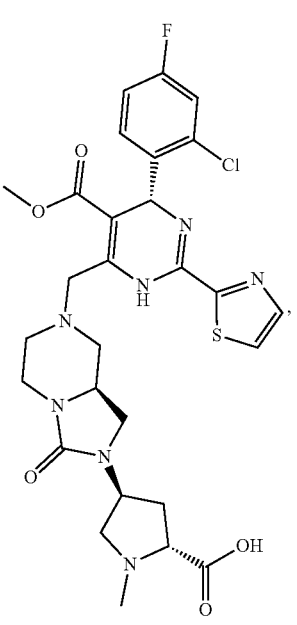

305
-continued
(7)
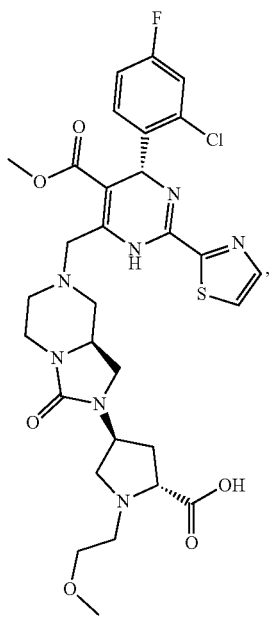
306
-continued
(9)
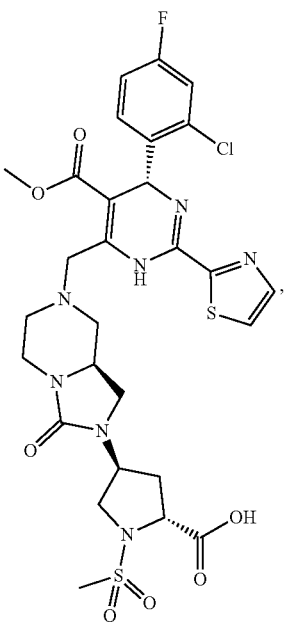
(8)
(10)
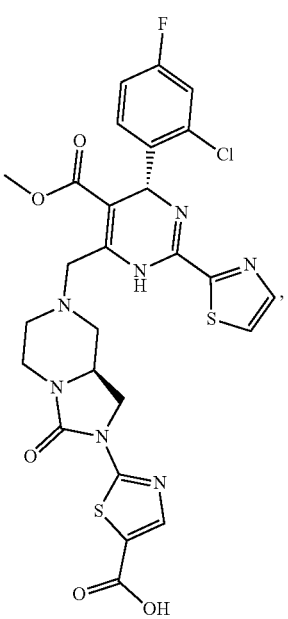

307
-continued
(11)
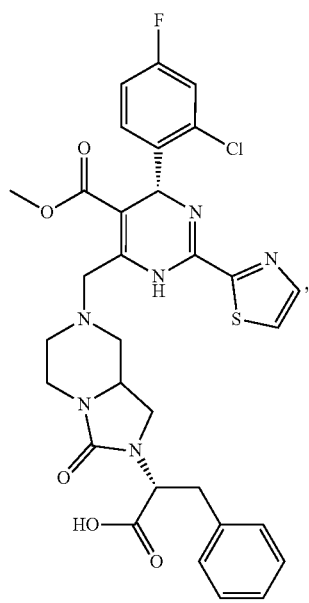
308
-continued
(13)
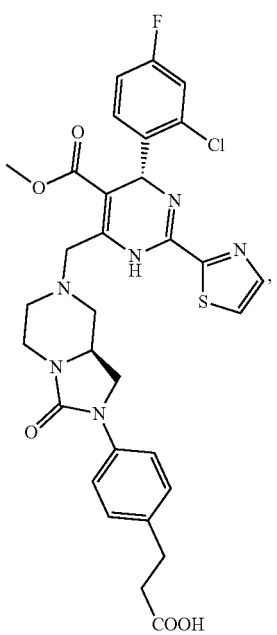
(12)
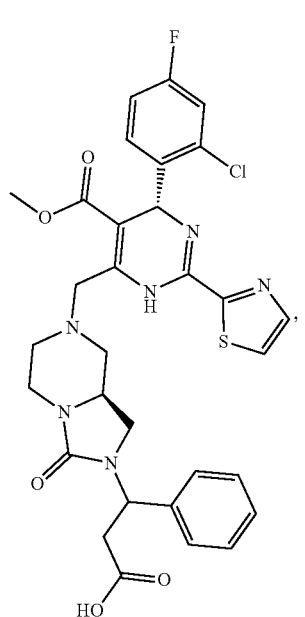
(14)
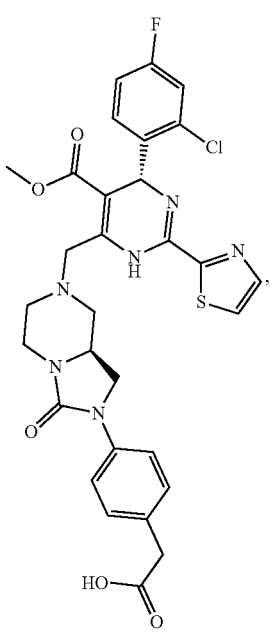

309
-continued
(15)
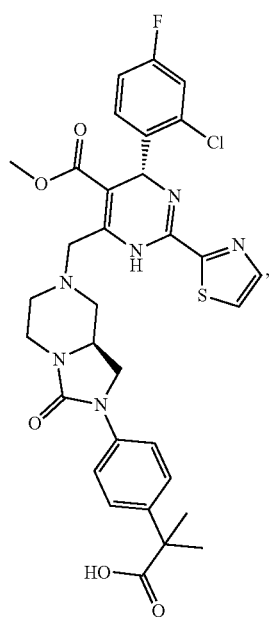
(16)
(17)
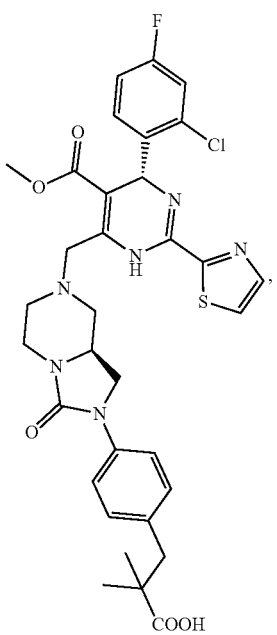
(18)
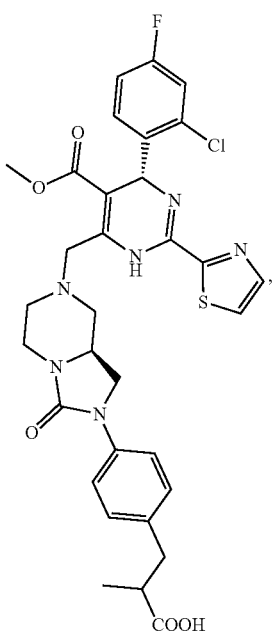

311
-continued
(19)
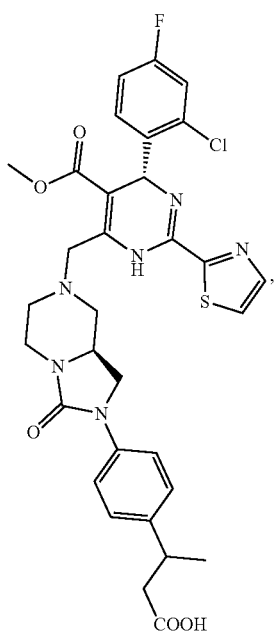
312
-continued
(21)
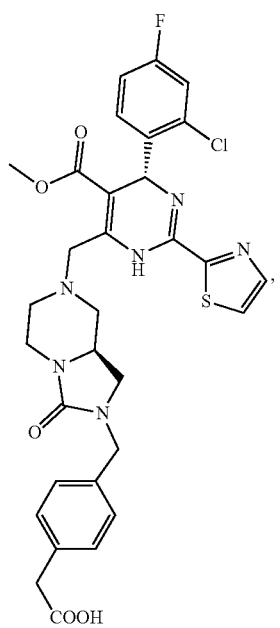
(20)
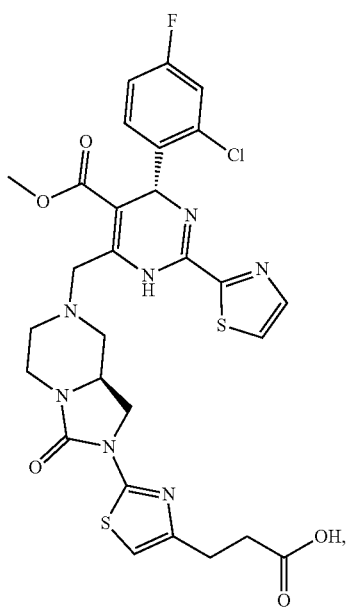
(22)
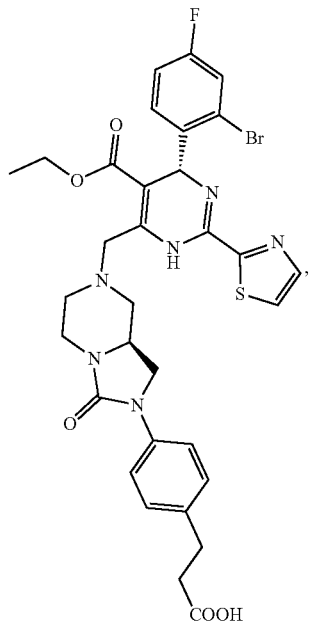

313
-continued
(23)
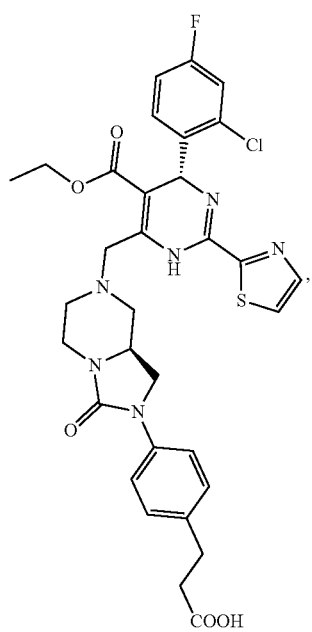
(24)
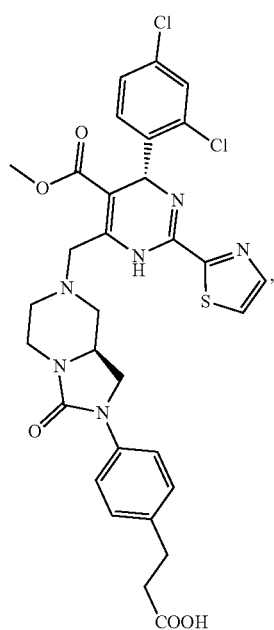
314
-continued
(25)
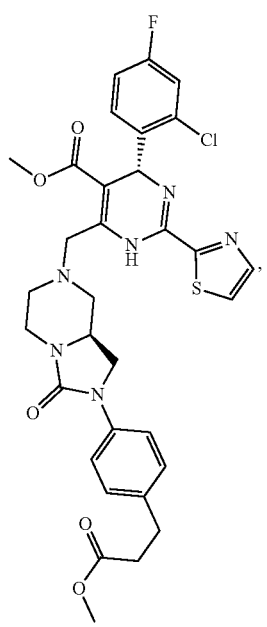
(26)
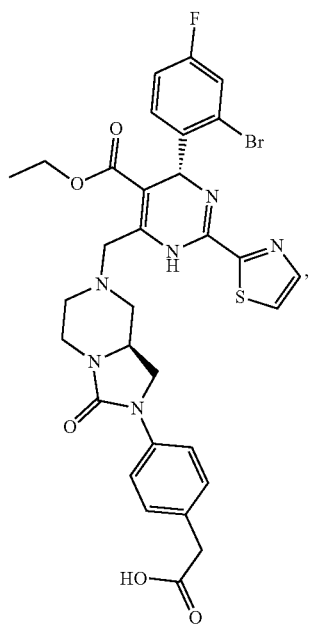

315
-continued
(27)
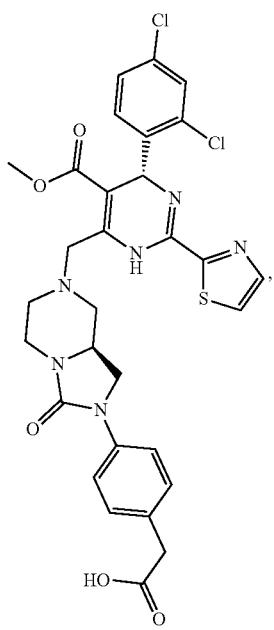
(28)
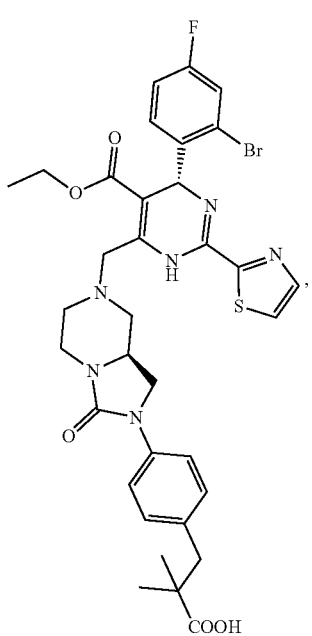
316
-continued
(29)
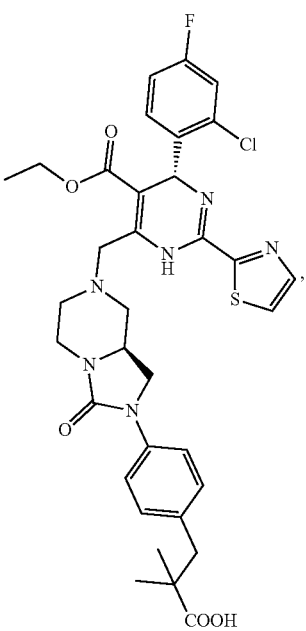
(30)
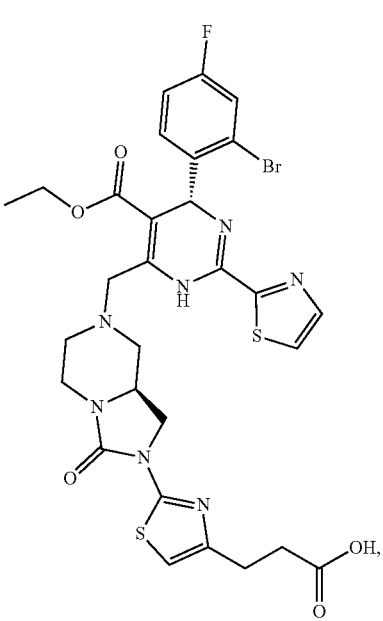

-continued
(31)
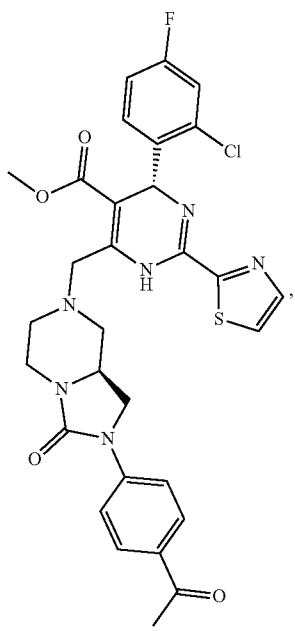
(32)
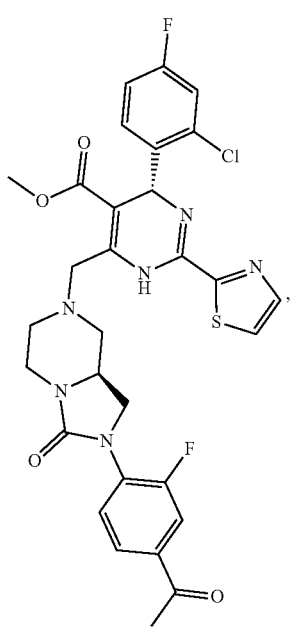
-continued
(33)
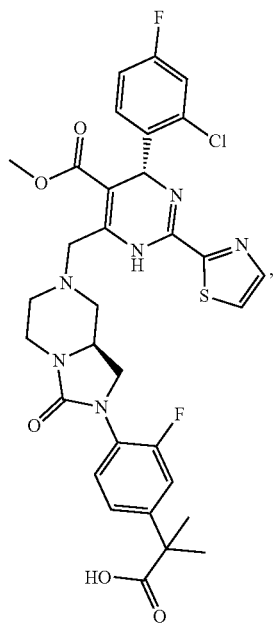
(34)
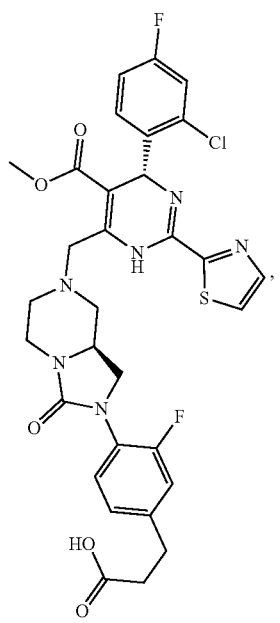

-continued
(35)
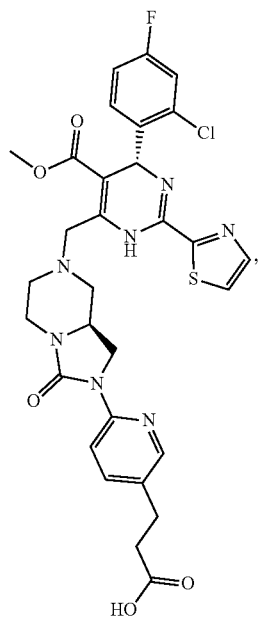
(37)
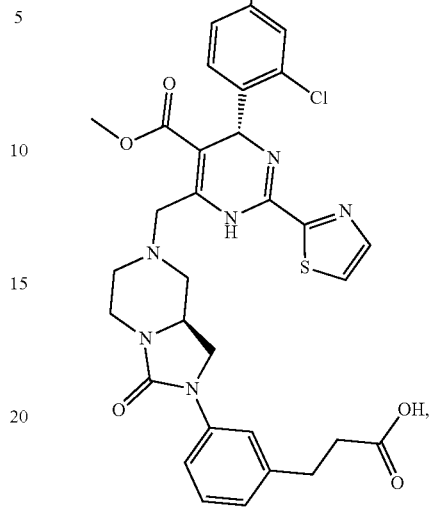
(36)
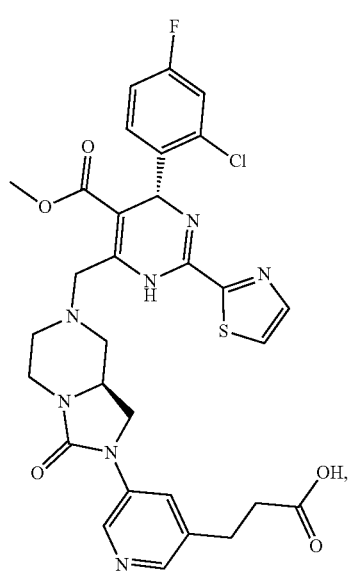
(38)
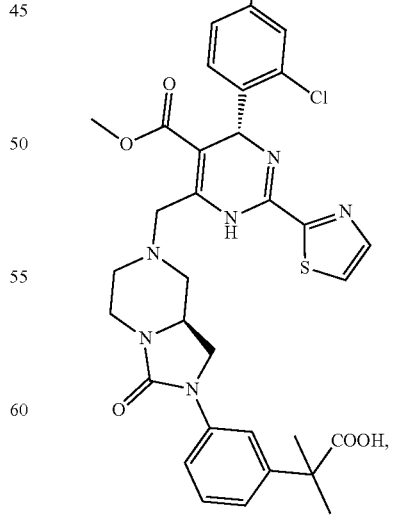

321
-continued
(39)
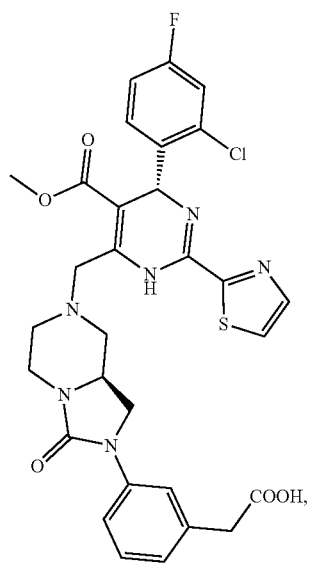
322
-continued
(41)
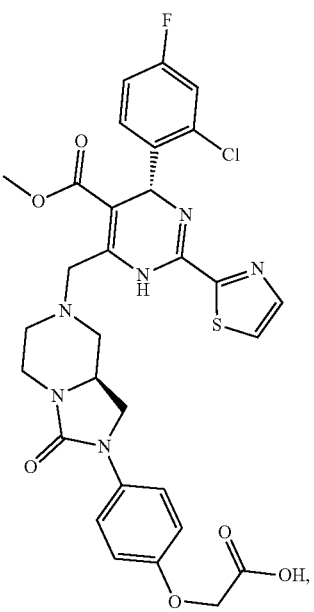
(40)
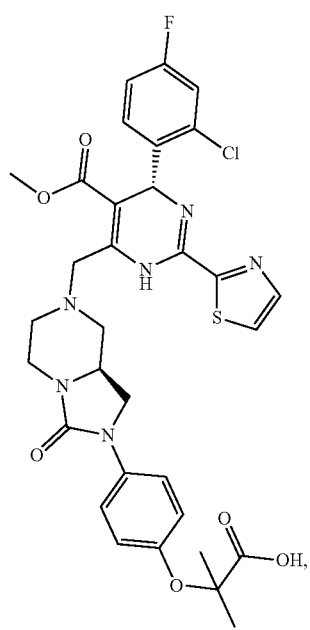
(42)
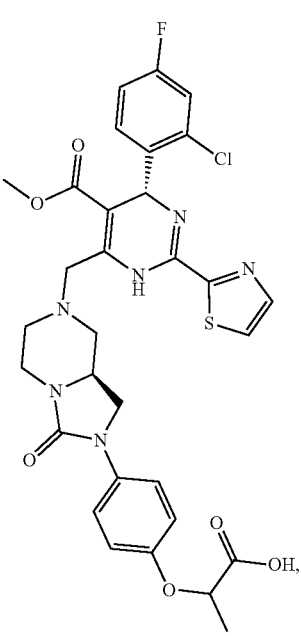

-continued
(43)
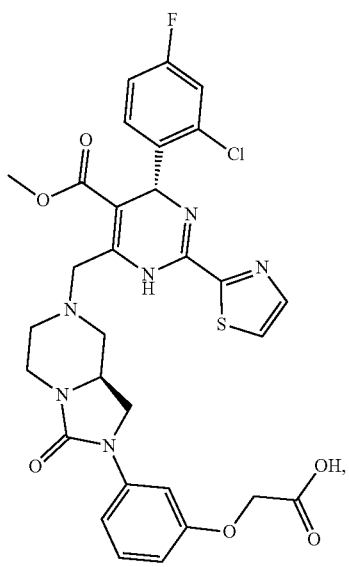
(45)
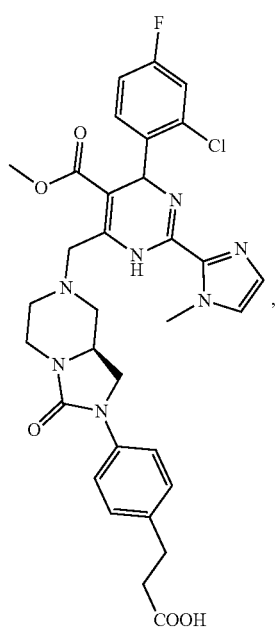
(44)
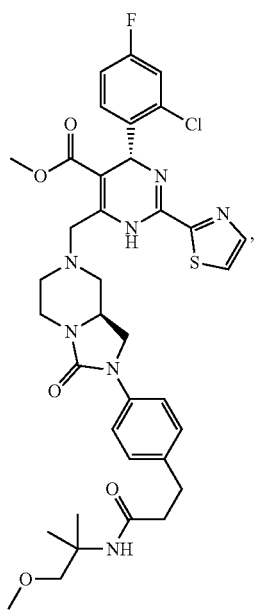
(46)
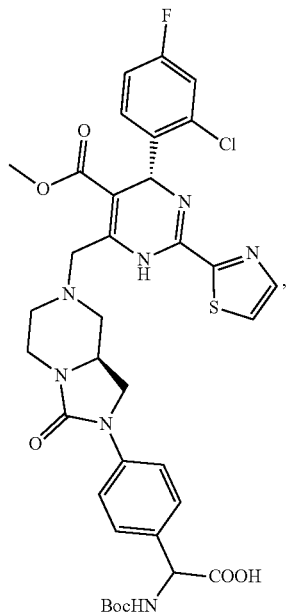

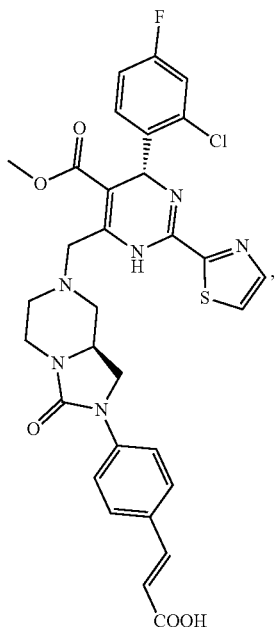
(47)
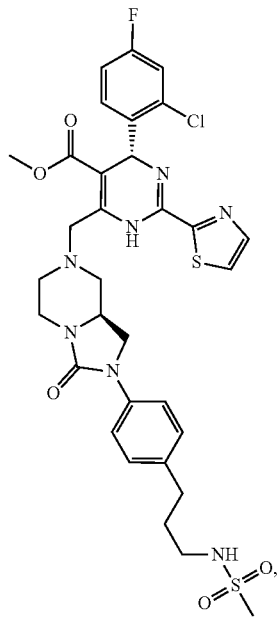
(49)
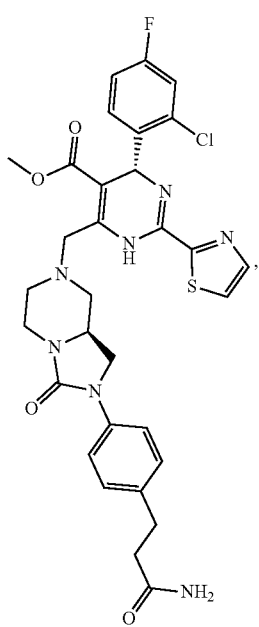
(48)
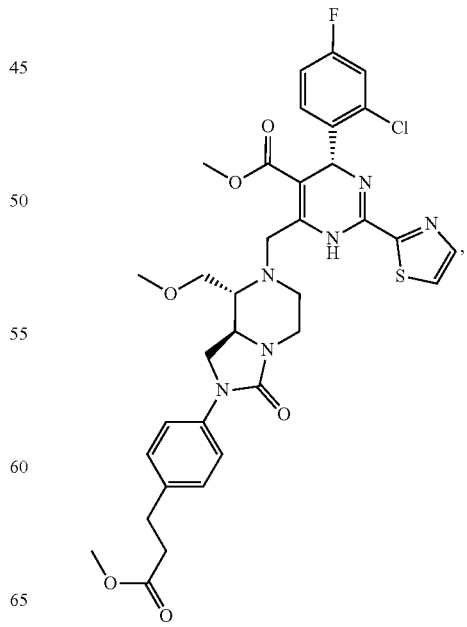
(50A)

-continued
(50B)
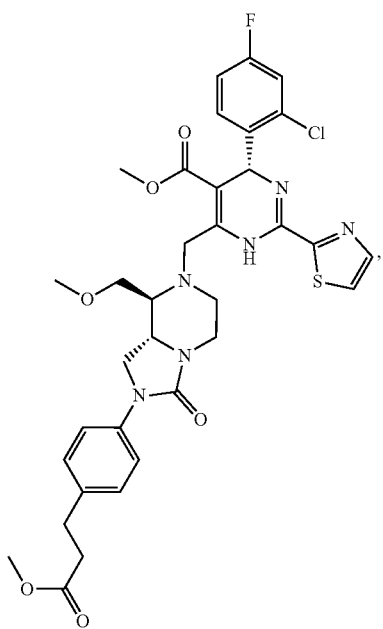
(51B)
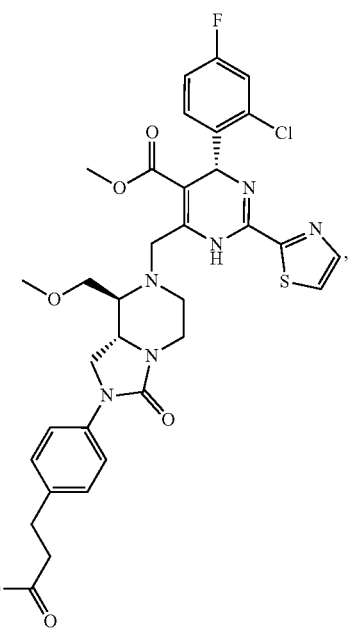
(51A)
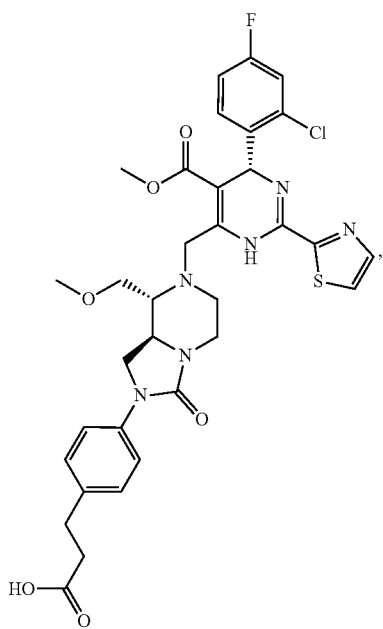
(52)
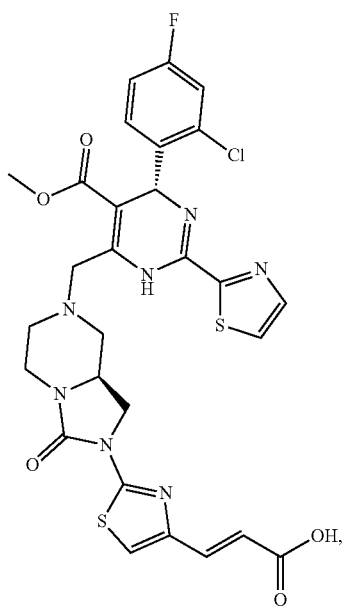

329
-continued
(53)
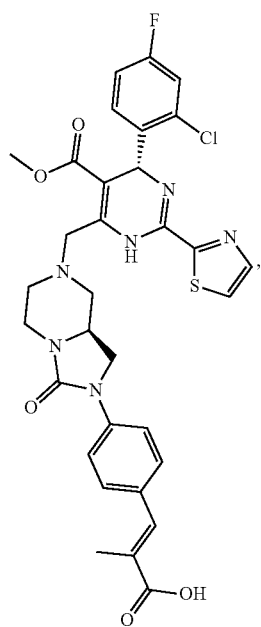
330
-continued
(55)
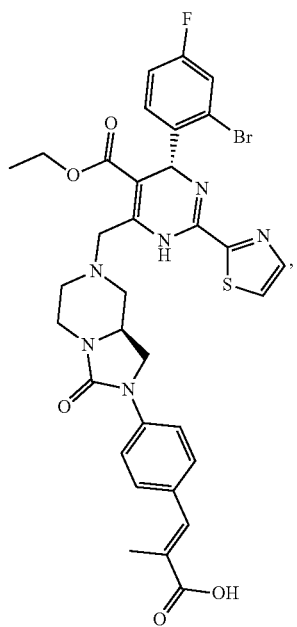
(54)
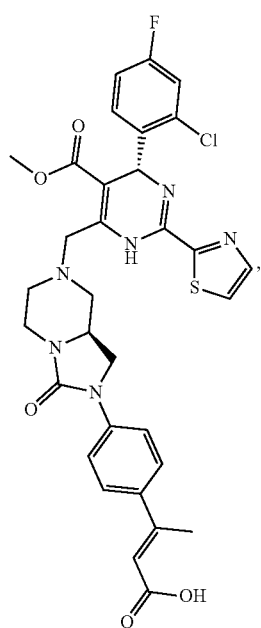
(56)
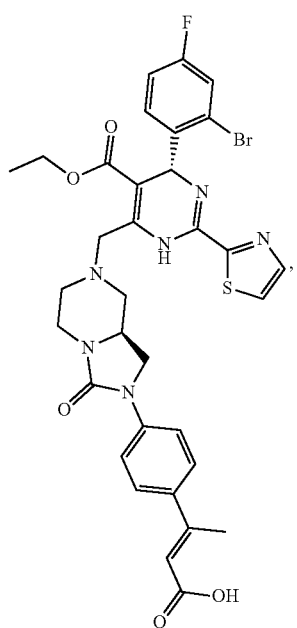

331
-continued
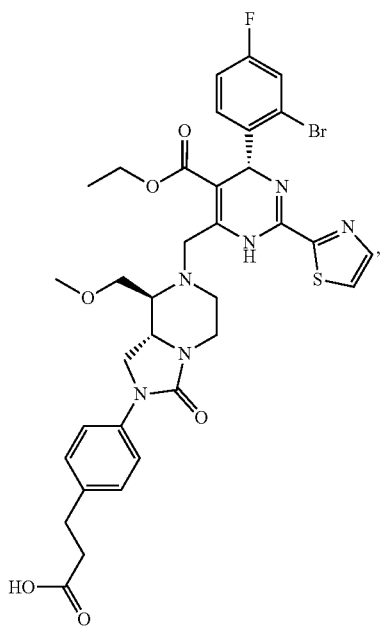
(57)
332
-continued
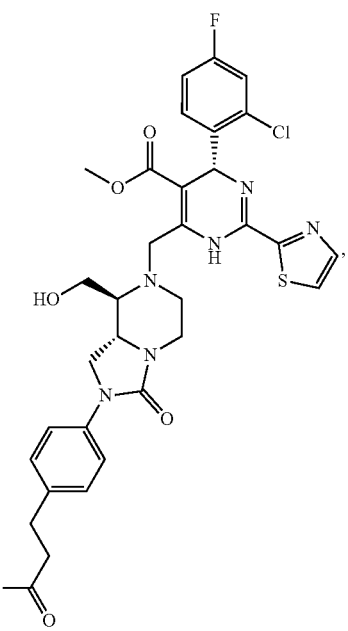
(58B)
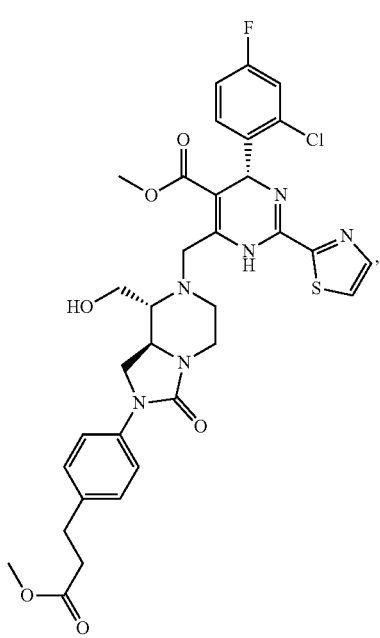
(58A)
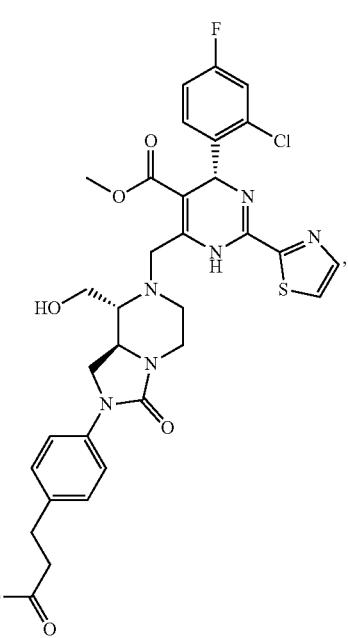
(59A)

333
-continued
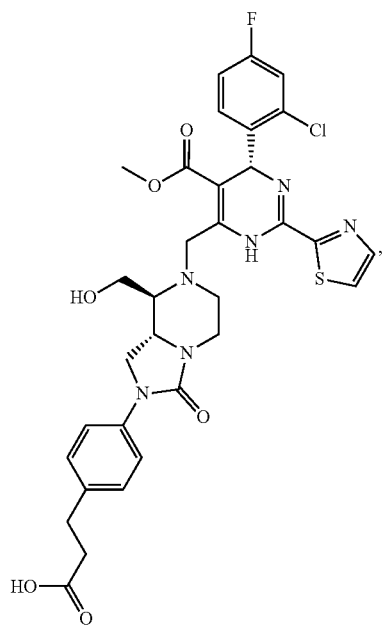
(59B)
334
-continued
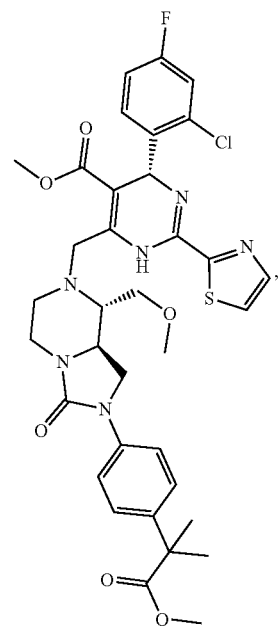
(60B)
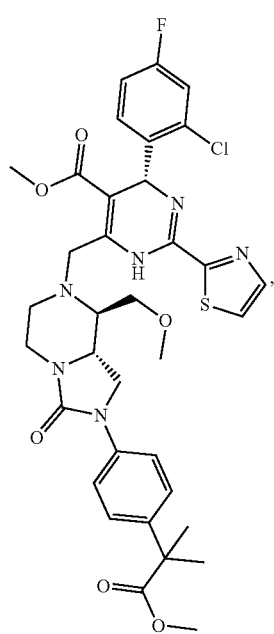
(60A)
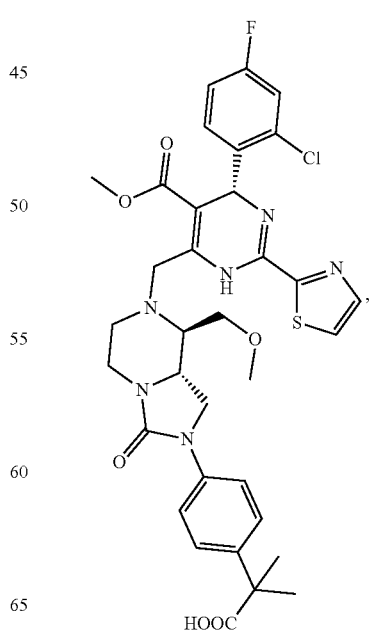
(61A)

335
-continued
(61B)
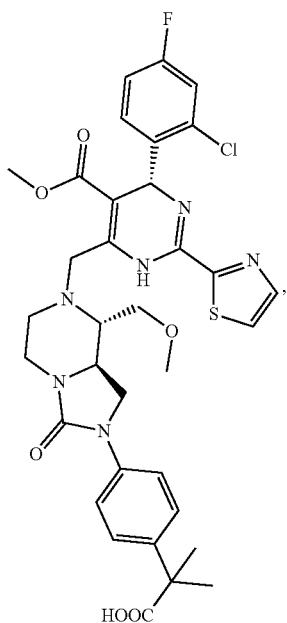
336
-continued
(63)
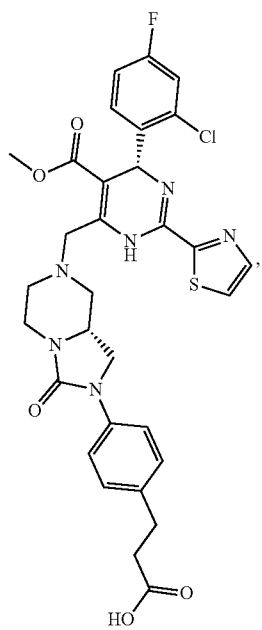
(62)
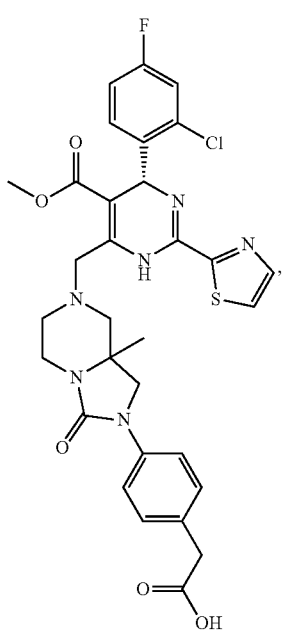
(64)
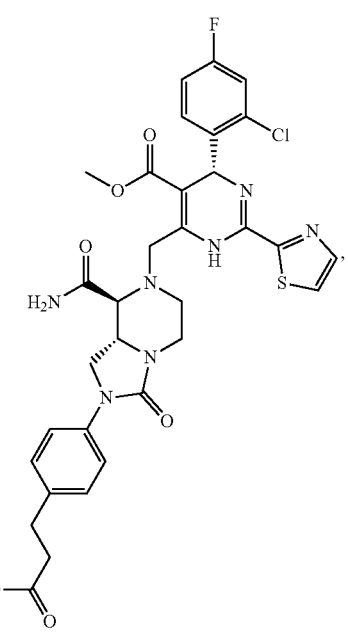

337
-continued
(65)
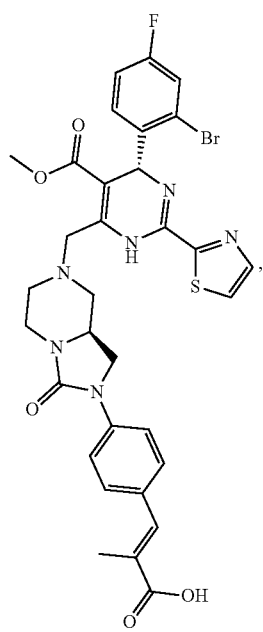
(66)
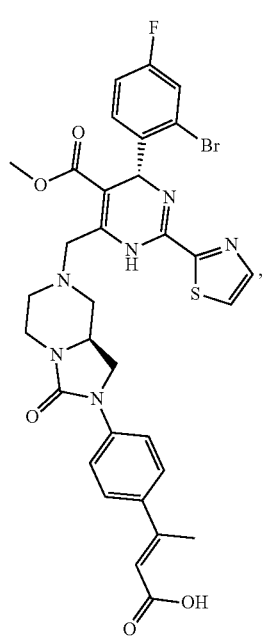
338
-continued
(67)
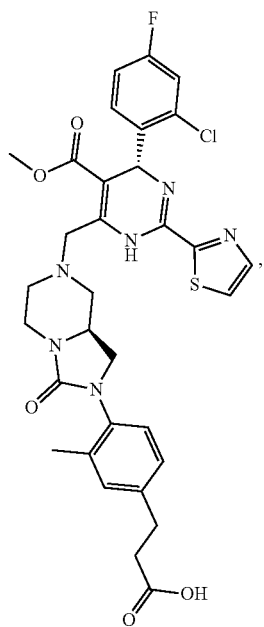
(68)
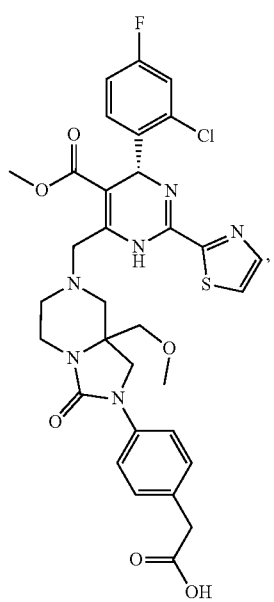

339
-continued
(69)
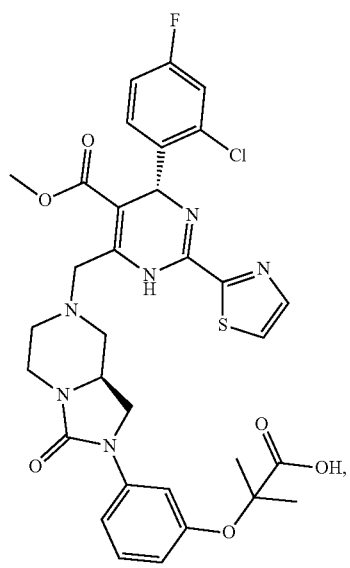
340
-continued
(71)
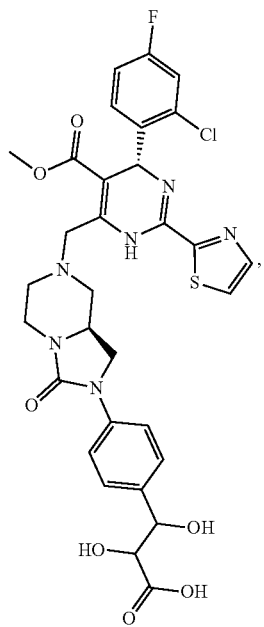
(70)
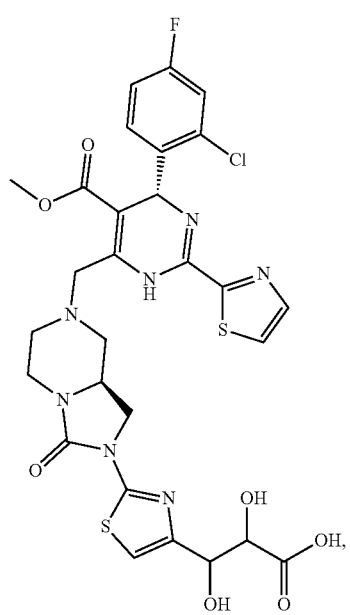
(72)
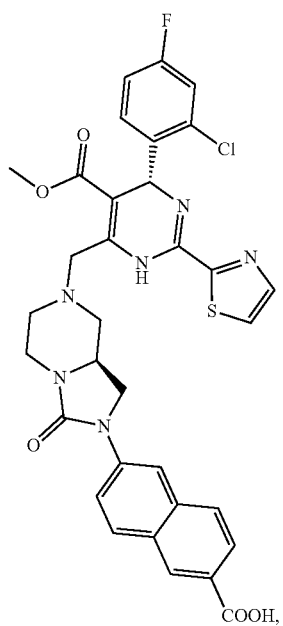

-continued
(73)
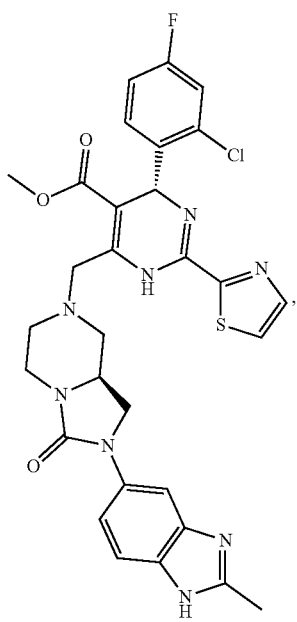
(74)
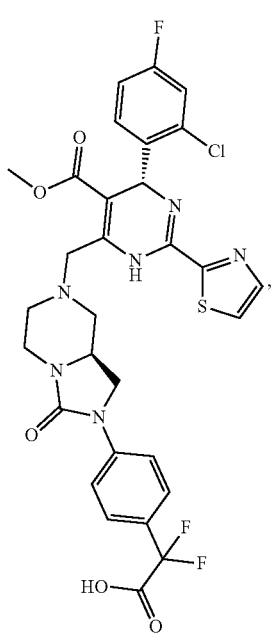
-continued
(75)
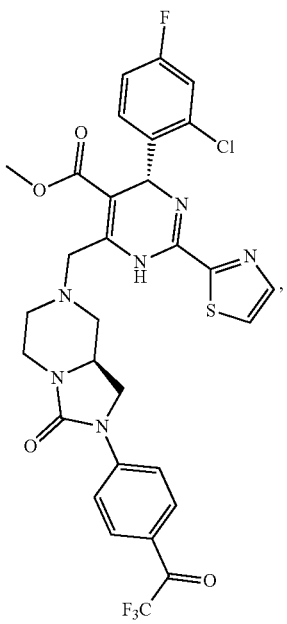
(76)
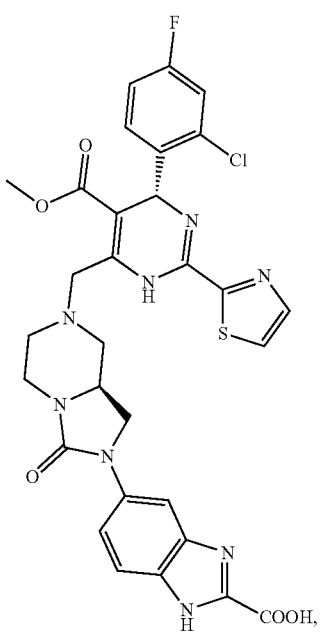

(77) 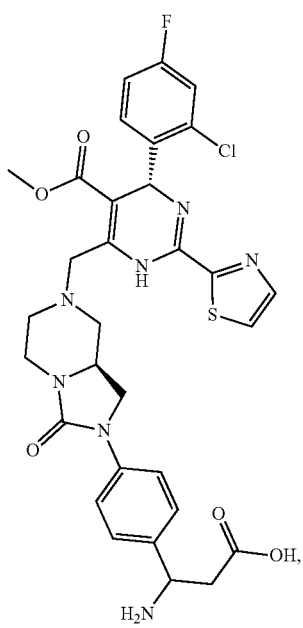
(78) 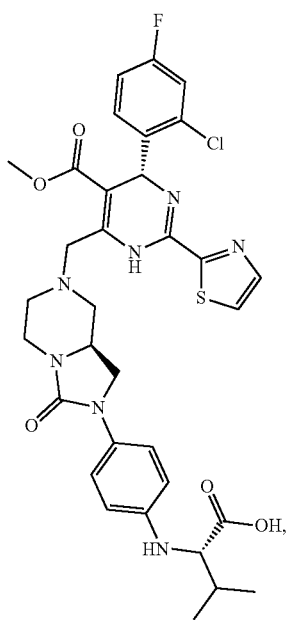
(79) 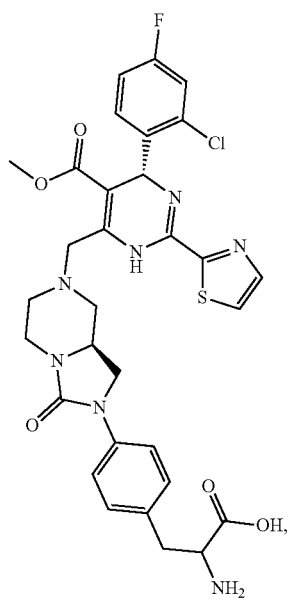
(80) 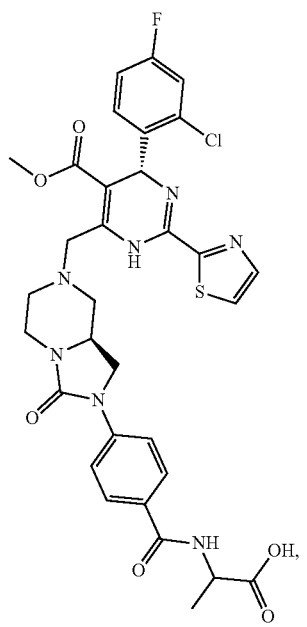

(83)
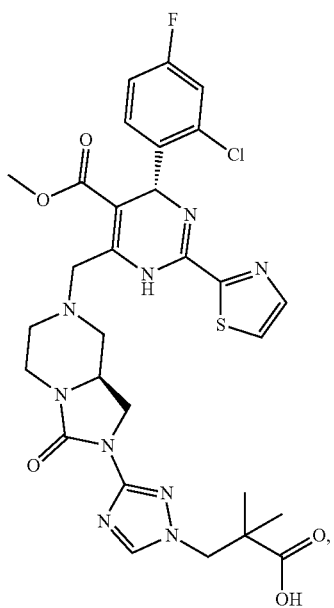
(84)
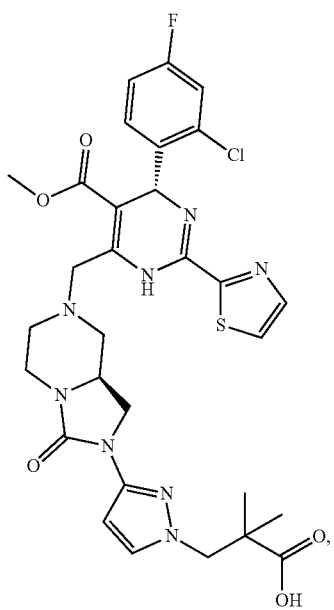
(85)
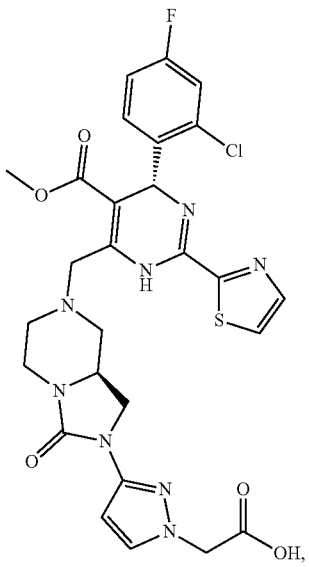
(86)
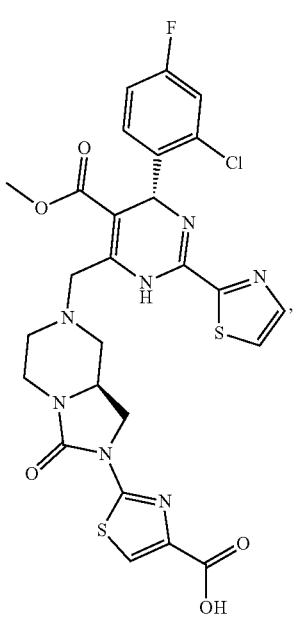

(87)
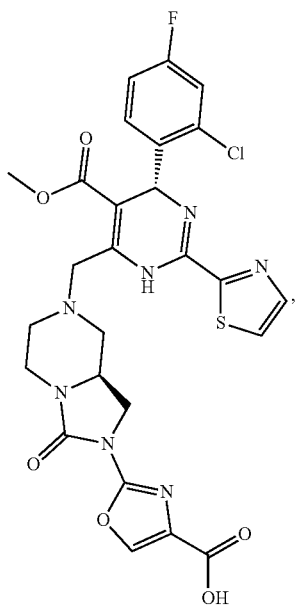
(88)
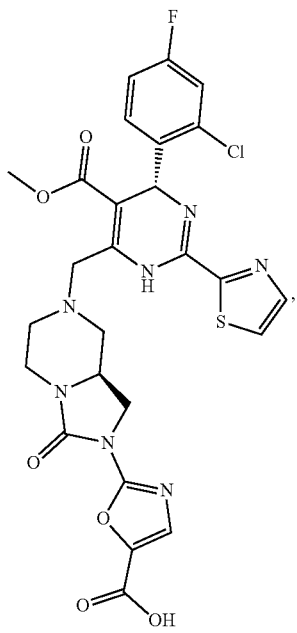
(90)
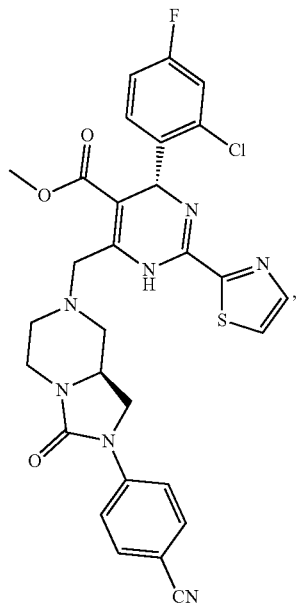
(91)
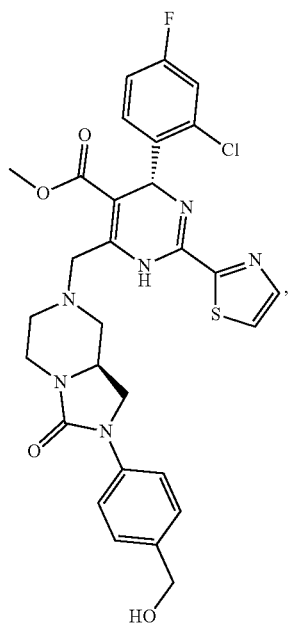

(92)
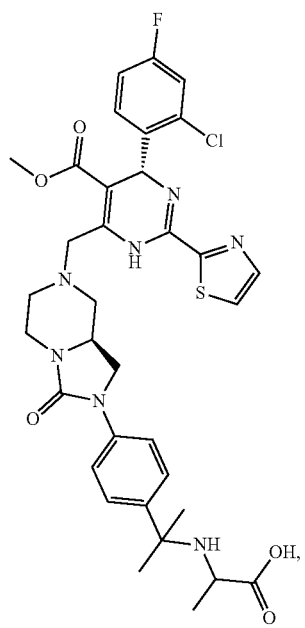
(93)
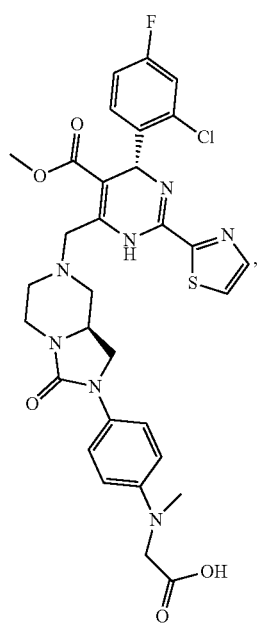
(95)
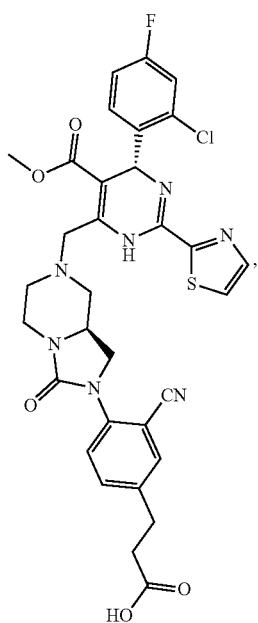
(96)
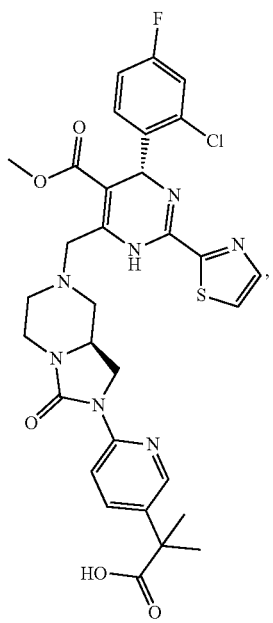

(97)
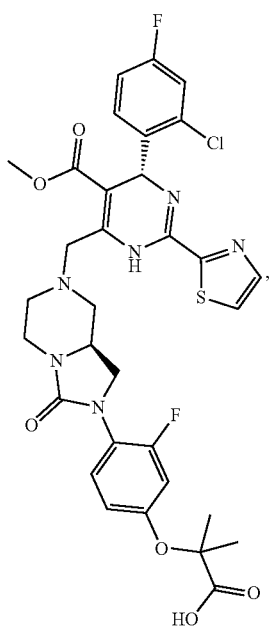
(98)
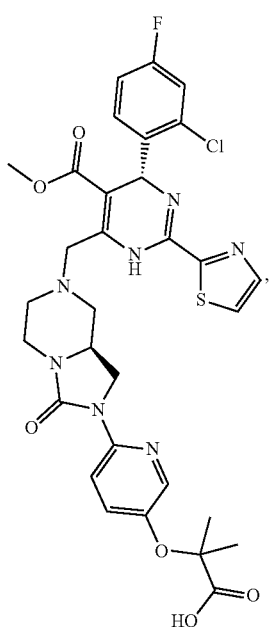
(99)
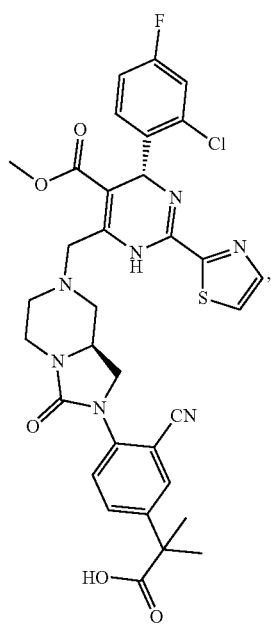
(100)
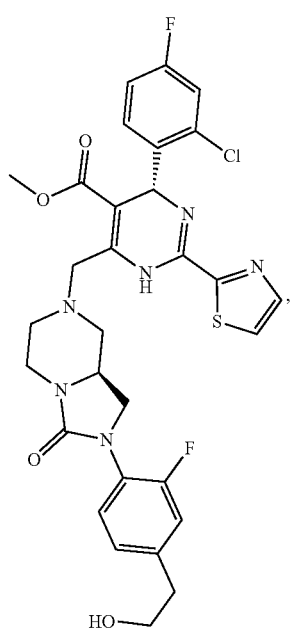

353
-continued
(101)
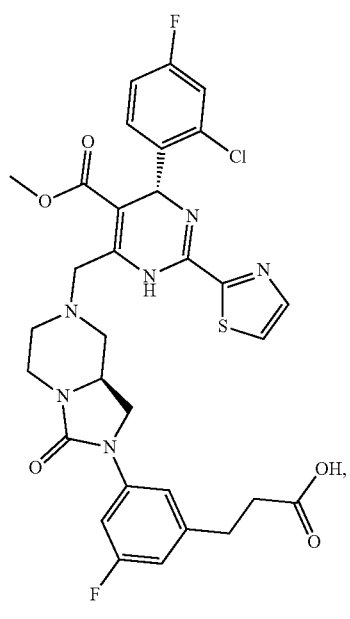
(102)
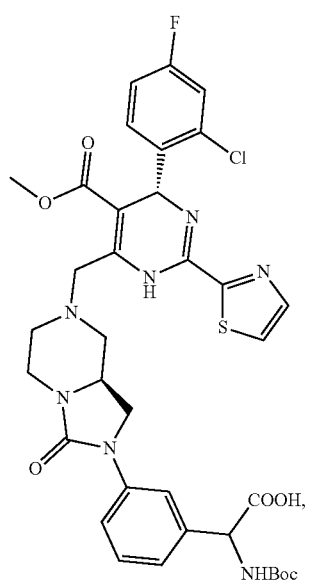
354
-continued
(103)
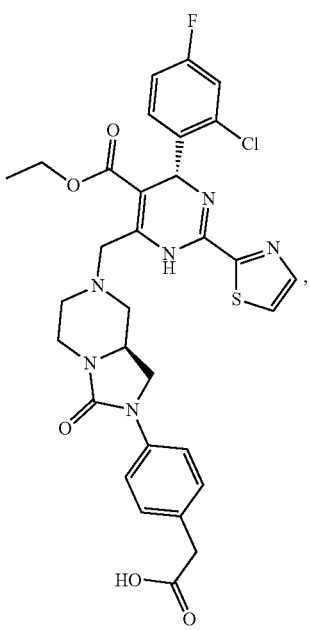
(104)
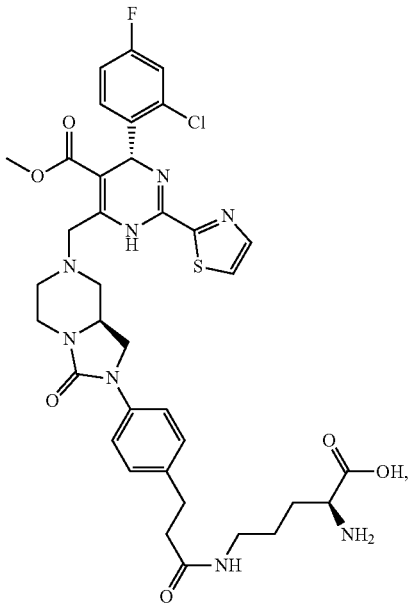

355
-continued
(105)
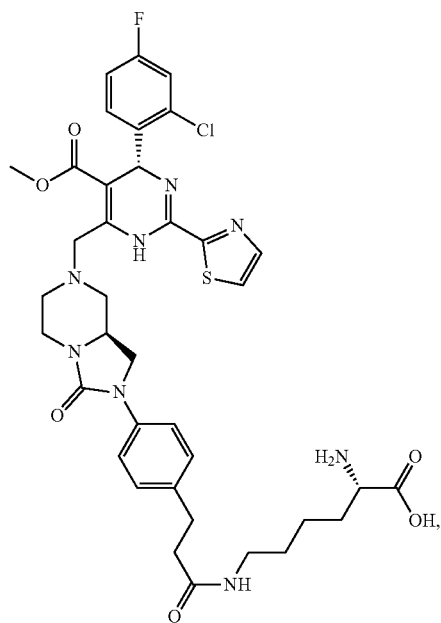
356
-continued
(107)
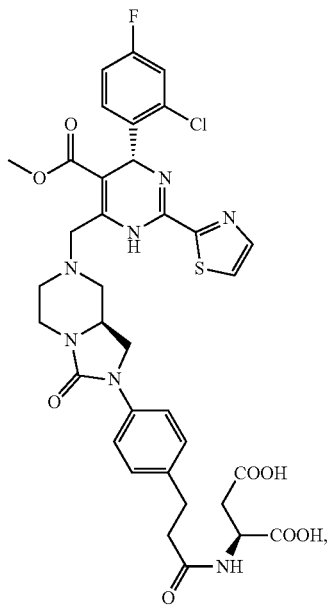
(106)
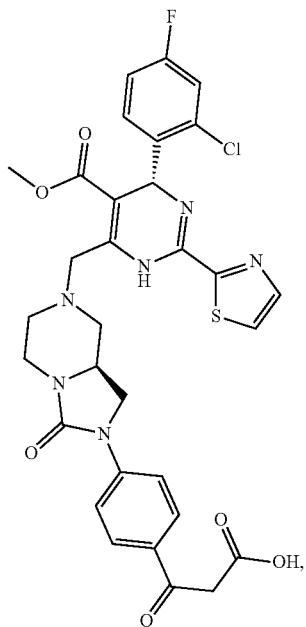
(109)

357
-continued
358
-continued
(110)
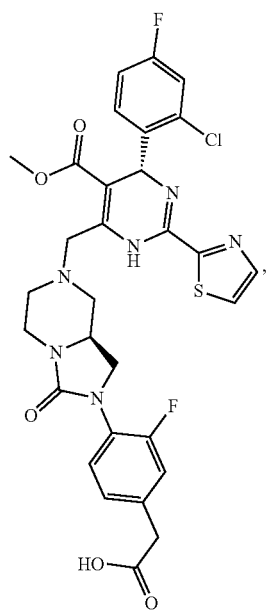
(112)
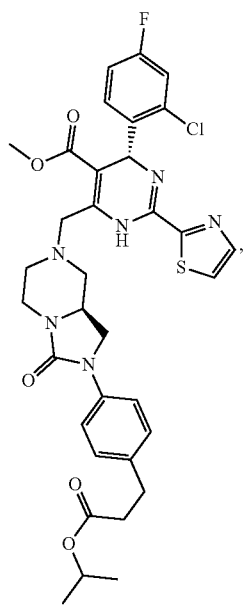
(111)
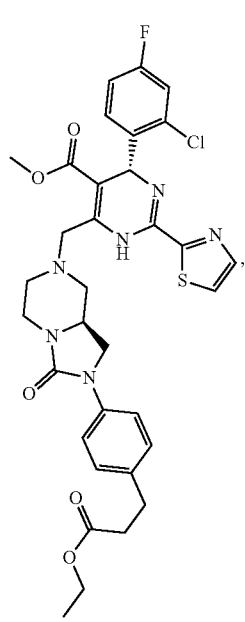
(114)
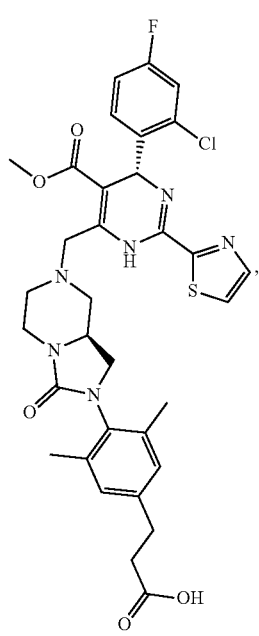

-continued
(115)
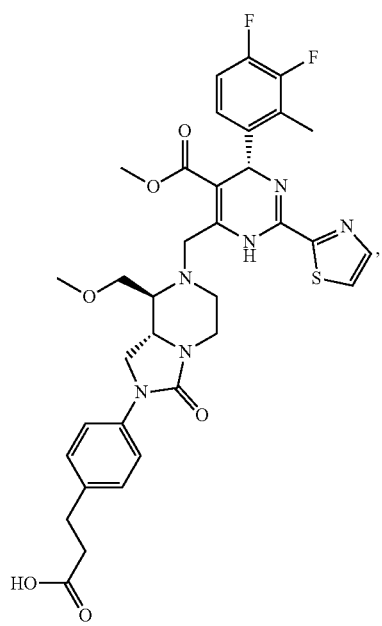
(116)
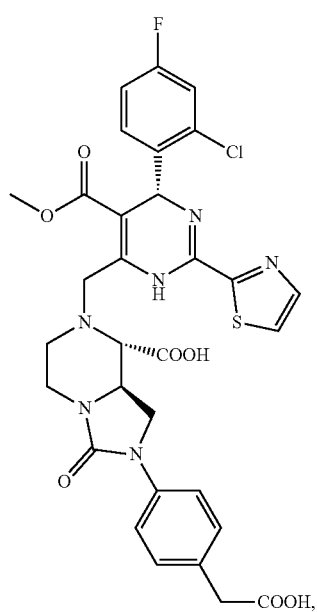
(117)
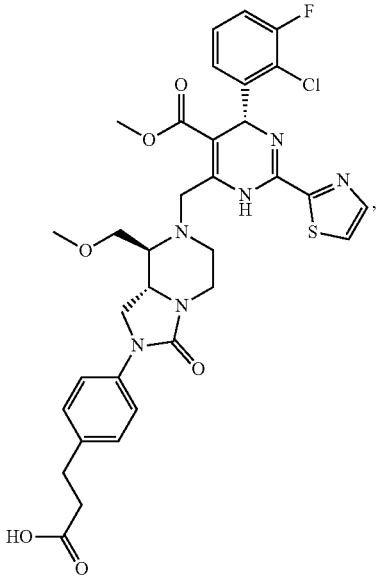
(118)
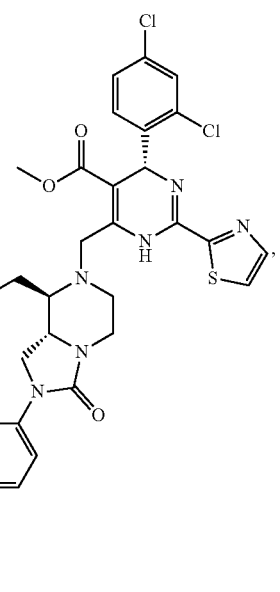

-continued
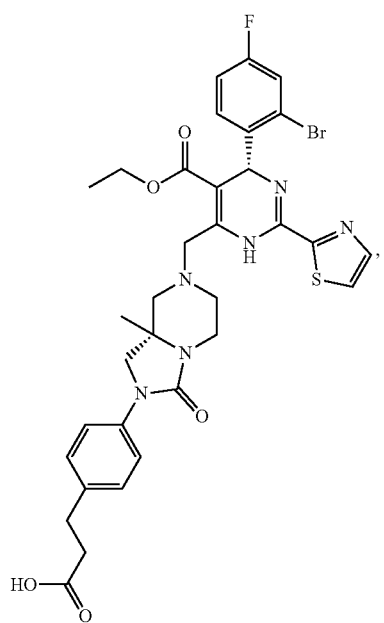
(119)
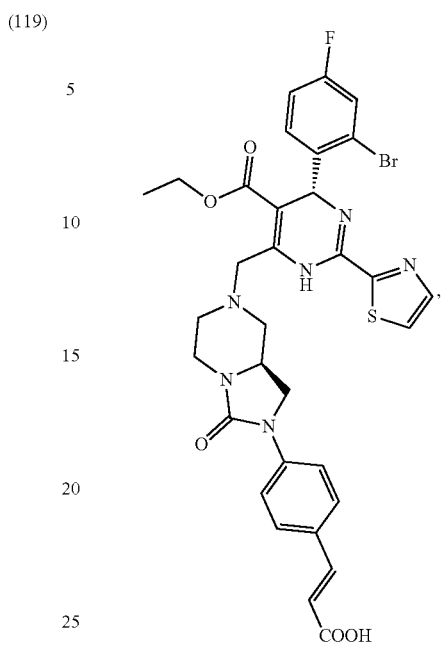
(121)
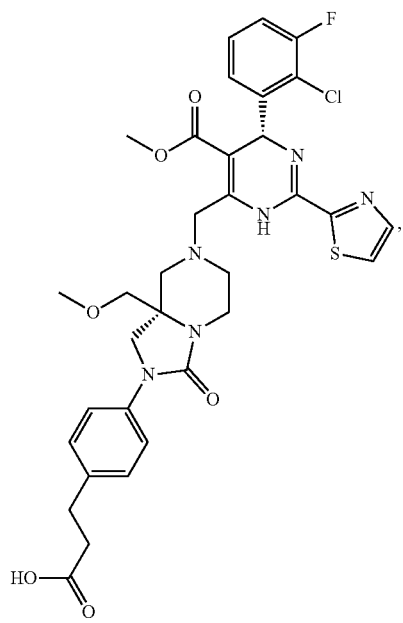
(120)
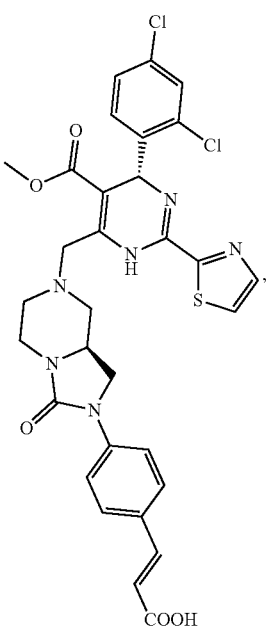
(122)

363
-continued
(123)
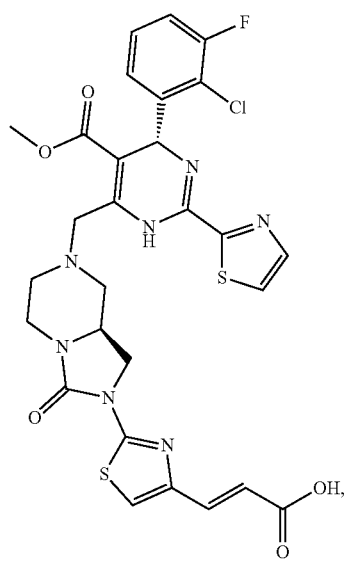
(124)
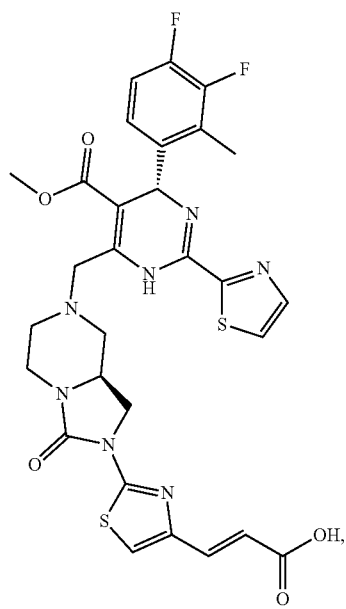
364
-continued
(125)
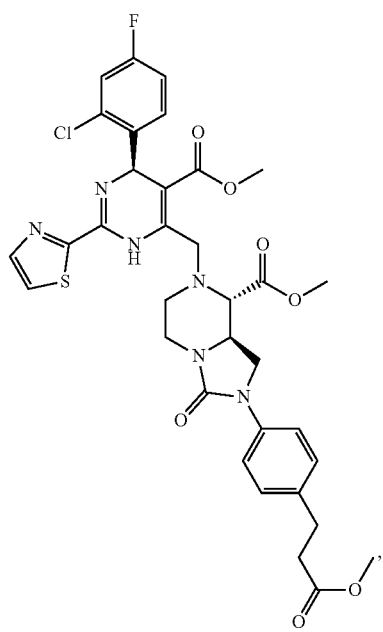
(126)
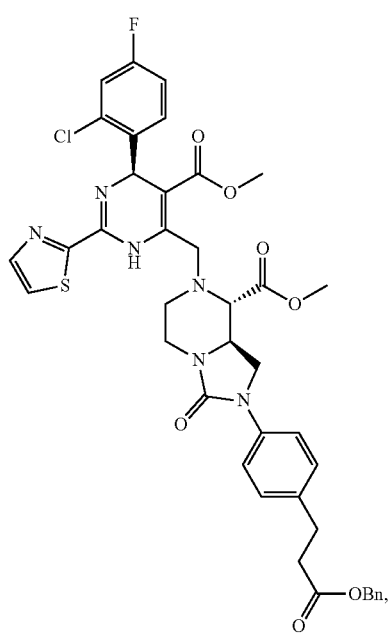

365
-continued
(127)
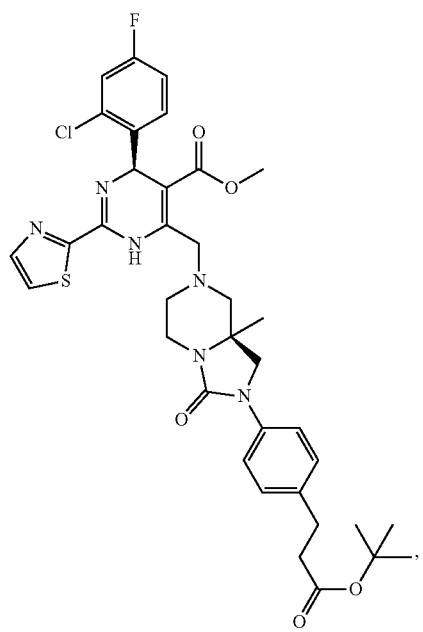
366
-continued
(129)
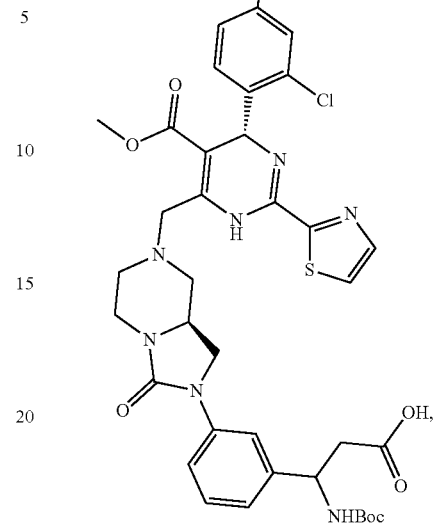
(128)
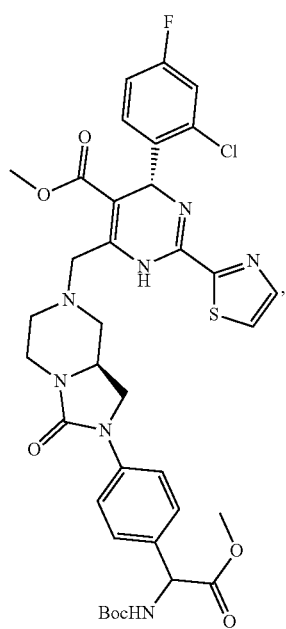
(130)
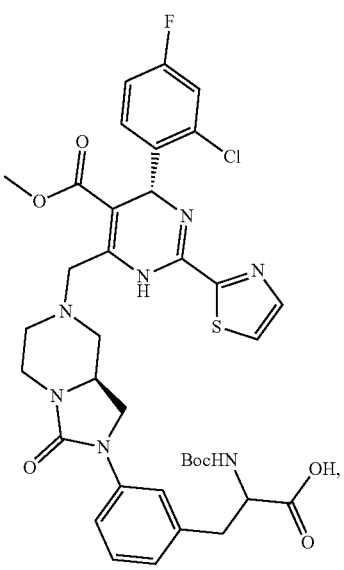

(131)
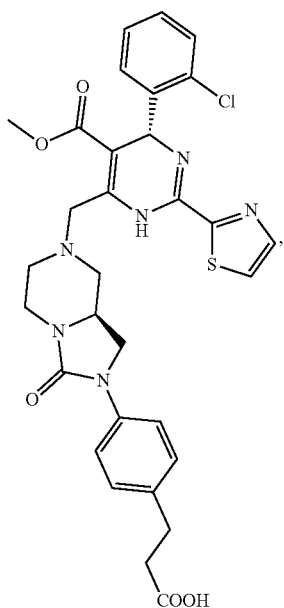
(133)
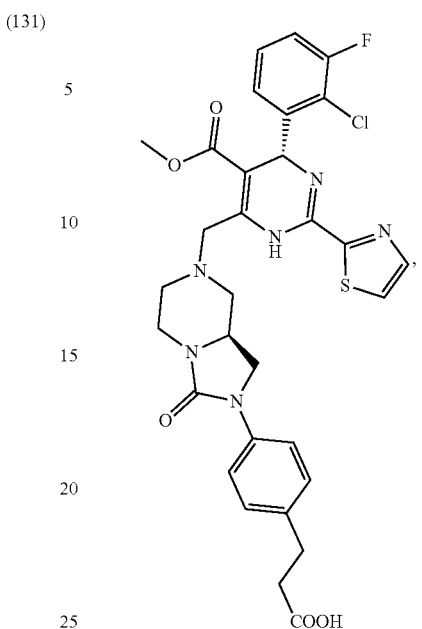
(132)
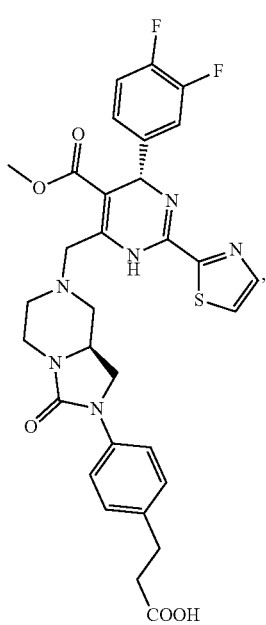
(134)
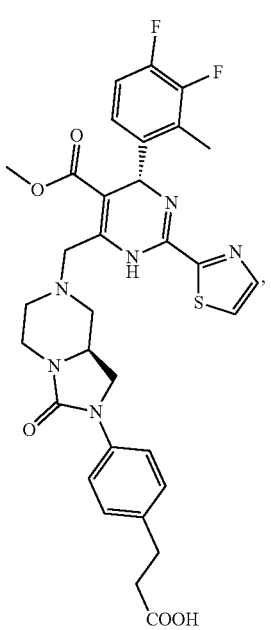

(135)
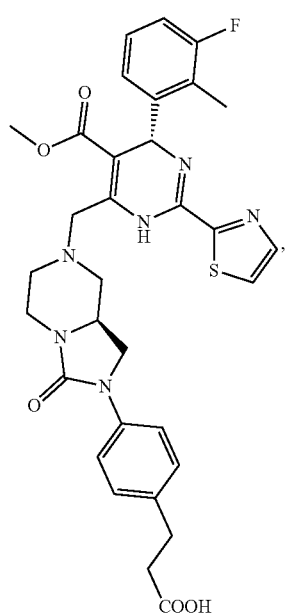
(136)
(137)
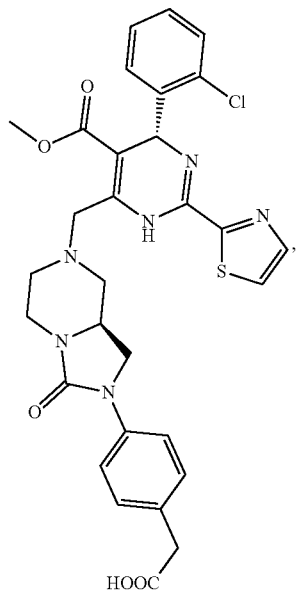
(138)

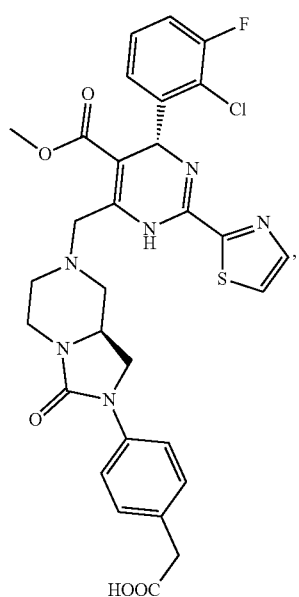
(139)
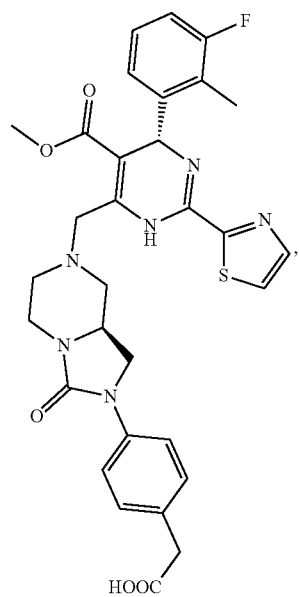
(141)
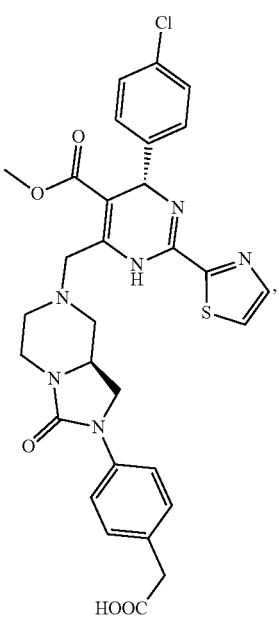
(140)
(142)

-continued
(143)
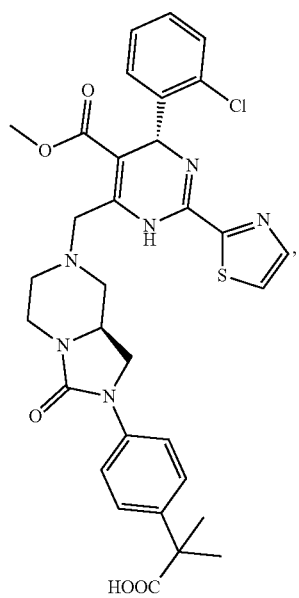
(145)
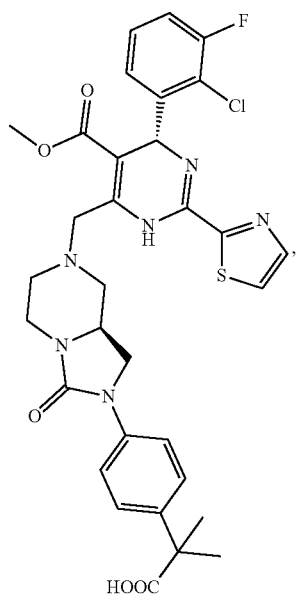
(144)
(146)
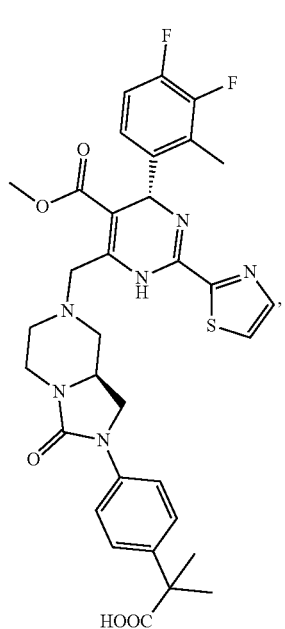

-continued
(147)
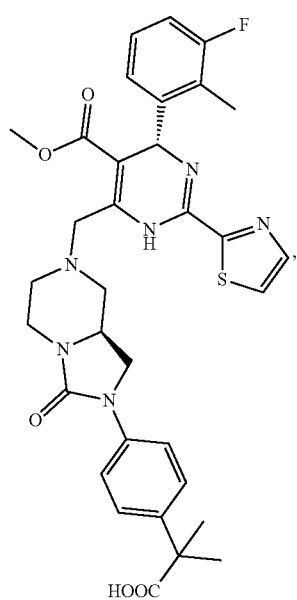
(148)
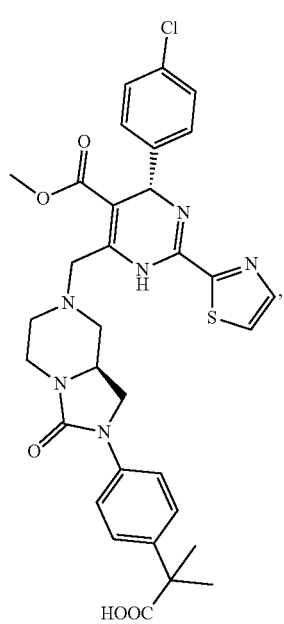
-continued
(149)
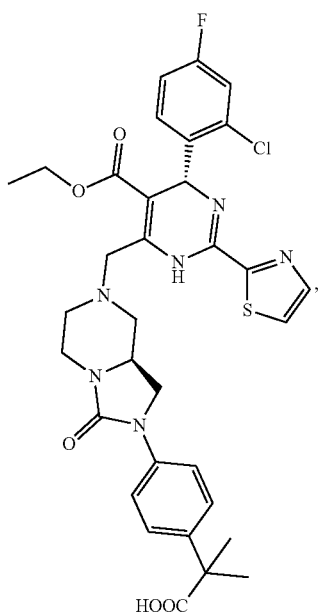
(150)
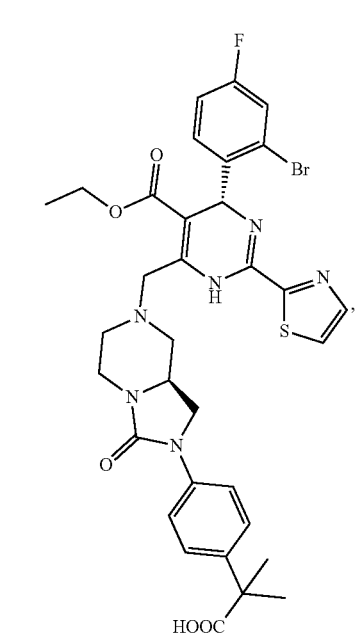

377
-continued
(151)
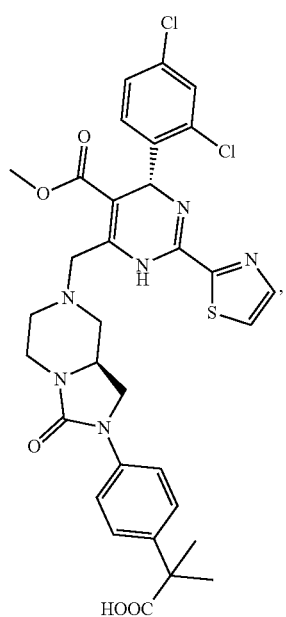
(152)
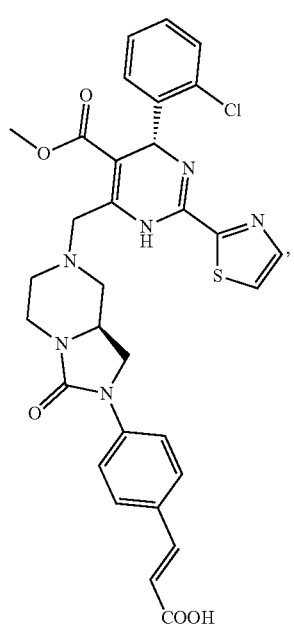
378
-continued
(153)
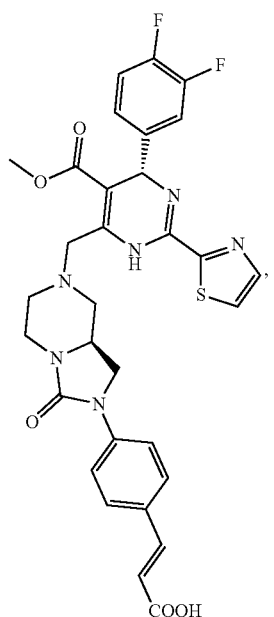
(154)
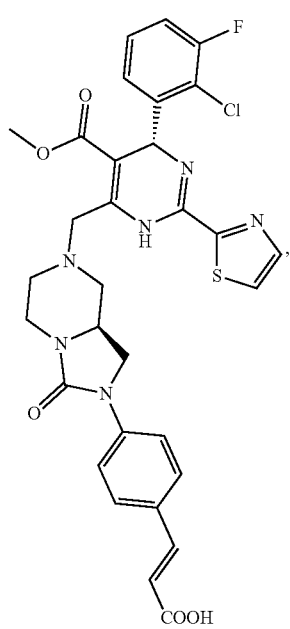

-continued
(155)
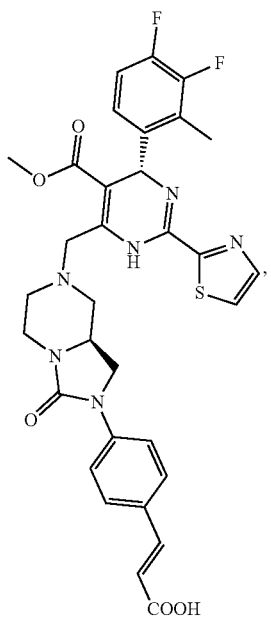
(157)
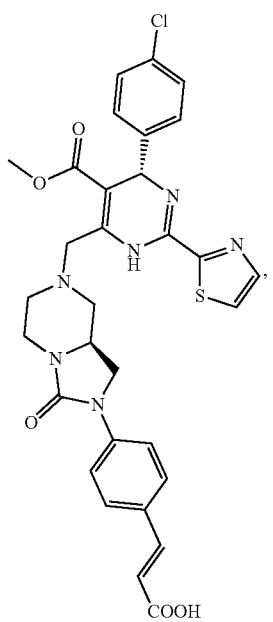
(156)
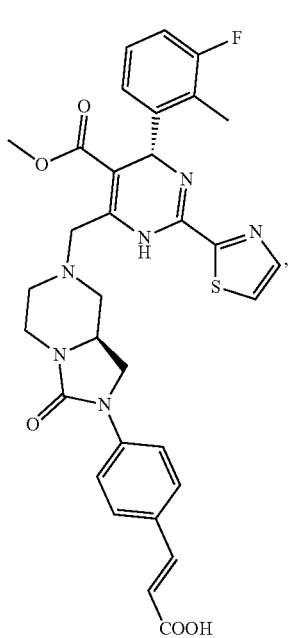
(158)
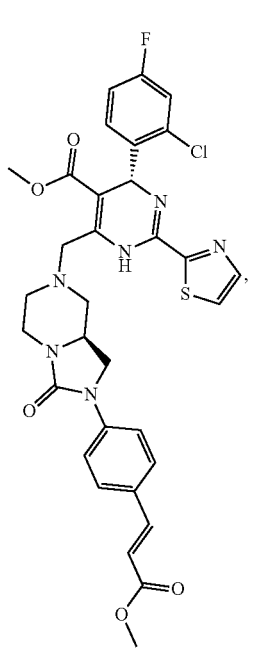

381
-continued
(159)
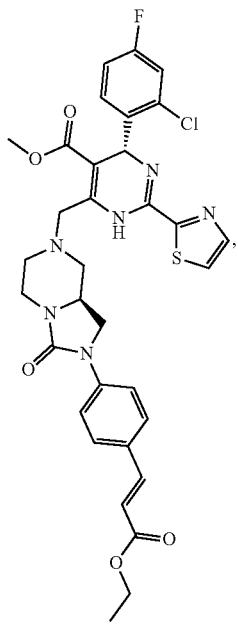
382
-continued
(161)
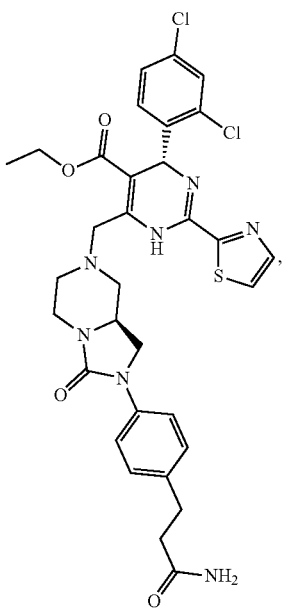
(160)
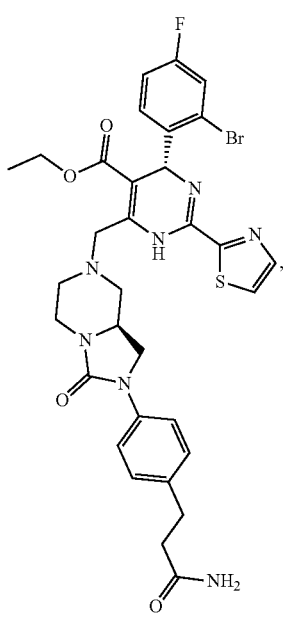
(162)
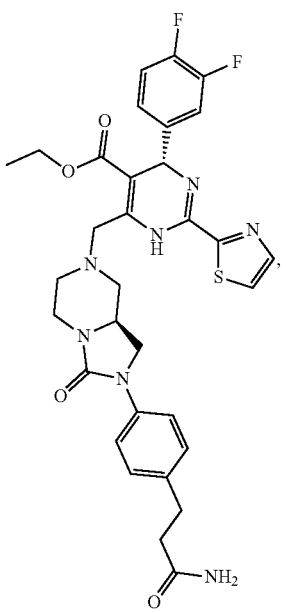

(163)
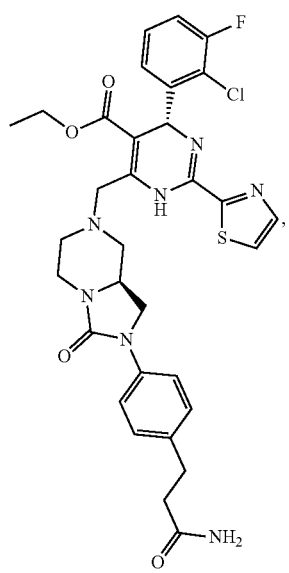
(164)
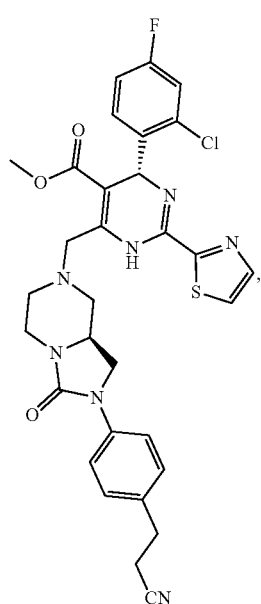
(166)
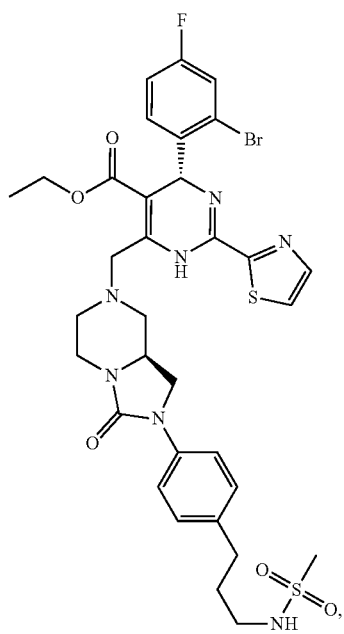
(167)
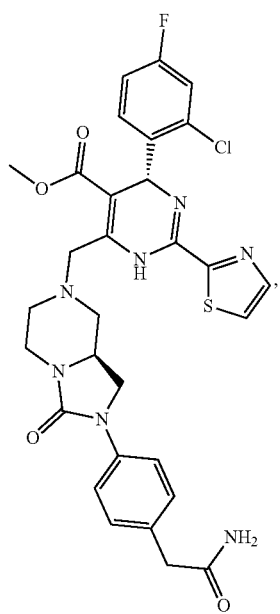

-continued
(168)
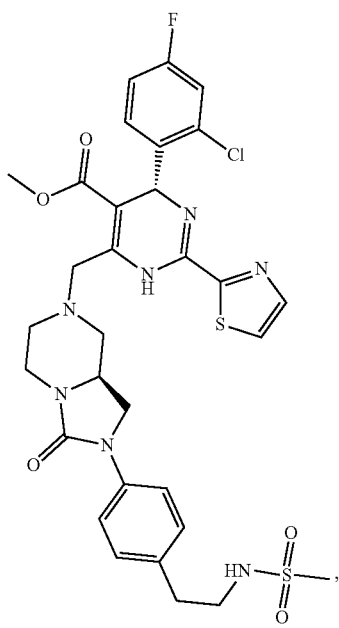
(169)
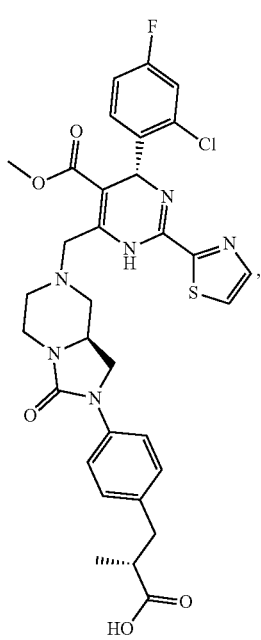
(170)
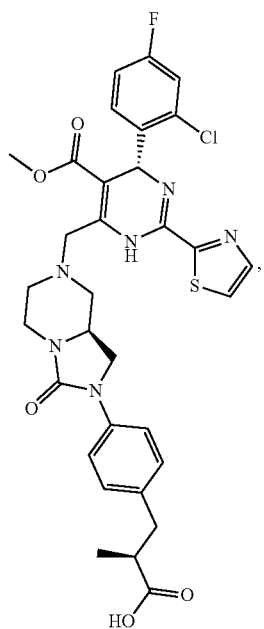
(171)
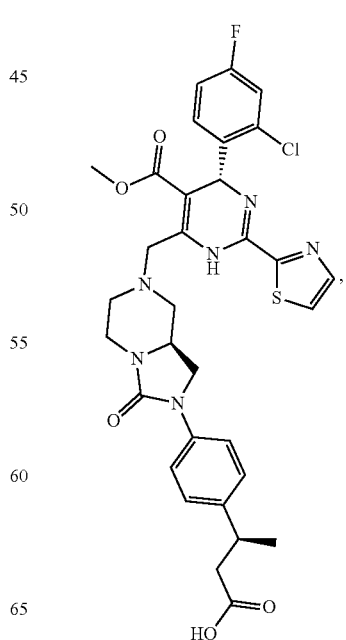

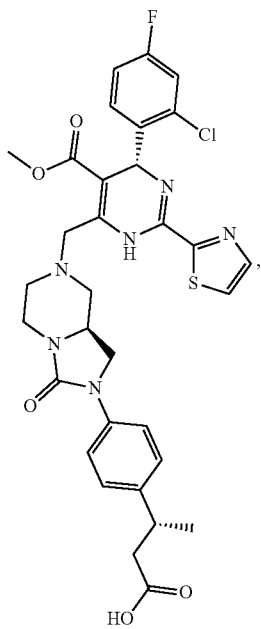
(172)
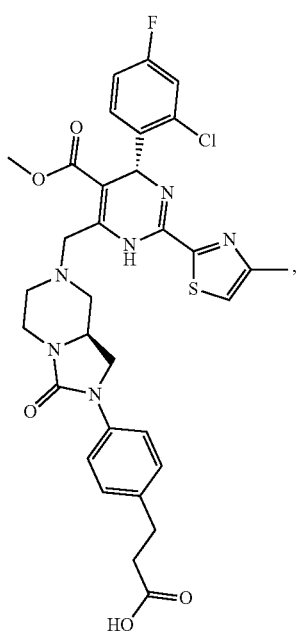
(173)
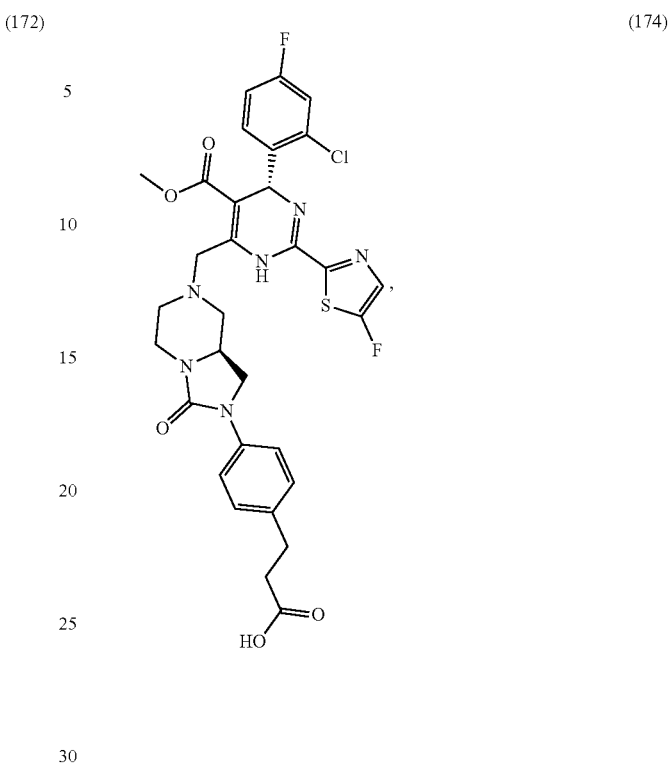
(174)
(175)

(176)
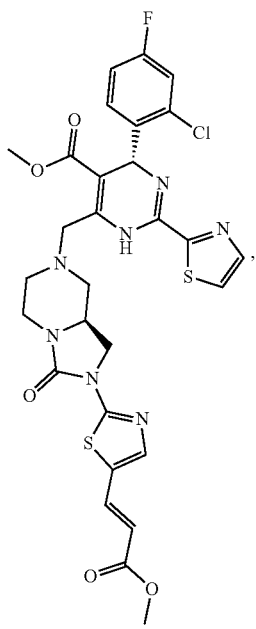
(177)
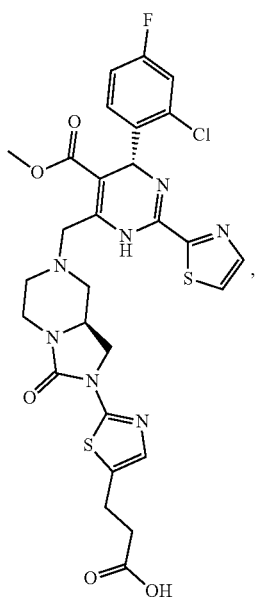
(178)
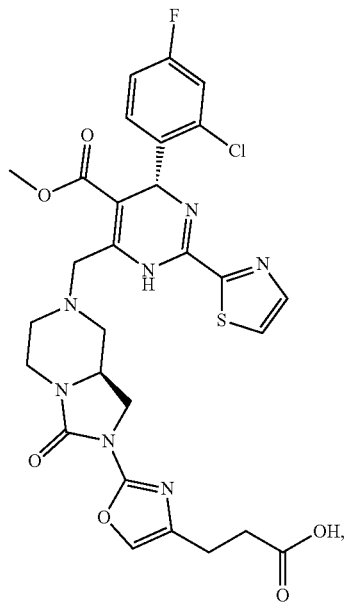
(179)
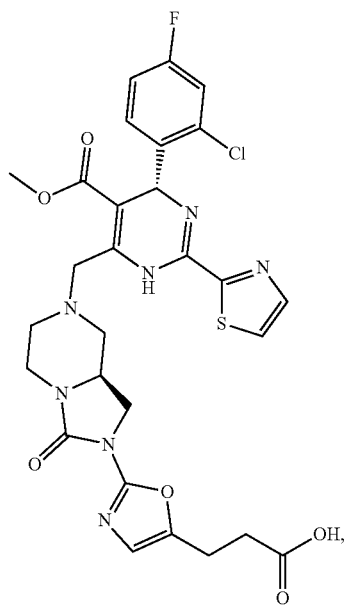

391
-continued
(180)
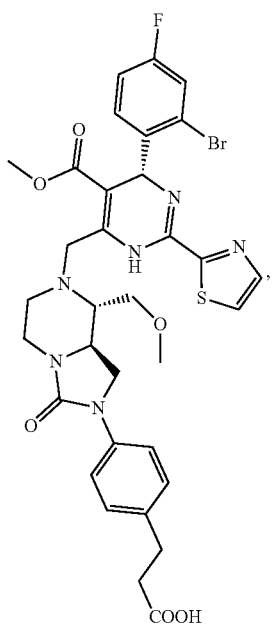
(181)
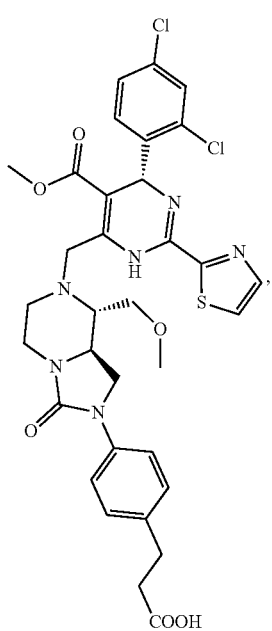
392
-continued
(182)
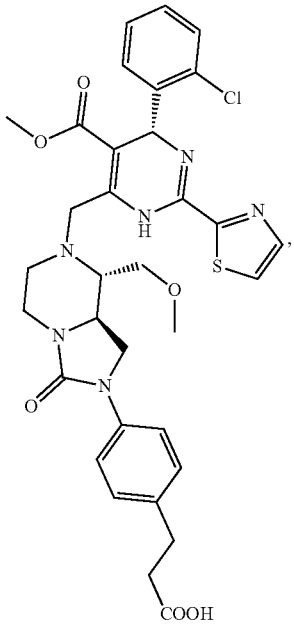
(183)
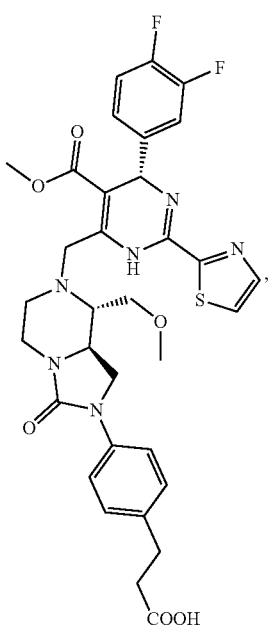

393
-continued
(184)
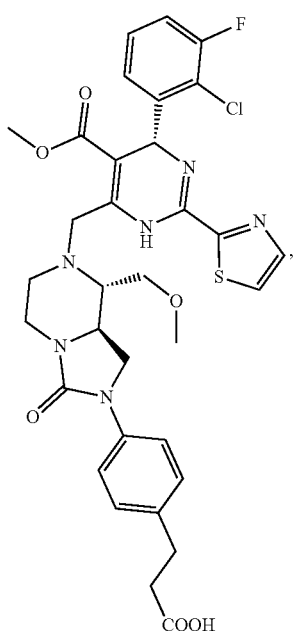
394
-continued
(186)
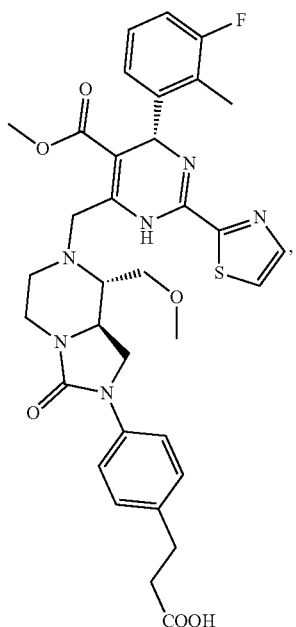
(185)
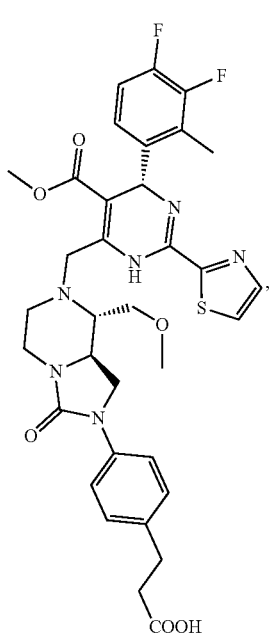
(187)
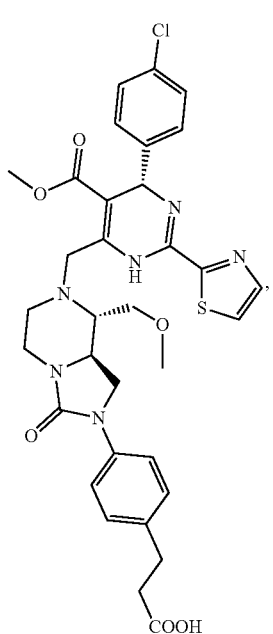

(188)
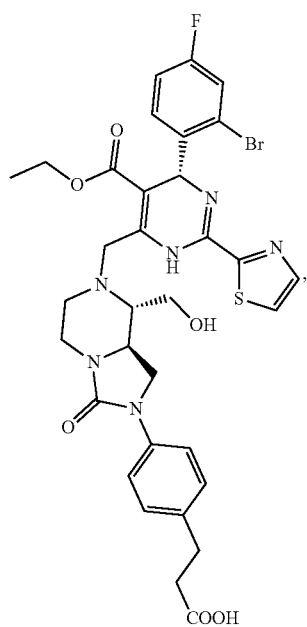
(189)
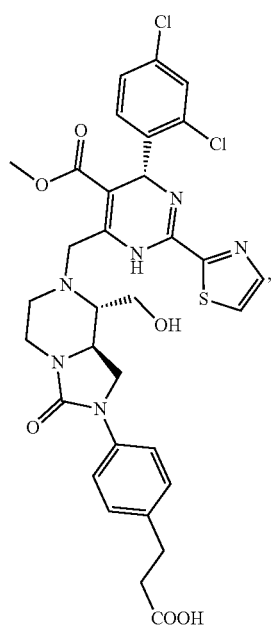
(190)
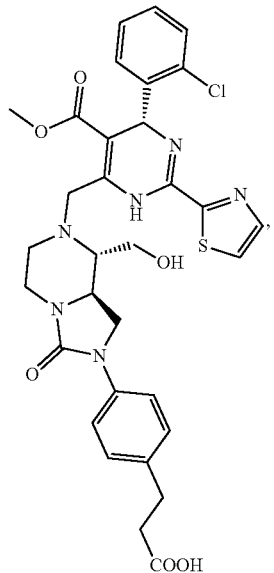
(191)

397
-continued
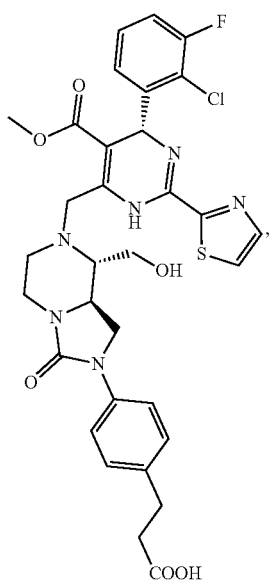
(192)
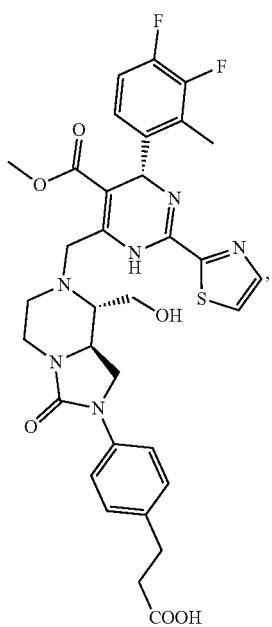
(193)
398
-continued
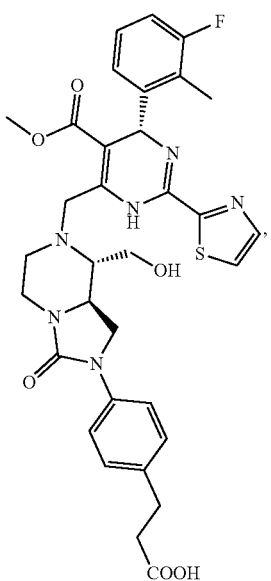
(194)
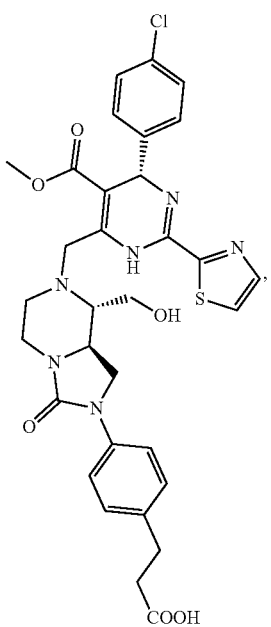
(195)

399
-continued
(196)
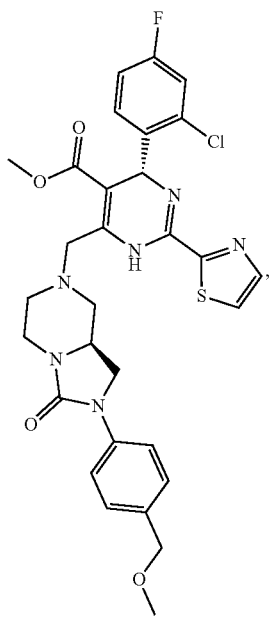
400
-continued
(198)
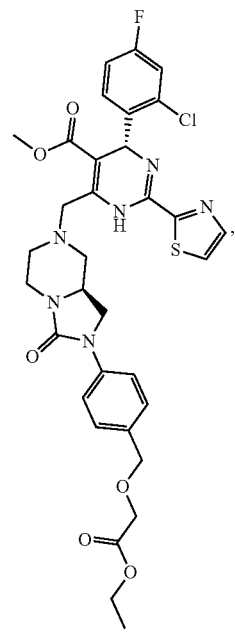
(197)
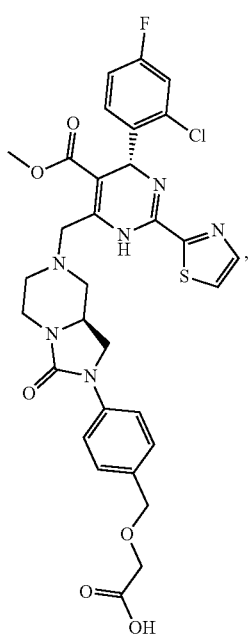
(199)
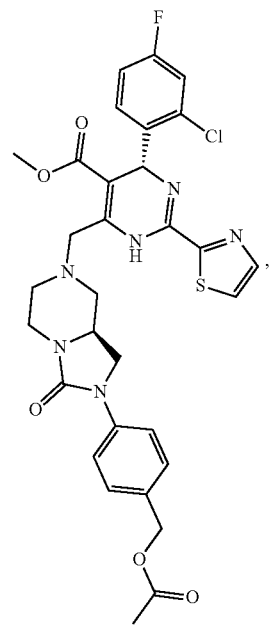

(200)
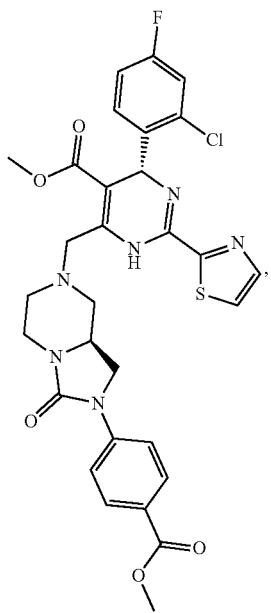
(202)
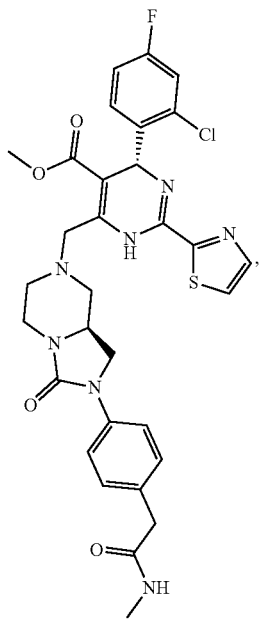
(201)
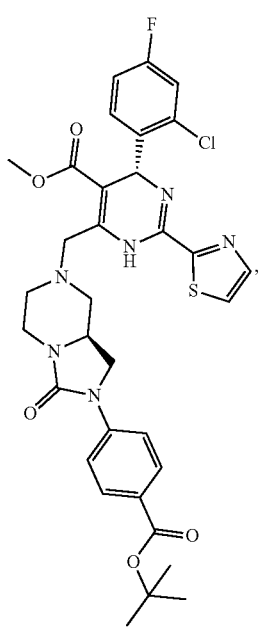
(203)
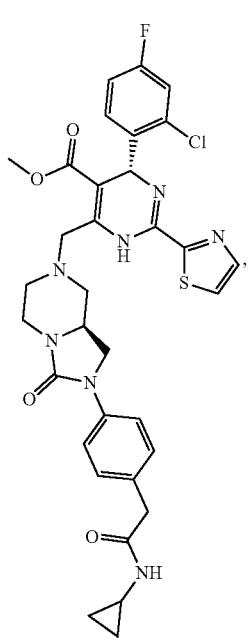

403
-continued
(204)
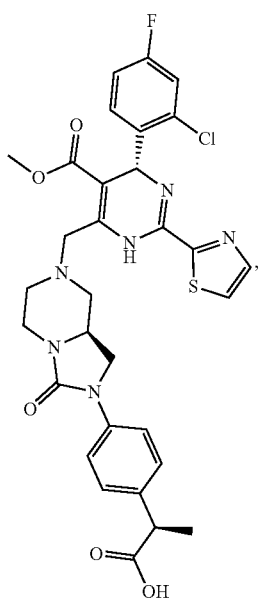
(205)
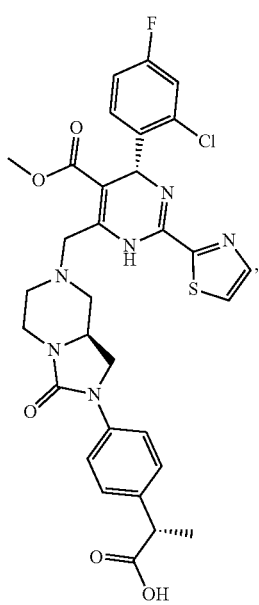
404
-continued
(206)
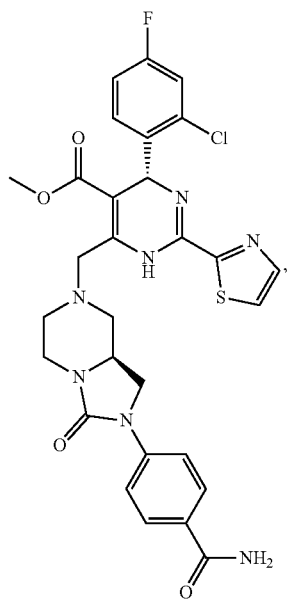
(207)
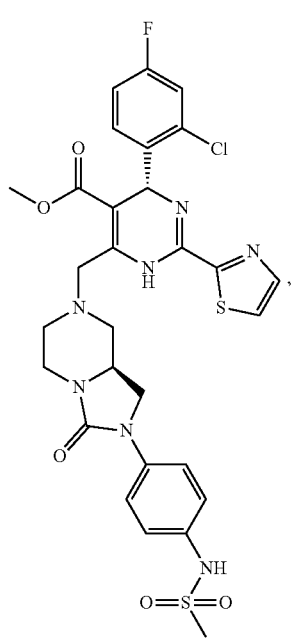

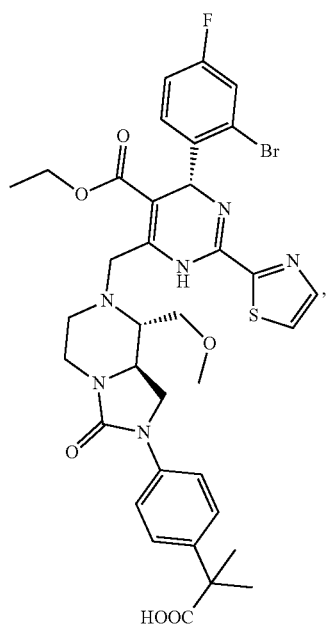
(208)
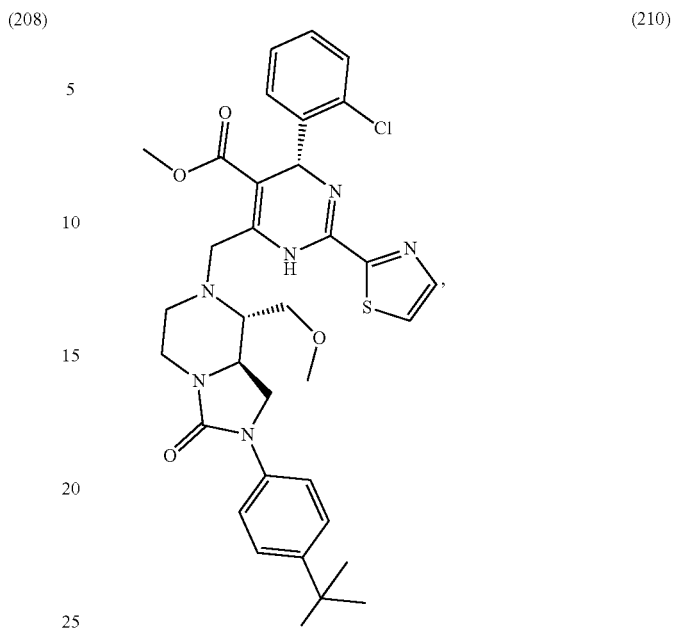
(210)
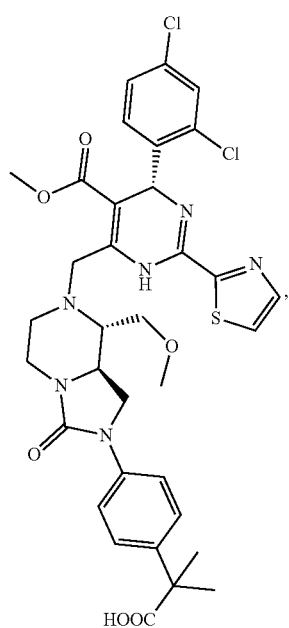
(209)
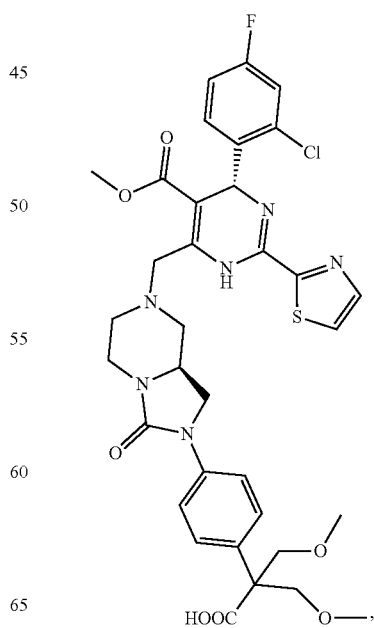
(211)

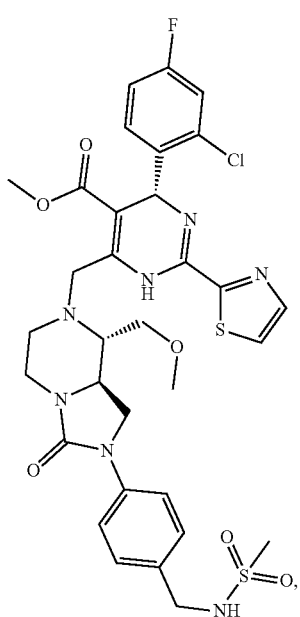

(212)

or a stereoisomer, a tautomer, an N-oxide, a solvate, a metabolite, a pharmaceutically acceptable salt or a prodrug thereof.

13. A pharmaceutical composition comprising the compound of claim 1 and a pharmaceutically acceptable adjuvant.

14. The pharmaceutical composition of claim 13 further comprising other anti-HBV drug, wherein the other anti-HBV drug is an HBV polymerase inhibitor, immunomodulator or interferon.

15. The pharmaceutical composition of claim 14, wherein the other anti-HBV drug is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, Euforavac, rintatolimod, Phosphazid, Heplisav, interferon α-2b, levamisole, or propagermanium.

16. A method of treating or lessening a virus disease comprising administering the compound of claim 1 to a patient in need thereof, wherein the virus disease is hepatitis B infection or a disease caused by hepatitis B infection.

17. The method of claim 16, wherein the disease caused by hepatitis B infection is hepatic cirrhosis or hepatocellular carcinogenesis.

18. A method of treating or lessening a virus disease comprising administering the pharmaceutical composition of claim 13 to a patient in need thereof, wherein the virus disease is hepatitis B infection or a disease caused by hepatitis B infection.

19. The method of claim 18, wherein the disease caused by hepatitis B infection is hepatic cirrhosis or hepatocellular carcinogenesis.

* * * * *